(12) United States Patent
Spears

(10) Patent No.: US 10,394,977 B2
(45) Date of Patent: Aug. 27, 2019

(54) METHOD AND APPARATUS FOR SHAPE-BASED ENERGY ANALYSIS OF SOLIDS

(71) Applicant: Robert E. Spears, Idaho Falls, ID (US)

(72) Inventor: Robert E. Spears, Idaho Falls, ID (US)

( * ) Notice: Subject to any disclaimer, the term of this patent is extended or adjusted under 35 U.S.C. 154(b) by 1436 days.

(21) Appl. No.: 14/298,522

(22) Filed: Jun. 6, 2014

(65) Prior Publication Data
US 2015/0356218 A1 Dec. 10, 2015

(51) Int. Cl.
G06F 17/50 (2006.01)
G01N 3/02 (2006.01)

(52) U.S. Cl.
CPC .......... *G06F 17/5018* (2013.01); *G01N 3/02* (2013.01)

(58) Field of Classification Search
CPC .............................. G06F 17/5018; G01N 3/02
See application file for complete search history.

(56) References Cited

U.S. PATENT DOCUMENTS

| | | | | |
|---|---|---|---|---|
| 5,984,511 A * | 11/1999 | Vasey-Glandon | ...... | G06F 17/50 345/420 |
| 8,249,837 B1 * | 8/2012 | Prabhu | ................ | G06F 17/5018 703/2 |
| 8,401,827 B2 | 3/2013 | Patnala | | |
| 8,467,997 B2 | 6/2013 | Hallquist et al. | | |
| 8,612,186 B2 | 12/2013 | Wu et al. | | |
| 2003/0204823 A1 * | 10/2003 | Armstrong | .............. | G06F 17/50 703/1 |
| 2004/0064295 A1 * | 4/2004 | Zhang | ................ | G06F 17/5018 703/2 |

(Continued)

OTHER PUBLICATIONS

Coutinho, A. L. G. A. et al. "Edge-based finite element techniques for non-linear solid mechanics problems" in: Int. J. Numer. Meth. Engng., 50: 2053-2068. 2001 [retrieved Jul. 24, 2017]. Retrieved from the Internet: < URL: http://onlinelibrary.wiley.com/doi/10.1002/nme.107/pdf> <doi:10.1002/nme.107>.*

(Continued)

*Primary Examiner* — Omar F Fernandez Rivas
*Assistant Examiner* — Robert S Brock
(74) *Attorney, Agent, or Firm* — Harness, Dickey & Pierce, P.L.C.

(57) ABSTRACT

A method of evaluating response of a physical structure to external stimulus includes defining a mesh of finite elements, each defined by edges, for a model of the physical structure. The method includes identifying a governing differential equation and associated complementary functions, which are each associated with a scalar multiplier. The method includes generating an energy optimization model that minimizes a difference between internal and external energies of the finite elements. The internal energy is based on strain energy in a volume defined by the edges of the finite element and resulting from deformations by the complementary functions. The external energy of each finite element is based on external work done by the external stimulus acting on the finite element as deformed by the complementary functions. The method includes solving the energy optimization model for the scalar multipliers and calculating a resulting parameter of interest of the physical structure.

20 Claims, 33 Drawing Sheets

(56) References Cited

U.S. PATENT DOCUMENTS

2008/0300831 A1* 12/2008 Taggart .............. G06F 17/5018 703/1
2019/0005171 A1* 1/2019 Zhang .................. G06F 17/156

OTHER PUBLICATIONS

Hutton, D. V., Fundamentals of Finite Element Analysis. McGraw-Hill, 2004 [retrieved on Aug. 2, 2017]. Retrieved from the Internet: <URL: http://research.iaun.ac.ir/pd/atrian/pdfs/UploadFile_2613.pdf>.*

Helm, Section 19.3: Second Order Differential Equations, Workbook 19: Differential Equations. pp. 30-50. 2008 [retrieved on Jul. 27, 2017]. Retrieved from the Internet: <http://epsassets.manchester.ac.uk/medialand/maths/helm/19_3.pdf >.*

Sydenstricker R.M., et al., Edge-Based Interface Elements for Solution of Three-Dimensional Geomechanical Problems. In: VECPAR 2002. Lecture Notes in Computer Science, vol. 2565. Springer, 2003 [retrieved on Jul. 24, 2017]. Retrieved from SpringerLink: <URL: https://link.springer.com/content/pdf/10.1007/3-540-36569-9_4.pdf>.*

Li, Y., "Edge based finite element simulation of eddy current phenomenon and its application to defect characterization." Retrospective Theses and Dissertations. Paper 1006. 2002 [retrieved Jul. 27, 2017]. Retrieved from the Internet: <URL: http://lib.dr.iastate.edu/cgi/viewcontent.cgi?article=2005&context=rtd>.*

Voss, Heinrich. "A new justification of finite dynamic element methods." In Numerical Treatment of Eigenvalue Problems vol. 4/Numerische Behandlung von Eigenwertaufgaben Band 4, pp. 232-242. Birkhäuser Basel, 1987. 10 pages (Year: 1987).*

Fraeijs De Veubeke, Baudouin. Duality in structural analysis by finite elements. No. SA-27. LTAS, 1971. pp. 323-355 (Year: 1971).*

Duarte, C. A., T. J. Liszka, W. W. Tworzydlo, and T. A. Westermann. "The Generalized Finite Element Method-Improving Finite Elements Through Meshless Technology." Structural Research Series 639 (2005). 50 pages (Year: 2005).*

Azene, Muluneh. "A finite element complementary energy formulation for plane elastoplastic stress analysis." PhD diss., Texas Tech University, 1979. 141 pages (Year: 1979).*

Arnold, Douglas N. "Mixed finite element methods for elliptic problems." Computer methods in applied mechanics and engineering 82, No. 1-3 (1990): 281-300. Obtained from http://www.academia.edu/download/43756796/rnixed.pdf on Dec. 20, 2018 (Year: 1990).*

Raviart, Pierre-Arnaud, and Jean-Marie Thomas. "A mixed finite element method for 2-nd order elliptic problems." In Mathematical aspects of finite element methods, pp. 292-315. Springer, Berlin, Heidelberg, 1977 (Year: 1977).*

Santos, H. A. F. A., P. M. Pimenta, and J. P. M. Almeida. "A hybrid-mixed finite element formulation for the geometrically exact analysis of three-dimensional framed structures." Computational Mechanics 48, No. 5 (2011): pp. 591-613 (Year: 2011).*

Ugural, A. C., 1999, "Stresses in Plates and Shells," Second Edition, Chapter 3—Elements of Plate-Bending Theory, The Ritz Method, pp. 97-98.

Simulia, Abaqus 6.12, Analysis User's Manual, vol. 4: Elements, 2012.

Hallquist, John O., LS-DYNA® Theory Manual, Livermore Software Technology Corporation, Mar. 2006.

LS-DYNA® Keyword User's Manual, vol. 1, Version 971, Livermore Software Technology Corporation, May 2007.

* cited by examiner

METHOD AND APPARATUS FOR SHAPE-BASED ENERGY ANALYSIS OF SOLIDS

STATEMENT OF GOVERNMENT RIGHTS

This invention was made with Government support under Prime Contract No. DE-AC07-05-ID14517 awarded by the Department of Energy. The Government has certain rights in this invention.

FIELD

The present disclosure relates to shape-based energy analysis and more particularly to shape-based energy analysis for solid models of physical objects.

BACKGROUND

The background description provided here is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Traditional finite element method (or, traditional finite element analysis) was developed in the 1960s and is currently the best numerical method for evaluating continua and structures. It is usually used to address problems too complicated to be addressed with classical analytical methods.

One usage of finite element analysis is to evaluate stresses (internal forces in a body resulting from externally-applied loads) in structural components. Consider the plate in FIG. 1. An engineer could be presented with or have developed a design where the plate in FIG. 1 is welded in place around its center hole and has to carry the pressure and edge loading shown in FIG. 2 and FIG. 3. Note that the loads in FIGS. 2-3 are put on the plate simultaneously but are shown in different plots for clarity. The engineer might have also selected (or received a specification for) the metal to be used in the plate so that the material properties are known for the plate.

To be a well-engineered component, the engineer wants to make the plate thick enough to carry the loads without having it be permanently deformed or break. Due to factors such as added cost and added weight, the engineer also doesn't want to make the plate thicker than necessary. Considering the material properties, the engineer may decide that the plate can carry a certain stress (for example only, 36,000 psi) before the plate is in danger of permanent deformation or breaking.

Establishing the stress in the plate is well suited for finite element analysis. Finite element analysis establishes the stresses and strains in the plate by breaking the plate into many pieces, or elements. The collection of elements is called a mesh. The elements are of a size and shape that can be numerically evaluated. The loads and the circular inner edge that is fixed in place are referred to as boundary conditions and are applied to the mesh. By simultaneously evaluating all of the elements at once, the stresses and strains can be approximated for the whole plate. In general, the finer the mesh is, the more accurate the stress results are.

FIGS. 4A-4B show an example of traditional finite element analysis results for this problem. In this case, shell elements are used. In general, shell elements are planar and the plate thickness is included in the element formulation (rather than in the physical element shape). In traditional finite element analysis, a shell element consists of a shape (like a triangle or quadrilateral) and points (called nodes) at corners and sometimes along an edge. The triangular elements in FIGS. 4A-4B have a node at each corner and at the center of each edge.

A node can translate or rotate and neighboring elements can share a node. Boundary conditions are applied to nodes and the elements numerically evaluate the stresses and strains that result from the node movement. On the edge that is fixed in place, the nodes are not allowed to move. In the rest of the model, the nodes move according to the stiffness of the elements relative to the applied loads. The nodal movements are the traditional finite element method's degrees of freedom. If a node can translate in the x-direction, y-direction, and z-direction and it can rotate about those same directions, it is said to have six degrees of freedom. The number of degrees of freedom in a finite element model determines how much computer computation is required to solve the problem.

FIG. 4A is a stress plot looking straight down on the plate. It is given in von Mises stress which is used for comparison with the 36,000 psi value defined earlier. The highest stresses are present at the central opening of the mounting plate and the lowest stresses are present at the outside corners. FIG. 4B is a displacement plot, where the deformation in the most positive z-direction is present at the central opening and the deformation in the most negative z-direction at the outside corners. The plate in this plot is rotated and the z displacement is magnified 75× to make it easier to see how the plate is deforming under the loading.

Considering the requirement that the stress be less than 36,000 psi, the engineer could ascertain that the plate in this example should be strengthened because it is overstressed (with a maximum stress of 4.361 e+04 psi, or 43,610 psi). For reference, the maximum displacement in the plate is 4.593e−03 inches or 0.004593 inches.

Element edges in the traditional finite element method must be a straight line between nodes. Consequently, many elements must be meshed (as in this example) to accurately approximate the curvature of a curved edge of the shape. The mesh in FIG. 4A is sufficient to produce accurate results. However, this comes with the cost of over 10,000 degrees of freedom that must be evaluated.

In FIG. 5A, a coarser mesh is applied, which makes the model more efficient to run—i.e., requiring less processing and memory resources. The gain in efficiency may be significant because the number of degrees of freedom to be evaluated is approximately 1/10 of the degrees of freedom of the fine mesh. However, the results are less accurate. Note in FIG. 5A that the circular edges are being followed less accurately (resulting in a jagged edge) and the stress results have significant inaccuracies. This inaccuracy is partially due to the elements not following the circular edge very well. It is also partially due to the elements' size and shape and how the numerical solution is formulated. If the mesh shown in FIG. 5A were the only mesh used to evaluate the problem, it would incorrectly appear that the stresses were acceptable (the maximum stress being approximately 26,840 psi). FIG. 5B similar shows a displacement plot generated using the coarse mesh.

SUMMARY

A method of evaluating response of a physical structure to external stimulus includes storing a structural model of the physical structure. The method includes defining a mesh for the structural model. The mesh includes a plurality of finite elements. Each element of the finite elements is defined by a plurality of edges of the element. The method includes identifying a governing differential equation for each of the plurality of finite elements. The method includes identifying, for each element of the plurality of finite elements, a plurality of complementary functions that satisfy the corresponding governing differential equation. Each of the plurality of complementary functions for each of the plurality of finite elements is associated with a respective scalar multiplier. The method includes generating an energy optimization model that minimizes a difference between internal energy of the plurality of finite elements and external energy of the plurality of finite elements. The internal energy of each finite element of the plurality of finite elements is based on strain energy in a volume of the finite element (i) defined by the edges of the finite element and (ii) resulting from deformations of the finite element by the plurality of complementary functions. The external energy of each finite element of the plurality of finite elements is based on external work done on the finite element by the external stimulus acting on the finite element as deformed by the plurality of complementary functions. The method includes solving the energy optimization model for the scalar multipliers. The method includes calculating a parameter of interest of the physical structure based on the solved scalar multipliers.

Some or all of the elements of the above methods can be implemented as instructions executable on a processor, where the instructions are stored on a non-transitory computer-readable medium. Further, some or all of the elements of the above methods can be implemented in an apparatus, such as a computing system that includes one or more processors, distributed among one or more computing devices, wherein the processors are collectively configured to execute instructions embodying elements of the above methods.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Overview

Figure 1:
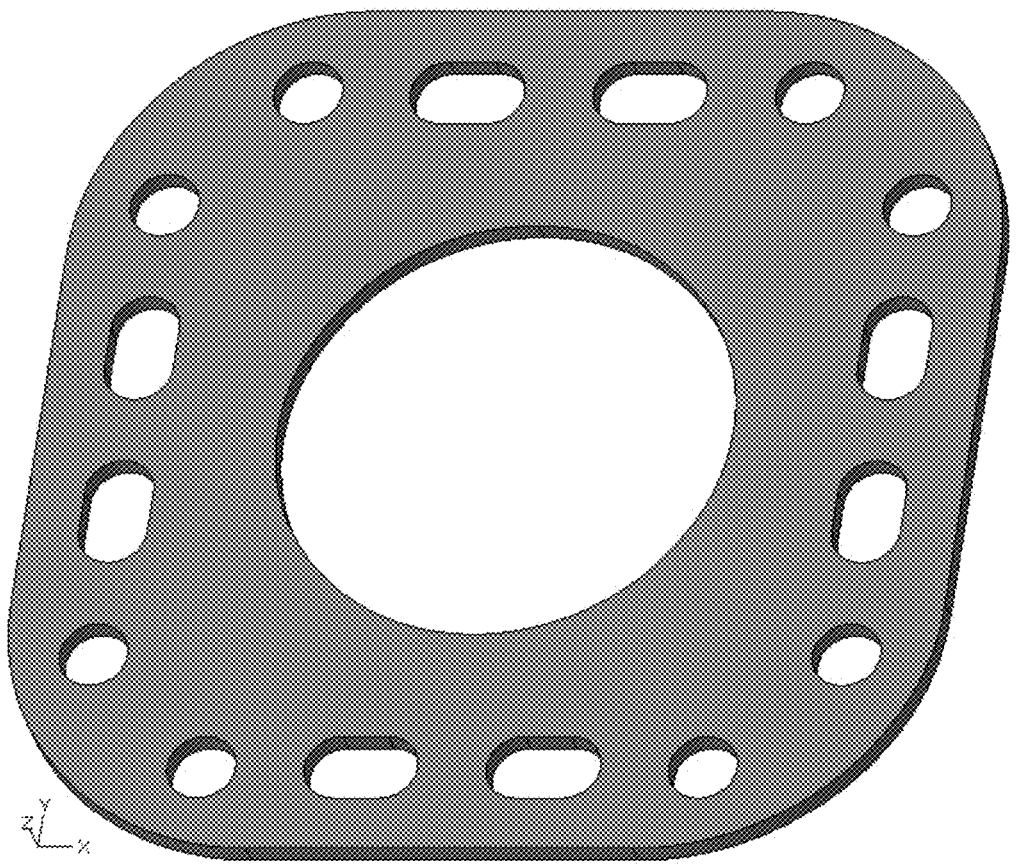
FIG. 1 is a perspective view of an example mounting plate structure.

Traditional finite element analysis relies on determining a governing differential equation and setting boundary conditions. Traditional finite element analysis operates to exactly meet the boundary conditions. Consequently, the degrees of freedom in the problem are translation (and rotation). A shape function is then energy optimized to approximate the governing equation.

Meanwhile, a method according to the present disclosure uses a logical set of functions where each function exactly conforms to the governing differential equation. Consequently, the degrees of freedom are on the shape being studied. Energy optimization is then used to best approximate the boundary conditions. In other words, the degrees of freedom are shape-related and on the element rather than being displacement- and rotation-related and on the nodes, as in traditional finite element analysis.

Any problem currently being solved with the traditional finite element method can instead be solved using the methods or apparatuses described in the present disclosure. This includes static models and dynamic models, allows for structural analysis, computational fluid dynamics, and multibody simulation, and may provide information on parameters such as mechanical stress and thermal stress. Further, acoustic-structural coupling and vibration may be analyzed.

According to the present disclosure, elements may be able to exactly fit curved surfaces/edges, unlike traditional finite element analysis, where elements are defined by series of straight lines between nodes. The straight line element boundaries of traditional finite element analysis may make meshing difficult for irregularly-shaped components. The method according to the present disclosure may allow elements to have any edge shape and may even allow "holes" or voids.

The method uses a logical set of functions where each function exactly conforms to the governing differential equation. To perform this method, the governing differential equation is identified. Then, a series of functions is established. One of these functions addresses the particular solution of the governing differential equation. The rest of the functions are each a complementary function, which causes the governing differential equation to equal zero. These functions could be simple polynomials or sine functions or any other function that satisfies the governing differential equation exactly. The desired features of the solver may drive the form of the functions selected.

Given that each complementary function results in the governing differential equation equaling zero, a constant can be multiplied to each without consequence. These constants are the degrees of freedom for this method. The sum of all the functions and associated constants produces a base equation for displacement. Having a base equation for displacement, differentiation can be used to establish functions for rotation, moment, force, stress, and strain.

An energy optimization is established, which incorporates internal energy (strain) and external work (associated with the applied loads). The internal energy is the strain energy within a given region (or element). The external work is the energy applied to the given element from an external source such as loads or boundary condition at the boundaries of the model or loads from a neighboring element. The optimization is set up in a manner similar to the Ritz Method, as it uses partial differentiation relative to the constants (representing the degrees of freedom) to establish an array and a vector. The array is then used similarly to how a stiffness matrix is used in the traditional finite element process. The vector is used similarly to how a force vector is used in the traditional finite element process.

This method differs from the Ritz Method as the Ritz Method follows the logic of traditional finite element analysis where the boundary conditions are exactly matched and the functions do not necessarily meet the governing equation. Because of these differences, a method according to the present disclosure may perform simultaneous optimizations of a given element relative to both displacement/rotation and force/moment.

The optimization equations are solved symbolically to produce an algebraic solution. If the algebraic solution is set up to address a single edge (and associated volume) of an element, elements of essentially any shape can be evaluated by summing contributions from multiple edges (which are not restricted to straight line shapes). Additional equations may be added that satisfy the governing differential equation if the energy optimization would not otherwise address all of the degrees of freedom.

Constraints, or limits, may be applied to the amplitudes of the degrees of freedom. Without these constraints, the optimization could cause the degrees of freedom to approach positive or negative infinity, which makes matrix inversion unstable. The linear set of equations may be represented by a square array multiplied by a degree-of-freedom vector and set equal to another vector. The coefficients of the vectors and arrays may be stored in a corresponding linear equation data structure For a given element or set of elements, this method produces a system of linear equations analogous to "F=k·x" in traditional finite element analysis. Consequently, a very similar matrix inverting solver can be used to solve for the degrees of freedom. If multiple regions interact, they can be combined into a larger square array multiplied by the combined degree of freedom vector, which equals a combined vector. The solution could be found using similar techniques to those used in traditional finite element analysis. Having found the degrees of freedom, they can be included into the base equation to show the results.

In various implementations, there are no integration points as in traditional finite element analysis, so it is not necessary to extrapolate results. Instead, the optimized stress, strain, etc. may be known for the entire volume of the model. The method may be described as taking a series of correctly-deforming functions and arranging them to best fit deformations associated with a given geometry and boundary conditions.

Comparison

The new method differs from the traditional finite element method in many ways (discussed in more detail below in Section A). As mentioned above, nodal translations are the degrees of freedom in the traditional finite element method. In a method according to the present disclosure (referred to as the "new method"), there are only elements that interrelate but no nodes. According to the new method, the numerical evaluation of an element is based on summing many accurate but simple deformation shapes. As selected by a numerically-optimized energy analysis, each simple deformation shape has a scale factor associated with it. These scale factors are the degrees of freedom for the new method.

Figure 6A:
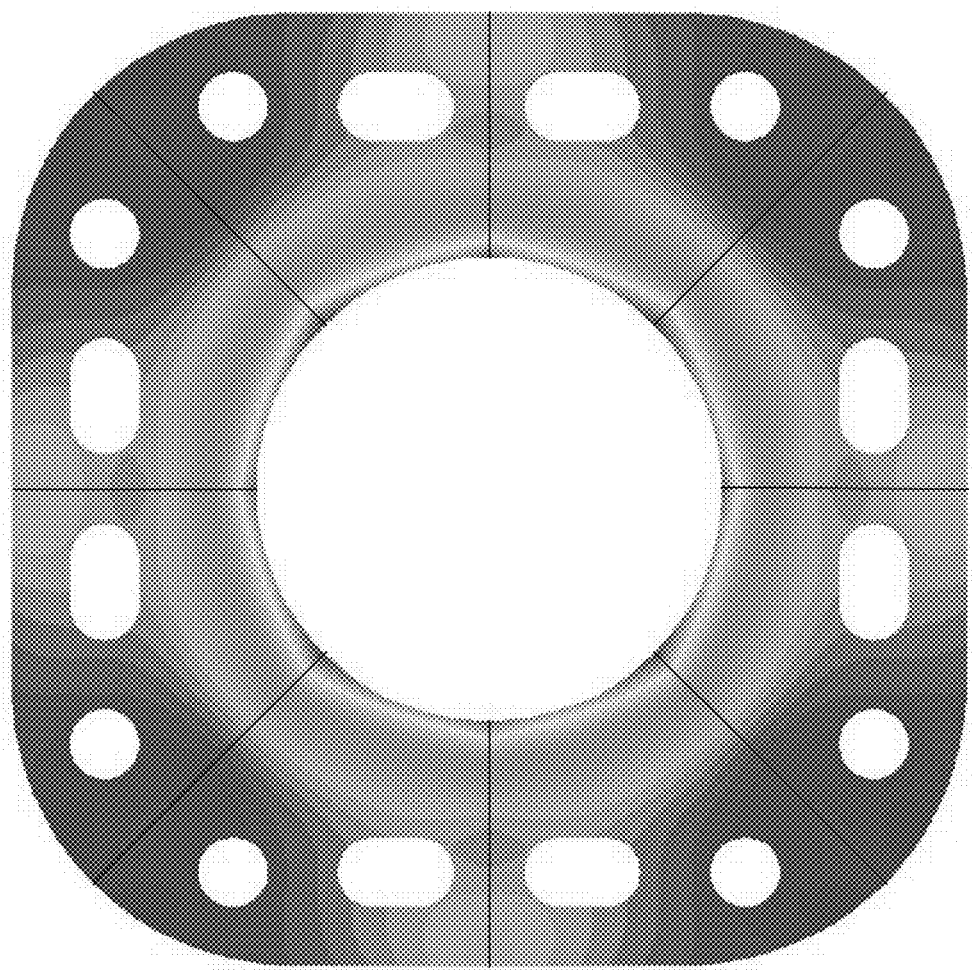
FIG. 6A is a stress plot of the plate of FIG. 1 under applied loads according to finite element methods as described in the present disclosure.

Having no nodes, the new method is unrestricted relative to number and shape of the edges for a single element and, further, holes are allowed in an element. As a result, the new method allows coarser meshes to be used. For example, the mounting plate of FIG. 1 may be divided into a mesh of 8 symmetric elements, as shown in FIG. 6A, and evaluated using the new method. Each of the eight elements can have 18 degrees of freedom, for a total of 144 degrees of freedom in the model.

Figure 6B:
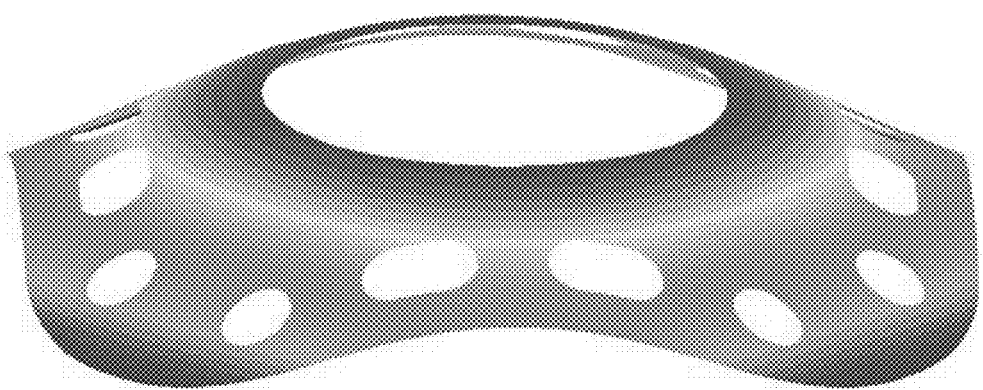
FIG. 6B is a displacement plot of the plate under applied loads according to finite element methods as described in the present disclosure.

In FIG. 6A, a gradient of von Mises stress is shown, with the maximum of 41,830 psi being at the central hole of the mounting plate and the minimum von Mises stress of 1,750 psi occurring at the outside corners of the mounting plate. In FIG. 6B, a gradient of displacement is shown with the maximum positive displacement of 0.000067 in. occurring at the central hole and the maximum negative displacement of −0.004765 in. occurring at the outside corners. To visually present the resulting deformed shape, the displacement plot of FIG. 6B is shown in a perspective view, with the magnitude of displacement magnified by 75×.

Specific results are discussed in greater detail in Section E below. Note that the stress and displacement results for this model using the new method compare closely to that of the finely meshed traditional finite element analysis, including correctly identifying that, according to the design limits, the plate is overstressed.

Because the mesh used by the new model has a dramatically lower number of degrees of freedom to evaluate, and consequently much lower processing burden, the new method may be preferable to the traditional finite element method. Note that, without a benchmark against which to compare, the new method may be evaluated using finer meshes than is shown in FIG. 6A. These finer meshes can confirm (or, in other situations, disprove) that the coarse mesh is sufficient to achieve a required level of accuracy. For most structures, the mesh required by the new method to achieve a similar accuracy will be coarser (fewer elements, and fewer total degrees of freedom) than the traditional finite element method.

As shown in FIG. 6A, the elements according to the new method follow the geometry of the mounting plate exactly, and consequently there is no inaccuracy associated with the multiple straight lines used by the traditional finite element method to approximate a curve. While the geometry and loading in this problem are particularly suitable for evaluation by the new model, in general the new method will give better accuracy per degree of freedom than would the traditional finite element method.

A further distinction referenced above is that the traditional finite element method requires that the boundary conditions be exactly met. For instance, where the nodes of the example mounting plate are fixed by the weld, they are not allowed to move according to the traditional finite element method. This reduces the ability of elements near the boundary condition to produce accurate stress results by artificially stiffening them.

The new method does not require that the boundary conditions be exactly met, meaning that the boundary conditions may be violated in the solution. In various implementations, the boundary conditions can be exactly enforced at the request of the user, with some of the tradeoffs discussed below. As shown in FIG. 6B, the new method depicts a slight positive displacement that occurs at the weld. This is not possible in real life, where the weld would prevent displacement of the plate. However, this local displacement inaccuracy (which causes the boundary conditions to be violated slightly) allows for an increase in the accuracy of the overall stress and displacement results.

Figure 5A:
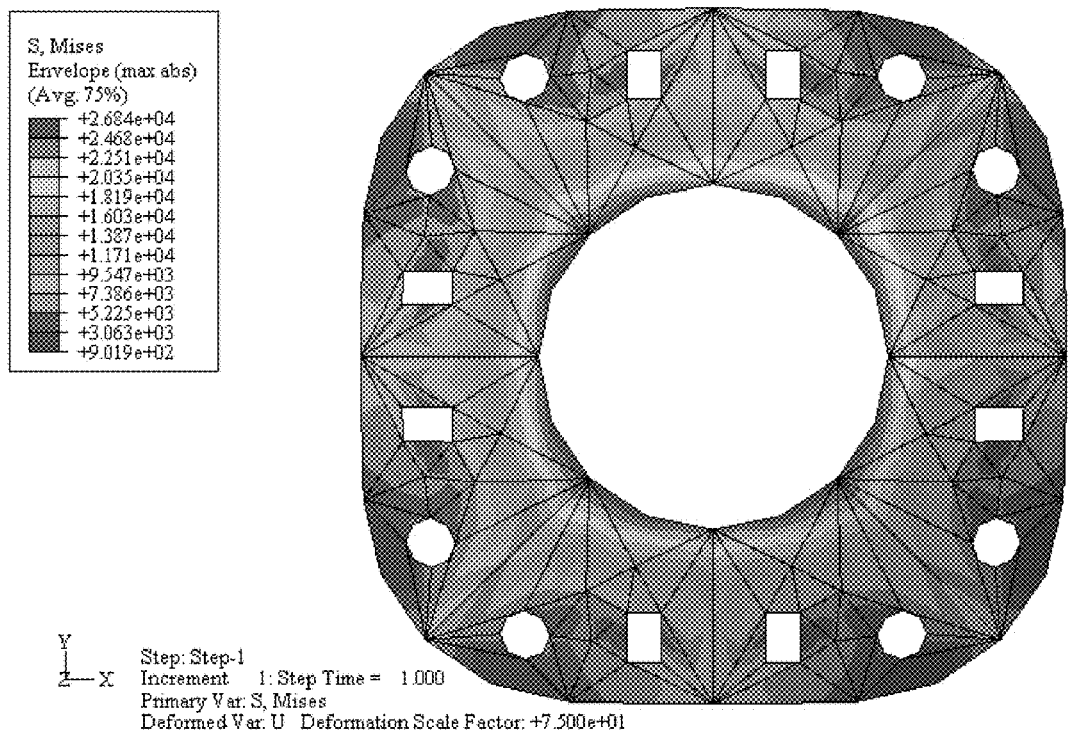
FIG. 5A is a stress plot of the plate of FIG. 1 under applied loads using traditional finite element analysis with a coarse mesh.
Figure 5B:
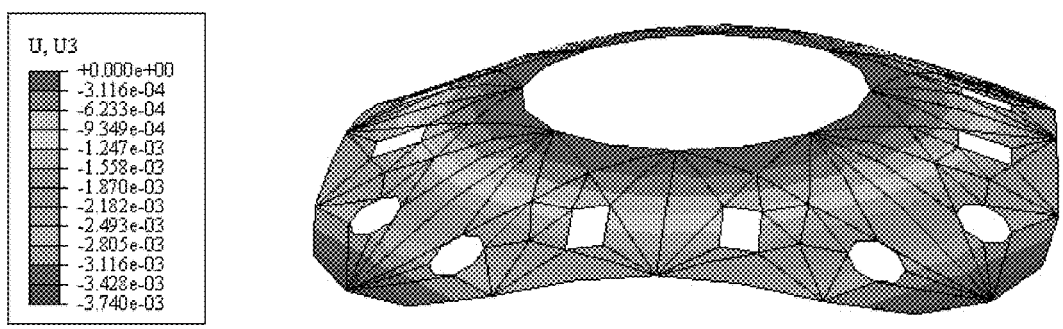
FIG. 5B is a displacement plot of the plate under applied loads with the coarse mesh.

For example, when comparing FIG. 6A to the traditional finite element method used in FIG. 5A, the significantly finer mesh of FIG. 5A has significantly less accurate stress results at the boundary condition (the center hole of the mounting plate), partially resulting from the inability of the traditional finite element method to allow for displacement inaccuracy at the boundary condition. The displacement of FIG. 6B is also significantly more accurate than the traditional finite element method results shown in FIG. 5B, as the small amount of local displacement inaccuracy at the boundary condition allowed for by the new method is offset by better displacement accuracy across the remainder of the structure.

Method and Apparatus

Figure 7:
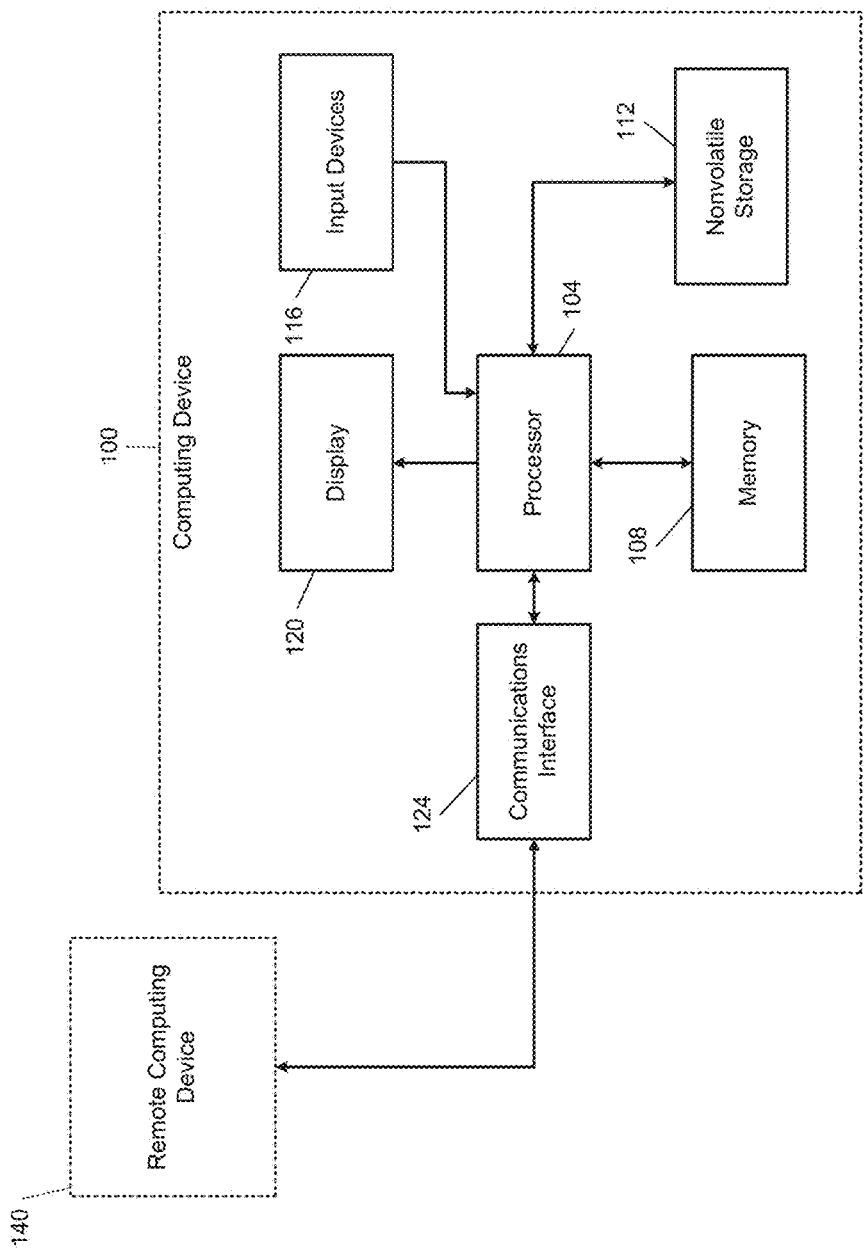
FIG. 7 is a high-level hardware diagram of an example computing device according to the present disclosure.

In FIG. 7, simplified hardware of an example implementation of a computing device 100 is shown. In various implementations, the computing device 100 is, or is part of, an apparatus that performs the methods described in the present disclosure.

A processor 104 executes instructions from a memory 108, and may operate on (read and/or write) data stored in the memory 108. Generally, the memory 108 includes volatile memory, such as dynamic random access memory. The processor 104 communicates, potentially via a chipset (not shown), with nonvolatile storage 112, which may include flash memory acting as a cache of instructions and/or data.

In various implementations, larger capacity and lower cost storage may also be included in the nonvolatile storage 112. For example, optical drives, tape drives, or magnetic storage media, such as hard drives, may be used to store data in the nonvolatile storage 112. Active portions of the data and/or instructions may be cached in the memory 108 and/or in flash portions of the nonvolatile storage 112.

Input devices 116 receive user input, and may include devices such as a keyboard, a mouse, a touchpad, a digitizer tablet, etc. A display 120 displays data to the user, and in various implementations, may be combined with a touch sensitive input device in the form of a touchscreen. A communications interface 124 allows the computing device 100 to communicate with other computing devices—for example, over a local area network or a wide area network, such as the Internet. The local area network may include a wired network or a wireless network.

The computing device 100 may interface with a remote computing device 140 via the communications interface 124. Some processing may be offloaded from the processor 104 to the remote computing device 140. The remote computing device 140 may be placed in a location where additional heat and noise can be generated without disturbing the user. The location may also satisfy other conditions, such as ready access to electrical power, the presence of backup power systems and fire suppression systems, and regulated environmental conditions, including temperature and/or humidity.

The remote computing device 140 may therefore perform tasks that would take significant amounts of time when executed on the processor 104. These tasks may be accelerated by the remote computing device 140, and the computing device 100 may be returned to use for other functions by the user while the remote computing device 140 is performing processing. The remote computing device 140 may service multiple users, and may interact with other remote computing devices (not shown) to load balance processing requests.

For simplicity of illustration, many well-known components, buses, and devices of common computing devices are omitted. For example only, audio inputs and outputs are not shown, graphics cards and accelerators are not shown, and technologies such as direct memory access (DMA) between the memory 108 and the nonvolatile storage 112 are not shown.

Figure 8:
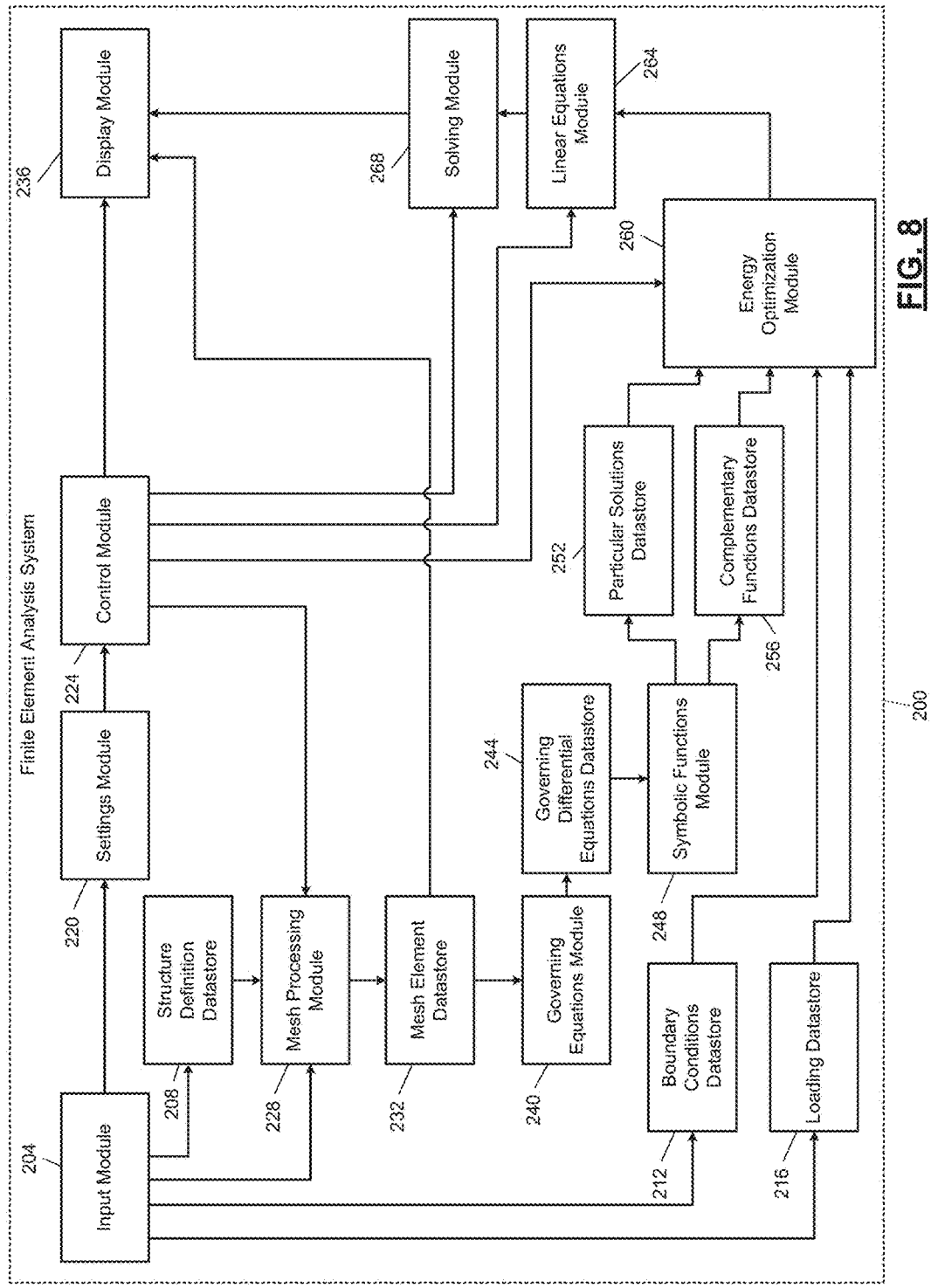
FIG. 8 is a functional block diagram of a system according to the principles of the present disclosure.

In FIG. 8, an input module 204 receives data about a structure, which may be parsed and stored in a structure definition datastore 208. For example only, datastores, such as the structure definition datastore 208, may reside in the nonvolatile storage 112, and may be cached in the memory 108. Information such as the structure of a solid may be received from a CAD (computer aided design) user interface and/or from a CAD file output by a supported CAD or CAE (computer aided engineering) program.

The term 'structure' is inclusive of continuous objects ("continua") and is not meant to imply that the analysis of the structure is limited to analyzing only "structural" responses (such as stress and strain) to applied forces. Instead, the new method may evaluate the response of the structure to other stimuli, including a thermal load (such as radiation, convection, and/or conduction loads).

The input module 204 also receives data regarding boundary conditions, which are stored in a boundary conditions datastore 212. The boundary conditions may include, as described above, solid connections between the structure and other structures and may specify locations of the structure whose physical displacement should remain close to zero. The input module 204 may also receive information regarding applied forces and loads, which is stored in a loading datastore 216.

The input module 204 may also receive settings specified by the user, such as through a graphical user interface, a command line interface, or a settings file. A settings module 220 stores these settings and uses them to control operation of a control module 224. The settings may include, for example, how fine of a mesh to use when creating a mesh of the structure. The density of the finite element mesh may vary throughout the structure—for example, depending on the anticipated change in stress levels of a particular area. Regions that experience high changes in stress may require a higher mesh density than those that experience little or no stress variation. Points of interest may include fracture points of previously tested material, fillets, corners, and high-stress areas.

The settings may also include a precision tolerance used when refining the mesh. As the mesh is refined, parameters of interest may begin to converge on a final value. Once this convergence leads to changes smaller than a set threshold, the process may be considered complete. The settings may also specify how edges of the finite elements in a mesh interact with each other, and may include a spring constant that defines how strongly coupled each edge is to adjacent edges. The settings module 220 may also store parameters such as material properties for constituent materials of the structure.

The control module 224 instructs a mesh processing module 228 to generate a mesh of finite elements based on the structure stored by the structure definition datastore 208. A mesh element datastore 232 stores the definition of the elements in the mesh, and may provide this definition to a display module for presentation to a user via a graphical user interface. The user may visually evaluate the mesh and provide changes via the input module 204 to refine the mesh according to the preferences and experience of the user.

A governing equations module 240 determines governing differential equations for each element in the mesh element datastore 232. In various implementations, a single governing equation may be used for many or all elements of the mesh element datastore 232. A governing differential equations datastore 244 includes data structures that represent the governing equations determined by the governing equations module 240.

A symbolic functions module 248 determines particular solutions and complementary functions that satisfy the governing differential equations from the governing differential equations datastore 244. A particular solutions datastore 252 stores the particular solution that solves each of the corresponding governing differential equations. Meanwhile, a complementary functions datastore 256 stores complementary functions that provide degrees of freedom, but evaluate to zero in the governing differential equation.

An energy optimization module 260 generates a model based on the particular solutions datastore 252, the complementary functions datastore 256, the boundary conditions datastore 212, and the loading datastore 216. This model represents the difference between internal energy (strains) and external energy (forces and loads), and may be optimized (e.g., reduced) in order to find an accurate solution for the finite element analysis.

A linear equations module 264 generates linear equations based on the energy optimization model, and a solving module 268 solves the linear equations from the linear equation module 264. A display module 236 provides information about the determined solution to the user, and may include text and figures. For example only, the figures may depict a gradient of parameters, such as stress or displacement, as shown in, for example, FIGS. 6A and 6B. The display module 236 may depict other parameters of interest, including moments (bending, torsional, etc.), strains, normal and shear strain, normal and shear stress, etc. Some or all of these parameters may be superimposed on a deformed 3D model of the structure that can be rotated, zoomed, or viewed in cross-section.

Figure 9A:
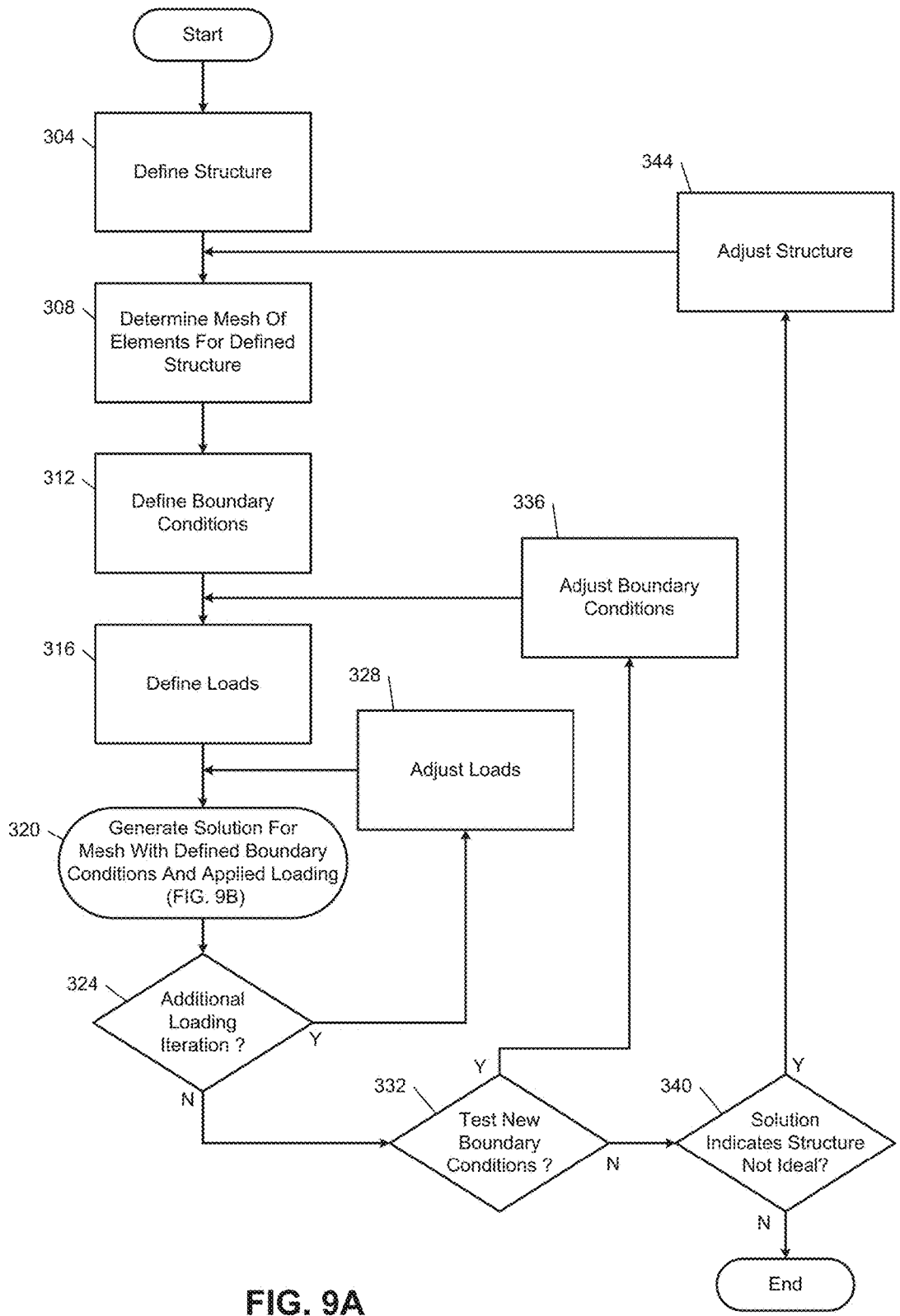
FIG. 9A is a flowchart demonstrating example operation of finite element analysis of a structure of interest.

In FIG. 9A, control begins at 304 where a structure is defined. At 308, control determines a mesh of elements for the defined structure. At 312, boundary conditions are defined for the structure. At 316, loads applied to the structure are defined. At 320, a solution for the mesh with the defined boundary conditions and applied loading is generated according to FIG. 9B. At 324, control determines whether an additional loading iteration should be performed. If so, control transfers to 328; otherwise, control continues at 332. Additional loading iterations may be performed to determine the structure's response to a variety of different magnitudes or locations of loads. At 328, the loads are adjusted and control returns to 320.

At 332, control determines whether new boundary conditions are to be tested. If so, control transfers to 336; otherwise, control continues at 340. At 336, control adjusts boundary conditions and returns to 316. For example, boundary conditions may be adjusted to determine the structure's reaction to different support and reinforcement patterns.

At 340, control determines whether the solution generated at 320 indicates that the structure is not ideal. If so, control transfers to 344; otherwise, control ends. In addition, at 340, results may be displayed to the user. The degrees of freedom solved for at 320 can be substituted into various equations to determine displacements, moments, strains, stresses, moments, torques, etc.

At 344, control allows the user to adjust the structure, and control returns to 308. The user may adjust the structure by, for example, increasing a thickness of a portion of the structure and/or identifying different material characteristics for the structure. A determination of whether the structure is ideal may be based on predefined limits that the user has set or determined for results such as stress or displacement. These limits may be defined in a manner that varies across the structure and/or may be expressed as maximum limits that should not be exceeded across the entire structure.

Figure 9B:
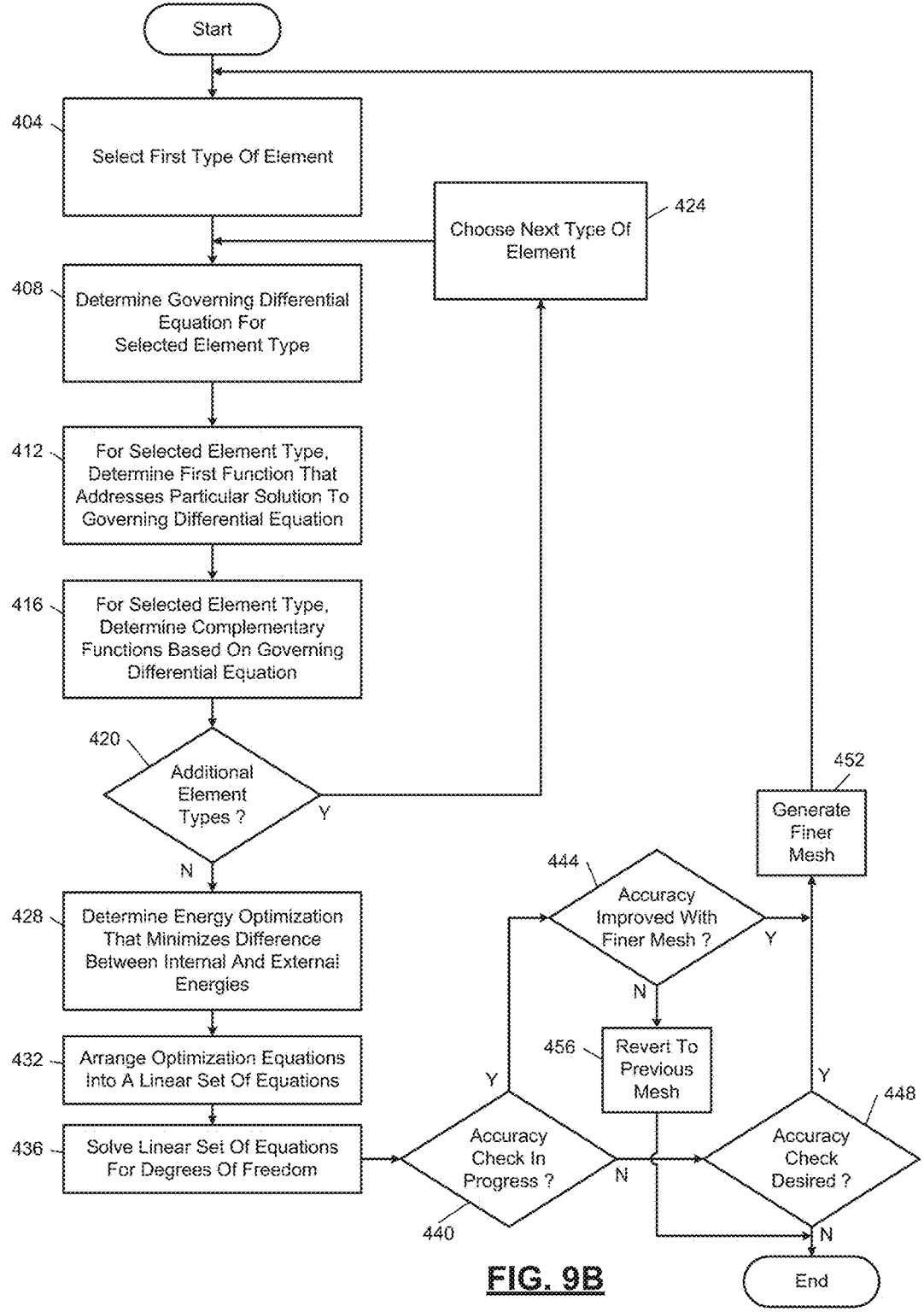
FIG. 9B is a flowchart demonstrating example operation of generating a solution for a finite element analysis mesh of a given structure.

In FIG. 9B, control begins to generate a solution at 404. At 404, control selects a first type of element from the mesh of elements and continues at 408. At 408, control determines a governing differential equation for the selected element type. In various implementations, governing differential equations may be predefined for a wide range of element types, and the appropriate governing differential equations are chosen based on the element types found in the mesh. Further, the range of stored governing differential equations may determine the set of mesh elements that can be used in creating the mesh. Using other mesh elements may require separate determination of the corresponding governing differential equations.

Multiple governing differential equations may be available for selection by the user. Each of the governing differential equations may have properties that make it more or less suitable in various scenarios. For example, governing differential equations may include polynomial terms, exponential terms, and/or trigonometric terms. For instance, in certain circumstances a governing differential equation having trigonometric terms may accurately reflect stress stiffening, and may therefore be selected in analyses where stress stiffening is of interest.

At 412, for the selected element type, control determines a first function that addresses a particular solution to the governing differential equation. At 416, for the selected element type, control determines one or more complementary functions based on the governing differential equation. In various implementations, the complementary functions may be predetermined for a given governing differential equation. In various implementations, a subset of the predetermined complementary functions may be selected. Additional complementary functions can be included in the subset to give additional degrees of freedom.

At 420, control determines whether additional element types are present in the mesh. If so, control transfers to 424; otherwise, control transfers to 428. At 428, control determines an energy optimization that minimizes the difference between internal and external energies of the structure. For a given element, the linear superposition of the particular solution to the governing differential equation and the associated complementary functions define how the element will deform. Essentially, the scalar multipliers for the complementary functions are varied to adjust the deformation of the element to reduce the difference between the internal energies created by the deformations and the external work imposed on the element by external work, including external forces, the effects of adjacent elements, and boundary conditions. The energy optimization creates a set of equations that quantify this difference.

For example, the area mapping array of Section E (below) can be used to determine the internal energies of the element in response to the particular solution and complementary functions. The edge mapping array of Section E can be used to determine the external work exerted on the element in response to the particular solution and complementary functions. In cases where there is a force (such as gravity) applied to the body of the element, and not just to the edges, the area mapping array can be used to also determine the external work exerted on the element by that force.

At 432, control transforms the optimization equations into a linear set of equations. At 436, control solves the linear set of equations for the degrees of freedom in the linear set of equations. The linear set of equations can be expressed in a standard matrix representation as $A \cdot x = B$, where A is an n-by-n matrix and x and B are n-element vectors. In the new method, the x vector is the set of scalar multipliers for the complementary functions of all of the elements in the mesh—i.e., the set of all degrees of freedom.

This form is analogous to the matrix of equations "$F = k \cdot x$" generated in traditional finite element analysis, in which k is referred to as a stiffness matrix. Consequently, a matrix-inverting solver similar to that used in the traditional finite element method can be used to solve for the degrees of freedom in the new method. The matrix in the new method, as in the traditional finite element method, may be banded—i.e., non-zero values are concentrated around the diagonal, and the upper-right and lower-left portions of the matrix are nearly all zeroes. As a result, solvers for the traditional finite element method may be more efficient than general linear equation solvers because they have been optimized to invert banded matrices.

At 440, control determines whether an accuracy check is in progress. If so, control transfers to 444; otherwise, control transfers to 448. At 448, control determines whether an accuracy check is desired. If so, control transfers to 452; otherwise, control ends and may return to, for example, FIG. 9A. At 452, an accuracy check is desired, and therefore, a finer mesh is generated for the defined structure. Control then returns to 404.

Referring back to 444, control determines whether accuracy of results, such as stress or displacement, has improved with the finer mesh generated by 452. If so, control transfers to 452 to generate a still finer mesh; otherwise, if the accuracy was not improved, control transfers to 456, where the previous mesh is reverted to. The previous mesh may be retained because the finer mesh requires more processing resources to solve but did not improve accuracy. Control of FIG. 9B then ends.

Section A—Fundamental Analysis

While the mounting plate above gives a specific example of an application of the new method, more general aspects of the new method as applied to structural analysis of a shell element are presented here. The analysis in the disclosure below can be applied analogously to other element types, such as beams and bricks.

This Section (Section A) provides equations for the formulation of a shell element. It then details a comparison of the equations used by the traditional finite element method versus those used by the new method to define a shell element and mesh.

Section B uses the equations from Section A that are relevant to the new method and performs an example problem where the new method shell element has all straight edges. The selected example problem has an exact solution so that the results can be compared for accuracy. Also, traditional finite element analysis results are compared to the exact solution.

Section C uses the equations from Section A that are relevant to the new method and additional equations from Section B and performs an example problem where the new method shell element has two straight edges and a circular edge. The selected example problem again has an exact solution so that the results can be compared for accuracy. Also, traditional finite element analysis results are compared to the exact solution.

Section D uses the equations from Section A that are relevant to the new method and additional equations from Section B and performs an example problem where the new method shell element has two straight edges and a general curved edge. The selected example problem shares the exact solution as used in Section C and the results are compared for accuracy.

Section E uses applicable equations from Sections A, B, and C to develop the example problem described in the Overview section. Traditional finite element analysis results are also run and compared to the new method results.

Sections A-E address a shell element in bending. To address in-plane deformations, a different set of shell equations is developed in Section F.

Outline

Section A demonstrates a relatively simple theoretical comparison of the traditional finite method with the new method. The comparison is performed using an example problem where a triangular shell element is evaluated for out of plane bending. The problem is kept as simple as possible relative to governing equations and element formulation to illustrate fundamental differences. This problem represents one possibility in a large family of problems that can be addressed with either method.

The comparison is described in several portions. The first portion (Shell Equations) provides equations relevant to the example problem. These equations represent one possible shell formulation and are true regardless of which method is performed. The second portion (Traditional FEA Method) derives the equations to perform a traditional finite element analysis. The third portion (New Method) derives equations for performing a finite element analysis using the new method. The differences are discussed in a fourth portion (Discussion).

The most significant difference in the two methods (as applied to the example problem) is how the base equation for displacement is established. In traditional FEA, the base equation for displacement is selected to exactly meet the boundary conditions and approximate the governing equation. In the new method, the base equation for displacement is selected to exactly meet the governing equation and approximate the boundary conditions. Both methods are energy optimized but the difference in base equations drives different methods of energy optimization. (It should be noted that the energy optimization shown for the traditional FEA is not the only approach, but it is one of the better ones. The selection of the base equation for displacement is representative of all traditional FEA approaches.)

Shell Equations

The shell equations presented here are for shell bending due to a distributed pressure, forces, and moments. For additional background on these equations, see Ugural, A. C., 1999, "Stresses in Plates and Shells," Second Edition, WCB/McGraw-Hill, Inc., Boston. In Ugural, these equations are identified as equations for "plates" and "shells" and are said to not carry a moment. In contrast, this disclosure uses the term "shell" to refer to a moment carrying element as is now common in the art.

Figure 10:
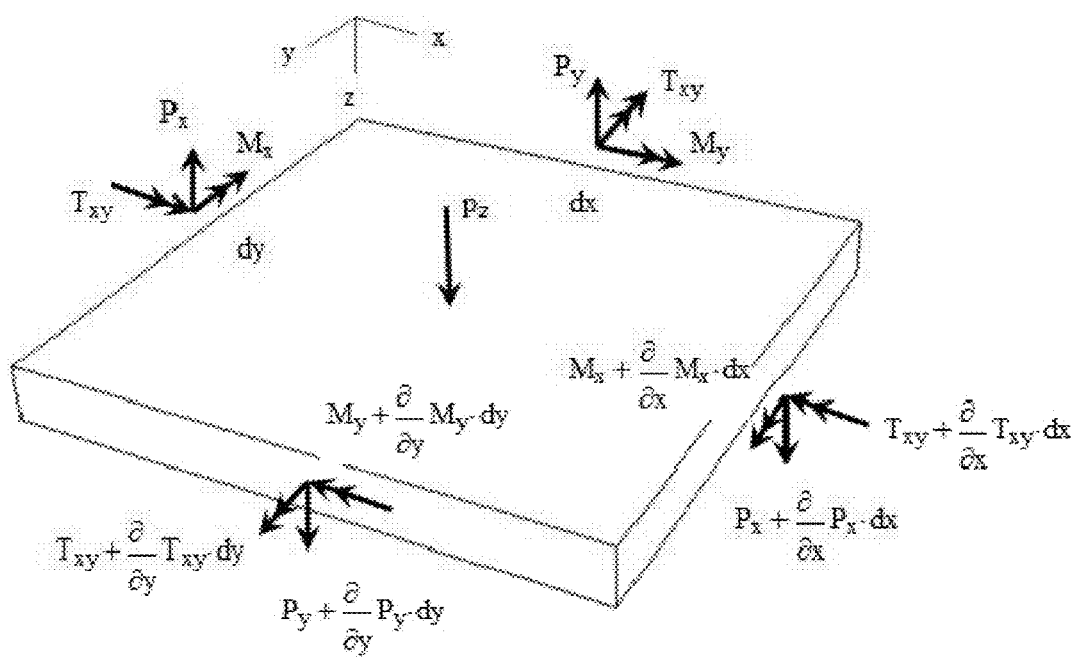
FIG. 10 is a free body diagram of a shell solid demonstrating pressures, moments, torsions, and shears.

FIG. 10 shows equilibrium in a shell for the considered problem.

$P_z$—Applied pressure $M_x$—Moment on the x-face perpendicular to the shell thickness and parallel to the x-face $M_y$—Moment on the y-face perpendicular to the shell thickness and parallel to the y-face $T_{xy}$—Torsion on the x-face and perpendicular to the x-face or torsion on the y-face and perpendicular to the y-face $P_x$—Shear on the x-face parallel to the shell thickness $P_y$—Shear on the y-face parallel to the shell thickness Eq. A-1 is the flexural rigidity, which in various implementations is a constant:

$$D = \frac{E \cdot t^3}{12 \cdot (1 - v^2)} \quad \text{Flexural rigidity} \qquad \text{Eq. A-1}$$

Where:

E—Modulus of elasticity v—Poisson's ratio t—Shell thickness

Eq. A-2 is the governing equation for this example:

$$\frac{d^4}{dx^4}w + 2 \cdot \frac{d^2}{dx^2}\frac{d^2}{dy^2}w + \frac{d^4}{dy^4}w = \frac{p_z}{D} \qquad \text{Eq. A-2}$$

Governing equation

Where:

w—Displacement perpendicular to the plane of the shell element

Eqs. A-3 to A-8 relate stress, strain, loads, and displacements $$M_x = -D \cdot \left( \frac{d^2}{dx^2} w + v \cdot \frac{d^2}{dy^2} w \right) \quad \text{Eq. A-3}$$

Bending moment on the x-face $$M_y = -D \cdot \left( \frac{d^2}{dy^2} w + v \cdot \frac{d^2}{dx^2} w \right)$$

Bending moment on the y-face $$T_{xy} = -D \cdot (1-v) \cdot \frac{\partial}{\partial x} \frac{\partial}{\partial y^2} w$$

Torsional moment on the x- or y-face $$P_x = -D \cdot \frac{\partial}{\partial x} \left( \frac{d^2}{dx^2} w + \frac{d^2}{dy^2} w \right) \quad \text{Eq. A-4}$$

Shear force on the x-face $$P_y = -D \cdot \frac{\partial}{\partial y} \left( \frac{d^2}{dx^2} w + \frac{d^2}{dy^2} w \right)$$

Shear force on the y-face $$\sigma_x = \frac{12 \cdot M_x \cdot z}{t^3} \quad \text{Eq. A-5}$$

Normal stress in the x-direction through the shell thickness $$\sigma_y = \frac{12 \cdot M_y \cdot z}{t^3}$$

Normal stress in the x-direction through the shell thickness $$T_{xy} = \frac{12 \cdot T_{xy} \cdot z}{t^3}$$

Shear stress through the shell thickness

Where:

z—Position along the z-axis (parallel to the thickness) considering an origin at the shell neutral axis $$\varepsilon_x = -z \cdot \frac{d^2}{dx^2} w \quad \text{Eq. A-6}$$

Normal strain in the x-direction through the shell thickness $$\varepsilon_y = -z \cdot \frac{d^2}{dy^2} w$$

Normal strain in the x-direction through the shell thickness $$Y_{xy} = -2 \cdot z \cdot \frac{\partial}{\partial x} \frac{\partial}{\partial y} w$$

Shear strain through the shell thickness $$\begin{pmatrix} \varepsilon_x \\ \varepsilon_y \\ Y_{xy} \end{pmatrix} = \frac{1}{E} \cdot \begin{bmatrix} 1 & -v & 0 \\ -v & 1 & 0 \\ 0 & 0 & 2 \cdot (1+v) \end{bmatrix} \cdot \begin{pmatrix} \sigma_x \\ \sigma_y \\ T_{xy} \end{pmatrix} \quad \text{Eq. A-7}$$

Strain as a function of stress at a point $$\begin{pmatrix} \sigma_x \\ \sigma_y \\ T_{xy} \end{pmatrix} = \frac{E}{1-v^2} \cdot \begin{bmatrix} 1 & v & 0 \\ v & 1 & 0 \\ 0 & 0 & \frac{1}{2} \cdot (1-v) \end{bmatrix} \cdot \begin{pmatrix} \varepsilon_x \\ \varepsilon_y \\ Y_{xy} \end{pmatrix}$$

Strain as a function of stress at a point $$\begin{pmatrix} M_x \\ M_y \\ T_{xy} \end{pmatrix} = \int_{-\frac{t}{2}}^{\frac{t}{2}} \begin{pmatrix} \sigma_x \\ \sigma_y \\ T_{xy} \end{pmatrix} \cdot z \, dz \quad \text{Eq. A-8}$$

Integral relationship between stress and moment (where the z-axis origin is at the neutral axis of the shell)

Traditional FEA Method

Figure 11:
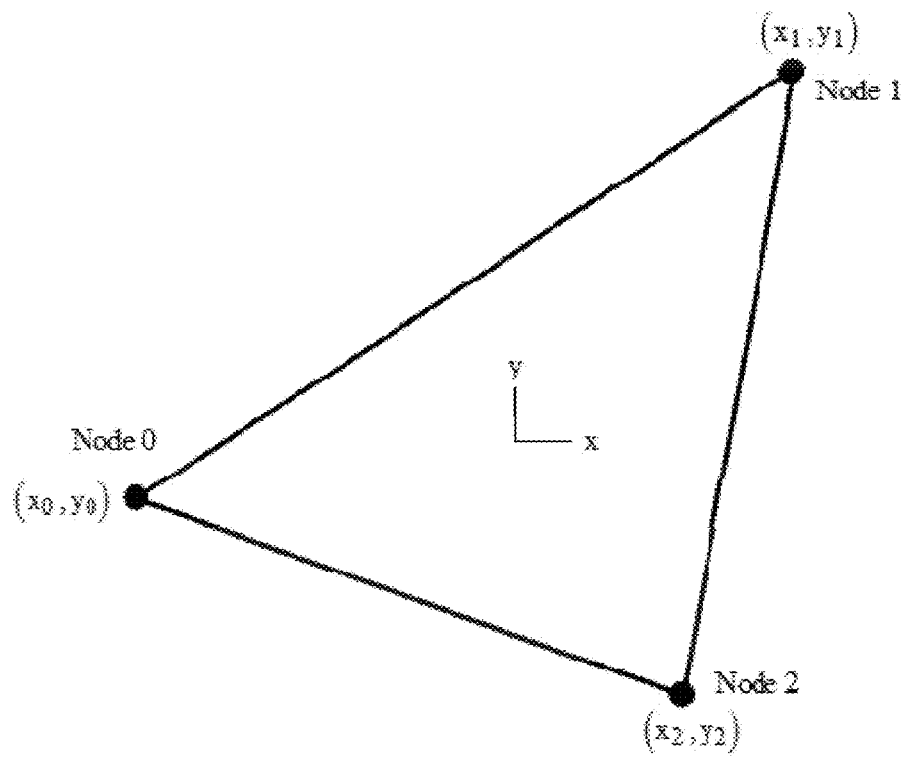
FIG. 11 is a graphical depiction of an example triangular shell with nodes and nodal positions identified according to the prior art.

FIG. 11 shows a triangular finite element according to traditional finite element analysis. There are three nodes and each node has three degrees of freedom. The degrees of freedom include an out of plane displacement and in plane angular rotations in the x- and y-directions.

This method starts by relating the element displacement to the displacement at the nodes with shape functions (Eq. A-9). The shape functions ensure that the applied displacements (and loads) are exactly met at the nodes. It is desirable that the shape functions approximate the governing equation (Eq. A-2) but this is not explicitly enforced in the shape of the shape functions.

The derivation for the shape functions are presented in Eqs. A-10 to A-16. The base equation for displacement (Eq. A-10) is presented first. This equation can be difficult to establish but is presented as if it is known for ease of presentation.

$w_e = Q \cdot \delta_e$ Element displacement as a function of nodal displacements  Eq. A-9

Where:
Q—Shape functions
$\delta_e$—Nodal displacements $$w_e = a_0 + a_1 \cdot x + a_2 \cdot y + a_3 \cdot x^2 + a_4 \cdot x \cdot y + a_5 \cdot y^2 + a_6 \cdot x^3 + a_7 \cdot (x^2 \cdot y + x \cdot y^2) + a_8 \cdot y^3 \quad \text{Eq. A-10}$$

or in matrix form:

$$w_e = (1 \; x \; y \; x^2 \; x \cdot y \; y^2 \; x^3 \; x^2 \cdot y + x \cdot y^2 \; y^3) \cdot \quad \text{Eq. A-11}$$
$$(a_0 \; a_1 \; a_2 \; a_3 \; a_4 \; a_5 \; a_6 \; a_7 \; a_8)^T$$
$$L = (1 \; x \; y \; x^2 \; x \cdot y \; y^2 \; x^3 \; x^2 \cdot y + x \cdot y^2 \; y^3)$$

Position variables $$a = (a_0 \; a_1 \; a_2 \; a_3 \; a_4 \; a_5 \; a_6 \; a_7 \; a_8)^T$$

Equation constants $$w_e = L \cdot a$$

Element displacement as a function of element position $$\theta = \frac{\partial}{\partial y} w \quad \text{Eq. A-12}$$

Angular rotation about the x-axis or $$\theta = 0 \; 0 \; 1 \; 0 \; x \; 2 \cdot y \; 0 \; x \cdot (x + 2 \cdot y)$$
$$3 \cdot y^2 \cdot (a_0 \; a_1 \; a_2 \; a_3 \; a_4 \; a_5 \; a_6 \; a_7 \; a_8)^T$$

$$\phi = \frac{\partial}{\partial x} w \quad \text{Eq. A-13}$$

Angular rotation about the y-axis or $$\phi = 0 \; 1 \; 0 \; 2 \cdot x \; y \; 0 \; 3 \cdot x^2$$
$$y \cdot (2 \cdot x + y) \; 0 \cdot (a_0 \; a_1 \; a_2 \; a_3 \; a_4 \; a_5 \; a_6 \; a_7 \; a_8)^T$$

Node 0    Node 1    Node 2      Eq. A-14
$$\delta_e = (w_0 \; \theta_0 \; \phi_0 \; w_1 \; \theta_1 \; w_2 \; \theta_2 \; \phi_2)^T$$

Nodal displacements

Using Eqs. A-11, A-12, and A-13 to find nodal displacement in Eq. A-14 produces:

$$\begin{pmatrix} w_0 \\ \theta_0 \\ \phi_0 \\ w_1 \\ \theta_1 \\ \phi_1 \\ w_2 \\ \theta_2 \\ \phi_2 \end{pmatrix} = \begin{pmatrix} 1 & x_0 & y_0 & x_0^2 & x_0 \cdot y_0 & y_0^2 & x_0^3 & x_0^2 \cdot y_0 + x_0 \cdot y_0^2 & y_0^3 \\ 0 & 0 & 1 & 0 & x_0 & 2 \cdot y_0 & 0 & x_0^2 + 2 \cdot y_0 \cdot x_0 & 3 \cdot y_0^2 \\ 0 & 1 & 0 & 2 \cdot x_0 & y_0 & 0 & 3 \cdot x_0^2 & y_0^2 + 2 \cdot x_0 \cdot y_0 & 0 \\ 1 & x_1 & y_1 & x_1^2 & x_1 \cdot y_1 & y_1^2 & x_1^3 & x_1^2 \cdot y_1 + x_1 y_1^2 & y_1^3 \\ 0 & 0 & 1 & 0 & x_1 & 2 \cdot y_1 & 0 & x_1^2 + 2 \cdot y_1 \cdot x_1 & 3 \cdot y_1^2 \\ 0 & 1 & 0 & 2 \cdot x_1 & y_1 & 0 & 3 \cdot x_1^2 & y_1^2 + 2 \cdot x_1 \cdot y_1 & 0 \\ 1 & x_2 & y_2 & x_2^2 & x_2 \cdot y_2 & y_2^2 & x_2^3 & x_2^2 \cdot y_2 + x_2 \cdot y_2^2 & y_2^3 \\ 0 & 0 & 1 & 0 & x_2 & 2 \cdot y_2 & 0 & x_2^2 + 2 \cdot y_2 \cdot x_2 & 3 \cdot y_2^2 \\ 0 & 1 & 0 & 2 \cdot x_2 & y_2 & 0 & 3 \cdot x_2^2 & y_2^2 + 2 \cdot x_2 \cdot y_2 & 0 \end{pmatrix} \cdot \begin{pmatrix} a_0 \\ a_1 \\ a_2 \\ a_3 \\ a_4 \\ a_5 \\ a_6 \\ a_7 \\ a_8 \end{pmatrix} \qquad \text{Eq. A-15}$$

or $$\delta_e = C \cdot a$$

Where:

C—Matrix that transforms the displacement equation constants into the nodal displacements Solving Eq. A-15 for the equation constants, substituting it into Eq. A-11, and equating to Eq. A-9 provides a means for defining the equation for the shape functions:

$$w_e = L \cdot a = L \cdot C^{-1} \cdot \delta_e = Q \cdot \delta_e$$

$$Q = L \cdot C^{-1} \text{ Shape functions} \qquad \text{Eq. A-16}$$

Eqs. A-17 to A-25 present stress, strain, load, and displacement relationships defined in a useful way for the traditional FEA method. Eq. A-17 is similar to Eq. A-6 and it is defined as a matter of convenience. The difference is that "z" has been taken out and the strain in Eq. A-15 is called the generalized strain. Eq. A-21 is similar to Eq. A-7 but is modified by including "z" to accommodate the generalized strain.

$$\begin{pmatrix} \varepsilon_{ex} \\ \varepsilon_{ey} \\ \gamma_{exy} \end{pmatrix} = \begin{pmatrix} -\dfrac{d^2}{dx^2} w \\ -\dfrac{d^2}{dy^2} w \\ -2 \cdot \dfrac{\partial}{\partial x} \dfrac{\partial}{\partial y} w \end{pmatrix} \qquad \text{Eq. A-17}$$

Generalized strain (defined for convenience)

or $$\varepsilon_e = B \cdot \delta_e$$

Representation for derivation

Where:

B—Matrix relating generalized element strains to nodal displacements

Introducing Eq. A-11 into Eq.

$$\begin{pmatrix} \varepsilon_{ex} \\ \varepsilon_{ey} \\ \gamma_{exy} \end{pmatrix} = \begin{pmatrix} -\dfrac{d^2}{dx^2} w \\ -\dfrac{d^2}{dy^2} w \\ -2 \cdot \dfrac{\partial}{\partial x} \dfrac{\partial}{\partial y} w \end{pmatrix} = \qquad \text{Eq. A-18}$$

$$\begin{pmatrix} 0 & 0 & 0 & -2 & 0 & 0 & -6 \cdot x & -2 \cdot y & 0 \\ 0 & 0 & 0 & 0 & 0 & -2 & 0 & -2 \cdot x & -6 \cdot y \\ 0 & 0 & 0 & 0 & -2 & 0 & 0 & -4 \cdot x - 4 \cdot y & 0 \end{pmatrix} \cdot \begin{pmatrix} a_0 \\ a_1 \\ a_2 \\ a_3 \\ a_4 \\ a_5 \\ a_6 \\ a_7 \\ a_8 \end{pmatrix}$$

or $$\varepsilon_e = H \cdot a$$

Where:

H—Matrix that relates the displacement equation constants to the generalized strain Solving Eq. A-15 for the equation constants, substituting it into Eq. A-18, and equating to Eq. A-17 provides a means for defining the matrix relating generalized element strains to nodal displacements:

$$\varepsilon_e = H \cdot C^{-1} \cdot \delta_e = B \cdot \delta_e$$

$B = H \cdot C^{-1}$ Matrix relating generalized element strains to nodal displacements  Eq. A-19

$$D' = \frac{E}{1-v^2} \cdot \begin{bmatrix} 1 & v & 0 \\ v & 1 & 0 \\ 0 & 0 & \frac{1}{2} \cdot (1-v) \end{bmatrix}$$ Eq. A-20

Constant array related to flexural rigidity (defined for convenience)

$$\begin{pmatrix} \sigma_x \\ \sigma_y \\ T_{xy} \end{pmatrix} = \frac{E}{1-v^2} \cdot \begin{bmatrix} 1 & v & 0 \\ v & 1 & 0 \\ 0 & 0 & \frac{1}{2} \cdot (1-v) \end{bmatrix} \cdot \begin{pmatrix} \varepsilon_{ex} \\ \varepsilon_{ey} \\ Y_{exy} \end{pmatrix}$$ Eq. A-21

Stress as a function of generalized strain
or
$\sigma_e = z \cdot D' \cdot \varepsilon_e$
Representation for derivation $$M_e = \int_{-\frac{t}{2}}^{\frac{t}{2}} \sigma_e \cdot z \, dz$$ Eq. A-22

Representation for derivation of Eq. A-8

Introducing Eq. A-21 into Eq. A-22 and rearranging:

$$M_e = \int_{-\frac{t}{2}}^{\frac{t}{2}} z \cdot D' \cdot \varepsilon_e \cdot z \, dz = \left( \int_{-\frac{t}{2}}^{\frac{t}{2}} z^2 \cdot D' \, dz \right) \cdot \varepsilon_e$$ Eq. A-23

$$M_e = \left( \int_{-\frac{t}{2}}^{\frac{t}{2}} z^2 \cdot D' \, dz \right) \cdot \varepsilon_e =$$

$$\left( \frac{D' \cdot t^3}{12} \right) \cdot \varepsilon_e = \left[ \frac{t^3}{12} \cdot \frac{E}{1-v^2} \cdot \begin{bmatrix} 1 & v & 0 \\ v & 1 & 0 \\ 0 & 0 & \frac{1}{2} \cdot (1-v) \end{bmatrix} \right] \cdot \varepsilon_e$$

$$D_m = \frac{E \cdot t^3}{12 \cdot (1-v^2)} \cdot \begin{bmatrix} 1 & v & 0 \\ v & 1 & 0 \\ 0 & 0 & \frac{1}{2} \cdot (1-v) \end{bmatrix}$$ Eq. A-24

Another constant array related to flexural rigidity (defined for convenience)

$M_e = D_m \cdot \varepsilon_e$ Eq. A-25

Moment as a function of generalized strain

Given the stress equations in a form convenient for FEA, optimization can be performed considering the variation of potential energy. The equation for variation of potential energy is given below.

$$\Delta \Pi = \sum_n \int \int (M_x \cdot \Delta \varepsilon_{ex} + M_y \cdot \Delta \varepsilon_{ey} + 2 \cdot T_x \cdot \Delta Y_{exy}) dx dy -$$ Eq. A-26

$$\sum_n \int \int (p \cdot \Delta w) dx dy = 0$$

Where:
Δ—Implies a small change in the variable that follows
Σ—Implies summing over "n" elements
n—Number of elements in the given problem Rearranging:

$$\sum_n \int \int \begin{pmatrix} \Delta \varepsilon_{ex} \\ \Delta \varepsilon_{ey} \\ \Delta Y_{exy} \end{pmatrix}^T \cdot \begin{pmatrix} M_x \\ M_y \\ T_{xy} \end{pmatrix} dx dy - \sum_n \int \int (p \cdot \Delta w) dx dy = 0$$

Where the superscript "T" implies the transpose of the array
Simplifying:

$$\sum_n \int \int \Delta \varepsilon_e^T \cdot M_e - p \cdot \Delta w \, dx dy = 0$$ Eq. A-27

Introducing Eqs. A-9, A-17, and A-25 into Eq. A-27 and rearranging:

$$\sum_n \int \int (B \cdot \Delta \delta_e)^T \cdot (D_m \cdot \varepsilon_e) - p \cdot (Q \cdot \Delta \delta_e) dx dy = 0$$ Eq. A-28

$$\sum_n \int \int \Delta \delta_e^T \cdot B^T \cdot D_m \cdot \varepsilon_e - \Delta \delta_e^T \cdot Q^T \cdot p \, dx dy = 0$$

$$\sum_n \int \int \Delta \delta_e^T \cdot B^T \cdot D_m \cdot (B \cdot \delta_e) - \Delta \delta_e^T \cdot Q^T \cdot p \, dx dy = 0$$

$$\sum_n \left[ \Delta \delta_e^T \cdot \left[ \left( \int \int B^T \cdot D_m \cdot B \, dx dy \right) \cdot \delta_e - \int \int Q^T \cdot p \, dx dy \right] \right] = 0$$

Defining:
$k_e = \iint B^T \cdot D_m \cdot B \, dx \, dy$ Stiffness matrix  Eq. A-29
$P_e = \iint Q^T \cdot p \, dx \, dy$ Nodal forces  Eq. A-30

Introducing Eqs. A-29 and A-30 into Eq. A-28:

$$\sum_n \Delta \delta_e^T \cdot (k_e \cdot \delta_e - P_e) = 0$$ Eq. A-31

$k_e \cdot \delta_e = P_e$ Eq. A-32
FEA equation relating loads and displacements for each element Summing all of the element contributions:
$\Delta \delta^T \cdot (K \cdot \delta - P) = 0$ Eq. A-33

Where:
δ—Summed nodal displacement
K—Summed stiffness matrix
P—Summed nodal forces $K \cdot \delta = P$ FEA equation relating summed loads and displacements  Eq. A-34 or $\delta = K^{-1} \cdot P$

For stable matrix inversion of the stiffness matrix in Eq. A-34, displacements must be defined to restrain all possible rigid body motions. These known displacements are included in the summed nodal displacements vector in Eq. A-34. Known external loads are also included in the summed nodal forces vector (though they are not a requirement for stable matrix inversion). If a displacement (degree of freedom) is known, then that degree of freedom is removed from the matrix inversion. Once the known degrees of freedom are removed and matrix inversion has been performed on the full model, then all of the variables related to stress, strain, load, and displacement can be found in every element.

New Method

Figure 12:
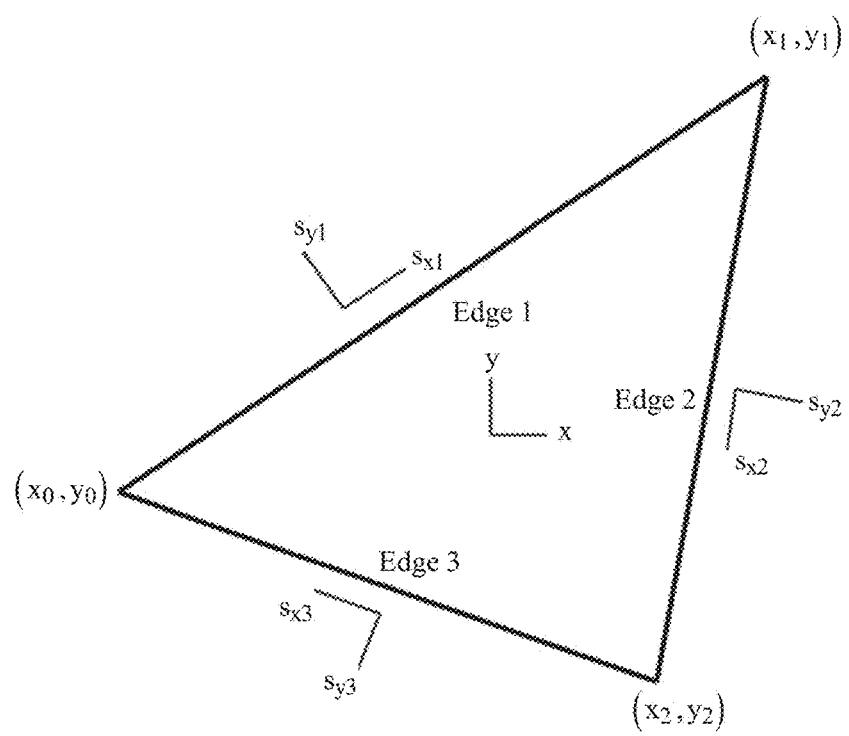
FIG. 12 is a graphical depiction of an example triangular shell with edges and edge ends identified according to the principles of the present disclosure.

This section describes the new method for the example problem. FIG. 12 shows the triangular finite element for the example problem. There are three edges and the number of degrees of freedom for the shell is not related to the geometry of the element (as opposed to traditional FEA where the number of nodes in an element sets the number of degrees of freedom in that element). Instead, the number of constants in the displacement equation (Eq. A-35) determines the number of degrees of freedom for the element. For this example, ten degrees of freedom are used. The deformations that are considered for the element include out of plane displacement and in plane angular rotations in the x- and y-directions (which are the same motions as considered in the traditional FEA description).

$$w = a_0 + a_1 \cdot x + a_2 \cdot y + a_3 \cdot x \cdot y + a_4 \cdot x^2 + a_5 \cdot y^2 +$$
$$a_6 \cdot x^2 \cdot y \ldots + a_7 \cdot x \cdot y^2 + a_8 \cdot x^3 + a_9 \cdot y^3 + \frac{p_z}{8 \cdot D} \cdot x^2 \cdot y^2$$

Eq. A-35

Displacement equation for the element or $$w = (a_0 \ a_1 \ a_2 \ a_3 \ a_4 \ a_5 \ a_6 \ a_7 \ a_8 \ a_9) \cdot$$
$$(1 \ x \ y \ x \cdot y \ x^2 \ y^2 \ x^2 \cdot y \ x \cdot y^2 \ x^3 \ y^3)^T$$
$$\ldots + \frac{p_z}{8 \cdot D} \cdot x^2 \cdot y^2$$

$$a = (a_0 \ a_1 \ a_2 \ a_3 \ a_4 \ a_5 \ a_6 \ a_7 \ a_8 \ a_9)$$

Degrees of freedom

In the displacement equation (Eq. A-35), the last term addresses the particular solution of the governing differential equation (Eq. A-2). Each of the other terms is a complementary function (which causes the governing differential equation to equal zero). Each complementary function has a degree of freedom assigned to it (as identified in Eq. A-35).

Having a displacement equation, the boundary conditions for the element are addressed with an energy optimization. The energy optimization selects degrees of freedom that best match the internal energy (strain energy of the element) to the external work (energy from the pressure load, edge shearing, edge moment, and edge torsion).

Area integrals and edge integrals are developed to allow energy optimization for the new method. The strain energy equation and the energy equation for the pressure load are both area integrals. The rest of the energy equations are edge integrals. The integrals for both the area and edges are developed for a single edge. Then the same integration is performed on all of the edges in succession to address all of the energy associated with the element. To this end, a slightly different strategy is used for the area integrals versus the edge integral. The area integrals use the coordinate system of the element and are derived as shown below in Eqs. A-36 to A-40. (A detailed discussion on how the strain energy is derived can be found in Ugural, 1999.)

The equation for stain energy in the element is given below:

$$U_e = \frac{D}{2} \cdot \int\int_A \left(\frac{d^2}{dx^2}w + \frac{d^2}{dy^2}w\right)^2 -$$

Eq. A-36

$$2 \cdot (1-v) \cdot \left[\frac{d^2}{dx^2}w \cdot \frac{d^2}{dy^2}w - \left(\frac{\partial}{\partial x}\frac{\partial}{\partial y}w\right)^2\right] dx\, dy$$

To generate an integral that can be performed along each successive edge, the curve representing the edge must be derived and incorporated into integral. Below is the derivation for the straight edges of the triangle.

$$y(x) = m \cdot x + b$$

Eq. A-37

Edge function for area integration $$m = \frac{y_{end} - y_{start}}{x_{end} - x_{start}}$$ Edge slope $$b = y_{start} - \frac{y_{end} - y_{start}}{x_{end} - x_{start}} \cdot x_{start}$$ Edge y-intercept for: $x_{end} - x_{start} \neq 0$ Where:

The subscript "start" implies the starting point on a given edge

The subscript "end" implies the ending point on a given edge

Introducing Eq. A-37 into Eq. A-36 and incorporating the x-position of the curve end points:

$$U_e = \frac{D}{2} \cdot \int_{x_{start}}^{x_{end}} \int_0^{m \cdot x + b} \left(\frac{d^2}{dx^2}w \ldots + \frac{d^2}{dy^2}w\right)^2 -$$
$$2 \cdot (1-v) \cdot \left[\frac{d^2}{dx^2}w \cdot \frac{d^2}{dy^2}w \ldots + -\left(\frac{\partial}{\partial x}\frac{\partial}{\partial y}w\right)^2\right] dy\, dx$$

Eq. A-38

If Eq. A-38 is performed on each successive edge, the summed values produce the area integral for the whole element. (Edges with no change in the x-direction are excluded from this summation as there is no change in energy for these edges in this formulation and they make Eq. A-37 unstable.)

Similar to that for strain energy, a derivation can be performed for the external work on the element from the applied pressure (which is also an area integral).

$$W_p = \int\int_A w \cdot p_z dx\, dy$$

Eq. A-39

Energy equation for the external work generated by the pressure load

Introducing Eq. A-37 into Eq. A-39 and incorporating the x-position of the curve end points:

$$W_p = \int_{x_{start}}^{x_{end}} \int_0^{m \cdot x + b} w \cdot p_z\, dy\, dx$$

Eq. A-40

The edge integrals, similar to the area integral formulation, are formulated for a single edge. Then each successive edge is summed to account for all of the edge energy. For convenience, however, the edge integrals are formulated in local coordinates. The local coordinates (as shown in FIG. 12) are defined in Eqs. A-41 to A-43.

| | | |
|---|---|---|
| $\Delta x = x_{end} - x_{start}$ | Edge length in the x-direction | Eq. A-41 |
| $\Delta y = y_{end} - y_{start}$ | Edge length in the y-direction | |
| $\Delta r = \sqrt{\Delta x^2 + \Delta y^2}$ | Length of the edge | |
| $\theta_x = \dfrac{\Delta x}{\Delta r}$ | Component in the x-direction | Eq. A-42 |
| $\theta_y = \dfrac{\Delta y}{\Delta r}$ | Component in the y-direction | |

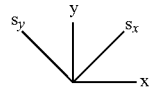

| | | |
|---|---|---|
| $s_x = \theta_x \cdot x + \theta_y \cdot y$ | Local x-direction in terms of the element coordinates | Eq. A-43 |
| $s_y = -\theta_y \cdot x + \theta_x \cdot y$ | Local y-direction in terms of the element coordinates | |
| or | | |
| $x = s_x \cdot \theta_x - s_y \cdot \theta_y$ | Element x-direction in terms of the local coordinates | |
| $y = s_x \cdot \theta_y + s_y \cdot \theta_x$ | Element y-direction in terms of the element coordinates | |

Given the local coordinates definition (Eq. A-43), edge displacements and loads can be defined in local coordinates (as shown in Eqs. A-44 to A-46).

$$w_s = a \cdot \begin{bmatrix} 1 \\ s_x \cdot \theta_x - s_y \cdot \theta_y \\ s_x \cdot \theta_y + s_y \cdot \theta_x \\ (s_x \cdot \theta_x - s_y \cdot \theta_y) \cdot (s_x \cdot \theta_y + s_y \cdot \theta_x) \\ (s_x \cdot \theta_x - s_y \cdot \theta_y)^2 \\ (s_x \cdot \theta_y + s_y \cdot \theta_x)^2 \\ (s_x \cdot \theta_x - s_y \cdot \theta_y)^2 \cdot (s_x \cdot \theta_y + s_y \cdot \theta_x) \\ (s_x \cdot \theta_x - s_y \cdot \theta_y) \cdot (s_x \cdot \theta_y + s_y \cdot \theta_x)^2 \\ (s_x \cdot \theta_x - s_y \cdot \theta_y)^2 \\ (s_x \cdot \theta_y + s_y \cdot \theta_x)^2 \end{bmatrix} + \quad \text{Eq. A-45}$$

$$\frac{p_z}{8 \cdot D} \cdot (s_x \cdot \theta_x - s_y \cdot \theta_y)^2 \cdot (s_x \cdot \theta_y + s_y \cdot \theta_x)^2$$

$$\theta_s = \frac{\partial}{\partial s_y} w_s$$

Bending rotation on the local y-face $$\phi_s = \frac{\partial}{\partial s_x} w_s$$

Torsional rotation on the local y-face

Redefining Eqs. A-3 and A-4 in local coordinates:

$$P_s = -D \cdot \left[ \frac{\partial}{\partial s_y} \left( \frac{d^2}{ds_y^2} w_s + \frac{d^2}{ds_x^2} w_s \right) \right] \quad \text{Eq. A-46}$$

Shear force on the local y-face $$M_s = -D \cdot \left( \frac{d^2}{ds_y^2} w_s + \frac{d^2}{ds_x^2} w_s \right)$$

Bending moment on the local y-face $$T_s = -D \cdot (1 - v) \cdot \frac{\partial}{\partial s_x} \frac{\partial}{\partial s_y} w_s$$

Torsional moment on the local y-face

This is followed by the edge energy integral for external work also in local coordinates (Eq. A-47).

$$W_e = \int_{s_{x\_start}}^{s_{x\_end}} P_s \cdot w_s - M_s \cdot \theta_s - T_s \cdot \phi_s \, ds_x \quad \text{Eq. A-47}$$

Edge energy integral for external work

Note: The subtraction of the moment and torsion is a matter of how the variables are defined. This is a summation of their contributions. The rotations could be defined as negative value and the negative signs in the edge energy integral would go away.

When considering the external work for this method, the external influences could be external displacements or external loads. For the external displacements, the energy integral is established considering the external displacement and the element loads. For the external loads, the energy integral is established considering the external loads and the element displacements. This results in two sets of external work integrals that need to be considered. Consequently, the total energy for the element is found by doubling the internal strain energy and subtracting external displacement based work and external load based work (as shown in Eq. A-48).

$$\Pi = 2U - (\Sigma W_P + \Sigma W_e)_w - (\Sigma W_P + \Sigma W_e)_P \text{ Total energy for an element} \quad \text{Eq. A-48}$$

Where:

$\Sigma$—Implies summing over all edges

The subscript "w" implies external work from external displacements

The subscript "P" implies external work from external loads

Writing Eq. A-48 for the example problem:

$$\Pi = 2 \cdot \left[ \begin{array}{l} \frac{D}{2} \cdot \int_{x_0}^{x_1} \int_0^{m_1 \cdot x + b_1} \left( \frac{d^2}{dx^2} w_e + \frac{d^2}{dy^2} w_e \right)^2 - 2 \cdot (1-v) \cdot \left[ \frac{d^2}{dx^2} w_e \cdot \frac{d^2}{dy^2} w_e - \left( \frac{\partial}{\partial x} \frac{\partial}{\partial y} w_e \right)^2 \right] dy\, dx \ldots + \\ \frac{D}{2} \cdot \int_{x_1}^{x_2} \int_0^{m_2 \cdot x + b_2} \left( \frac{d^2}{dx^2} w_e + \frac{d^2}{dy^2} w_e \right)^2 - 2 \cdot (1-v) \cdot \left[ \frac{d^2}{dx^2} w_e \cdot \frac{d^2}{dy^2} w_e - \left( \frac{\partial}{\partial x} \frac{\partial}{\partial y} w_e \right)^2 \right] dy\, dx \ldots + \\ \frac{D}{2} \cdot \int_{x_2}^{x_0} \int_0^{m_3 \cdot x + b_3} \left( \frac{d^2}{dx^2} w_e + \frac{d^2}{dy^2} w_e \right)^2 - 2 \cdot (1-v) \cdot \left[ \frac{d^2}{dx^2} w_e \cdot \frac{d^2}{dy^2} w_e - \left( \frac{\partial}{\partial x} \frac{\partial}{\partial y} w_e \right)^2 \right] dy\, dx \end{array} \right] \ldots +$$

$$\left\{ \begin{array}{l} \int_{x_0}^{x_1} \int_0^{m_1 \cdot x + b_1} w_e \cdot p_z\, dy\, dx + \int_{x_1}^{x_2} \int_0^{m_2 \cdot x + b_2} w_e \cdot p_z\, dy\, dx + \int_{x_2}^{x_0} \int_0^{m_3 \cdot x + b_3} w_e \cdot p_z\, dy\, dx \ldots + \\ \int_{s_{x1\_0}}^{s_{x1\_1}} P_{s1} \cdot w_{s1}\, ds_{x1} - \int_{s_{x1\_0}}^{s_{x1\_1}} M_{s1} \cdot \theta_{s1}\, ds_{x1} - \int_{s_{x1\_0}}^{s_{x1\_1}} T_{s1} \cdot \phi_{s1}\, ds_{x1} \ldots + \\ \int_{s_{x2\_0}}^{s_{x2\_1}} P_{s2} \cdot w_{s2}\, ds_{x2} - \int_{s_{x2\_0}}^{s_{x2\_1}} M_{s2} \cdot \theta_{s2}\, ds_{x2} - \int_{s_{x2\_0}}^{s_{x2\_1}} T_{s2} \cdot \phi_{s2}\, ds_{x2} \ldots + \\ \int_{s_{x3\_0}}^{s_{x3\_1}} P_{s3} \cdot w_{s3}\, ds_{x3} - \int_{s_{x3\_0}}^{s_{x3\_1}} M_{s3} \cdot \theta_{s3}\, ds_{x3} - \int_{s_{x3\_0}}^{s_{x3\_1}} T_{s3} \cdot \phi_{s3}\, ds_{x3} \end{array} \right\}_w$$

$$\left\{ \begin{array}{l} \int_{x_0}^{x_1} \int_0^{m_1 \cdot x + b_1} w_e \cdot p_z\, dy\, dx + \int_{x_1}^{x_2} \int_0^{m_2 \cdot x + b_2} w_e \cdot p_z\, dy\, dx + \int_{x_2}^{x_0} \int_0^{m_3 \cdot x + b_3} w_e \cdot p_z\, dy\, dx \ldots + \\ \int_{s_{x1\_0}}^{s_{x1\_1}} P_{s1} \cdot w_{s1}\, ds_{x1} - \int_{s_{x1\_0}}^{s_{x1\_1}} M_{s1} \cdot \theta_{s1}\, ds_{x1} - \int_{s_{x1\_0}}^{s_{x1\_1}} T_{s1} \cdot \phi_{s1}\, ds_{x1} \ldots + \\ \int_{s_{x2\_0}}^{s_{x2\_1}} P_{s2} \cdot w_{s2}\, ds_{x2} - \int_{s_{x2\_0}}^{s_{x2\_1}} M_{s2} \cdot \theta_{s2}\, ds_{x2} - \int_{s_{x2\_0}}^{s_{x2\_1}} T_{s2} \cdot \phi_{s2}\, ds_{x2} \ldots + \\ \int_{s_{x3\_0}}^{s_{x3\_1}} P_{s3} \cdot w_{s3}\, ds_{x3} - \int_{s_{x3\_0}}^{s_{x3\_1}} M_{s3} \cdot \theta_{s3}\, ds_{x3} - \int_{s_{x3\_0}}^{s_{x3\_1}} T_{s3} \cdot \phi_{s3}\, ds_{x3} \end{array} \right\}_p$$

Eq. A-49

Where the numbered subscripts indicate which of the three edges are being integrated and "_0 and "_1" indicate the start and end of an edge respectively.

Having the total energy equation for the element, the optimization is performed by minimizing based on the degrees of freedom (as shown in Eq. A-50).

$$\frac{\partial}{\partial a_0} \Pi = 0 \quad \text{Energy optimization} \qquad \text{Eq. A-49}$$

$$\frac{\partial}{\partial a_1} \Pi = 0$$

$$\frac{\partial}{\partial a_2} \Pi = 0$$

-continued $$\vdots$$

$$\frac{\partial}{\partial a_9} \Pi = 0$$

Evaluating the partial differential equations for the energy optimization produces a system of linear equations. Eq. A-51 shows the matrix form of this equation considering a single element. Eq. A-52 shows the equation for all of the elements in a model.

$$U_m \cdot a + U_b = 0 \quad \text{Linear equation for optimized degrees of freedom for a single element} \qquad \text{Eq. A-51}$$

Where:

$U_m$—Array constants determined with the partial differential equations $U_b$—Vector constants determined with the partial differential equations $$U_M \cdot a + U_B = 0 \text{ Linear equation for optimized degrees of freedom for all of the elements} \quad \text{Eq. A-52}$$

or $$a = U_M^{-1} \cdot (-U_B)$$

Where:
$U_M$—Array constants summed for all of the elements in the model
$U_B$—Vector constants summed for all of the elements in the model Performing the energy optimization in this way, the displacement based portion of the external work from the pressure load does not contribute and therefore it does not need to be considered. This is because the load is the constant pressure and if the displacement is defined as external, there are no degrees of freedom in the integral. Thus, the partial differential equations relative to the degrees of freedom are all equal to zero.

The remaining strain energy and work terms may cause significant tedium in solving integrals to get them to an algebraic form. This can be performed with relative ease using modern symbolic solvers (or a numerical integration could be performed). The approach used in the example problem establishes a way to get all of the energy integrals solved for a single straight edge of any length, position, or angle. Once the algebraic form is found, it can be applied to each edge successively to find the array and vector in Eq. A-51. This same solution could be used on an element with any number of straight edges with no additional derivation necessary.

As in the traditional finite element analysis, the new method requires displacement restraints sufficient to prevent any rigid body motion for stable matrix inversion (of Eq. A-52). A relatively easy way to incorporate this is to perform integrals along restrained edges and write equations to equate the average edge displacement to the average external displacement. In the example problem, the strain energy equation (Eq. A-36) prevents the first three degrees of freedom (i.e. $a_0$, $a_1$, and $a_2$) from being included (which is to be expected). The average edge displacement equations can be summed as needed to produce three linear equations. These linear equations can be added to the linear equations for the first three degrees of freedom and stable matrix inversion is then possible. Another technique would be to add virtual springs to the restrained edges that span between the element displacement and the desired external displacement. Including the energy of these springs makes a stable matrix inversion and makes it possible to vary how strongly the displacement at the boundaries is enforced.

At element to element boundaries, external displacements and loads are based on the neighboring element. At a boundary condition, either the external displacement is known or the external load is known. As previously discussed, the external work in the new method is established with an external displacement (or load) and the element load (or displacement). Where the external displacement (or load) at a boundary condition is not known then both the displacement and load from the element are considered for the external work. Given that the work is subtracted from the strain energy in the energy optimization, this approach effectively removes the energy associated with the unknown boundary condition from the energy optimization. After Eq. A-52 is solved, then the displacement (or load) that was not known can be found based on the solved element degrees of freedom.

Discussion

As noted in the Outline, the most significant difference in the two methods (as applied to the example problem) is how the base equation for displacement is established. In traditional FEA, the base equation for displacement (Eq. A-10) is selected to exactly meet the boundary conditions and approximate the governing equation. In the new method, the base equation for displacement (Eq. A-35) is selected to exactly meet the governing equation and approximate the boundary conditions. Both methods are energy optimized but the difference in base equations drives different methods of energy optimization. (It should be noted that the energy optimization shown for the traditional FEA is not the only approach, but it is one of the better ones. The selection of the base equation for displacement is representative of all traditional FEA approaches.)

The boundary conditions (at the nodes) being exactly met in traditional FEA reduces the ability of the shape functions to accurately predict stresses/strains in the element. The result is a relatively stiff response that tends to under predict the stresses/strains. (This may be counteracted by an inability to follow a curved edge that could cause the stresses to go higher.) In the new method, neither boundary conditions nor stresses/strains in the element are enforced to be exactly met. Consequently, energy optimization can better utilize the degrees of freedom to predict both boundary conditions and stresses/strains.

If the displacement equation can produce an exact solution given the geometry and boundary conditions and that same displacement equation is appropriate for traditional FEA and the new method, then both methods should produce the same results. (This is the case with beam elements.) As the displacement equation becomes less adequate for the given geometry and boundary conditions, the new method should produce results that are closer to correct due to the boundary conditions not having to be exactly met.

Another difference in the two methods not really highlighted in the example problem is that the new method does not require straight edges. Additionally, the number of edges does not force a change in the number of degrees of freedom as in traditional finite element analysis. This means that an element can have any number of edges and they can be of any size or shape. The element can also have "holes" without consequence.

Also not highlighted in this example is the situation where neighboring elements have different numbers of degrees of freedom. In traditional finite element analysis, neighboring elements may have differing numbers of degrees of freedom if they are a similar order and similar degrees of freedom per node (i.e. linear triangular and linear quadrilateral are easily combined but linear triangles and parabolic triangles are not easily combined). With the new method, neighboring elements may have different degrees of freedom or even different governing equations. It is a good idea to have a similar curve following the edge on each element (but this comes at less consequence than traditional finite elements of different orders sharing nodes because the new method does a best fit match at the edges).

Section B
Outline

In this section, algebraic equations for evaluating an element with straight sides are developed. Second, a simple triangular element is evaluated to find displacement and stress results. As validation, the triangular element is defined with geometry, loading, and boundary conditions to match a well-known problem that has an exact solution. Third, the results are compared with the exact solution and traditional finite element results.

The evaluation is described in several portions. The first portion (Displacement Equation) shows an approach to establish a valid displacement equation. The second portion (Area Integrals for a Straight Edge) shows an approach to convert the area integrals (from Section A, Eqs. A-38 and A-40) into an algebraic form. The third portion (Edge Integrals for a Straight Edge) shows an approach to convert the edge integrals (from Section A, Eq. A-47) into an algebraic form. The fourth portion (Model Formulation) defines values for material properties, element geometry, boundary conditions, and the algebraic forms of the area and edge integrals. The fifth portion (Rigid Body Motions) defines an approach to address rigid body motions. The approach used in the example equates the average edge displacement of the element with the average edge displacement defined by the boundary conditions. The sixth portion (Degrees of Freedom and Results Plots) solves the energy optimization (from Section A, Eq. A-51) and uses the results to plot element displacement and stress. The seventh portion (Comparison with Traditional Finite Element Analysis) compares the new method displacement and stress results with the exact solution and four traditional finite element models. The evaluation results are discussed in an eighth portion (Discussion).

The test model for the example problem is a thin plate that is 5 inches by 5 inches by 0.1 inches thick. All of the edges are fixed and there is a 300 psi pressure applied evenly over the surface. The material properties include a Young's modulus of 2.99938e7 psi and a Poisson's ratio of 0.29.

Table B-1 provides a comparison summary of the theoretical, new model, and traditional finite element results for stress and displacement (with percent error from theoretical).

Displacement Equation

As discussed in Section A, the displacement equation exactly solves the governing equation. To this end, a relatively easy way to establish the displacement equation is shown in Eqs. B-1 to B-8. For this example, the displacement equation is polynomial based.

$$w = c_0 + c_1 \cdot x + c_2 \cdot y + c_3 \cdot x^2 + c_4 \cdot x \cdot y + c_5 \cdot y^2 + c_6 \cdot x^3 \ldots + \\ c_7 \cdot x^2 \cdot y + c_8 \cdot x \cdot y^2 + c_9 \cdot y^3 + c_{10} \cdot x^4 + c_{11} \cdot x^3 \cdot y \ldots + \\ c_{12} \cdot x^2 \cdot y^2 + c_{13} \cdot x \cdot y^3 + c_{14} \cdot y^4 + c_{15} \cdot x^5 + c_{16} \cdot x^4 \cdot y \ldots + \\ c_{17} \cdot x^3 \cdot y^2 + c_{18} \cdot x^2 \cdot y^3 + c_{19} \cdot x \cdot y^4 + c_{20} \cdot y^5$$

Eq. B-1

General polynomial for generating the displacement equation $$\frac{\partial^4}{\partial x^4} w + 2 \cdot \frac{\partial^2}{\partial x^2} \frac{\partial^2}{\partial y^2} w + \frac{\partial^4}{\partial y^4} w = \frac{p_z}{D}$$

Eq. B-2

Governing equation

Introducing Eq. B-1 into Eq. B-2 and solving:

$$\frac{\partial^4}{\partial x^4}\begin{pmatrix} c_0 + c_1 \cdot x + c_2 \cdot y + c_3 \cdot x^2 + c_4 \cdot x \cdot y + c_5 \cdot y^2 + \\ c_6 \cdot x^3 \ldots + c_7 \cdot x^2 \cdot y + c_8 \cdot x \cdot y^2 + c_9 \cdot y^3 + \\ c_{10} \cdot x^4 + c_{11} \cdot x^3 \cdot y \ldots + c_{12} \cdot x^2 \cdot y^2 + \\ c_{13} \cdot x \cdot y^3 + c_{14} \cdot y^4 + c_{15} \cdot x^5 + c_{16} \cdot x^4 \cdot y \ldots + \\ c_{17} \cdot x^3 \cdot y^2 + c_{18} \cdot x^2 \cdot y^3 + c_{19} \cdot x \cdot y^4 + c_{20} \cdot y^5 \end{pmatrix} \ldots +$$

Eq. B-3

$$2 \cdot \frac{\partial^2}{\partial x^2} \frac{\partial^2}{\partial y^2} \begin{pmatrix} \begin{pmatrix} c_0 + c_1 \cdot x + c_2 \cdot y + c_3 \cdot x^2 + c_4 \cdot x \cdot y + c_5 \cdot y^2 + \\ c_6 \cdot x^3 \ldots + c_7 \cdot x^2 \cdot y + c_8 \cdot x \cdot y^2 + c_9 \cdot y^3 + \\ c_{10} \cdot x^4 + c_{11} \cdot x^3 \cdot y \ldots + c_{12} \cdot x^2 \cdot y^2 + \\ c_{13} \cdot x \cdot y^3 + c_{14} \cdot y^4 + c_{15} \cdot x^5 + c_{16} \cdot x^4 \cdot y \ldots + \\ c_{17} \cdot x^3 \cdot y^2 + c_{18} \cdot x^2 \cdot y^3 + c_{19} \cdot x \cdot y^4 + c_{20} \cdot y^5 \end{pmatrix} \end{pmatrix} \ldots +$$

$$\frac{\partial^4}{\partial y^4} \begin{pmatrix} \begin{pmatrix} c_0 + c_1 \cdot x + c_2 \cdot y + c_3 \cdot x^2 + c_4 \cdot x \cdot y + c_5 \cdot y^2 + \\ c_6 \cdot x^3 \ldots + c_7 \cdot x^2 \cdot y + c_8 \cdot x \cdot y^2 + c_9 \cdot y^3 + \\ c_{10} \cdot x^4 + c_{11} \cdot x^3 \cdot y \ldots + c_{12} \cdot x^2 \cdot y^2 + \\ c_{13} \cdot x \cdot y^3 + c_{14} \cdot y^4 + c_{15} \cdot x^5 + c_{16} \cdot x^4 \cdot y \ldots + \\ c_{17} \cdot x^3 \cdot y^2 + c_{18} \cdot x^2 \cdot y^3 + c_{19} \cdot x \cdot y^4 + c_{20} \cdot y^5 \end{pmatrix} \end{pmatrix} = \frac{p_o}{D}$$

|  | Theoretical values[1] | New model[2] | Parabolic triangular 8 element[3] | Parabolic triangular 64 element[2] | Parabolic triangular 256 element | Linear quadrilateral 900 element[3] |
|---|---|---|---|---|---|---|
| Maximum von Mises stress [ksi] | 205.7 | 225.9 (+9.8%) | 41.6 (−79.8%) | 181.2 (−11.9%) | 200.3 (−2.6%) | 178.7 (−13.1%) |
| Maximum displacement [in] | 0.0866 | 0.0868 (+0.3%) | 0.02927 (−66.2%) | 0.08902 (+2.8%) | 0.08837 (+2.1%) | 0.08755 (+1.1%) |
| Degrees of freedom | N/A | 144 | 75 | 435 | 1635 | 2883 |

[1]The theoretical value is 230.8 ksi, but this is only in one direction. Converting it to von Mises stress produces the 205.7 ksi value.
[2]The test model was run with one 18 degree of freedom element and symmetry. The degrees of freedom for the test model is shown as 144 to reflect the degrees of freedom as if it were an 8 element model. This is the relevant number of degrees of freedom for comparison with the other models.
[3]The high stress should occur in the center of an edge. The 8 parabolic triangle element model showed the high stress in the center of the plate. The table value is from the center of an edge.

$$24 \cdot c_{10} + 8 \cdot c_{12} + 24 \cdot c_{14} \ldots + 120 \cdot c_{15} \cdot x + 24 \cdot c_{17} \cdot x +$$
$$24 \cdot c_{19} \cdot x \ldots + 120 \cdot c_{20} \cdot y + 24 \cdot c_{16} \cdot y + 24 \cdot c_{18} \cdot y = \frac{p_o}{D}$$

Eq. B-3

Constants equation

The x and y variables in Eq. B-3 can be anything. Consequently, the constants associated with each variable (and the constants not associated with a variable) are used to ensure that Eq. B-3 is true. This produces the following three equations.

$$24 \cdot c_{10} + 8 \cdot c_{12} + 24 \cdot c_{14} = \frac{p_o}{D} \implies \begin{array}{l} c_{12} = \frac{p_o}{8 \cdot D} - 3 \cdot \\ c_{14} - 3 \cdot c_{10} \end{array}$$

Eq. B-4

$$(120 \cdot c_{15} + 24 \cdot c_{17} + 24 \cdot c_{19}) \cdot x = 0 \implies c_{19} = -5 \cdot c_{15} - c_{17}$$

$$(120 \cdot c_{20} + 24 \cdot c_{16} + 24 \cdot c_{18}) \cdot y = 0 \implies c_{18} = -5 \cdot c_{20} - c_{16}$$

Substituting Eq. B-4 into Eq. B-1 and gathering terms:

$$w = c_0 + c_1 \cdot x + c_2 \cdot y + c_3 \cdot x^2 + c_4 \cdot x \cdot y + c_5 \cdot y^2 + c_6 \cdot x^3 +$$
$$c_7 \cdot x^2 \cdot y + c_8 \cdot x \cdot y^2 \ldots + c_9 \cdot y^3 + c_{10} \cdot x^4 + c_{11} \cdot x^3 \cdot y +$$
$$\left(\frac{p_o}{8 \cdot D} - 3 \cdot c_{14} - 3 \cdot c_{10}\right) \cdot x^2 \cdot y^2 + c_{13} \cdot x \cdot y^3 \ldots + c_{14} \cdot y^4 +$$
$$c_{15} \cdot x^5 + c_{16} \cdot x^4 \cdot y + c_{17} \cdot x^3 \cdot y^2 + (-5 \cdot c_{15} - c_{17}) \cdot x^2 \cdot y^3 \ldots +$$
$$(-5 \cdot c_{17} - c_{17}) \cdot x^2 \cdot y^3 \ldots + (-5 \cdot c_{20} - c_{16}) \cdot x \cdot y^4 + c_{20} \cdot y^5$$

Eq. B-5

$$w = c_0 + c_1 \cdot x + c_2 \cdot y + c_3 \cdot x^2 + c_4 \cdot x \cdot y + c_5 \cdot y^2 +$$
$$c_6 \cdot x^3 + c_7 \cdot x^2 \cdot y + c_8 \cdot x \cdot y^2 \ldots + c_9 \cdot y^3 +$$
$$c_{10} \cdot (x^4 - 3 \cdot x^2 \cdot y^2) + c_{11} \cdot x^3 \cdot y + \frac{p_o}{8 \cdot D} \cdot x^2 \cdot y^2 +$$
$$c_{13} \cdot x \cdot y^3 \ldots + c_{14} \cdot (y^4 - 3 \cdot x^2 \cdot y^2) +$$
$$c_{15} \cdot (x^5 - 5 \cdot x \cdot y^4) + c_{16} \cdot (x^4 \cdot y - x^2 \cdot y^3) \ldots +$$
$$c_{17} \cdot (x^3 \cdot y^2 - x \cdot y^4) + c_{20} \cdot (y^5 - 5 \cdot x^2 \cdot y^3)$$

Reordering, renaming, and scaling constants:

$$w = a_0 + a_1 \cdot x + a_2 \cdot y + a_3 \cdot x \cdot y + a_4 \cdot x^2 + a_5 \cdot y^2 + a_6 \cdot x^2 \cdot y +$$
$$a_7 \cdot x \cdot y^2 \ldots + a_8 \cdot x^3 + a_9 \cdot y^3 + a_{10} \cdot x^3 \cdot y + a_{11} \cdot x \cdot y^3 +$$
$$a_{12} \cdot (x^4 - 3 \cdot x^2 \cdot y^2) \ldots + a_{13} \cdot (y^4 - 3 \cdot x^2 \cdot y^2) +$$
$$a_{14} \cdot (x^4 \cdot y - x^2 \cdot y^3) + a_{15} \cdot (x \cdot y^4 - x^3 \cdot x^2) \ldots +$$
$$a_{16} \cdot (x^5 - 5 \cdot x^3 \cdot y^2) + a_{17} \cdot (y^5 - 5 \cdot x^2 \cdot y^3) + \frac{p_z}{8 \cdot D} \cdot x^2 \cdot y^2$$

Eq. B-6

Displacement equation with 18 degrees of freedom

The variables x, y, and w in the displacement equation (Eq. B-6) have length units. In this form, the constants also have units. To make the constants not have units a length constant is added. This constant can be useful later to reduce the number magnitude difference in the array being inverted. This can be helpful numerically for the matrix inversion.

Arranging Eq. B-6 into a matrix form and adding the length constant:

$$w = \begin{pmatrix} a_0 \\ a_1 \\ a_2 \\ a_3 \\ a_4 \\ a_5 \\ a_6 \\ a_7 \\ a_8 \\ a_9 \\ a_{10} \\ a_{11} \\ a_{12} \\ a_{13} \\ a_{14} \\ a_{15} \\ a_{16} \\ a_{17} \end{pmatrix}^T \cdot \begin{bmatrix} 1 \cdot r' \\ x \\ y \\ x \cdot y \cdot r'^{-1} \\ x^2 \cdot r'^{-1} \\ y^2 \cdot r'^{-1} \\ x^2 \cdot y \cdot r'^{-2} \\ x \cdot y^2 \cdot r'^{-2} \\ x^3 \cdot r'^{-2} \\ y^3 \cdot r'^{-2} \\ x^3 \cdot y \cdot r'^{-3} \\ x \cdot y^3 \cdot r'^{-3} \\ (x^4 - 3 \cdot x^2 \cdot y^2) \cdot r'^{-3} \\ (y^4 - 3 \cdot x^2 \cdot y^2) \cdot r'^{-3} \\ (x^4 \cdot y - x^2 \cdot y^3) \cdot r'^{-4} \\ (x \cdot y^4 - x^3 \cdot y^2) \cdot r'^{-4} \\ (x^5 - 5 \cdot x^3 \cdot y^2) \cdot r'^{-4} \\ (y^5 - 5 \cdot x^2 \cdot y^3) \cdot r'^{-4} \end{bmatrix} + \frac{p_z}{8 \cdot D} \cdot x^2 \cdot y^2$$

Eq. B-7

Displacement equation with length constant

Where:

r'—Length constant used to make the degrees of freedom ($a_0$ to $a_{17}$) unitless Degrees of freedom $a = (a_0\ a_1\ a_2\ a_3\ a_4\ a_5\ a_6\ a_7\ a_8\ a_9\ a_{10}\ a_{11}\ a_{12}\ a_{13}\ a_{14}\ a_{15}\ a_{16}\ a_{17})$ Eq. B-8

In the displacement equation (Eq. B-7), the last term addresses the particular solution of the governing differential equation (Eq. B-2). Each of the other terms is a complementary function, which causes the governing differential equation to equal zero. Each complementary function has a degree of freedom assigned to it (as identified in Eqs. B-7 and B-8).

Area Integrals for a Straight Edge

Recalling the strain energy for the element (Eq. A-38) and the external work due to the pressure load (Eq. A-40), there are two area integrals to be addressed in the total energy equation for the element (Eq. A-48 or A-49) and the energy optimization (Eq. A-49). The energy optimization lends itself to be broken into pieces, evaluated to form algebraic solutions, and then summed back together. All of the integrals will be addressed in this manner. When broken out the of the energy optimization, the strain energy and the external work due to the pressure load appear as in Eqs. B-9 and B-10.

$$U_i = \frac{\partial}{\partial a_i}\left[\frac{D}{2}\cdot\int_{x_0}^{x_1}\int_0^{m_1\cdot x+b_1}\left(\frac{\partial^2}{\partial x^2}w+\frac{\partial^2}{\partial y^2}w\right)^2-\right.$$
$$\left. 2\cdot(1-v)\cdot\left[\frac{\partial^2}{\partial x^2}w\cdot\frac{\partial^2}{\partial y^2}w-\left(\frac{\partial}{\partial x}\frac{\partial}{\partial y}w\right)^2\right]dy\,dx\right]$$
Eq. B-9

Strain energy linear equations in the energy optimization $$w_{p_i} = \frac{\partial}{\partial a_i}\left(\int_{x_0}^{x_1}\int_0^{m_1\cdot x+b_1} w\cdot p_z\, dy\, dx\right)$$
Eq. B-10

External work due to the pressure load linear equations in the energy optimization Where the subscript "i" represents a degree of freedom (from 0 to 17)

Note: The variables $x_0$, $x_1$, $m_1$, and $b_1$ are defined as though the first edge is being evaluated. The resulting derivation, however, is applicable to all of the edges in the example problem.

Considering the strain energy (Eq. B-9) can produce a very large and complex algebraic form, it is desirable to find ways to make this process as easy and efficient as possible. It is clear that the strain energy equation will result in a symmetric array multiplied by the degree of freedom vector plus a vector related to the external pressure terms in the displacement equation. Also apparent is that once the partial derivative is applied, all of the degrees of freedom will have a power of 1. Finally, the application of the partial differential equations on the displacement equations lowers the power and number of degrees of freedom involved. These observations are useful in simplifying the strain energy integral (as shown in Eqs. B-11 to B-13).

Defining: $w_{xx} = \frac{\partial^2}{\partial x^2} w$, $w_{yy} = \frac{\partial^2}{\partial y^2} w$, and $w_{xy} = \frac{\partial^2}{\partial x \partial y} w$ or
Eq. B-11

$$w_{xx} = a^T \cdot \begin{bmatrix} 0 \\ 0 \\ 0 \\ 0 \\ 2\cdot r'^{-1} \\ 0 \\ 2\cdot y\cdot r'^{-2} \\ 0 \\ 6\cdot x\cdot r'^{-2} \\ 0 \\ 6\cdot x\cdot y\cdot r'^{-3} \\ 0 \\ (12\cdot x^2 - 6\cdot y^2)\cdot r'^{-3} \\ -6\cdot y^2\cdot r'^{-3} \\ -2\cdot y\cdot (y^2 - 6\cdot x^2)\cdot r'^{-4} \\ -6\cdot x\cdot y^2\cdot r'^{-4} \\ 10\cdot x\cdot (2\cdot x^2 - 3\cdot y^2)\cdot r'^{-4} \\ -10\cdot y^3\cdot r'^{-4} \end{bmatrix} + \frac{p_z\cdot y^2}{4\cdot D}$$

$$w_{yy} = a^T \cdot \begin{bmatrix} 0 \\ 0 \\ 0 \\ 0 \\ 0 \\ 2\cdot r'^{-1} \\ 0 \\ 2\cdot x\cdot r'^{-2} \\ 0 \\ 6\cdot y\cdot r'^{-2} \\ 0 \\ 6\cdot x\cdot y\cdot r'^{-3} \\ -6\cdot x^2\cdot r'^{-3} \\ -6\cdot (x^2 - 2\cdot y^2)\cdot r'^{-3} \\ -6\cdot x^2\cdot y\cdot r'^{-4} \\ -2\cdot x\cdot (x^2 - 6\cdot y^2)\cdot r'^{-4} \\ -10\cdot x^3\cdot r'^{-4} \\ (20\cdot y^3 - 30\cdot x^2\cdot y)\cdot r'^{-4} \end{bmatrix} + \frac{p_z\cdot x^2}{4\cdot D}$$ and $$w_{xy} = a^T \cdot \begin{bmatrix} 0 \\ 0 \\ 0 \\ 1\cdot r'^{-1} \\ 0 \\ 0 \\ 2\cdot x\cdot r'^{-2} \\ 2\cdot y\cdot r'^{-2} \\ 0 \\ 0 \\ 3\cdot x^2\cdot r'^{-3} \\ 3\cdot y^2\cdot r'^{-3} \\ -12\cdot x\cdot y\cdot r'^{-3} \\ -12\cdot x\cdot y\cdot r'^{-3} \\ 2\cdot x\cdot (2\cdot x^2 - 3\cdot y^2)\cdot r'^{-4} \\ (4\cdot y^3 - 6\cdot x^2\cdot y)\cdot r'^{-4} \\ -30\cdot x^2\cdot y\cdot r'^{-4} \\ -30\cdot x\cdot y^2\cdot r'^{-4} \end{bmatrix} + \frac{p_z\cdot x\cdot y}{2\cdot D}$$

Introducing Eq. B-11 into Eq. B-10 and rearranging:

$$U_i = \frac{\partial}{\partial a_i}\left[\frac{D}{2}\cdot\int_{x_0}^{x_1}\int_0^{m_1\cdot x+b_1}(w_{xx}+w_{yy})^2 - \right.$$
$$\left. 2\cdot(1-v)\cdot(w_{xx}\cdot w_{yy} - w_{xy}^2)dy\,dx\right]$$
Eq. B-12

$$U_i = \frac{D}{2}\cdot\int_{x_0}^{x_1}\int_0^{m_1\cdot x+b_1}\frac{\partial}{\partial a_i}$$
$$[(w_{xx}+w_{yy})^2 - 2\cdot(1-v)\cdot(w_{xx}\cdot w_{yy} - w_{xy}^2)]dy\,dx$$

-continued $$U_i = \frac{D}{2} \cdot \int_{x_0}^{x_1} \int_0^{m_1 \cdot x + b_1} 2 \cdot (w_{xx} + w_{yy}) \cdot \frac{\partial}{\partial a_i}(w_{xx} + w_{yy}) \ldots +$$

$$-2 \cdot (1-v) \cdot \left( w_{xx} \cdot \frac{\partial}{\partial a_i} w_{yy} + w_{yy} \cdot \frac{\partial}{\partial a_i} w_{xx} - 2 \cdot w_{xy} \cdot \frac{\partial}{\partial a_i} w_{xy} \right) dy\, dx$$

The integral in Eq. B-12 represents one row that is to be summed into the $U_m$ array (in Eq. A-51) and one position that is to be summed into the $U_b$ vector (in Eq. A-51). Considering the portion that is to be summed into the $U_m$ array (in Eq. A-51), a further definition can be made to identify each position in the array (as shown in Eq. B-13).

$$U_{i,j} = \frac{D}{2} \cdot \int_{x_0}^{x_1} \int_0^{m_1 \cdot x + b_1} 2 \cdot (w_{xx} + w_{yy})_j \cdot \frac{\partial}{\partial a_i}(w_{xx} + w_{yy}) \ldots + \quad \text{Eq. B-13}$$

$$-2 \cdot (1-v) \cdot \left( w_{xx_j} \cdot \frac{\partial}{\partial a_i} w_{yy} + w_{yy_j} \cdot \frac{\partial}{\partial a_i} w_{xx} - 2 \cdot w_{xy_j} \cdot \frac{\partial}{\partial a_i} w_{xy} \right) dy\, dx$$

Equation to find array terms

Where the subscript "j" represents the portion of an expression related to a degree of freedom (from 0 to 17).

Eq. B-13 identifies the term in the array on the ith row and jth column. Considering Eq. B-11, one term in one expression can be found as shown in Eq. B-14.

$$\int_{x_0}^{x_1} \int_0^{m_1 \cdot x + b_1} w_{xx_{18}} \cdot \frac{\partial}{\partial a_{17}} w_{yy} dy\, dx = \quad \text{Eq. B-14}$$

$$\int_{x_0}^{x_1} \int_0^{m_1 \cdot x + b_1} (-10 \cdot y^3 \cdot r'^{-4}) \cdot (-10 \cdot x^3 \cdot r'^{-4}) dy\, dx$$

Example where $i = 17$ and $j = 18$ for one expression in Eq. B-13.

Definitions similar to that in Eq. B-14 are made for all of the array positions and for all of the terms in Eq. B-13. Considering that there is a limited number of possible polynomial expressions (given Eqs. B-11 and B-13), a generalized representation for Eq. B-14 can be defined (as shown in Eqs. B-15 and B-16).

$$(w_{xx} + w_{yy})_j = \begin{pmatrix} \alpha_0 \\ \alpha_1 \\ \alpha_2 \\ \alpha_3 \\ \alpha_4 \\ \alpha_5 \\ \alpha_6 \\ \alpha_7 \\ \alpha_8 \\ \alpha_9 \end{pmatrix}^T \begin{pmatrix} x^3 \\ x^2 \\ x \\ 1 \\ x^2 \cdot y \\ x \cdot y \\ y \\ x \cdot y^2 \\ y^2 \\ y^3 \end{pmatrix} \text{ and} \quad \text{Eq. B-15}$$

or $w_{xx_j} =$ or $w_{yy_j} =$ or $w_{xy_j} =$ $$\frac{\partial}{\partial a_i}(w_{xx} + w_{yy}) = \begin{pmatrix} \beta_0 \\ \beta_1 \\ \beta_2 \\ \beta_3 \\ \beta_4 \\ \beta_5 \\ \beta_6 \\ \beta_7 \\ \beta_8 \\ \beta_9 \end{pmatrix}^T \begin{pmatrix} x^3 \\ x^2 \\ x \\ 1 \\ x^2 \cdot y \\ x \cdot y \\ y \\ x \cdot y^2 \\ y^2 \\ y^3 \end{pmatrix}$$

or $\frac{\partial}{\partial a_i} w_{xx} =$ or $\frac{\partial}{\partial a_i} w_{yy} =$ or $\frac{\partial}{\partial a_i} w_{xy} =$ Where $(\alpha_0\ \alpha_1\ \alpha_2\ \alpha_3\ \alpha_4\ \alpha_5\ \alpha_6\ \alpha_7\ \alpha_8\ \alpha_9)$ and $(\beta_0\ \beta_1\ \beta_2\ \beta_3\ \beta_4\ \beta_5\ \beta_6\ \beta_7\ \beta_8\ \beta_9)$ represent possible definitions for the constants in Eq. B-11.

Since Eq. B-15 can represent all possible outcomes for Eq. B-11, all of the terms similar to Eq. B-14 can be evaluated with a single generalized integration (Eq. B-16).

$$\text{Int} = \int_{x_0}^{x_1} \int_0^{m_1 \cdot x + b_1} \left[ \begin{pmatrix} \alpha_0 \\ \alpha_1 \\ \alpha_2 \\ \alpha_3 \\ \alpha_4 \\ \alpha_5 \\ \alpha_6 \\ \alpha_7 \\ \alpha_8 \\ \alpha_9 \end{pmatrix}^T \begin{pmatrix} x^3 \\ x^2 \\ x \\ 1 \\ x^2 \cdot y \\ x \cdot y \\ y \\ x \cdot y^2 \\ y^2 \\ y^3 \end{pmatrix} \right] \cdot \left[ \begin{pmatrix} \beta_0 \\ \beta_1 \\ \beta_2 \\ \beta_3 \\ \beta_4 \\ \beta_5 \\ \beta_6 \\ \beta_7 \\ \beta_8 \\ \beta_9 \end{pmatrix}^T \begin{pmatrix} x^3 \\ x^2 \\ x \\ 1 \\ x^2 \cdot y \\ x \cdot y \\ y \\ x \cdot y^2 \\ y^2 \\ y^3 \end{pmatrix} \right] dy\, dx \quad \text{Eq. B-16}$$

Generalized or integration $$\text{Int} = \int_{x_0}^{x_1}\int_{0}^{m_1 \cdot x + b_1} \begin{pmatrix} \alpha_9 \cdot \beta_9 \\ \alpha_8 \cdot \beta_9 + \alpha_9 \cdot \beta_8 \\ \alpha_7 \cdot \beta_9 + \alpha_9 \cdot \beta_7 \\ \alpha_6 \cdot \beta_9 + \alpha_9 \cdot \beta_6 + \alpha_8 \cdot \beta_8 \\ \alpha_5 \cdot \beta_9 + \alpha_9 \cdot \beta_5 + \alpha_7 \cdot \beta_8 + \alpha_8 \cdot \beta_7 \\ \alpha_4 \cdot \beta_9 + \alpha_9 \cdot \beta_4 + \alpha_7 \cdot \beta_7 \\ \alpha_3 \cdot \beta_9 + \alpha_9 \cdot \beta_3 + \alpha_6 \cdot \beta_8 + \alpha_8 \cdot \beta_6 \\ \alpha_2 \cdot \beta_9 + \alpha_9 \cdot \beta_2 + \alpha_5 \cdot \beta_8 + \alpha_6 \cdot \beta_7 + \alpha_7 \cdot \beta_6 + \alpha_8 \cdot \beta_5 \\ \alpha_1 \cdot \beta_9 + \alpha_9 \cdot \beta_1 + \alpha_4 \cdot \beta_8 + \alpha_5 \cdot \beta_7 + \alpha_7 \cdot \beta_5 + \alpha_8 \cdot \beta_4 \\ \alpha_0 \cdot \beta_9 + \alpha_9 \cdot \beta_0 + \alpha_4 \cdot \beta_7 + \alpha_7 \cdot \beta_4 \\ \alpha_3 \cdot \beta_8 + \alpha_8 \cdot \beta_3 + \alpha_6 \cdot \beta_6 \\ \alpha_2 \cdot \beta_8 + \alpha_3 \cdot \beta_7 + \alpha_7 \cdot \beta_3 + \alpha_8 \cdot \beta_2 + \alpha_5 \cdot \beta_6 + \alpha_6 \cdot \beta_5 \\ \alpha_1 \cdot \beta_8 + \alpha_2 \cdot \beta_7 + \alpha_7 \cdot \beta_2 + \alpha_8 \cdot \beta_1 + \alpha_4 \cdot \beta_6 + \alpha_5 \cdot \beta_5 + \alpha_6 \cdot \beta_4 \\ \alpha_0 \cdot \beta_8 + \alpha_1 \cdot \beta_7 + \alpha_7 \cdot \beta_1 + \alpha_8 \cdot \beta_0 + \alpha_4 \cdot \beta_5 + \alpha_5 \cdot \beta_4 \\ \alpha_0 \cdot \beta_7 + \alpha_7 \cdot \beta_0 + \alpha_4 \cdot \beta_4 \\ \alpha_3 \cdot \beta_6 + \alpha_6 \cdot \beta_3 \\ \alpha_2 \cdot \beta_6 + \alpha_3 \cdot \beta_5 + \alpha_5 \cdot \beta_3 + \alpha_6 \cdot \beta_2 \\ \alpha_1 \cdot \beta_6 + \alpha_2 \cdot \beta_5 + \alpha_3 \cdot \beta_4 + \alpha_4 \cdot \beta_3 + \alpha_5 \cdot \beta_2 + \alpha_6 \cdot \beta_1 \\ \alpha_0 \cdot \beta_6 + \alpha_1 \cdot \beta_5 + \alpha_2 \cdot \beta_4 + \alpha_4 \cdot \beta_2 + \alpha_5 \cdot \beta_1 + \alpha_6 \cdot \beta_0 \\ \alpha_0 \cdot \beta_5 + \alpha_1 \cdot \beta_4 + \alpha_4 \cdot \beta_1 + \alpha_5 \cdot \beta_0 \\ \alpha_0 \cdot \beta_4 + \alpha_4 \cdot \beta_0 \\ \alpha_3 \cdot \beta_3 \\ \alpha_2 \cdot \beta_3 + \alpha_3 \cdot \beta_2 \\ \alpha_1 \cdot \beta_3 + \alpha_2 \cdot \beta_2 + \alpha_3 \cdot \beta_1 \\ \alpha_0 \cdot \beta_3 + \alpha_1 \cdot \beta_2 + \alpha_2 \cdot \beta_1 + \alpha_3 \cdot \beta_0 \\ \alpha_0 \cdot \beta_2 + \alpha_1 \cdot \beta_1 + \alpha_2 \cdot \beta_0 \\ \alpha_0 \cdot \beta_1 + \alpha_1 \cdot \beta_0 \\ \alpha_0 \cdot \beta_0 \end{pmatrix}^T \cdot \begin{pmatrix} y^6 \\ y^5 \\ x \cdot y^5 \\ y^4 \\ x \cdot y^4 \\ x^2 \cdot y^4 \\ y^3 \\ x \cdot y^3 \\ x^2 \cdot y^3 \\ x^3 \cdot y^3 \\ y^2 \\ x \cdot y^2 \\ x^2 \cdot y^2 \\ x^3 \cdot y^2 \\ x^4 \cdot y^2 \\ y \\ x \cdot y \\ x^2 \cdot y \\ x^3 \cdot y \\ x^4 \cdot y \\ x^5 \cdot y \\ 1 \\ x \\ x^2 \\ x^3 \\ x^4 \\ x^5 \\ x^6 \end{pmatrix} \, dy\, dx$$

Performing the integration in Eq. B-16 results in Eq. B-17

$$\text{Int} = CvtU(\alpha,\beta)^T \cdot SU_{01}(x_0, x_1, m_1, b_1) \quad \text{Eq. B-17}$$

Where:

$CvtU(\alpha,\beta)$—Vector containing constant equations (must be evaluated many times per edge)

$SU_{01}(x_0, x_1, m_1, b_1)$—Generalized integration vector (must be evaluated once per edge)

$$CvtU(\alpha, \beta) = \begin{pmatrix} \alpha_9 \cdot \beta_9 \\ \alpha_8 \cdot \beta_9 + \alpha_9 \cdot \beta_8 \\ \alpha_7 \cdot \beta_9 + \alpha_9 \cdot \beta_7 \\ \alpha_6 \cdot \beta_9 + \alpha_9 \cdot \beta_6 + \alpha_8 \cdot \beta_8 \\ \alpha_5 \cdot \beta_9 + \alpha_9 \cdot \beta_5 + \alpha_7 \cdot \beta_8 + \alpha_8 \cdot \beta_7 \\ \alpha_4 \cdot \beta_9 + \alpha_9 \cdot \beta_4 + \alpha_7 \cdot \beta_7 \\ \alpha_3 \cdot \beta_9 + \alpha_9 \cdot \beta_3 + \alpha_6 \cdot \beta_8 + \alpha_8 \cdot \beta_6 \\ \alpha_2 \cdot \beta_9 + \alpha_9 \cdot \beta_2 + \alpha_5 \cdot \beta_8 + \alpha_6 \cdot \beta_7 + \alpha_7 \cdot \beta_6 + \alpha_8 \cdot \beta_5 \\ \alpha_1 \cdot \beta_9 + \alpha_9 \cdot \beta_1 + \alpha_4 \cdot \beta_8 + \alpha_5 \cdot \beta_7 + \alpha_7 \cdot \beta_5 + \alpha_8 \cdot \beta_4 \\ \alpha_0 \cdot \beta_9 + \alpha_9 \cdot \beta_0 + \alpha_4 \cdot \beta_7 + \alpha_7 \cdot \beta_4 \\ \alpha_3 \cdot \beta_8 + \alpha_8 \cdot \beta_3 + \alpha_6 \cdot \beta_6 \\ \alpha_2 \cdot \beta_8 + \alpha_3 \cdot \beta_7 + \alpha_7 \cdot \beta_3 + \alpha_8 \cdot \beta_2 + \alpha_5 \cdot \beta_6 + \alpha_6 \cdot \beta_5 \\ \alpha_1 \cdot \beta_8 + \alpha_2 \cdot \beta_7 + \alpha_7 \cdot \beta_2 + \alpha_8 \cdot \beta_1 + \alpha_4 \cdot \beta_6 + \alpha_5 \cdot \beta_5 + \alpha_6 \cdot \beta_4 \\ \alpha_0 \cdot \beta_8 + \alpha_1 \cdot \beta_7 + \alpha_7 \cdot \beta_1 + \alpha_8 \cdot \beta_0 + \alpha_4 \cdot \beta_5 + \alpha_5 \cdot \beta_4 \\ \alpha_0 \cdot \beta_7 + \alpha_7 \cdot \beta_0 + \alpha_4 \cdot \beta_4 \\ \alpha_3 \cdot \beta_6 + \alpha_6 \cdot \beta_3 \\ \alpha_2 \cdot \beta_6 + \alpha_3 \cdot \beta_5 + \alpha_5 \cdot \beta_3 + \alpha_6 \cdot \beta_2 \\ \alpha_1 \cdot \beta_6 + \alpha_2 \cdot \beta_5 + \alpha_3 \cdot \beta_4 + \alpha_4 \cdot \beta_3 + \alpha_5 \cdot \beta_2 + \alpha_6 \cdot \beta_1 \\ \alpha_0 \cdot \beta_6 + \alpha_1 \cdot \beta_5 + \alpha_2 \cdot \beta_4 + \alpha_4 \cdot \beta_2 + \alpha_5 \cdot \beta_1 + \alpha_6 \cdot \beta_0 \\ \alpha_0 \cdot \beta_5 + \alpha_1 \cdot \beta_4 + \alpha_4 \cdot \beta_1 + \alpha_5 \cdot \beta_0 \\ \alpha_0 \cdot \beta_4 + \alpha_4 \cdot \beta_0 \\ \alpha_3 \cdot \beta_3 \\ \alpha_2 \cdot \beta_3 + \alpha_3 \cdot \beta_2 \\ \alpha_1 \cdot \beta_3 + \alpha_2 \cdot \beta_2 + \alpha_3 \cdot \beta_1 \\ \alpha_0 \cdot \beta_3 + \alpha_1 \cdot \beta_2 + \alpha_2 \cdot \beta_1 + \alpha_3 \cdot \beta_0 \\ \alpha_0 \cdot \beta_2 + \alpha_1 \cdot \beta_1 + \alpha_2 \cdot \beta_0 \\ \alpha_0 \cdot \beta_1 + \alpha_1 \cdot \beta_0 \\ \alpha_0 \cdot \beta_0 \end{pmatrix}$$

Eq. B-18 is defined because of the large size of the expressions in the vector. The three stacked vectors are shown on the three pages below.

Eq. B-18

$SU_{01}(x_0, x_1, m_1, b_1) =$
  $stack(SU_{01a}(x_0, x_1, m_1, b_1), SU_{01b}(x_0, x_1, m_1, b_1), SU_{01c}(x_0, x_1, m_1, b_1))$ $SU_{01a}(x_0, x_1, m_1, b_1) =$ $$\begin{bmatrix}
\frac{b_1^7 \cdot x_1}{7} - \frac{b_1^7 \cdot x_0}{7} - \frac{b_1^6 \cdot m_1 \cdot x_0^2}{2} + \frac{b_1^6 \cdot m_1 \cdot x_1^2}{2} - b_1^5 \cdot m_1^2 \cdot x_0^3 + b_1^5 \cdot m_1^2 \cdot x_1^3 - \frac{5 \cdot b_1^4 \cdot m_1^3 \cdot x_0^4}{4} + \frac{5 \cdot b_1^4 \cdot m_1^3 \cdot x_1^4}{4} \ldots + \\
-b_1^3 \cdot m_1^4 \cdot x_0^5 + b_1^3 \cdot m_1^4 \cdot x_1^5 - \frac{b_1^2 \cdot m_1^5 \cdot x_0^6}{2} + \frac{b_1 \cdot m_1^5 \cdot x_1^6}{2} - \frac{b_1 \cdot m_1^6 \cdot x_0^7}{7} + \frac{b_1 \cdot m_1^6 \cdot x_1^7}{7} - \frac{m_1^7 \cdot x_0^8}{56} + \frac{m_1^7 \cdot x_1^8}{56} \\
\frac{b_1^6 \cdot x_1}{6} - \frac{b_1^6 \cdot x_0}{6} - \frac{b_1^5 \cdot m_1 \cdot x_0^2}{2} + \frac{b_1^5 \cdot m_1 \cdot x_1^2}{2} - \frac{5 \cdot b_1^4 \cdot m_1^2 \cdot x_0^3}{6} + \frac{5 \cdot b_1^4 \cdot m_1^2 \cdot x_1^3}{6} - \frac{5 \cdot b_1^3 \cdot m_1^3 \cdot x_0^4}{6} \ldots + \\
\frac{5 \cdot b_1^3 \cdot m_1^3 \cdot x_1^4}{6} - \frac{b_1^2 \cdot m_1^4 \cdot x_0^5}{2} + \frac{b_1^2 \cdot m_1^4 \cdot x_0^5}{2} - \frac{b_1 \cdot m_1^5 \cdot x_0^6}{6} + \frac{b_1 \cdot m_1^5 \cdot x_1^6}{6} - \frac{m_1^6 \cdot x_0^7}{42} + \frac{m_1^6 \cdot x_1^7}{42} \\
\frac{b_1^6 \cdot x_1^2}{12} - \frac{b_1^6 \cdot x_0^2}{12} - \frac{b_1^5 \cdot m_1 \cdot x_0^3}{3} + \frac{b_1^5 \cdot m_1 \cdot x_1^3}{3} - \frac{5 \cdot b_1^4 \cdot m_1^2 \cdot x_0^4}{8} + \frac{5 \cdot b_1^4 \cdot m_1^2 \cdot x_1^4}{8} - \frac{2 \cdot b_1^3 \cdot m_1^3 \cdot x_0^5}{3} \ldots + \\
\frac{2 \cdot b_1^3 \cdot m_1^3 \cdot x_1^5}{3} - \frac{5 \cdot b_1^2 \cdot m_1^4 \cdot x_0^6}{12} \quad \frac{5 \cdot b_1^2 \cdot m_1^4 \cdot x_1^6}{12} - \frac{b_1 \cdot m_1^5 \cdot x_0^7}{7} + \frac{b_1 \cdot m_1^5 \cdot x_1^7}{7} - \frac{m_1^6 \cdot x_0^8}{48} + \frac{m_1^6 \cdot x_1^8}{48} \\
\frac{b_1^5 \cdot x_1}{5} - \frac{b_1^5 \cdot x_0}{5} - \frac{b_1^4 \cdot m_1 \cdot x_0^2}{2} + \frac{b_1^4 \cdot m_1 \cdot x_1^2}{2} - \frac{2 \cdot b_1^3 \cdot m_1^2 \cdot x_0^3}{3} + \frac{2 \cdot b_1^3 \cdot m_1^2 \cdot x_1^3}{3} \ldots +
\end{bmatrix}$$

$$\begin{bmatrix}
-\frac{b_1^2 \cdot m_1^3 \cdot x_0^4}{2} + \frac{b_1^2 \cdot m_1^3 \cdot x_1^4}{2} - \frac{b_1 \cdot m_1^4 \cdot x_0^5}{5} + \frac{b_1 \cdot m_1^4 \cdot x_1^5}{5} - \frac{m_1^5 \cdot x_0^6}{30} + \frac{m_1^5 \cdot x_1^6}{30} \\
\frac{b_1^5 \cdot x_1^2}{10} - \frac{b_1^5 \cdot x_0^2}{10} - \frac{b_1^4 \cdot m_1 \cdot x_0^2}{3} + \frac{b_1^4 \cdot m_1 \cdot x_1^3}{3} - \frac{b_1^3 \cdot m_1^2 \cdot x_0^4}{2} + \frac{b_1^3 \cdot m_1^2 \cdot x_1^4}{2} \ldots + \\
-\frac{2 \cdot b_1^2 \cdot m_1^3 \cdot x_0^5}{5} + \frac{2 \cdot b_1^2 \cdot m_1^3 \cdot x_1^5}{5} - \frac{b_1 \cdot m_1^4 \cdot x_0^6}{6} + \frac{b_1 \cdot m_1^4 \cdot x_1^6}{6} - \frac{m_1^5 \cdot x_0^7}{35} + \frac{m_1^5 \cdot x_1^7}{35} \\
\frac{b_1^5 \cdot x_1^3}{15} - \frac{b_1^5 \cdot x_0^3}{15} - \frac{b_1^4 \cdot m_1 \cdot x_0^4}{4} + \frac{b_1^4 \cdot m_1 \cdot x_1^4}{4} - \frac{2 \cdot b_1^3 \cdot m_1^2 \cdot x_0^5}{5} + \frac{2 \cdot b_1^3 \cdot m_1^2 \cdot x_1^5}{5} \ldots + \\
-\frac{b_1^2 \cdot m_1^3 \cdot x_0^6}{3} + \frac{b_1^2 \cdot m_1^3 \cdot x_1^6}{3} - \frac{b_1 \cdot m_1^4 \cdot x_0^7}{7} + \frac{b_1 \cdot m_1^4 \cdot x_1^7}{7} - \frac{m_1^5 \cdot x_0^8}{40} + \frac{m_1^5 \cdot x_1^8}{40} \\
\frac{b_1^4 \cdot x_1}{4} - \frac{b_1^4 \cdot x_0}{4} - \frac{b_1^3 \cdot m_1 \cdot x_0^2}{2} + \frac{b_1^3 \cdot m_1 \cdot x_1^2}{2} - \frac{b_1^2 \cdot m_1^2 \cdot x_0^3}{2} \ldots + \\
\frac{b_1^2 \cdot m_1^2 \cdot x_1^3}{2} - \frac{b_1 \cdot m_1^3 \cdot x_0^4}{4} + \frac{b_1 \cdot m_1^3 \cdot x_1^4}{4} - \frac{m_1^4 \cdot x_0^5}{20} + \frac{m_1^4 \cdot x_1^5}{20}
\end{bmatrix}$$

$SU_{01b}(x_0, x_1, m_1, b_1) =$ $$\begin{bmatrix} \frac{b_1^4 \cdot x_1^2}{8} - \frac{b_1^4 \cdot x_0^2}{8} - \frac{b_1^3 \cdot m_1 \cdot x_0^3}{3} + \frac{b_1^3 \cdot m_1 \cdot x_1^3}{3} - \frac{3 \cdot b_1^2 \cdot m_1^2 \cdot x_0^4}{8} + \ldots \\ \frac{3 \cdot b_1^2 \cdot m_1^2 \cdot x_1^4}{8} - \frac{b_1 \cdot m_1^3 \cdot x_0^5}{5} + \frac{b_1 \cdot m_1^3 \cdot x_1^5}{5} - \frac{m_1^4 \cdot x_0^6}{24} + \frac{m_1^4 \cdot x_1^6}{24} \\ \frac{b_1^4 \cdot x_1^3}{12} - \frac{b_1^4 \cdot x_0^3}{12} - \frac{b_1^3 \cdot m_1 \cdot x_0^4}{4} + \frac{b_1^3 \cdot m_1 \cdot x_1^4}{4} - \frac{3 \cdot b_1^2 \cdot m_1^2 \cdot x_0^5}{10} \ldots + \\ \frac{3 \cdot b_1^2 \cdot m_1^2 \cdot x_1^5}{10} - \frac{b_1 \cdot m_1^3 \cdot x_0^6}{6} + \frac{b_1 \cdot m_1^3 \cdot x_1^6}{6} - \frac{m_1^4 \cdot x_0^7}{28} + \frac{m_1^4 \cdot x_1^7}{28} \\ \frac{b_1^4 \cdot x_1^4}{16} - \frac{b_1^4 \cdot x_0^4}{16} - \frac{b_1^3 \cdot m_1 \cdot x_0^5}{5} + \frac{b_1^3 \cdot m_1 \cdot x_1^5}{5} - \frac{b_1^2 \cdot m_1^2 \cdot x_0^6}{4} \ldots + \\ \frac{b_1^2 \cdot m_1^2 \cdot x_1^6}{4} - \frac{b_1 \cdot m_1^3 \cdot x_0^7}{7} + \frac{b_1 \cdot m_1^3 \cdot x_1^7}{7} - \frac{m_1^4 \cdot x_0^8}{32} + \frac{m_1^4 \cdot x_1^8}{32} \\ -\frac{(x_0 - x_1) \cdot (2 \cdot b_1 + m_1 \cdot x_0 + m_1 \cdot x_1) \cdot (2 \cdot b_1^2 + 2 \cdot b_1 \cdot m_1 \cdot x_0 + 2 \cdot b_1 \cdot m_1 \cdot x_1 + m_1^2 \cdot x_0^2 + m_1^2 \cdot x_1^2)}{12} \\ \frac{b_1^3 \cdot x_1^2}{6} - \frac{b_1^3 \cdot x_0^2}{6} - \frac{b_1^2 \cdot m_1 \cdot x_0^3}{3} + \frac{b_1^2 \cdot m_1 \cdot x_1^3}{3} - \frac{b_1 \cdot m_1^2 \cdot x_0^4}{4} + \frac{b_1 \cdot m_1^2 \cdot x_1^4}{4} - \frac{m_1^3 \cdot x_0^5}{15} + \frac{m_1^3 \cdot x_1^5}{15} \\ \frac{b_1^3 \cdot x_1^3}{9} - \frac{b_1^3 \cdot x_0^3}{9} - \frac{b_1^2 \cdot m_1 \cdot x_0^4}{4} + \frac{b_1^2 \cdot m_1 \cdot x_1^4}{4} - \frac{b_1 \cdot m_1^2 \cdot x_0^5}{5} + \frac{b_1 \cdot m_1^2 \cdot x_1^5}{5} - \frac{m_1^3 \cdot x_0^6}{18} + \frac{m_1^3 \cdot x_1^6}{18} \\ \frac{b_1^3 \cdot x_1^4}{12} - \frac{b_1^3 \cdot x_0^4}{12} - \frac{b_1^2 \cdot m_1 \cdot x_0^5}{5} + \frac{b_1^2 \cdot m_1 \cdot x_1^5}{5} - \frac{b_1 \cdot m_1^2 \cdot x_0^6}{6} + \frac{b_1 \cdot m_1^2 \cdot x_1^6}{6} - \frac{m_1^3 \cdot x_0^7}{21} + \frac{m_1^3 \cdot x_1^7}{21} \end{bmatrix}$$

$SU_{01c}(x_0, x_1, m_1, b_1) =$ $$\begin{bmatrix} \frac{b_1^3 \cdot x_1^5}{15} - \frac{b_1^3 \cdot x_0^5}{15} - \frac{b_1^2 \cdot m_1 \cdot x_0^5}{6} + \frac{b_1^2 \cdot m_1 \cdot x_1^6}{6} - \frac{b_1 \cdot m_1^2 \cdot x_0^7}{7} + \frac{b_1 \cdot m_1^2 \cdot x_1^7}{7} - \frac{m_1^3 \cdot x_0^8}{24} + \frac{m_1^3 \cdot x_1^8}{24} \\ \frac{b_1^2 \cdot x_1}{2} - \frac{b_1^2 \cdot x_0}{2} - \frac{b_1 \cdot m_1 \cdot x_0^2}{2} + \frac{b_1 \cdot m_1 \cdot x_1^2}{2} - \frac{m_1^2 \cdot x_0^3}{6} + \frac{m_1^2 \cdot x_1^3}{6} \\ \frac{b_1^2 \cdot x_1^2}{4} - \frac{b_1^2 \cdot x_0^2}{4} - \frac{b_1 \cdot m_1 \cdot x_0^3}{3} + \frac{b_1 \cdot m_1 \cdot x_1^3}{3} - \frac{m_1^2 \cdot x_0^4}{8} + \frac{m_1^2 \cdot x_1^4}{8} \\ \frac{b_1^2 \cdot x_1^3}{6} - \frac{b_1^2 \cdot x_0^3}{6} - \frac{b_1 \cdot m_1 \cdot x_0^4}{4} + \frac{b_1 \cdot m_1 \cdot x_1^4}{4} - \frac{m_1^2 \cdot x_0^5}{10} + \frac{m_1^2 \cdot x_1^5}{10} \\ \frac{b_1^2 \cdot x_1^4}{8} - \frac{b_1^2 \cdot x_0^4}{8} - \frac{b_1 \cdot m_1 \cdot x_0^5}{5} + \frac{b_1 \cdot m_1 \cdot x_1^5}{5} - \frac{m_1^2 \cdot x_0^6}{12} + \frac{m_1^2 \cdot x_1^6}{12} \\ \frac{b_1^2 \cdot x_1^5}{10} - \frac{b_1^2 \cdot x_0^5}{10} - \frac{b_1 \cdot m_1 \cdot x_0^6}{6} + \frac{b_1 \cdot m_1 \cdot x_1^6}{6} - \frac{m_1^2 \cdot x_0^7}{14} + \frac{m_1^2 \cdot x_1^7}{14} \\ \frac{b_1^2 \cdot x_1^6}{12} - \frac{b_1^2 \cdot x_0^6}{12} - \frac{b_1 \cdot m_1 \cdot x_0^7}{7} + \frac{b_1 \cdot m_1 \cdot x_1^7}{7} - \frac{m_1^2 \cdot x_0^8}{16} + \frac{m_1^2 \cdot x_1^8}{16} \end{bmatrix}$$

$$-\frac{(x_0 - x_1) \cdot (2 \cdot b_1 + m_1 \cdot x_0 + m_1 \cdot x_1)}{2}$$

$$\frac{m_1 \cdot x_1^3}{3} - \frac{b_1 \cdot x_0^2}{2} - \frac{m_1 \cdot x_0^3}{3} + \frac{b_1 \cdot x_1^2}{2}$$

$$\frac{m_1 \cdot x_1^4}{4} - \frac{b_1 \cdot x_0^3}{3} - \frac{m_1 \cdot x_0^4}{4} + \frac{b_1 \cdot x_1^3}{3}$$

$$\frac{m_1 \cdot x_1^5}{5} - \frac{b_1 \cdot x_0^4}{4} - \frac{m_1 \cdot x_0^5}{5} + \frac{b_1 \cdot x_1^4}{4}$$

$$\frac{m_1 \cdot x_1^6}{6} - \frac{b_1 \cdot x_0^5}{5} - \frac{m_1 \cdot x_0^6}{6} + \frac{b_1 \cdot x_1^5}{5}$$

$$\frac{m_1 \cdot x_1^7}{7} - \frac{b_1 \cdot x_0^6}{6} - \frac{m_1 \cdot x_0^7}{7} + \frac{b_1 \cdot x_1^6}{6}$$

$$\frac{m_1 \cdot x_1^8}{8} - \frac{b_1 \cdot x_0^7}{7} - \frac{m_1 \cdot x_0^8}{8} + \frac{b_1 \cdot x_1^7}{7}$$

An equation similar to Eq. B-13 can be written for the portion of the strain energy relative to the external pressure. This is shown in Eq. B-19. Eq. B-19 represents one position that is to be summed into the $U_b$ vector (in Eq. A-51).

$$U_{i,p} = \frac{D}{2} \cdot \int_{x_0}^{x_1} \int_0^{m_1 \cdot x + b_1} 2 \cdot (w_{xx} + w_{yy})_p \cdot \frac{\partial}{\partial a_i}(w_{xx} + w_{yy}) \ldots + \quad \text{Eq. B-19}$$

$$-2 \cdot (1 - v) \cdot$$

$$\left( w_{xx_p} \cdot \frac{\partial}{\partial a_i} w_{yy} + w_{yy_p} \cdot \frac{\partial}{\partial a_i} w_{xx} - 2 \cdot w_{xy_p} \cdot \frac{\partial}{\partial a_i} w_{xy} \right) dy\, dx$$

Where the subscript "p" indicates the portion of the equation related to the external pressure It is clear that the approach used to evaluate Eq. B-13 will work for Eq. B-19 also. Considering this, the following definitions can be made to perform the integration numerically. The first definitions are to produce arrays (shown in Eq. B-20, B-21, and B-22) representing constants for the three equations found in Eq. B-11. Each column of each array represents the appropriate constant vector shown in Eq. B-15. The number of columns then matches the number of degrees of freedom. (This generates a very sparse array and coding it into an actual finite element solver could be done much more efficiently by reducing the calculation down to where adding or multiplying by zero did not occur. For simplicity of discussion, the sparse array is defined here.) An example of how the array is defined is shown below.

Considering the 12th degree of freedom and the pressure terms as examples, Eq. B-11 produces the results for the 12th degree of freedom as shown below. The pressure term can be viewed similar to a degree of freedom for evaluation and is also shown below.

$$\frac{\partial}{\partial a_{12}} w_{xx} = w_{xx_{12}} = (12 \cdot x^2 - 6 \cdot y^2) \cdot r'^{-3}; \quad w_{xx_p} = \frac{p_z \cdot y^2}{4 \cdot D}$$

Putting these definitions in the form of Eq. B-15:

$$w_{xx_{12}} = \frac{1}{r'^3} \cdot \begin{pmatrix} 0 \\ 12 \\ 0 \\ 0 \\ 0 \\ 0 \\ 0 \\ 0 \\ -6 \\ 0 \end{pmatrix}^T \begin{pmatrix} x^3 \\ x^2 \\ x \\ 1 \\ x^2 \cdot y \\ x \cdot y \\ y \\ x \cdot y^2 \\ y^2 \\ y^3 \end{pmatrix} ==> U_{xx}^{(12)} = \frac{1}{r'^3} \cdot \begin{pmatrix} 0 \\ 12 \\ 0 \\ 0 \\ 0 \\ 0 \\ 0 \\ 0 \\ -6 \\ 0 \end{pmatrix}$$

The 12th column in the $U_{xx}$ array defined in Eq. B-20.

and $$w_{xx_p} = \frac{p_z}{D} \cdot \begin{pmatrix} 0 \\ 0 \\ 0 \\ 0 \\ 0 \\ 0 \\ 0 \\ 0 \\ \frac{1}{4} \\ 0 \end{pmatrix}^T \begin{pmatrix} x^3 \\ x^2 \\ x \\ 1 \\ x^2 \cdot y \\ x \cdot y \\ y \\ x \cdot y^2 \\ y^2 \\ y^3 \end{pmatrix} ==> U_{xxp} = \frac{p_z}{D} \cdot \begin{pmatrix} 0 \\ 0 \\ 0 \\ 0 \\ 0 \\ 0 \\ 0 \\ 0 \\ \frac{1}{4} \\ 0 \end{pmatrix}$$

The the $U_{xxp}$ vector defined in Eq. B-20.

Eqs. B-20, B-21, and B-22 are the arrays for defining the constant vectors defined in Eq. B-15. One vector is assigned for each degree of freedom and then a vector is defined relative to the pressure load.

$U_{xx}(r') :=$ Eq. B-20

$$\begin{pmatrix} 0 & 0 & 0 & 0 & 0 & 0 & 0 & 0 & 0 & 0 & 0 & 0 & 0 & 0 & 0 & 20 \cdot r'^{-4} & 0 \\ 0 & 0 & 0 & 0 & 0 & 0 & 0 & 0 & 0 & 0 & 0 & 12 \cdot r'^{-3} & 0 & 0 & 0 & 0 & 0 \\ 0 & 0 & 0 & 0 & 0 & 0 & 0 & 6 \cdot r'^{-2} & 0 & 0 & 0 & 0 & 0 & 0 & 0 & 0 & 0 \\ 0 & 0 & 0 & 0 & 2 \cdot r'^{-1} & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 12 \cdot r'^{-4} & 0 & 0 & 0 & 0 \\ 0 & 0 & 0 & 0 & 0 & 0 & 0 & 0 & 0 & 6 \cdot r'^{-3} & 0 & 0 & 0 & 0 & 0 & 0 & 0 \\ 0 & 0 & 0 & 0 & 0 & 0 & 2 \cdot r'^{-2} & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & -6 \cdot r'^{-4} & -30 \cdot r'^{-4} & 0 & 0 \\ 0 & 0 & 0 & 0 & 0 & 0 & 0 & 0 & 0 & 0 & -6 \cdot r'^{-3} & -6 \cdot r'^{-3} & 0 & 0 & 0 & 0 & 0 \\ 0 & 0 & 0 & 0 & 0 & 0 & 0 & 0 & 0 & 0 & 0 & 0 & 0 & -2 \cdot r'^{-4} & 0 & 0 & -10 \cdot r'^{-4} \end{pmatrix}$$

$U_{xxp}(D, p_z) := \frac{p_z}{D} \cdot \begin{pmatrix} 0 & 0 & 0 & 0 & 0 & 0 & 0 & 0 & \frac{1}{4} & 0 \end{pmatrix}^T$ $U_{yy}(r') :=$ Eq. B-21

$$\begin{pmatrix} 0 & 0 & 0 & 0 & 0 & 0 & 0 & 0 & 0 & 0 & 0 & 0 & 0 & 0 & -2 \cdot r'^{-4} & -10 \cdot r'^{-4} & 0 \\ 0 & 0 & 0 & 0 & 0 & 0 & 0 & 0 & 0 & 0 & 0 & -6 \cdot r'^{-3} & -6 \cdot r'^{-3} & 0 & 0 & 0 & 0 \\ 0 & 0 & 0 & 0 & 0 & 0 & 0 & 2 \cdot r'^{-2} & 0 & 0 & 0 & 0 & 0 & 0 & 0 & 0 & 0 \\ 0 & 0 & 0 & 0 & 0 & 2 \cdot r'^{-1} & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & -6 \cdot r'^{-4} & 0 & 0 & -30 \cdot r'^{-4} & 0 \\ 0 & 0 & 0 & 0 & 0 & 0 & 0 & 0 & 0 & 6 \cdot r'^{-3} & 0 & 0 & 0 & 0 & 0 & 0 & 0 \\ 0 & 0 & 0 & 0 & 0 & 0 & 0 & 6 \cdot r'^{-2} & 0 & 0 & 0 & 0 & 0 & 0 & 0 & 0 & 0 \\ 0 & 0 & 0 & 0 & 0 & 0 & 0 & 0 & 0 & 0 & 0 & 0 & 12 \cdot r'^{-4} & 0 & 0 & 0 & 0 \\ 0 & 0 & 0 & 0 & 0 & 0 & 0 & 0 & 0 & 0 & 0 & 12 \cdot r'^{-3} & 0 & 0 & 0 & 0 & 0 \\ 0 & 0 & 0 & 0 & 0 & 0 & 0 & 0 & 0 & 0 & 0 & 0 & 0 & 0 & 0 & 20 \cdot r'^{-4} \end{pmatrix}$$

$U_{yyp}(D, p_z) := \frac{p_z}{D} \cdot \begin{pmatrix} 0 & \frac{1}{4} & 0 & 0 & 0 & 0 & 0 & 0 & 0 & 0 \end{pmatrix}^T$ $U_{xy}(r') :=$ Eq. B-22

$$\begin{pmatrix} 0 & 0 & 0 & 0 & 0 & 0 & 0 & 0 & 0 & 0 & 0 & 0 & 0 & 4 \cdot r'^{-4} & 0 & 0 & 0 \\ 0 & 0 & 0 & 0 & 0 & 0 & 0 & 0 & 3 \cdot r'^{-3} & 0 & 0 & 0 & 0 & 0 & 0 & 0 & 0 \\ 0 & 0 & 0 & 0 & 0 & 2 \cdot r'^{-2} & 0 & 0 & 0 & 0 & 0 & 0 & 0 & 0 & 0 & 0 & 0 \\ 0 & 0 & r'^{-1} & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & -6 \cdot r'^{-4} & -30 \cdot r'^{-4} & 0 & 0 & 0 \\ 0 & 0 & 0 & 0 & 0 & 0 & 0 & 0 & 0 & -12 \cdot r'^{-3} & -12 \cdot r'^{-3} & 0 & 0 & 0 & 0 & 0 & 0 \\ 0 & 0 & 0 & 0 & 0 & 0 & 2 \cdot r'^{-2} & 0 & 0 & 0 & 0 & 0 & 0 & 0 & 0 & 0 & 0 \\ 0 & 0 & 0 & 0 & 0 & 0 & 0 & 0 & 0 & 0 & 0 & -6 \cdot r'^{-4} & 0 & 0 & -30 \cdot r'^{-4} & 0 & 0 \\ 0 & 0 & 0 & 0 & 0 & 0 & 0 & 0 & 3 \cdot r'^{-3} & 0 & 0 & 0 & 0 & 0 & 0 & 0 & 0 \\ 0 & 0 & 0 & 0 & 0 & 0 & 0 & 0 & 0 & 0 & 0 & 0 & 4 \cdot r'^{-4} & 0 & 0 & 0 & 0 \end{pmatrix}$$

$U_{xyp}(D, p_z) := \frac{p_z}{D} \cdot \begin{pmatrix} 0 & 0 & 0 & 0 & 0 & \frac{1}{2} & 0 & 0 & 0 & 0 \end{pmatrix}^T$ At this point, all of the definitions necessary for an algebraic form of Eq. B-9 have been defined. These equations can be used to generate array constants and vector constants consistent with Eq. A-50. This is performed with the subroutines (Su.) below. While these subroutines are illustrated in a Mathcad format, other mathematical or general programming languages could be used instead. Su. B-1 assembles an array relative to the degrees of freedom based on Eq. B-14 and using Eq. B-17. Su. B-2 performs a similar role except it is relative to the pressure term.

$$Int_U(A_{\alpha\alpha}, A_{\beta\beta}, A_{\alpha\beta}, s_{01}, D, v) := \quad \text{Su. B-1}$$

$$\begin{vmatrix} out_{cols(A_{\alpha\alpha})-1, cols(A_{\alpha\alpha})-1} \leftarrow 0 \\ \text{for } j \in 0 \ldots cols(A_{\alpha\alpha}) - 1 \\ \quad \text{for } i \in j \ldots cols(A_{\alpha\alpha}) - 1 \\ \quad\quad dx\_dy \leftarrow \begin{pmatrix} CvtU\left(A_{\alpha\alpha}^{(i)} + A_{\beta\beta}^{(i)}, A_{\alpha\alpha}^{(j)} + A_{\beta\beta}^{(j)}\right)^T \ldots + \\ CvtU\left(A_{\alpha\alpha}^{(j)} + A_{\beta\beta}^{(j)}, A_{\alpha\alpha}^{(i)} + A_{\beta\beta}^{(i)}\right)^T \end{pmatrix} \cdot s_{01} \\ \quad\quad dxdy \leftarrow \left(CvtU\left(A_{\alpha\alpha}^{(i)} + A_{\beta\beta}^{(i)}\right)^T + CvtU\left(A_{\alpha\alpha}^{(j)} + A_{\beta\beta}^{(j)}\right)^T\right) \cdot s_{01} \\ \quad\quad dxy \leftarrow \left(CvtU\left(A_{\alpha\beta}^{(i)} + A_{\alpha\beta}^{(j)}\right)^T + CvtU\left(A_{\alpha\beta}^{(j)} + A_{\alpha\beta}^{(i)}\right)^T\right) \cdot s_{01} \\ \quad\quad out_{i,j} \leftarrow \frac{D}{2} \cdot [dx\_dy - 2 \cdot (1-v) \cdot (dxdy - dxy)] \\ \quad\quad out_{j,i} \leftarrow out_{i,j} \\ out \end{vmatrix}$$

$$Int_{Up}(A_{\alpha\alpha}, A_{\beta\beta}, A_{\alpha\beta}, A_{\rho\alpha\alpha}, A_{\rho\beta\beta}, A_{\rho\alpha\beta}, s_{01}, D, v) := \quad \text{Su. B-2}$$

$$\begin{vmatrix} out_{cols(A_{\alpha\alpha})-1} \leftarrow 0 \\ \text{for } j \in 0 \ldots cols(A_{\alpha\alpha}) - 1 \\ \quad dx\_dy \leftarrow \begin{pmatrix} CvtU\left(A_{\alpha\alpha}^{(i)} + A_{\beta\beta}^{(i)}, A_{\rho\alpha\alpha} + A_{\rho\beta\beta}\right)^T \ldots + \\ CvtU\left(A_{\rho\alpha\alpha} + A_{\rho\beta\beta}, A_{\alpha\alpha}^{(i)} + A_{\beta\beta}^{(i)}\right)^T \end{pmatrix} \cdot s_{01} \\ \quad dxdy \leftarrow \left(CvtU\left(A_{\alpha\alpha}^{(i)} + A_{\rho\beta\beta}\right)^T + CvtU\left(A_{\rho\alpha\alpha} + A_{\beta\beta}^{(i)}\right)^T\right) \cdot s_{01} \\ \quad dxy \leftarrow \left(CvtU\left(A_{\alpha\beta}^{(i)} + A_{\rho\alpha\beta}\right)^T + CvtU\left(A_{\rho\alpha\beta} + A_{\alpha\beta}^{(i)}\right)^T\right) \cdot s_{01} \\ \quad out_i \leftarrow \frac{D}{2} \cdot [dx\_dy - 2 \cdot (1-v) \cdot (dxdy - dxy)] \\ out \end{vmatrix}$$

Eq. B-23 defines the functions for the generation of the strain energy constants array and constants vector respectively.

$$U_o(x_0, x_1, m_1, b_1, r', D, v) := Int_U(U_{xx}(r'), U_{xy}(r'), SU_{01}(x_0, x_1, b_1), D, v)$$

$$U_{pz}(x_0, x_1, m_1, b_1, r', D, v, p_z) := Int_{Up}(U_{xx}(r'), U_{yy}(r'), U_{xy}(r'), U_{xxp}(D, p_z), U_{yyp}(D, p_z), U_{xyp}(D, p_z), SU_{01}(x_0, x_1, m_1, b_1), D, v) \quad \text{Eq. B-23}$$

The other area integral to be addressed is Eq. B-10 for the pressure load. This is evaluated by introducing Eq. B-7 into Eq. B-10 and evaluating the partial differential equations relative to the degrees of freedom. This produces Eq. B-23

Eq. B-23

$$W_{p_i} = \frac{\partial}{\partial a_i} \int_{x_0}^{x_1} \int_0^{m_1 \cdot x + b_1} \begin{pmatrix} a_0 \\ a_1 \\ a_2 \\ a_3 \\ a_4 \\ a_5 \\ a_6 \\ a_7 \\ a_8 \\ a_9 \\ a_{10} \\ a_{11} \\ a_{12} \\ a_{13} \\ a_{14} \\ a_{15} \\ a_{16} \\ a_{17} \end{pmatrix}^T \begin{pmatrix} 1 \cdot r' \\ x \\ y \\ x \cdot y \cdot r'^{-1} \\ x^2 \cdot r'^{-1} \\ y^2 \cdot r'^{-1} \\ x^2 \cdot y \cdot r'^{-2} \\ x \cdot y^2 \cdot r'^{-2} \\ x^3 \cdot r'^{-2} \\ y^3 \cdot r'^{-2} \\ x^3 \cdot y \cdot r'^{-3} \\ x \cdot y^3 \cdot r'^{-3} \\ (x^4 - 3 \cdot x^2 \cdot y^2) \cdot r'^{-3} \\ (y^4 - 3 \cdot x^2 \cdot y^2) \cdot r'^{-3} \\ (x^4 \cdot y - x^2 \cdot y^3) \cdot r'^{-4} \\ (x \cdot y^4 - x^3 \cdot y^2) \cdot r'^{-4} \\ (x^5 - 5 \cdot x^3 \cdot y^2) \cdot r'^{-4} \\ (y^5 - 5 \cdot x^2 \cdot y^3) \cdot r'^{-4} \end{pmatrix} + \frac{p_z}{8 \cdot D} \cdot x^2 \cdot y^2 \cdot p_z \, dy \, dx$$

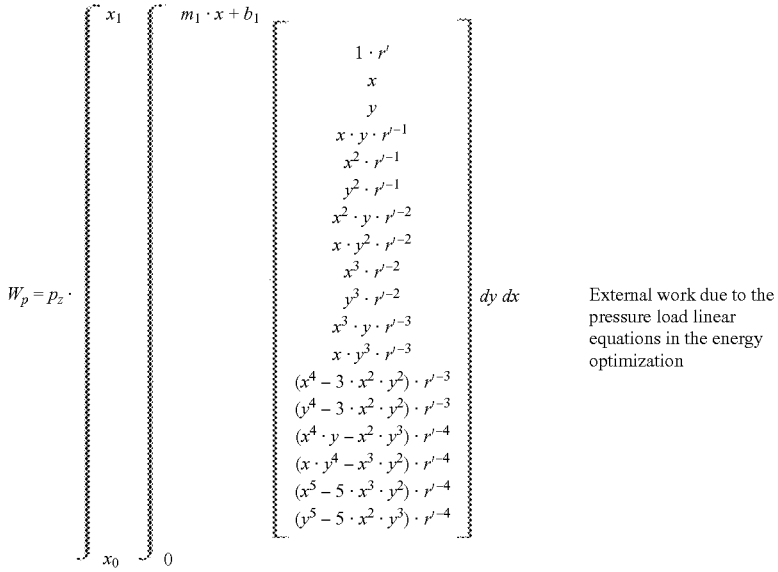

External work due to the pressure load linear equations in the energy optimization Observing Eq. B-23 and the integral portion of Eq. B-16, it is apparent that Equation B-23 can be evaluated with portions of Eq. B-18. Eq. B-24 defines a function relating the integration in Eq. B-23 to Eq. B-18.

$$CvtU''(s_{01}, r') := \begin{Bmatrix} s_{01_{21}} \cdot r' \\ s_{01_{22}} \\ s_{01_{15}} \\ s_{01_{16}} \cdot r'^{-1} \\ s_{01_{23}} \cdot r'^{-1} \\ s_{01_{10}} \cdot r'^{-1} \\ s_{01_{17}} \cdot r'^{-2} \\ s_{01_{11}} \cdot r'^{-2} \\ s_{01_{24}} \cdot r'^{-2} \\ s_{01_{6}} \cdot r'^{-2} \\ s_{01_{18}} \cdot r'^{-3} \\ s_{01_{7}} \cdot r'^{-3} \\ (s_{01_{25}} - 3 \cdot s_{01_{12}}) \cdot r'^{-3} \\ (s_{01_{3}} - 3 \cdot s_{01_{12}}) \cdot r'^{-3} \\ (s_{01_{19}} - s_{01_{8}}) \cdot r'^{-4} \\ (s_{01_{4}} - s_{01_{13}}) \cdot r'^{-4} \\ (s_{01_{26}} - 5 \cdot s_{01_{13}}) \cdot r'^{-4} \\ (s_{01_{1}} - 5 \cdot s_{01_{8}}) \cdot r'^{-4} \end{Bmatrix}$$ Eq. B-24

Displacement equation with length constant

Where:

$s_{01}$—Variable representing the vector from Eq. B-18

Using Eq. B-18 in Eq. B-24 and Eq. B-24 in Eq. B-23, an algebraic form of Eq. B-10 can be found (as shown in Eq. B-25). Eq. B-25 defines the functions for the constants vector to address the pressure load.

$$U_p(x_0,x_1,m_1,b_1,r',D,v,p_z) := p_z \cdot CvtU''(SU_{01}(x_0,x_1,m_1,b_1),r')$$ Eq. B-25

Edge Integrals for a Straight Edge

Recalling the edge energy integral (Eq. A-47), there are three edge loads and three edge displacements to be addressed in the total energy equation for the element (Eq. A-48 or A-49) and the energy optimization (Eq. A-49). The energy optimization lends itself to be broken into pieces, evaluated to form algebraic solutions, and then summed back together. All of the integrals will be addressed in this manner. When broken out the of the energy optimization, the edge energies appear as in Eq. B-26.

$$W_{eP_i} = \frac{d}{da_i} \int_{s_0}^{s_1} P_s \cdot w_s(a) ds_x = \int_{s_0}^{s_1} P_s \cdot \frac{d}{da_i} w_s(a) ds_x$$

Edge energy considering an Eq. B-26(a) external shear load $$W_{eM_i} = \frac{d}{da_i} \int_{s_0}^{s_1} M_s \cdot \theta_s(a) ds_x = \int_{s_0}^{s_1} M_s \cdot \frac{d}{da_i} \theta_s(a) ds_x$$

Edge energy considering an Eq. B-26(b) external moment $$W_{eT_i} = \frac{d}{da_i} \int_{s_0}^{s_1} T_s \cdot \phi_s(a) ds_x = \int_{s_0}^{s_1} T_s \cdot \frac{d}{da_i} \phi_s(a) ds_x$$

Edge energy considering an Eq. B-26(c) external torsion $$W_{ew_i} = \frac{d}{da_i} \int_{s_0}^{s_1} P_s(a) \cdot w_s ds_x = \int_{s_0}^{s_1} w_s \cdot \frac{d}{da_i} P_s(a) ds_x$$

Edge energy considering an Eq. B-26(d) external shear displacement $$W_{e\theta_i} = \frac{d}{da_i} \int_{s_0}^{s_1} M_s(a) \cdot \theta_s ds_x = \int_{s_0}^{s_1} \theta_s \cdot \frac{d}{da_i} M_s(a) ds_x$$

Edge energy considering an Eq. B-26(e) external bending rotation $$W_{e\phi_i} = \frac{d}{da_i} \int_{s_0}^{s_1} T_s(a) \cdot \phi_s ds_x = \int_{s_0}^{s_1} \phi_s \cdot \frac{d}{da_i} T_s(a) ds_x$$

Edge energy considering an Eq. B-26(f) external torsional rotation

Where:

$s_0$—Start of the edge in the local x-direction Also, "(a)" implies that the variable is a function of the degrees of freedom.

$s_1$—End of the edge in the local x-direction

In general, the equations in Eq. B-26 represent one position that is to be summed into the $U_b$ vector (in Eq. A-51) for the element or one row to be summed into the $U_m$ array (in Eq. A-51) for a neighboring element. (In the case where a boundary condition is not known, this can represent one row to be summed into the $U_m$ array (in Eq. A-51) for the element but this is a special case that is discussed more later.)

The external loads and displacements may have any function as long as it can be expressed in terms of the local x-direction. It is very common for boundary conditions to just be constant (which is easily addressed). Neighboring elements will cause external loads and displacements based on their displacement equation. For this example, the external loads will be based on a polynomial equation relevant to the displacement equation of the formulated element. (Consequently, neighboring elements could have the same number or less degrees of freedom and a similar displacement equation and this formulation would not need to be modified.) Considering this approach, Eq. B-27 shows the needed polynomial forms for the displacements and loads (with respect to Eqs. A-44 to A-46).

$w(s) = w_{s0} + w_{s1} \cdot s_x + w_{s2} \cdot s_x^2 + w_{s3} \cdot s_x^3 + w_{s4} \cdot s_x^4 + w_{s5} \cdot s_x^5$ Displacement    Eq. B-27(a)

$\theta(s) = \theta_{s0} + \theta_{s1} \cdot s_x + \theta_{s2} \cdot s_x^2 + \theta_{s3} \cdot s_x^3 + \theta_{s4} \cdot s_x^4$ Bending rotation    Eq. B-27(b)

$\phi(s) = \phi_{s0} + \phi_{s1} \cdot s_x + \phi_{s2} \cdot s_x^2 + \phi_{s3} \cdot s_x^3 + \phi_{s4} \cdot s_x^4$ Torsional rotation    Eq. B-27(c)

$P(s) = P_{s0} + P_{s1} \cdot s_x + P_{s2} \cdot s_x^2$ Shear force    Eq. B-27(d)

$M(s) = M_{s0} + M_{s1} \cdot s_x + M_{s2} \cdot s_x^2 + M_{s3} \cdot s_x^3$ Bending moment    Eq. B-27(e)

$T(s) = T_{s0} + T_{s1} \cdot s_x + T_{s2} \cdot s_x^2 + T_{s3} \cdot s_x^3$ Torsional moment    Eq. B-27(f)

Where the subscript "s" implies that it is a polynomial constant and the number that follows the "s" identifies where it occurs in the polynomial. (It should be noted that the constants are only constants relative to the Eq. B-26 integration. They may be a function of other variables and/or the degrees of freedom.)

Similar to the area integrals addressed earlier, the edge integrals (Eq. B-26) can produce a very large and complex algebraic form. Consequently, it is desirable to find ways to make this process as easy and efficient as possible. To this end, another generalized integration is defined (as shown in Eq. B-28) that addresses possible integrals that occur when Eq. B-27 is introduced into Eq. B-26.

$$Int' = \int_{s_0}^{s_1} \begin{pmatrix} \alpha'_0 \\ \alpha'_1 \\ \alpha'_2 \\ \alpha'_3 \\ \alpha'_4 \\ \alpha'_5 \end{pmatrix}^T \begin{pmatrix} s_x^1 \\ s_x^2 \\ s_x^3 \\ s_x^4 \\ s_x^5 \end{pmatrix} \cdot \left[ \begin{pmatrix} \beta'_0 \\ \beta'_1 \\ \beta'_2 \\ \beta'_3 \\ \beta'_4 \\ \beta'_5 \end{pmatrix}^T \begin{pmatrix} s_x^1 \\ s_x^2 \\ s_x^3 \\ s_x^4 \\ s_x^5 \end{pmatrix} \right] fs_x \qquad \text{Eq. B-28}$$

Generalized integration

Where $(\alpha'_0\ \alpha'_1\ \alpha'_2\ \alpha'_3\ \alpha'_4\ \alpha'_5)$ and $(\beta'_0\ \beta'_1\ \beta'_2\ \beta'_3\ \beta'_4\ \beta'_5)$ represent possible definitions for the Eq. B-27 polynomial constants when introduced into Eq. B-26. Solving the integral in Eq. B-28 produces Eq. B-29.

$$Int' = \int_{s_0}^{s_1} \begin{Bmatrix} \alpha'_0 \cdot \beta'_0 \\ \alpha'_0 \cdot \beta'_1 + \alpha'_1 \cdot \beta'_0 \\ \alpha'_0 \cdot \beta'_2 + \alpha'_1 \cdot \beta'_1 + \alpha'_2 \cdot \beta'_0 \\ \alpha'_0 \cdot \beta'_3 + \alpha'_1 \cdot \beta'_2 + \alpha'_2 \cdot \beta'_1 + \alpha'_3 \cdot \beta'_0 \\ \alpha'_0 \cdot \beta'_4 + \alpha'_1 \cdot \beta'_3 + \alpha'_2 \cdot \beta'_2 + \alpha'_3 \cdot \beta'_1 + \alpha'_4 \cdot \beta'_0 \\ \alpha'_0 \cdot \beta'_5 + \alpha'_1 \cdot \beta'_4 + \alpha'_2 \cdot \beta'_3 + \alpha'_3 \cdot \beta'_2 + \alpha'_4 \cdot \beta'_1 + \alpha'_5 \cdot \beta'_0 \\ \alpha'_1 \cdot \beta'_5 + \alpha'_2 \cdot \beta'_4 + \alpha'_3 \cdot \beta'_3 + \alpha'_4 \cdot \beta'_2 + \alpha'_5 \cdot \beta'_1 \\ \alpha'_2 \cdot \beta'_5 + \alpha'_3 \cdot \beta'_4 + \alpha'_4 \cdot \beta'_3 + \alpha'_5 \cdot \beta'_2 \\ \alpha'_3 \cdot \beta'_5 + \alpha'_4 \cdot \beta'_4 + \alpha'_5 \cdot \beta'_3 \\ \alpha'_4 \cdot \beta'_5 + \alpha'_5 \cdot \beta'_4 \\ \alpha'_5 \cdot \beta'_5 \end{Bmatrix}^T \cdot \begin{Bmatrix} 1 \\ s \\ s^2 \\ s^3 \\ s^3 \\ s^4 \\ s^5 \\ s^6 \\ s^7 \\ s^8 \\ s^9 \\ s^{10} \end{Bmatrix} ds \qquad \text{Eq. B-29}$$

-continued $$Int' = \begin{Bmatrix} \alpha'_0 \cdot \beta'_0 \\ \alpha'_0 \cdot \beta'_1 + \alpha'_1 \cdot \beta'_0 \\ \alpha'_0 \cdot \beta'_2 + \alpha'_1 \cdot \beta'_1 + \alpha'_2 \cdot \beta'_0 \\ \alpha'_0 \cdot \beta'_3 + \alpha'_1 \cdot \beta'_2 + \alpha'_2 \cdot \beta'_1 + \alpha'_3 \cdot \beta'_0 \\ \alpha'_0 \cdot \beta'_4 + \alpha'_1 \cdot \beta'_3 + \alpha'_2 \cdot \beta'_2 + \alpha'_3 \cdot \beta'_1 + \alpha'_4 \cdot \beta'_0 \\ \alpha'_0 \cdot \beta'_5 + \alpha'_1 \cdot \beta'_4 + \alpha'_2 \cdot \beta'_3 + \alpha'_3 \cdot \beta'_2 + \alpha'_4 \cdot \beta'_1 + \alpha'_5 \cdot \beta'_0 \\ \alpha'_1 \cdot \beta'_5 + \alpha'_2 \cdot \beta'_4 + \alpha'_3 \cdot \beta'_3 + \alpha'_4 \cdot \beta'_2 + \alpha'_5 \cdot \beta'_1 \\ \alpha'_2 \cdot \beta'_5 + \alpha'_3 \cdot \beta'_4 + \alpha'_4 \cdot \beta'_3 + \alpha'_5 \cdot \beta'_2 \\ \alpha'_3 \cdot \beta'_5 + \alpha'_4 \cdot \beta'_4 + \alpha'_5 \cdot \beta'_3 \\ \alpha'_4 \cdot \beta'_5 + \alpha'_5 \cdot \beta'_4 \\ \alpha'_5 \cdot \beta'_5 \end{Bmatrix}^T \begin{Bmatrix} s_1 - s_0 \\ \frac{1}{2} \cdot (s_1^2 - s_0^2) \\ \frac{1}{3} \cdot (s_1^3 - s_0^3) \\ \frac{1}{4} \cdot (s_1^4 - s_0^4) \\ \frac{1}{5} \cdot (s_1^5 - s_0^5) \\ \frac{1}{6} \cdot (s_1^6 - s_0^6) \\ \frac{1}{7} \cdot (s_1^7 - s_0^7) \\ \frac{1}{8} \cdot (s_1^8 - s_0^8) \\ \frac{1}{9} \cdot (s_1^9 - s_0^9) \\ \frac{1}{10} \cdot (s_1^{10} - s_0^{10}) \\ \frac{1}{11} \cdot (s_1^{11} - s_0^{11}) \end{Bmatrix}$$

Eq. B-29 can be defined as algebraic functions as in Eq. B-30

$$Int' = Cvt(\alpha',\beta')^T \cdot s_{0\_1}(s_0, s_1) \qquad \text{Eq. B-30}$$

Where:

$Cvt(\alpha',\beta')$—Vector containing constant equations (must be evaluated many times per edge)

$S_{0\_1}(s_0, s_1)$—Generalized integration vector (must be evaluated once per edge)

$$Cvt(\alpha', \beta') := \begin{pmatrix} \alpha'_0 \cdot \beta'_0 \\ \alpha'_0 \cdot \beta'_1 + \alpha'_1 \cdot \beta'_0 \\ \alpha'_0 \cdot \beta'_2 + \alpha'_1 \cdot \beta'_1 + \alpha'_2 \cdot \beta'_0 \\ \alpha'_0 \cdot \beta'_3 + \alpha'_1 \cdot \beta'_2 + \alpha'_2 \cdot \beta'_1 + \alpha'_3 \cdot \beta'_0 \\ \alpha'_0 \cdot \beta'_4 + \alpha'_1 \cdot \beta'_3 + \alpha'_2 \cdot \beta'_2 + \alpha'_3 \cdot \beta'_1 + \alpha'_4 \cdot \beta'_0 \\ \alpha'_0 \cdot \beta'_5 + \alpha'_1 \cdot \beta'_4 + \alpha'_2 \cdot \beta'_3 + \alpha'_3 \cdot \beta'_2 + \alpha'_4 \cdot \beta'_1 + \alpha'_5 \cdot \beta'_0 \\ \alpha'_1 \cdot \beta'_5 + \alpha'_2 \cdot \beta'_4 + \alpha'_3 \cdot \beta'_3 + \alpha'_4 \cdot \beta'_2 + \alpha'_5 \cdot \beta'_1 \\ \alpha'_2 \cdot \beta'_5 + \alpha'_3 \cdot \beta'_4 + \alpha'_4 \cdot \beta'_3 + \alpha'_5 \cdot \beta'_2 \\ \alpha'_3 \cdot \beta'_5 + \alpha'_4 \cdot \beta'_4 + \alpha'_5 \cdot \beta'_3 \\ \alpha'_4 \cdot \beta'_5 + \alpha'_5 \cdot \beta'_4 \\ \alpha'_5 \cdot \beta'_5 \end{pmatrix}$$

-continued $$S_{0-1}(s_0, s_1) := \begin{bmatrix} s_1 - s_0 \\ \frac{1}{2} \cdot (s_1^2 - s_0^2) \\ \frac{1}{3} \cdot (s_1^3 - s_0^3) \\ \frac{1}{4} \cdot (s_1^4 - s_0^4) \\ \frac{1}{5} \cdot (s_1^5 - s_0^5) \\ \frac{1}{6} \cdot (s_1^6 - s_0^6) \\ \frac{1}{7} \cdot (s_1^7 - s_0^7) \\ \frac{1}{8} \cdot (s_1^8 - s_0^8) \\ \frac{1}{9} \cdot (s_1^9 - s_0^9) \\ \frac{1}{10} \cdot (s_1^{10} - s_0^{10}) \\ \frac{1}{11} \cdot (s_1^{11} - s_0^{11}) \end{bmatrix}$$

Referring back to Eq. B-27, the constants can occur from an external source or from the element being evaluated. Eqs. B-31 to B-36 establish these equations for the element being evaluated. They are developed by evaluating/rearranging Eqs. A-44 to A-46.

Eq. B-31

$$w_s = \begin{Bmatrix} w_{s0} \\ w_{s1} \\ w_{s2} \\ w_{s3} \\ w_{s4} \\ w_{s5} \end{Bmatrix} \cdot \begin{Bmatrix} 1 \\ s_x \\ s_x^2 \\ s_x^3 \\ s_x^4 \\ s_x^5 \end{Bmatrix} \quad \text{Where: } \begin{Bmatrix} w_{s0} \\ w_{s1} \\ w_{s2} \\ w_{s3} \\ w_{s4} \\ w_{s5} \end{Bmatrix} = C_{w\_a} \cdot a + C_{w\_p} \quad \text{Displacement equation in local coordinates} \quad C_{w\_p}(\theta_x, \theta_y, s_y, r', D, \nu, p_z) := \frac{p_z}{8 \cdot D}$$

$$C_{w\_a}(\theta_x, \theta_y, s_y, r', D, \nu, p_z) = \frac{1}{r'^4} \cdot [\text{matrix of terms}]$$

(Full matrix expansion of displacement coefficients with terms involving $r'$, $s_y$, $\theta_x$, $\theta_y$ powers as shown in the equation array.)

-continued $$\frac{\partial}{\partial s_y} w_s = \theta_s = \frac{1}{r'^4} \begin{Bmatrix} \theta_{s0} \\ \theta_{s1} \\ \theta_{s2} \\ \theta_{s3} \\ \theta_{s4} \end{Bmatrix}^T \cdot \begin{bmatrix} 0 & 0 & 0 & 4 \cdot s_y^3 \cdot \theta_x^2 \cdot \theta_y^2 \\ -r'^4 \cdot \theta_y & 0 & 0 & -6 \cdot s_y^2 \cdot \theta_x \cdot \theta_y \cdot (\theta_x^2 - \theta_y^2) \\ r'^4 \cdot \theta_x & 0 & 0 & 2 \cdot s_y \cdot (\theta_x^4 - 4 \cdot \theta_x^2 \theta_y^2 + \theta_y^4) \\ -2 \cdot r'^3 \cdot s_y \cdot \theta_x \cdot \theta_y^2 & r'^3 \cdot (\theta_x^2 - \theta_y^2) & 0 & 2 \cdot \theta_x \cdot \theta_y \cdot (\theta_x^2 - \theta_y^2) \\ 2 \cdot r'^3 \cdot s_y \cdot \theta_x^2 \cdot \theta_y & -2 \cdot r'^3 \cdot \theta_x \cdot \theta_y & 0 & 0 \\ 3 \cdot r'^3 \cdot s_y \cdot \theta_x \cdot \theta_y^2 & 2 \cdot r'^3 \cdot \theta_x \cdot \theta_y & 0 & \\ -3 \cdot r'^3 \cdot s_y \cdot \theta_x^2 \cdot \theta_y & r'^2 \cdot s_y^2 \cdot \theta_x \cdot (\theta_x^2 - 2 \cdot \theta_y^2) & 0 & \\ 3 \cdot r'^2 \cdot s_y \cdot \theta_y^3 & -r'^2 \cdot s_y^2 \cdot \theta_y \cdot (\theta_y^2 - 2 \cdot \theta_x^2) & 0 & \\ -4 \cdot r'^2 \cdot s_y^3 \cdot \theta_x \cdot \theta_y^3 & -3 \cdot r'^2 \cdot s_y^2 \cdot \theta_y \cdot \theta_x^2 & r'^2 \cdot \theta_y^2 \cdot (\theta_x^2 - 3 \cdot \theta_y^2) & \\ -4 \cdot r'^2 \cdot s_y^3 \cdot \theta_y^3 \cdot \theta_x & 3 \cdot r'^2 \cdot s_y^2 \cdot \theta_x \cdot \theta_y^2 & -r'^2 \cdot \theta_y^2 \cdot (\theta_y^2 - 3 \cdot \theta_x^2) & \\ 4 \cdot r' \cdot s_y^3 \cdot \theta_x^2 \cdot \theta_y^2 \cdot (\theta_x^2 - 3 \cdot \theta_y^2) & 6 \cdot r' \cdot s_y^2 \cdot \theta_x \cdot \theta_y \cdot (\theta_x^2 - \theta_y^2) & -6 \cdot r' \cdot s_y \cdot \theta_x \cdot \theta_y \cdot (\theta_x^2 - \theta_y^2) & \\ 4 \cdot r' \cdot s_y^3 \cdot \theta_y^2 \cdot (3 \cdot \theta_x^2 - \theta_y^2) & 6 \cdot r' \cdot s_y^2 \cdot \theta_x^2 \cdot (\theta_x^2 - 3 \cdot \theta_y^2) & 6 \cdot r' \cdot s_y \cdot \theta_x \cdot \theta_y \cdot (3 \cdot \theta_x^2 - \theta_y^2) & \\ -5 \cdot s_y^4 \cdot \theta_y \cdot \theta_x \cdot (2 \cdot \theta_x^4 - 7 \cdot \theta_x^2 \theta_y^2 + \theta_y^4) & 4 \cdot s_y^3 \cdot \theta_y \cdot (\theta_x^4 - 7 \cdot \theta_x^2 \theta_y^2 + 7 \cdot \theta_y^4) & 2 \cdot r' \cdot s_y \cdot \theta_x \cdot (\theta_x^4 - 12 \cdot \theta_x^2 \theta_y^2 + 5 \cdot \theta_y^4) & \\ -5 \cdot s_y^4 \cdot \theta_x^2 \cdot \theta_y \cdot (\theta_x^2 - 2 \cdot \theta_y^2) & 4 \cdot s_y^3 \cdot \theta_x \cdot (\theta_x^4 - 12 \cdot \theta_x^2 \theta_y^2 + 7 \cdot \theta_y^4) & -2 \cdot r' \cdot s_y \cdot \theta_y \cdot (3 \cdot \theta_x^4 - 12 \cdot \theta_x^2 \theta_y^2 + \theta_y^4) & \\ -5 \cdot s_y^4 \cdot \theta_y^3 \cdot (\theta_y^2 - 5 \cdot \theta_x^2) & -60 \cdot s_y^3 \cdot \theta_x \cdot \theta_y^2 \cdot (\theta_x^2 - \theta_y^2) & -10 \cdot s_y \cdot \theta_y \cdot (\theta_x^4 - 8 \cdot \theta_x^2 \theta_y^2 + 3 \cdot \theta_y^4) & \\ 5 \cdot s_y^4 \cdot \theta_x^3 \cdot (\theta_x^2 - 5 \cdot \theta_y^2) & 60 \cdot s_y^3 \cdot \theta_y \cdot \theta_x^2 \cdot (\theta_x^2 - \theta_y^2) & -10 \cdot s_y \cdot \theta_y \cdot (3 \cdot \theta_x^4 - 8 \cdot \theta_x^2 \theta_y^2 + \theta_y^4) & \end{bmatrix}$$

$C_{\theta\_a}(\theta_x, \theta_y, s_y, r', D, v) = C_{\theta\_a} \cdot a + C_{\theta\_p}$ Bending rotation equation in local coordinates $C_{\theta\_p}(\theta_x, \theta_y, s_y, r', D, v, p_z) := \frac{p_z}{8 \cdot D}$ Eq. B-32

$$\frac{\partial}{\partial s_x} w_s = \phi_s = \begin{Bmatrix} \phi_{s0} \\ \phi_{s1} \\ \phi_{s2} \\ \phi_{s3} \\ \phi_{s4} \\ \phi_{s5} \end{Bmatrix}^T \cdot \begin{bmatrix} 1 \\ s_x \\ s_x^2 \\ s_x^3 \\ s_x^4 \\ s_x^5 \end{bmatrix} = C_{\phi\_a} \cdot a + C_{\phi\_p} \quad \text{Torsional rotation equation in local coordinates} \quad C_{\phi\_p}(\theta_x, \theta_y, s_y, r', D, v, p_z) := \frac{p_z}{8 \cdot D} \cdot \begin{bmatrix} -2 \cdot s_y^3 \cdot \theta_x \cdot \theta_y \\ 2 \cdot s_y^2 \cdot (\theta_x^2 - 4 \cdot \theta_x^2 \theta_y^2 + \theta_y^4) \\ 6 \cdot s_y \cdot \theta_x \cdot \theta_y \cdot (\theta_x^2 - \theta_y^2) \\ 4 \cdot \theta_x^2 \cdot \theta_y^2 \\ 0 \end{bmatrix}$$

Eq. B-33

$$C_{\phi\_a}(\theta_x, \theta_y, s_y, r', D, v) = \frac{1}{r'^4} \cdot \begin{bmatrix} 0 & 0 & 0 & 0 \\ r'^4 \cdot \theta_y & 0 & 0 & 0 \\ r'^4 \cdot \theta_y & 0 & 0 & 0 \\ 2 \cdot r'^3 \cdot s_y \cdot \theta_x \cdot (\theta_x^2 - \theta_y^2) & 2 \cdot r'^3 \cdot \theta_x \cdot \theta_y & 0 & 0 \\ -2 \cdot r'^3 \cdot s_y \cdot \theta_x \cdot \theta_y & 2 \cdot r'^3 \cdot \theta_y^2 & 0 & 0 \\ 2 \cdot r'^3 \cdot s_y \cdot \theta_x \cdot \theta_y & 2 \cdot r'^3 \cdot \theta_y^2 & 0 & 0 \\ r'^2 \cdot s_y^2 \cdot \theta_y \cdot (\theta_y^2 - 2 \cdot \theta_x^2) & 2 \cdot r'^2 \cdot s_y^2 \cdot \theta_x \cdot \theta_y & 0 & 0 \\ r'^2 \cdot s_y^2 \cdot \theta_x \cdot (\theta_x^2 - 2 \cdot \theta_y^2) & -2 \cdot r'^2 \cdot s_y^2 \cdot \theta_y \cdot \theta_x^2 & 0 & 0 \\ 3 \cdot r'^2 \cdot s_y^2 \cdot \theta_x^2 \cdot \theta_y & -6 \cdot r'^2 \cdot s_y \cdot \theta_x \cdot \theta_y^2 & 3 \cdot r'^2 \cdot \theta_x^2 \cdot \theta_y & 0 \\ 3 \cdot r'^2 \cdot s_y^2 \cdot \theta_x \cdot \theta_y^2 & 6 \cdot r'^2 \cdot s_y \cdot \theta_x \cdot \theta_y^2 & 3 \cdot r'^2 \cdot \theta_x \cdot \theta_y^2 & 0 \\ -r' \cdot s_y^3 \cdot \theta_x^2 \cdot (\theta_x^2 - 3 \cdot \theta_y^2) & -6 \cdot r' \cdot s_y^2 \cdot \theta_x \cdot \theta_y \cdot (\theta_x^2 - 3 \cdot \theta_y^2) & 3 \cdot r' \cdot s_y \cdot \theta_x^2 \cdot \theta_y^2 & 4 \cdot r' \cdot \theta_x^3 \cdot \theta_y \\ r' \cdot s_y^3 \cdot \theta_y^2 \cdot (\theta_y^2 - 3 \cdot \theta_x^2) & 6 \cdot r' \cdot s_y^2 \cdot \theta_x \cdot \theta_y \cdot (3 \cdot \theta_y^2 - 5 \cdot \theta_x^2) & -3 \cdot r' \cdot s_y^2 \cdot \theta_y^2 \cdot (\theta_y^2 - 3 \cdot \theta_x^2) & 4 \cdot r' \cdot \theta_x \cdot \theta_y^3 \\ 2 \cdot r' \cdot s_y^3 \cdot \theta_x \cdot \theta_y \cdot (\theta_x^2 - 7 \cdot \theta_y^2) & -6 \cdot r' \cdot s_y^2 \cdot \theta_x \cdot (\theta_x^4 + 6 \cdot \theta_x^2 \cdot \theta_y^2 - 5 \cdot \theta_y^4) & 6 \cdot r' \cdot s_y \cdot \theta_x \cdot \theta_y \cdot (3 \cdot \theta_x^2 - 5 \cdot \theta_y^2) & 4 \cdot r' \cdot \theta_x \cdot (\theta_x^4 - 7 \cdot \theta_x^2 \cdot \theta_y^2 + 2 \cdot \theta_y^4) \\ -2 \cdot r' \cdot s_y^3 \cdot \theta_x \cdot \theta_y \cdot (\theta_x^2 - 7 \cdot \theta_y^2) & -6 \cdot r' \cdot s_y^2 \cdot \theta_x \cdot (\theta_x^4 - 6 \cdot \theta_x^2 \cdot \theta_y^2 + \theta_y^4) & -6 \cdot r' \cdot s_y \cdot \theta_x \cdot \theta_y \cdot (3 \cdot \theta_x^2 - 5 \cdot \theta_y^2) & 4 \cdot r' \cdot \theta_y \cdot (\theta_y^4 - 7 \cdot \theta_x^2 \cdot \theta_y^2 + 2 \cdot \theta_x^4) \\ s_y^4 \cdot \theta_y \cdot \theta_x \cdot (2 \cdot \theta_x^4 - 7 \cdot \theta_x^2 \cdot \theta_y^2 + 2 \cdot \theta_y^4) & -3 \cdot s_y^3 \cdot \theta_x \cdot (7 \cdot \theta_x^4 - 12 \cdot \theta_x^2 \cdot \theta_y^2 + \theta_y^4) & -2 \cdot s_y^3 \cdot \theta_x \cdot (\theta_x^4 - 12 \cdot \theta_x^2 \cdot \theta_y^2 + 7 \cdot \theta_y^4) & 4 \cdot s_y \cdot \theta_x \cdot \theta_y \cdot (2 \cdot \theta_x^4 - 7 \cdot \theta_x^2 \cdot \theta_y^2 + 2 \cdot \theta_y^4) & 5 \cdot \theta_x^2 \cdot \theta_y \cdot \theta_x^4 - 5 \cdot \theta_x^3 \cdot \theta_y^2 \\ s_y^4 \cdot \theta_x \cdot \theta_y \cdot (2 \cdot \theta_x^4 - 7 \cdot \theta_x^2 \cdot \theta_y^2 + 2 \cdot \theta_y^4) & -3 \cdot s_y^3 \cdot \theta_y \cdot (\theta_y^4 - 12 \cdot \theta_x^2 \cdot \theta_y^2 + 7 \cdot \theta_x^4) & 2 \cdot s_y^3 \cdot \theta_y \cdot (\theta_y^4 - 12 \cdot \theta_x^2 \cdot \theta_y^2 + 7 \cdot \theta_x^4) & -4 \cdot s_y \cdot \theta_x \cdot \theta_y \cdot (2 \cdot \theta_x^4 - 7 \cdot \theta_x^2 \cdot \theta_y^2 + 2 \cdot \theta_y^4) & 5 \cdot \theta_x \cdot \theta_y^4 - 5 \cdot \theta_x^3 \cdot \theta_y^2 \\ -15 \cdot s_y^4 \cdot \theta_x \cdot \theta_y^2 \cdot (\theta_x^2 - 3 \cdot \theta_y^2) & 10 \cdot s_y^3 \cdot \theta_x^2 \cdot \theta_y \cdot (\theta_x^2 - 3 \cdot \theta_y^2) & -15 \cdot s_y^2 \cdot \theta_x \cdot \theta_y^2 \cdot (\theta_x^2 - 3 \cdot \theta_y^2) & -60 \cdot s_y \cdot \theta_x^2 \cdot \theta_y \cdot \theta_x^2 \cdot \theta_y^2 & 5 \cdot \theta_x^3 \cdot \theta_y^2 - 5 \cdot \theta_y^4 \\ 15 \cdot s_y^4 \cdot \theta_y \cdot \theta_x^2 \cdot (\theta_x^2 - 3 \cdot \theta_y^2) & -10 \cdot s_y^3 \cdot \theta_x \cdot (\theta_x^4 + 8 \cdot \theta_x^2 \cdot \theta_y^2 + 3 \cdot \theta_y^4) & -15 \cdot s_y^2 \cdot \theta_x \cdot \theta_y \cdot (3 \cdot \theta_x^4 + 8 \cdot \theta_x^2 \cdot \theta_y^2 + 3 \cdot \theta_y^4) & -60 \cdot s_y \cdot \theta_x \cdot \theta_y^2 \cdot \theta_x^2 \cdot \theta_y & 5 \cdot \theta_y^3 \cdot \theta_x^2 - 5 \cdot \theta_y^2 \end{bmatrix}^T$$

$$-D \cdot \left[ \frac{\partial}{\partial s_y} \left( \frac{d^2}{ds_y^2} w_s + \frac{d^2}{ds_x^2} w_s \right) \right] = P_s = \begin{bmatrix} P_{s0} \\ P_{s1} \\ P_{s2} \end{bmatrix}^T \cdot \begin{bmatrix} 1 \\ s_x \\ s_x^2 \end{bmatrix} \quad \text{Shear load equation in local coordinates} \quad \text{Where:} \begin{bmatrix} P_{s0} \\ P_{s1} \\ P_{s2} \end{bmatrix} = C_{P\_a} \cdot a + C_{P\_p} \quad C_{P\_p}(\theta_x, \theta_y, s_y, r', D, v, p_z) := \frac{p_z}{8 \cdot D} \cdot \begin{bmatrix} -4 \cdot D \cdot s_y \cdot (\theta_x^2 + \theta_y^2)^2 \\ 0 \\ 0 \end{bmatrix}$$

Eq. B-34

$C_{P\_d}(\theta_x, \theta_y, s_y, r', D, v) =$ $$\frac{D}{r'^4} \cdot \begin{bmatrix} 0 & 0 & 0 \\ 0 & 0 & 0 \\ 0 & 0 & 0 \\ 0 & 0 & 0 \\ 0 & 0 & 0 \\ -2 \cdot r'^2 \cdot \theta_x \cdot (\theta_x^2 + \theta_y^2) & 0 & 0 \\ 2 \cdot r'^2 \cdot \theta_y \cdot (\theta_x^2 + \theta_y^2) & 0 & 0 \\ 6 \cdot r'^2 \cdot \theta_y \cdot (\theta_x^2 + \theta_y^2) & 0 & 0 \\ -6 \cdot r'^2 \cdot \theta_x \cdot (\theta_x^2 + \theta_y^2) & 0 & 0 \\ 12 \cdot r' \cdot s_y \cdot \theta_x \cdot (\theta_x^2 + \theta_y^2) & 0 & 0 \\ 12 \cdot r' \cdot s_y \cdot \theta_y \cdot (\theta_x^2 + \theta_y^2) & 0 & 0 \\ 6 \cdot s_y^2 \cdot (\theta_x^4 + \theta_y^4) & -6 \cdot r' \cdot (\theta_x^4 - \theta_y^4) & 0 \\ -12 \cdot r' \cdot s_y \cdot (\theta_x^4 + \theta_y^4) & -6 \cdot r' \cdot (\theta_x^4 - \theta_y^4) & 0 \\ 6 \cdot s_y^2 \cdot \theta_x \cdot (\theta_y^2 - 3 \cdot \theta_x^2) \cdot (\theta_x^2 + \theta_y^2) & 24 \cdot r' \cdot s_y \cdot \theta_x \cdot \theta_y \cdot (\theta_x^2 + \theta_y^2) & 0 \\ -6 \cdot s_y^2 \cdot \theta_y \cdot (\theta_y^2 - 3 \cdot \theta_x^2) \cdot (\theta_x^2 + \theta_y^2) & -24 \cdot r' \cdot s_y \cdot \theta_x \cdot \theta_y \cdot (\theta_x^2 + \theta_y^2) & 0 \\ 30 \cdot s_y^2 \cdot \theta_y \cdot (\theta_y^2 - 3 \cdot \theta_x^2) \cdot (\theta_x^2 + \theta_y^2) & -12 \cdot s_y \cdot \theta_y \cdot (\theta_y^2 - 3 \cdot \theta_x^2) \cdot (\theta_x^2 + \theta_y^2) & -6 \cdot \theta_x \cdot (\theta_x^2 - 3 \cdot \theta_y^2) \cdot (\theta_x^2 + \theta_y^2) \\ -30 \cdot s_y^2 \cdot \theta_x \cdot (\theta_y^2 - 3 \cdot \theta_x^2) \cdot (\theta_x^2 + \theta_y^2) & -12 \cdot s_y \cdot \theta_x \cdot (\theta_y^2 - 3 \cdot \theta_x^2) \cdot (\theta_x^2 + \theta_y^2) & 6 \cdot \theta_y \cdot (\theta_y^2 - 3 \cdot \theta_x^2) \cdot (\theta_x^2 + \theta_y^2) \\ & 60 \cdot s_y \cdot \theta_y \cdot (\theta_x^2 - 3 \cdot \theta_y^2) \cdot (\theta_x^2 + \theta_y^2) & -30 \cdot \theta_y \cdot (\theta_x^2 - 3 \cdot \theta_y^2) \cdot (\theta_x^2 + \theta_y^2) \\ & 60 \cdot s_y \cdot \theta_x \cdot (\theta_y^2 - 3 \cdot \theta_x^2) \cdot (\theta_x^2 + \theta_y^2) & 30 \cdot \theta_x \cdot (\theta_y^2 - 3 \cdot \theta_x^2) \cdot (\theta_x^2 + \theta_y^2) \end{bmatrix}$$

Bending moment equation in local coordinates $$-D \cdot \left\{ \frac{d^2}{ds_y^2} w_s + v \cdot \frac{d^2}{ds_x^2} w_s \right\} = M_s = \begin{Bmatrix} M_{s0} \\ M_{s1} \\ M_{s2} \\ M_{s3} \end{Bmatrix}^T \cdot \begin{Bmatrix} 1 \\ s_x \\ s_x^2 \\ s_x^3 \end{Bmatrix} \quad \text{Where:} \quad \begin{Bmatrix} M_{s0} \\ M_{s1} \\ M_{s2} \\ M_{s3} \end{Bmatrix} = C_{M\_a} \cdot a + C_{M\_p} \quad C_{M\_p}(\theta_x, \theta_y, s_y, r', D, v, p_z) := \frac{p_z}{8 \cdot D} \cdot \begin{bmatrix} -2 \cdot D \cdot s_y^2 \cdot (v \cdot \theta_x^4 + v \cdot \theta_y^4 + 6 \cdot \theta_x \cdot \theta_y^4 + v \cdot \theta_x^2 \theta_y^2)^2 \\ -12 \cdot D \cdot s_y \cdot \theta_x \cdot \theta_y \cdot (\theta_x^2 \theta_y^2) \cdot (v-1) \\ -2 \cdot D \cdot (\theta_x^4 + \theta_y^4 - 4 \cdot \theta_x^2 \theta_y^2 + 6 \cdot v \cdot \theta_x^2 \theta_y^2) \\ 0 \end{bmatrix}$$

Eq. B-35

-continued $$C_{M\_a}(\theta_x, \theta_y, s_y, r', D, v) = \frac{D}{r'^4} \cdot$$

$$\begin{bmatrix}
0 & 0 \\
0 & 0 \\
0 & 0 \\
-2 \cdot r'^3 \cdot \theta_x \cdot \theta_y \cdot (v-1) & 0 \\
-2 \cdot r'^3 \cdot (v \cdot \theta_x^2 + \theta_y^2) & 0 \\
-2 \cdot r'^3 \cdot (\theta_x^2 + v \cdot \theta_y^2) & 0 \\
-2 \cdot r'^2 \cdot s_y \cdot \theta_x \cdot (v \cdot \theta_x^2 + 2 \cdot v \cdot \theta_y^2 + 3 \cdot \theta_y^2) & -2 \cdot r'^2 \cdot \theta_y \cdot (3 \cdot v \cdot \theta_x^2 + 2 \cdot \theta_x^2 + \theta_y^2) \\
2 \cdot r'^2 \cdot s_y \cdot \theta_y \cdot (v \cdot \theta_y^2 + 2 \cdot v \cdot \theta_x^2 + 3 \cdot \theta_x^2) & -2 \cdot r'^2 \cdot \theta_x \cdot (3 \cdot v \cdot \theta_y^2 + 2 \cdot \theta_x^2 + \theta_y^2) \\
6 \cdot r'^2 \cdot s_y \cdot \theta_y \cdot (v \cdot \theta_x^2 + \theta_y^2) & -6 \cdot r'^2 \cdot \theta_x \cdot (v \cdot \theta_x^2 + \theta_y^2) \\
-6 \cdot r'^2 \cdot s_y \cdot \theta_x \cdot (\theta_x^2 + v \cdot \theta_y^2) & -6 \cdot r'^2 \cdot \theta_y \cdot (\theta_x^2 + v \cdot \theta_y^2) \\
6 \cdot r' \cdot s_y^2 \cdot \theta_y \cdot (v \cdot \theta_x^2 + v \cdot \theta_y^2 + 2 \cdot \theta_y^2) & -6 \cdot r' \cdot s_y \cdot (v \cdot \theta_x^4 + 3 \cdot \theta_x^2 \cdot \theta_y^2 + 3 \cdot v \cdot \theta_x^2 \cdot \theta_y^2)^2 \\
6 \cdot r' \cdot s_y^2 \cdot \theta_x \cdot (v \cdot \theta_y^2 + v \cdot \theta_x^2 + 2 \cdot \theta_x^2) & 6 \cdot r' \cdot s_y \cdot (v \cdot \theta_y^4 + 3 \cdot v \cdot \theta_x^2 \cdot \theta_y^2 + 3 \cdot v \cdot \theta_x^2 \cdot \theta_y^2)^2 \\
6 \cdot r' \cdot s_y^2 \cdot (v \cdot \theta_x^4 + v \cdot \theta_y^4 + 2 \cdot \theta_x^4 + 6 \cdot \theta_x^2 \cdot \theta_y^2 + 6 \cdot v \cdot \theta_x^2 \cdot \theta_y^2)^2 & -12 \cdot r' \cdot s_y \cdot \theta_x \cdot \theta_y \cdot (3 \cdot v \cdot \theta_x^2 + 5 \cdot v \cdot \theta_y^2 + 5 \cdot \theta_x^2 + 3 \cdot \theta_y^2)^2 \\
6 \cdot r' \cdot s_y^2 \cdot (v \cdot \theta_x^4 + v \cdot \theta_y^4 + 2 \cdot \theta_y^4 + 6 \cdot \theta_x^2 \cdot \theta_y^2 + 6 \cdot v \cdot \theta_x^2 \cdot \theta_y^2)^2 & 12 \cdot r' \cdot s_y \cdot \theta_x \cdot \theta_y \cdot (3 \cdot v \cdot \theta_y^2 + 5 \cdot v \cdot \theta_x^2 + 5 \cdot \theta_y^2 + 3 \cdot \theta_x^2)^2 \\
2 \cdot s_y^3 \cdot \theta_x \cdot (v \cdot \theta_x^4 + 7 \cdot v \cdot \theta_y^4 + 10 \cdot \theta_y^4 + 2 \cdot v \cdot \theta_x^2 \cdot \theta_y^2 + 12 \cdot v \cdot \theta_x^2 \cdot \theta_y^2)^2 & 6 \cdot s_y^2 \cdot \theta_y \cdot (7 \cdot v \cdot \theta_x^4 + v \cdot \theta_y^4 + 4 \cdot \theta_x^4 + 2 \cdot v \cdot \theta_x^2 \cdot \theta_y^2 + 14 \cdot \theta_x^2 \cdot \theta_y^2 + 12 \cdot v \cdot \theta_x^2 \cdot \theta_y^2)^2 \\
-2 \cdot s_y^3 \cdot \theta_y \cdot (7 \cdot v \cdot \theta_x^4 + v \cdot \theta_y^4 + 10 \cdot \theta_x^4 + 2 \cdot v \cdot \theta_x^2 \cdot \theta_y^2 + 12 \cdot v \cdot \theta_x^2 \cdot \theta_y^2)^2 & 6 \cdot s_y^2 \cdot \theta_x \cdot (v \cdot \theta_x^4 + 7 \cdot v \cdot \theta_y^4 + 4 \cdot \theta_y^4 + 2 \cdot v \cdot \theta_x^2 \cdot \theta_y^2 + 14 \cdot \theta_x^2 \cdot \theta_y^2 + 12 \cdot v \cdot \theta_x^2 \cdot \theta_y^2)^2 \\
-10 \cdot s_y^3 \cdot \theta_y \cdot (3 \cdot v \cdot \theta_x^4 + v \cdot \theta_y^4 + 2 \cdot \theta_x^4 + 10 \cdot \theta_x^2 \cdot \theta_y^2 + 6 \cdot v \cdot \theta_x^2 \cdot \theta_y^2)^2 & 30 \cdot s_y^2 \cdot \theta_x \cdot (v \cdot \theta_x^4 + 3 \cdot v \cdot \theta_y^4 + 6 \cdot \theta_y^4 + 6 \cdot v \cdot \theta_x^2 \cdot \theta_y^2 + 8 \cdot v \cdot \theta_x^2 \cdot \theta_y^2)^2 \\
10 \cdot s_y^3 \cdot \theta_x \cdot (v \cdot \theta_x^4 + 3 \cdot v \cdot \theta_y^4 + 2 \cdot \theta_y^4 + 10 \cdot \theta_x^2 \cdot \theta_y^2 + 6 \cdot v \cdot \theta_x^2 \cdot \theta_y^2)^2 & 30 \cdot s_y^2 \cdot \theta_y \cdot (3 \cdot v \cdot \theta_x^4 + v \cdot \theta_y^4 + 6 \cdot \theta_x^4 + 6 \cdot v \cdot \theta_x^2 \cdot \theta_y^2 + 8 \cdot v \cdot \theta_x^2 \cdot \theta_y^2)^2 \\
\end{bmatrix}$$

-continued $$\begin{Bmatrix} 0 \\ 0 \\ 0 \\ 0 \\ 0 \\ 0 \\ 0 \\ 0 \\ -6 \cdot r' \cdot \theta_x \cdot \theta_y \cdot (2 - v \cdot \theta_x^2 \theta_y^2) \\ -6 \cdot r' \cdot \theta_x \cdot \theta_y \cdot (2 - v \cdot \theta_y^2 + \theta_x^2 \theta_y^2) \\ 6 \cdot r' \cdot (\theta_x^4 - 2 \cdot v \cdot \theta_x^4 + \theta_y^4 + 6 \cdot \theta_x^2 \theta_y^2 + 6 \cdot v \cdot \theta_x^2 \theta_y^2) \\ 6 \cdot r' \cdot (\theta_x^4 - 2 \cdot v \cdot \theta_y^4 + \theta_y^4 + 6 \cdot \theta_x^2 \theta_y^2 + 6 \cdot v \cdot \theta_x^2 \theta_y^2) \\ 6 \cdot s_y \cdot \theta_x \cdot (\theta_x^4 - 4 \cdot v \cdot \theta_x^4 + \theta_y^4 + 7 \cdot \theta_y^4 + 12 \cdot \theta_x^2 \theta_y^2 + 14 \cdot v \cdot \theta_x^2 \theta_y^2) \\ -6 \cdot s_y \cdot \theta_y \cdot (7 \cdot \theta_x^4 - 2 \cdot v \cdot \theta_x^4 + \theta_y^4 + 4 \cdot v \cdot \theta_y^4 + 12 \cdot \theta_x^2 \theta_y^2 + 14 \cdot v \cdot \theta_x^2 \theta_y^2) \\ -30 \cdot s_y \cdot \theta_y \cdot (3 \cdot \theta_x^4 - 6 \cdot v \cdot \theta_x^4 + \theta_y^4 + 8 \cdot \theta_x^2 \theta_y^2 + 6 \cdot v \cdot \theta_x^2 \theta_y^2) \\ 30 \cdot s_y \cdot \theta_x \cdot (\theta_x^4 - 6 \cdot v \cdot \theta_x^4 + 3 \cdot \theta_y^4 + 8 \cdot \theta_x^2 \theta_y^2 + 6 \cdot v \cdot \theta_x^2 \theta_y^2) \\ 0 \\ 0 \\ 0 \\ 0 \\ 0 \\ 0 \\ 0 \\ 0 \\ 2 \cdot \theta_y \cdot (7 \cdot \theta_x^4 - 10 \cdot v \cdot \theta_x^4 + \theta_y^4 + 12 \cdot \theta_x^2 \theta_y^2 + 10 \cdot v \cdot \theta_x^2 \theta_y^2) \\ 2 \cdot \theta_x \cdot (\theta_x^4 - 10 \cdot v \cdot \theta_x^4 + 7 \cdot \theta_y^4 + 12 \cdot \theta_x^2 \theta_y^2 + 10 \cdot v \cdot \theta_x^2 \theta_y^2) \\ 30 \cdot \theta_x \cdot \theta_y^4 - 20 \cdot v \cdot \theta_x \cdot \theta_y^5 + 10 \cdot \theta_x^5 - 80 \cdot \theta_x^3 \theta_y^2 + 100 \cdot v \cdot \theta_x^3 \theta_y^2 \\ 30 \cdot \theta_x^4 \cdot \theta_y - 20 \cdot v \cdot \theta_x^5 \theta_y + 10 \cdot \theta_y^5 - 80 \cdot \theta_x^2 \theta_y^3 + 100 \cdot v \cdot \theta_x^2 \theta_y^3 \end{Bmatrix}^T$$

Eq. B-36

$$-D \cdot (1-v) \cdot \frac{\partial}{\partial s_x} \frac{\partial}{\partial s_y} w_s = T_s = \begin{Bmatrix} T_{s0} \\ T_{s1} \\ T_{s2} \\ T_{s3} \end{Bmatrix}^T \cdot \begin{Bmatrix} 1 \\ s_x \\ s_x^2 \\ s_x^3 \end{Bmatrix}$$ Torsional moment equation in local coordinates Where: $\begin{Bmatrix} T_{s0} \\ T_{s1} \\ T_{s2} \\ T_{s3} \end{Bmatrix} = C_{T\_a} \cdot a + C_{T\_p}$ $$C_{T\_p}(\theta_x, \theta_y, s_y, r', D, v, p_z) := \frac{p_z}{8 \cdot D} \cdot \begin{bmatrix} -6 \cdot D \cdot s_y^2 \cdot \theta_x \cdot \theta_y \cdot (\theta_x^2 \theta_y^2) \cdot (v-1) \\ 4 \cdot D \cdot s_y \cdot (v-1) \cdot (\theta_x^4 - 4 \cdot \theta_x^2 \theta_y^2 + \theta_y^4) \\ 6 \cdot D \cdot \theta_x \cdot \theta_y \cdot (\theta_x^2 - \theta_y^2) \cdot (v-1) \\ 0 \end{bmatrix}$$

$$C_{T\_d}(\theta_x, \theta_y, s_y, r', D, v) = \frac{D \cdot (v-1)}{r'^4} \cdot$$

$$\begin{bmatrix}
0 & 0 & 0 \\
0 & 0 & 0 \\
0 & 0 & 0 \\
r'^3 \cdot (\theta_x^2 - \theta_y^2) & 0 & 0 \\
-2 \cdot r'^3 \cdot \theta_x \cdot \theta_y & 0 & 0 \\
2 \cdot r'^3 \cdot \theta_x \cdot \theta_y & 0 & 0 \\
2 \cdot r'^2 \cdot s_y \cdot \theta_y \cdot (\theta_y^2 - 2 \cdot \theta_x^2) & 2 \cdot r'^2 \cdot \theta_x \cdot (\theta_x^2 - 2 \cdot \theta_y^2) & 0 \\
2 \cdot r'^2 \cdot s_y \cdot \theta_x \cdot (\theta_x^2 - 2 \cdot \theta_y^2) & -2 \cdot r'^2 \cdot \theta_y \cdot (\theta_y^2 - 2 \cdot \theta_x^2) & 0 \\
6 \cdot r'^2 \cdot s_y \cdot \theta_x \cdot \theta_y^2 & -6 \cdot r'^2 \cdot \theta_x^2 \cdot \theta_y & 0 \\
6 \cdot r'^2 \cdot s_y \cdot \theta_x^2 \cdot \theta_y & 6 \cdot r'^2 \cdot \theta_x \cdot \theta_y^2 & 0 \\
-3 \cdot r' \cdot s_y^2 \cdot \theta_y^2 \cdot (\theta_y^2 - 3 \cdot \theta_x^2) & -12 \cdot r' \cdot s_y \cdot \theta_x \cdot \theta_y \cdot (\theta_x^2 \theta_y^2) & 3 \cdot r' \cdot \theta_x^2 \cdot (\theta_x^2 - 3 \cdot \theta_y^2) \\
3 \cdot r' \cdot s_y^2 \cdot \theta_x^2 \cdot (\theta_x^2 - 3 \cdot \theta_y^2) & 12 \cdot r' \cdot s_y \cdot \theta_x \cdot \theta_y \cdot (\theta_x^2 \theta_y^2) & -3 \cdot r' \cdot \theta_y^2 \cdot (\theta_y^2 - 3 \cdot \theta_x^2) \\
6 \cdot r' \cdot s_y^2 \cdot \theta_x \cdot \theta_y \cdot (3 \cdot \theta_x^2 - 5 \cdot \theta_y^2) & -12 \cdot r' \cdot s_y \cdot (\theta_x^4 - 6 \cdot \theta_x^2 \theta_y^2 + \theta_y^4) & 6 \cdot r' \cdot \theta_x \cdot \theta_y \cdot (3 \cdot \theta_y^2 - 5 \cdot \theta_x^2) \\
-6 \cdot r' \cdot s_y^2 \cdot \theta_x \cdot \theta_y \cdot (3 \cdot \theta_y^2 - 5 \cdot \theta_x^2) & -12 \cdot r' \cdot s_y \cdot (\theta_x^4 - 6 \cdot \theta_x^2 \theta_y^2 + \theta_y^4) & -6 \cdot r' \cdot \theta_x \cdot \theta_y \cdot (3 \cdot \theta_x^2 - 5 \cdot \theta_y^2) \\
4 \cdot s_y^3 \cdot \theta_y \cdot (2 \cdot \theta_x^4 - 7 \cdot \theta_x^2 \theta_y^2 + \theta_y^4) & -6 \cdot s_y^2 \cdot \theta_x \cdot (\theta_x^4 - 12 \cdot \theta_x^2 \theta_y^2 + 7 \cdot \theta_y^4) & -6 \cdot s_y \cdot \theta_y \cdot (7 \cdot \theta_x^4 - 12 \cdot \theta_x^2 \theta_y^2 + \theta_y^4) \\
4 \cdot s_y^3 \cdot \theta_x \cdot (\theta_x^4 - 7 \cdot \theta_x^2 \theta_y^2 + 2 \cdot \theta_y^4) & 6 \cdot s_y^2 \cdot \theta_y \cdot (7 \cdot \theta_x^4 - 12 \cdot \theta_x^2 \theta_y^2 + \theta_y^4) & -6 \cdot s_y \cdot \theta_x \cdot (\theta_x^4 - 12 \cdot \theta_x^2 \theta_y^2 + 7 \cdot \theta_y^4) \\
-60 \cdot s_y^3 \cdot \theta_x \cdot \theta_y^2 \cdot (\theta_x^2 \theta_y^2) & 30 \cdot s_y^2 \cdot \theta_y \cdot (3 \cdot \theta_x^4 - 8 \cdot \theta_x^2 \theta_y^2 + \theta_y^4) & -30 \cdot s_y \cdot \theta_x \cdot (\theta_x^4 - 8 \cdot \theta_x^2 \theta_y^2 + 3 \cdot \theta_y^4) \\
60 \cdot s_y^3 \cdot \theta_x^2 \cdot \theta_y \cdot (\theta_x^2 \theta_y^2) & -30 \cdot s_y^2 \cdot \theta_x \cdot (\theta_x^4 - 8 \cdot \theta_x^2 \theta_y^2 + 3 \cdot \theta_y^4) & -30 \cdot s_y \cdot \theta_y \cdot (3 \cdot \theta_x^4 - 8 \cdot \theta_x^2 \theta_y^2 + \theta_y^4)
\end{bmatrix}^T$$

(with additional column entries: $\ldots, 4 \cdot \theta_x^5 - 28 \cdot \theta_x^3 \cdot \theta_y^2 + 8 \cdot \theta_x \cdot \theta_y^4$, $28 \cdot \theta_x^2 \cdot \theta_y^3 - 8 \cdot \theta_x^4 \cdot \theta_y - 4 \cdot \theta_y^5$, $60 \cdot \theta_x^2 \cdot \theta_y^3 - 60 \cdot \theta_x^4 \cdot \theta_y$, $60 \cdot \theta_x \cdot \theta_y^4 - 60 \cdot \theta_x^3 \cdot \theta_y^2$)

At this point, most of the derivation needed for the edge energy has been completed. Similar to the formulation of the area integrals, the formulation from here forward uses a strategy to aid in simplicity of discussion rather than trying to be most efficient. (This strategy generates sparse arrays and coding it into an actual finite element solver could be done much more efficiently by reducing the calculation down to where adding or multiplying by zero does not occur.)

Recalling Eq. B-26, further derivation can be done to make use of Eqs. B-31 to B-36. Detailed derivation is performed on Eq. B-26(a) as an example. The other equations in Eq. B-26 follow the same derivation pattern. In Eq. B-26(a), the edge energy is calculated considering an edge load (from a boundary condition or neighboring element) acting on the edge displacement of the element. Consequently, the edge displacement is defined by Eq. B-31. Introducing Eq. B-31 into Eq. B-26(a) allows the following derivation to produce Eq. B-37.

$$\int_{s_0}^{s_1} P_s \cdot \frac{d}{da_i} w_s(a) ds_x = \qquad \text{Eq. B-37}$$

$$\int_{s_0}^{s_1} \left[ \begin{pmatrix} P_{s0} \\ P_{s1} \\ P_{s2} \end{pmatrix}^T \cdot \begin{pmatrix} 1 \\ s_x \\ s_x^2 \end{pmatrix} \right] \cdot \frac{d}{da_i} \begin{pmatrix} w_{s0} \\ w_{s1} \\ w_{s2} \\ w_{s3} \\ w_{s4} \\ w_{s5} \end{pmatrix}^T \begin{pmatrix} 1 \\ s_x \\ s_x^2 \\ s_x^3 \\ s_x^4 \\ s_x^5 \end{pmatrix} ds_x$$

$$\int_{s_0}^{s_1} P_s \cdot \frac{d}{da_i} w_s(a) ds_x =$$

$$\int_{s_0}^{s_1} \left[ \begin{pmatrix} P_{s0} \\ P_{s1} \\ P_{s2} \end{pmatrix}^T \cdot \begin{pmatrix} 1 \\ s_x \\ s_x^2 \end{pmatrix} \right] \cdot \frac{d}{da_i} (C_{w\_a} \cdot a + C_{w\_p})^T \cdot \begin{pmatrix} 1 \\ s_x \\ s_x^2 \\ s_x^3 \\ s_x^4 \\ s_x^5 \end{pmatrix} ds_x$$

$$\int_{s_0}^{s_1} P_s \cdot \frac{d}{da_i} w_s(a) ds_x = \int_{s_0}^{s_1} \left[ \begin{pmatrix} P_{s0} \\ P_{s1} \\ P_{s2} \end{pmatrix}^T \cdot \begin{pmatrix} 1 \\ s_x \\ s_x^2 \end{pmatrix} \right] \cdot C_{w\_a}^{(i)T} \cdot \begin{pmatrix} 1 \\ s_x \\ s_x^2 \\ s_x^3 \\ s_x^4 \\ s_x^5 \end{pmatrix} ds_x$$

Where the bracketed "i" implies the ith column of the array and the superscript "T" implies the transpose.

Su. B-3 assembles a vector based on Eq. B-30 to put equations like Eq. B-37 into an algebraic form. This subroutine can be used for all of the equations in Eq. B-26.

$$Int_v(A_\alpha, V_\beta, s_{01}) := \begin{vmatrix} no \leftarrow 5 \\ A_{\alpha no,0} \leftarrow 0 \text{ if rows } (A_\alpha) - 1 < no \\ V_{\beta no,0} \leftarrow 0 \text{ if rows } (V_\beta) - 1 < no \\ out_{cols(A_\alpha)-1, cols(V_\beta)-1} \leftarrow 0 \\ \text{for } j \in 0 \ldots cols(V_\beta) - 1 \\ \quad \text{for } i \in 0 \ldots cols(A_\alpha) - 1 \\ \quad \quad out_{i,j} \leftarrow Cvt(A_\alpha^{(i)}, V_\beta^{(j)})^T \cdot s_{01} \\ out \end{vmatrix} \quad \text{Su. B-3}$$

Where:

$A_\alpha$—The element based array ("$C_{w\_a}$" for Eq. B-37)

$V_\beta$—The element based vector/array ("($P_{s0}$ $P_{s1}$ $P_{s2}$)" for Eq. B-37)

$s_{01}$—The vector results of $S_{0\_1}(s_0, s_1)$ in Eq. B-30

For simplicity in later subroutine definitions, it is desirable to pull the load constants out of Eq. B-37 as shown in Eq. B-38(a). Eq. B-38 shows the desirable definitions for all the equations in Eq. B-26. This is not a required step but is necessary for this description of the problem solution.

$$\int_{s_0}^{s_1} P_s \cdot \frac{d}{da_i} w_s(a) ds_x = C_P^T \cdot (P_{s0} \quad P_{s1} \quad P_{s2})^T \qquad \text{Eq. B-38(a)}$$

$$\int_{s_0}^{s_1} M_s \cdot \frac{d}{da_i} \theta_s(a) ds_x = C_M^T \cdot (M_{s0} \quad M_{s1} \quad M_{s2} \quad M_{s3})^T \qquad \text{Eq. B-38(b)}$$

$$\int_{s_0}^{s_1} T_s \cdot \frac{d}{da_i} \phi_s(a) ds_x = C_T^T \cdot (T_{s0} \quad T_{s1} \quad T_{s2} \quad T_{s3})^T \qquad \text{Eq. B-38(c)}$$

$$\int_{s_0}^{s_1} w_s \cdot \frac{d}{da_i} P_s(a) ds_x = C_w^T \cdot (w_{s0} \quad w_{s1} \quad w_{s2} \quad w_{s4} \quad w_{s5})^T \qquad \text{Eq. B-38(d)}$$

$$\int_{s_0}^{s_1} \theta_s \cdot \frac{d}{da_i} M_s(a) ds_x = C_\theta^T \cdot (\theta_{s0} \quad \theta_{s1} \quad \theta_{s2} \quad \theta_{s3} \quad \theta_{s4})^T \qquad \text{Eq. B-38(e)}$$

$$\int_{s_0}^{s_1} \phi_s \cdot \frac{d}{da_i} T_s(a) ds_x = C_\phi^T \cdot (\phi_{s0} \quad \phi_{s1} \quad \phi_{s2} \quad \phi_{s3} \quad \phi_{s4})^T \qquad \text{Eq. B-38(f)}$$

Where the constants $C_P$, $C_M$, $C_T$, $C_W$, $C_\Theta$, and $C_\phi$ are the algebraic form of the integrals without the corresponding external load/displacement constants.

The constants in Eq. B-38 can be defined using the functions in Eq. B-39. These functions use Su B-3 along with Eqs. B-31 to B-36. The identity matrices are used to produce the desired results in the form of Eq. B-38. Each column of the given identity matrix causes the integral to be solved considering the external load is the one that exists in only one row. This makes it possible for each corresponding external load/displacement constant to be represented individually in the output array.

$$C_P(\theta_x, \theta_y, s_y, s_1, r', D, v) := \qquad \text{Eq. B-39(a)}$$

$$Int_v \left[ C_{w\_a}(\theta_x, \theta_y, s_y, r', D, v), \begin{pmatrix} -1 & 0 & 0 \\ 0 & -1 & 0 \\ 0 & 0 & -1 \end{pmatrix}, S_{0\_1}(s_0, s_1) \right]^T$$

-continued $$C_M(\theta_x, \theta_y, s_y, s_0, s_1, r', D, v) :=$$ Eq. B-39(b)

$$Int_v\left[C_{\theta\_a}(\theta_x, \theta_y, s_y, r', D, v), \begin{pmatrix} 1 & 0 & 0 & 0 \\ 0 & 1 & 0 & 0 \\ 0 & 0 & 1 & 0 \\ 0 & 0 & 0 & 1 \end{pmatrix}^T, S_{0\_1}(s_0, s_1)\right]$$

$$C_T(\theta_x, \theta_y, s_y, s_0, s_1, r', D, v) :=$$ Eq. B-39(c)

$$Inv_v\left[C_{\phi\_a}(\theta_x, \theta_y, s_y, r', D, v), \begin{pmatrix} 1 & 0 & 0 & 0 \\ 0 & 1 & 0 & 0 \\ 0 & 0 & 1 & 0 \\ 0 & 0 & 0 & 1 \end{pmatrix}^T, S_{0\_1}(s_0, s_1)\right]$$

$$C_w(\theta_x, \theta_y, s_y, s_0, s_1, r', D, v) :=$$ Eq. B-39(d)

$$\left[ Inv_v \middle| C_{P\_a}(\theta_x, \theta_y, s_y, r', D, v), \right.$$

$$\left. \begin{pmatrix} -1 & 0 & 0 & 0 & 0 & 0 \\ 0 & -1 & 0 & 0 & 0 & 0 \\ 0 & 0 & -1 & 0 & 0 & 0 \\ 0 & 0 & 0 & -1 & 0 & 0 \\ 0 & 0 & 0 & 0 & -1 & 0 \\ 0 & 0 & 0 & 0 & 0 & -1 \end{pmatrix}^T, S_{0\_1}(s_0, s_1) \right]$$

$$C_\theta(\theta_x, \theta_y, s_y, s_0, s_1, r', D, v) := Int_v$$ Eq. B-39(e)

$$\left[C_{M\_a}(\theta_x, \theta_y, s_y, r', D, v), \begin{pmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{pmatrix}^T, S_{0\_1}(s_0, s_1)\right]$$

$$C_\phi(\theta_x, \theta_y, s_y, s_0, s_1, r', D, v) := Int_v$$ Eq. B-39(f)

$$\left[C_{T\_a}(\theta_x, \theta_y, s_y, r', D, v), \begin{pmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{pmatrix}^T, S_{0\_1}(s_0, s_1)\right]$$

At this point, all of the definitions necessary for an algebraic form of Eq. B-26 have been defined. These equations are now used to generate array constants and vector constants consistent with Eq. A-50. Recalling the last paragraph of the New Model section of Section A, there are three possibilities for the external loads/displacements. These include a known external load/displacement, an external load/displacement produced by a neighboring element, or an external load/displacement that is not known. As an example, Eq. B-38(a) is defined for these three possibilities in Eq. B-40. A similar approach can be used for all of the equations in Eq. B-38.

$$C_P^T \cdot \begin{pmatrix} P_{s0} \\ P_{s1} \\ P_{s2} \end{pmatrix} = C_P^T \cdot \begin{pmatrix} Constant_{s0} \\ Constant_{s1} \\ Constant_{s2} \end{pmatrix}$$ Eq. B-40(a)

For a known external load,
the polynomial constants describing the local
change in load on the edge are used for
the load constants. The result is a vector
that sums into the vector $U_b$ in Eq. A-50.

$$C_P^T \cdot \begin{pmatrix} P_{s0} \\ P_{s1} \\ P_{s2} \end{pmatrix} = C_P^T \cdot \begin{pmatrix} function_{s0} \\ function_{s1} \\ functions_{s2} \end{pmatrix}$$ Eq. B-40(b)

For an external load produced by a neighboring element,
the polynomial constants describing the load are functions
of the degrees of freedom of the neighboring
element. The result is a vector that sums into the vector
$U_b$ in Eq. A-50 and effects the neighboring element
$U_m$ array (in Eq. A-50 for the neighboring element).

$$C_P^T \cdot \begin{pmatrix} P_{s0} \\ P_{s1} \\ P_{s2} \end{pmatrix} = C_P^T \cdot C_{P\_a} \cdot a \ldots + C_P^T \cdot C_{P\_p}$$ Eq. B-40(c)

Where $C_{P\_a}$ and $C_{P\_a}$ are identified in Eq. B-34

For an external load that is not known,
the internal loading on the element edge is applied. This
is done so that when this work is subtracted
from the internal energy, its energy contribution
(that is unknown until the model results are found)
is effectively removed from the optimization. The
result is a vector $(C_P^T \cdot C_{P\_p})$ that sums in the
vector $U_b$ in Eq. A-50 and an array $(C_P^T \cdot C_{P\_a})$
that sums into the array $U_m$ in Eq. A-50.

Model Formulation

Figure 13:
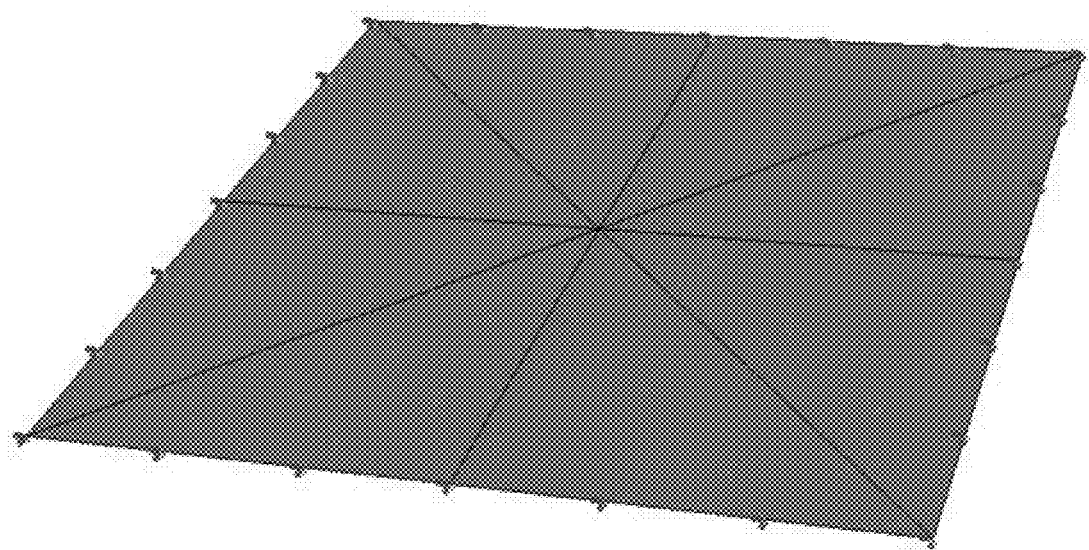
FIG. 13 is a perspective view of an example plate structure with a fixed edge and distributed pressure load.
Figure 14:
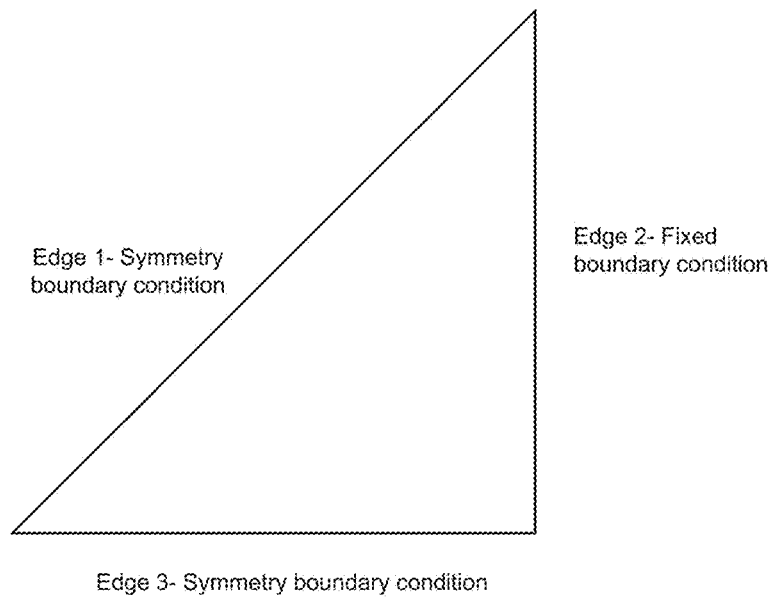
FIG. 14 is a graphical depiction of one of the elements into which the plate structure of FIG. 13 is divided.

The test model (as shown in FIG. 13) is a thin plate that is 5 inches by 5 inches by 0.1 inches thick. All of the edges are fixed and there is a 300 psi pressure applied evenly over the surface. Considering symmetry, a single triangular element with symmetry restraints can be used to evaluate the whole plate. The evaluated portion of the plate is identified in FIG. 13 and shown with boundary conditions identified in FIG. 14. This problem is selected because a single, simple element can be used to solve it. Also, the exact solution is well known and can be used for comparison.

Material Properties and Geometry

The material properties and element geometry are listed below.

E:=29.9938·10$^6$ Modulus of elasticity
v:=0.29 Poisson's ratio
t:=0.1 Thickness $$D := \frac{E \cdot t^3}{12 \cdot (1 - v^2)}$$

Flexural rigidity $D = 2.729 \times 10^3$ x:=(0 2.5 2.5)$^T$ Endpoints in the x-direction for the triangular element
y:=(0 2.5 0)$^T$ Endpoints in the y-direction for the triangular element
r':=15 Length dimension used to make the degrees of freedom unitless. (The value of 15 is arbitrarily selected as a good value relative to matrix inversion. This is the integer value that makes the matrix determinant and matrix inverse determinant closest to one.)

The length dimension used to make the degrees of freedom unitless is an interesting variable. If this variable is much less than 0.025 or much greater than 250 for this example problem, it causes the matrix inversion (in Eq. A-51) to be so unstable that Mathcad gives an error. The stress and displacement results reported in Table B-1 are correct for length dimension values from about 5 to about 250. As the length dimension value goes up, the accuracy tends to get better (as compared to the exact solution).

Element Definitions and Boundary Conditions

The equations derived for this example are only for straight edges. The element definition variables are organized to accept other shapes for the edges. For this example, only the straight edge aspects will be discussed.

For the element definitions, three simple arrays are defined to guide the process of formulating an element. The first is an area mapping array as shown below. The area mapping array guides the area integral solutions for each edge. Each row represents an edge. The first column has a zero to indicate that the edge is linear. The next two columns are the indices for the start and end edge endpoints. The last two columns are not used for linear edges. The edges need to be defined in a clockwise manner for the edge integrals to be properly defined.

$$a_{map} := \begin{pmatrix} 0 & 0 & 1 & 0 & 0 \\ 0 & 1 & 2 & 0 & 0 \\ 0 & 2 & 0 & 0 & 0 \end{pmatrix}$$

Area mapping array

The second array is an edge mapping array as shown below. The edge mapping array guides the edge integral solutions for each edge. For this example, the two arrays are the same and the numbers mean the same thing. However, it is important that these be defined separately because they are not always the same.

$$e_{map} := \begin{pmatrix} 0 & 0 & 1 & 0 & 0 \\ 0 & 1 & 2 & 0 & 0 \\ 0 & 2 & 0 & 0 & 0 \end{pmatrix}$$

Edge mapping array

The third array (as shown below) is a boundary conditions mapping array that corresponds to the edge mapping array. Each row of this array identifies active boundary conditions for the corresponding row in the edge mapping array. A zero indicates that the external displacement/load is unknown. A one indicates that the external displacement/load is known. Each column represents a displacement/load as identified below. Considering that this is a single element problem, all of the boundary conditions consist of a known displacement/load and the corresponding load/displacement is not known. For this element, the first and third edges have symmetry boundary conditions and the second edge is fixed in displacement.

$$\text{map} := \begin{pmatrix} w & \theta & \phi & P & M & T \\ 0 & 1 & 0 & 1 & 0 & 1 \\ 1 & 1 & 1 & 0 & 0 & 0 \\ 0 & 1 & 0 & 1 & 0 & 1 \end{pmatrix}$$

Boundary conditions mapping array

The boundary conditions are defined as arrays where each column corresponds with an edge defined in the edge mapping array and each row corresponds with a displacement/load constant defined in Eq. B-38. The pressure loading is defined as a scalar value.

$$P_e = \begin{pmatrix} 0 & 0 & 0 \\ 0 & 0 & 0 \\ 0 & 0 & 0 \end{pmatrix} \text{Shear load} \quad M_e = \begin{pmatrix} 0 & 0 & 0 \\ 0 & 0 & 0 \\ 0 & 0 & 0 \\ 0 & 0 & 0 \end{pmatrix} \text{Bending moment}$$

$$T_e = \begin{pmatrix} 0 & 0 & 0 \\ 0 & 0 & 0 \\ 0 & 0 & 0 \\ 0 & 0 & 0 \\ 0 & 0 & 0 \end{pmatrix} \text{Torsional moment} \quad w_e = \begin{pmatrix} 0 & 0 & 0 \\ 0 & 0 & 0 \\ 0 & 0 & 0 \\ 0 & 0 & 0 \\ 0 & 0 & 0 \\ 0 & 0 & 0 \end{pmatrix} \text{Displacement}$$

$$\theta_e = \begin{pmatrix} 0 & 0 & 0 \\ 0 & 0 & 0 \\ 0 & 0 & 0 \\ 0 & 0 & 0 \\ 0 & 0 & 0 \end{pmatrix} \text{Bending rotation} \quad \phi_e = \begin{pmatrix} 0 & 0 & 0 \\ 0 & 0 & 0 \\ 0 & 0 & 0 \\ 0 & 0 & 0 \\ 0 & 0 & 0 \end{pmatrix} \text{Torsional rotation}$$

$p_z := -300$  Distributed pressure

Continuing with the element definition, functions are defined in Eq. B-41 which establish edge slope and edge y-intercept. These are for the area integrals and the equations were defined in Eq. A-37.

$$m_{ofunc}(x_0, x_1, y_0, y_1) := \frac{y_1 - y_0}{x_1 - x_0} \qquad \text{Eq. B-41}$$

Edge slope $$b_{ofunc}(x_0, x_1, y_0, y_1) := y_0 - \frac{y_1 - y_0}{x_1 - x_0} \cdot x_0$$

Edge y-intercept

Functions are also defined in Eq. B-42 which establish functions relevant to the edge integrals. These equations were defined in Eqs. A-41 to A-43.

$$\Delta r_{func}(x_0, x_1, y_0, y_1) := \sqrt{(x_1 - x_0)^2 + (y_1 - y_0)^2} \quad \text{Eq. B-42}$$

Length of the edge $$\theta_{xfunc}(x_0, x_1, y_0, y_1) := \frac{x_1 - x_0}{\Delta r_{func}(x_0, x_1, y_0, y_1)}$$

Component in the x-direction $$\theta_{yfunc}(x_0, x_1, y_0, y_1) := \frac{y_1 - y_0}{\Delta r_{func}(x_0, x_1, y_0, y_1)}$$

Component in the y-direction $$s_{x0func}(x_0, x_1, y_0, y_1) :=$$

$$\theta_{xfunc}(x_0, x_1, y_0, y_1) \cdot x_0 \ldots + \theta_{yfunc}(x_0, x_1, y_0, y_1) \cdot y_0$$

Local x-position at the start of the edge $$s_{x1func}(x_0, x_1, y_0, y_1) :=$$

$$\theta_{xfunc}(x_0, x_1, y_0, y_1) \cdot x_1 \ldots + \theta_{yfunc}(x_0, x_1, y_0, y_1) \cdot y_1$$

Local x-position at the start of the edge $$s_{yfunc}(x_0, x_1, y_0, y_1) :=$$

$$-\theta_{yfunc}(x_0, x_1, y_0, y_1) \cdot x_0 \ldots + \theta_{xfunc}(x_0, x_1, y_0, y_1) \cdot y_0$$

Local y-position of the edge

The area mapping array and edge mapping array are defined in simple terms to make input logical and simple. Eqs. B-41 and B-42 can be used to put these arrays in a form that is more convenient for use in subroutines. Sus. B-4 and B-5 perform this function. These subroutines are used as a way to automate the process and as a way to ensure that division by zero doesn't occur (as it could if $x_0 = x_1$ in Eq. B-41).

Su. B-4 uses the area mapping array, endpoints in the x-direction vector, endpoints in the y-direction vector, and Eq. B-41 to generate an area mapping array for calculation. The area mapping array for calculation has columns of starting x-position, ending x-position, slope, y-intercept, and an additional column (not used for linear edges) respectively. The rows of the area mapping array for calculation have the same meaning as those in the area mapping array.

Su. B-5 uses the edge mapping array, endpoints in the x-direction vector, endpoints in the y-direction vector, and Eq. B-42 to generate an area mapping array for calculation. The edge mapping array for calculation has columns of component in the x-direction, component in the y-direction, local y-position, local starting x-position, and local ending x-position respectively. The rows of the edge mapping array for calculation have the same meaning as those in the edge mapping array.

$$a_c := \begin{vmatrix} out_{T_{4,rows(a_{map})-1}} \leftarrow 0 \\ \text{for } i \in 0 \ldots \text{rows}(a_{map}) - 1 \\ \begin{vmatrix} out_{T_{0,i}} \leftarrow x_{a_{map_{i,1}}} \\ out_{T_{1,i}} \leftarrow x_{a_{map_{i,2}}} \\ \text{if } x_{a_{map_{i,1}}} \neq x_{a_{map_{i,2}}} \wedge a_{map_{i,0}} = 0 \\ \begin{vmatrix} out_{T_{2,i}} \leftarrow m_{ofunc}\left(x_{a_{map,i,1}}, x_{a_{map,i,2}}, y_{a_{map,i,1}}, y_{a_{map,i,2}}\right) \\ out_{T_{2,i}} \leftarrow m_{ofunc}\left(x_{a_{map,i,1}}, x_{a_{map,i,2}}, y_{a_{map,i,1}}, y_{a_{map,i,2}}\right) \end{vmatrix} \end{vmatrix} \\ out_T^T \end{vmatrix} \quad \text{Su. B-4}$$

$$\begin{array}{cccc} x_0, & x_1, & m_1, & b_1 \\ \end{array}$$
$$a_c = \begin{pmatrix} 0 & 2.5 & 1 & 0 & 0 \\ 2.5 & 2.5 & 0 & 0 & 0 \\ 2.5 & 0 & 0 & 0 & 0 \end{pmatrix}$$

Area mapping array for calculation $$e_c := \begin{vmatrix} out_{T_{4,rows(e_{map})-1}} \leftarrow 0 \\ \text{for } i \in 0 \ldots \text{rows}(e_{map}) - 1 \\ \text{if } e_{map_{i,0}} = 0 \\ \begin{vmatrix} p \leftarrow e_{map_{i,1}} \\ q \leftarrow e_{map_{i,2}} \\ out_T^{(i)} \leftarrow \begin{pmatrix} \theta_{xfunc}(x_p, x_q, y_p, y_q) \\ \theta_{yfunc}(x_p, x_q, y_p, y_q) \\ s_{yfunc}(x_p, x_q, y_p, y_q) \\ s_{x0func}(x_p, x_q, y_p, y_q) \\ s_{x1func}(x_p, x_q, y_p, y_q) \end{pmatrix} \end{vmatrix} \\ out_T^T \end{vmatrix} \quad \text{Su. B-5}$$

$$\begin{array}{ccccc} \theta_x, & \theta_y, & s_y, & s_0, & s_1 \end{array}$$
$$e_c = \begin{pmatrix} 0.707 & 0.707 & 0 & 0 & 3.536 \\ 0 & -1 & 2.5 & -2.5 & 0 \\ -1 & 0 & 0 & -2.5 & 0 \end{pmatrix}$$

Edge mapping array for calculation

Considering the equations for the area integrals, Su. B-6 produces an array which includes all of the area integration data for the element in the example problem. This array is the portion of the $U_b$ vector (in Eq. A-51) related to the area integrals augmented to the portion of the $U_m$ array (in Eq. A-51) related to the area integrals. This subroutine starts by populating the output array and vector with zeros. It then calculates the algebraic form of the strain energy and work of the pressure load for each row of the area mapping array. The factor of 2 on the strain energy array and vector is from Eq. A-48.

Su. B-6

$$U'_{o\_el} := \begin{vmatrix} k_{17, 17} \leftarrow 0 \\ F_{17} \leftarrow 0 \\ \text{for } i \in 0 \ldots \text{rows}(a_{map}) - 1 \\ \quad \text{if } a_{map_{i,0}} = 0 \wedge a_{c_{i,0}} \neq a_{c_{i,1}} \\ \quad \quad \begin{vmatrix} k \leftarrow 2 \cdot U_o(a_{c_{i,0}}, a_{c_{i,1}}, a_{c_{i,2}}, a_{c_{i,3}}, r', D, v) + k \\ F \leftarrow 2 \cdot U_{pz}(a_{c_{i,0}}, a_{c_{i,1}}, a_{c_{i,2}}, a_{c_{i,3}}, r', D, v, p_z) + F \\ F \leftarrow 2 \cdot U_p(a_{c_{i,0}}, a_{c_{i,1}}, a_{c_{i,2}}, a_{c_{i,3}}, r', D, v, p_z) + F \end{vmatrix} \\ \text{augment }(F, k) \end{vmatrix}$$

$$U'_{o\_el} = \begin{pmatrix}
14062.5 & 0 & 0 & 0 & 0 & 0 & 0 & 0 & 0 & 0 & 0 & 0 & 0 & 0 & 0 & 0 & 0 & 0 \\
1562.5 & 0 & 0 & 0 & 0 & 0 & 0 & 0 & 0 & 0 & 0 & 0 & 0 & 0 & 0 & 0 & 0 & 0 \\
781.25 & 0 & 0 & 0 & 0 & 0 & 0 & 0 & 0 & 0 & 0 & 0 & 0 & 0 & 0 & 0 & 0 & 0 \\
-41.02 & 0 & 0 & 0 & 107.64 & 0 & 0 & 23.92 & 11.96 & 0 & 0 & 4.49 & 1.5 & -8.97 & -8.97 & 0.4 & -0.4 & -2.99 & -1.99 \\
73.57 & 0 & 0 & 0 & 0 & 303.22 & 87.93 & 16.85 & 9.77 & 101.07 & 14.66 & 6.32 & 1.83 & 17.39 & -5.43 & 1.3 & -0.4 & 1.99 & -1.52 \\
-149.09 & 0 & 0 & 0 & 0 & 87.93 & 303.22 & 4.89 & 33.69 & 29.31 & 50.54 & 1.83 & 6.32 & -6.53 & -5.43 & -0.39 & 0.4 & -1.99 & -3.01 \\
-34.24 & 0 & 0 & 0 & 23.92 & 16.85 & 4.89 & 7.38 & 3.6 & 6.32 & 1.22 & 1.73 & 0.56 & -1.37 & -2.81 & 0.23 & -0.15 & -0.79 & -0.7 \\
-44.53 & 0 & 0 & 0 & 11.96 & 9.77 & 33.69 & 3.6 & 6.2 & 3.66 & 6.32 & 0.84 & 1.14 & -2.47 & -2.32 & -0.03 & -0.01 & -0.83 & -0.83 \\
-22.66 & 0 & 0 & 0 & 0 & 101.07 & 29.31 & 6.32 & 3.66 & 37.9 & 5.5 & 0.53 & 0.73 & 6.96 & -2.17 & 0.54 & -0.17 & 0.83 & -0.63 \\
-38.22 & 0 & 0 & 0 & 0 & 14.66 & 50.54 & 1.22 & 6.32 & 5.5 & 12.63 & 0.49 & 1.68 & -1.43 & -0.37 & -0.11 & 0.18 & -0.5 & -0.77 \\
-10.18 & 0 & 0 & 0 & 4.49 & 6.32 & 1.83 & 1.76 & 0.84 & 2.53 & 0.49 & 0.48 & 0.15 & -0.07 & -0.67 & 0.07 & -0.04 & -0.16 & -0.18 \\
-9.16 & 0 & 0 & 0 & 1.5 & 1.83 & 6.32 & 0.56 & 1.14 & 0.73 & 1.68 & 0.15 & 0.28 & -0.45 & -0.3 & -0.01 & 0.02 & -0.16 & -0.18 \\
22.14 & 0 & 0 & 0 & -8.97 & 17.39 & -6.53 & -1.37 & -2.47 & 6.96 & -1.43 & -0.07 & -0.45 & 3.36 & 1.15 & 0.12 & -0 & 0.84 & 0.4 \\
24.28 & 0 & 0 & 0 & -8.97 & -5.43 & -5.43 & -2.81 & -2.32 & -2.17 & -0.37 & -0.67 & -0.3 & 1.15 & 1.77 & -0.06 & 0.09 & 0.49 & 0.43 \\
-0.45 & 0 & 0 & 0 & 0.4 & 1.3 & -0.39 & 0.23 & -0.03 & 0.54 & -0.11 & 0.07 & -0.01 & 0.12 & -0.06 & 0.02 & -0.01 & 0.01 & -0 \\
0.62 & 0 & 0 & 0 & 0.4 & -0.4 & 0.4 & -0.15 & -0.01 & -0.17 & 0.18 & -0.04 & 0.02 & -0 & 0.09 & -0.01 & 0.01 & 0.01 & 0.01 \\
8.9 & 0 & 0 & 0 & -2.99 & 1.99 & -1.99 & -0.79 & -0.83 & 0.83 & -0.5 & -0.16 & -0.16 & 0.84 & 0.49 & 0.01 & 0.01 & 0.26 & 0.16 \\
8.46 & 0 & 0 & 0 & -1.99 & -1.52 & -3.01 & -0.7 & -0.83 & -0.63 & -0.77 & -0.18 & -0.18 & 0.04 & 0.43 & -0 & 0.01 & 0.16 & 0.16
\end{pmatrix}$$

Considering the equations for the edge integrals, Su. B-7 produces an array which includes all of the edge integration data for the element in the example problem. This array is the portion of the $U_b$ vector (in Eq. A-51) related to the edge integrals augmented to the portion of the $U_m$ array (in Eq. A-51) related to the edge integrals. This subroutine starts by populating the output array and vector with zeros. It then calculates the algebraic form of the edge integrals for each row of the edge mapping array. The boundary conditions mapping array uses the logic discussed with Eq. B-40 to determine the correct algorithm for addressing the displacement/load situation.

$$U''_{ed} := \begin{vmatrix} k_{17,17} \leftarrow 0 \\ F_{17} \leftarrow 0 \\ \text{for } i \in 0 \ldots \text{rows}(e_{map}) - 1 \\ \quad \begin{vmatrix} \text{if } e_{map_{i,0}} = 0 \\ \quad \begin{vmatrix} \text{if } map_{i,0} = 0 \\ \quad \begin{vmatrix} k \leftarrow C_w(e_{c_{i,0}}, e_{c_{i,1}}, e_{c_{i,2}}, e_{c_{i,3}}, e_{c_{i,4}}, r', D, v)^T \cdot C_{w\_d}(e_{c_{i,0}}, e_{c_{i,1}}, e_{c_{i,2}}, r', D, v) + k \\ F \leftarrow C_w(e_{c_{i,0}}, e_{c_{i,1}}, e_{c_{i,2}}, e_{c_{i,3}}, e_{c_{i,4}}, r', D, v)^T \cdot C_{w\_p}(e_{c_{i,0}}, e_{c_{i,1}}, e_{c_{i,2}}, r', D, v, p_z) + F \end{vmatrix} \\ \quad \begin{vmatrix} F \leftarrow C_w(e_{c_{i,0}}, e_{c_{i,1}}, e_{c_{i,2}}, e_{c_{i,3}}, e_{c_{i,4}}, r', D, v)^T \cdot w_e^{\langle i \rangle} + F \text{ if } map_{i,0} = 1 \end{vmatrix} \\ \text{if } map_{i,1} = 0 \\ \quad \begin{vmatrix} k \leftarrow C_\theta(e_{c_{i,0}}, e_{c_{i,1}}, e_{c_{i,2}}, e_{c_{i,3}}, e_{c_{i,4}}, r', D, v)^T \cdot C_{\theta\_d}(e_{c_{i,0}}, e_{c_{i,1}}, e_{c_{i,2}}, r', D, v) + k \\ F \leftarrow C_\theta(e_{c_{i,0}}, e_{c_{i,1}}, e_{c_{i,2}}, e_{c_{i,3}}, e_{c_{i,4}}, r', D, v)^T \cdot C_{\theta\_p}(e_{c_{i,0}}, e_{c_{i,1}}, e_{c_{i,2}}, r', D, v, p_z) + F \end{vmatrix} \\ \quad \begin{vmatrix} F \leftarrow C_\theta(e_{c_{i,0}}, e_{c_{i,1}}, e_{c_{i,2}}, e_{c_{i,3}}, e_{c_{i,4}}, r', D, v)^T \cdot \theta_e^{\langle i \rangle} + F \text{ if } map_{i,1} = 1 \end{vmatrix} \\ \text{if } map_{i,2} = 0 \\ \quad \begin{vmatrix} k \leftarrow C_\phi(e_{c_{i,0}}, e_{c_{i,1}}, e_{c_{i,2}}, e_{c_{i,3}}, e_{c_{i,4}}, r', D, v)^T \cdot C_{\phi\_d}(e_{c_{i,0}}, e_{c_{i,1}}, e_{c_{i,2}}, r', D, v) + k \\ F \leftarrow C_\phi(e_{c_{i,0}}, e_{c_{i,1}}, e_{c_{i,2}}, e_{c_{i,3}}, e_{c_{i,4}}, r', D, v)^T \cdot C_{\phi\_p}(e_{c_{i,0}}, e_{c_{i,1}}, e_{c_{i,2}}, r', D, v, p_z) + F \end{vmatrix} \\ \quad \begin{vmatrix} F \leftarrow C_\phi(e_{c_{i,0}}, e_{c_{i,1}}, e_{c_{i,2}}, e_{c_{i,3}}, e_{c_{i,4}}, r', D, v)^T \cdot \phi_e^{\langle i \rangle} + F \text{ if } map_{i,2} = 1 \end{vmatrix} \\ \text{if } map_{i,3} = 0 \end{vmatrix} \end{vmatrix}$$

Su. B-7

-continued $$U^r{}_{el} = \begin{cases} \begin{vmatrix} k \leftarrow C_P(e_{c_i,0}, e_{c_i,1}, e_{c_i,2}, e_{c_i,3}, e_{c_i,4}, r', D, v)^T \cdot C_{P\_d}(e_{c_i,0}, e_{c_i,1}, e_{c_i,2}, r', D, v) + k \\ F \leftarrow C_P(e_{c_i,0}, e_{c_i,1}, e_{c_i,2}, e_{c_i,3}, e_{c_i,4}, r', D, v)^T \cdot C_{P\_p}(e_{c_i,0}, e_{c_i,1}, e_{c_i,2}, r', D, v, p_z) + F \end{vmatrix} \\ \text{if } map_{i,4} = 0 \\ \begin{vmatrix} F \leftarrow C_P(e_{c_i,0}, e_{c_i,1}, e_{c_i,2}, e_{c_i,3}, e_{c_i,4}, r', D, v)^T \cdot (P_e^{<e>}) + F \text{ if } map_{i,3} = 1 \\ k \leftarrow C_M(e_{c_i,0}, e_{c_i,1}, e_{c_i,2}, e_{c_i,3}, e_{c_i,4}, r', D, v)^T \cdot C_{M\_d}(e_{c_i,0}, e_{c_i,1}, e_{c_i,2}, r', D, v) + k \\ F \leftarrow C_M(e_{c_i,0}, e_{c_i,1}, e_{c_i,2}, e_{c_i,3}, e_{c_i,4}, r', D, v)^T \cdot C_{M\_p}(e_{c_i,0}, e_{c_i,1}, e_{c_i,2}, r', D, v, p_z) + F \\ F \leftarrow C_M(e_{c_i,0}, e_{c_i,1}, e_{c_i,2}, e_{c_i,3}, e_{c_i,4}, r', D, v)^T \cdot (-M_e^{<e>}) + F \text{ if } map_{i,4} = 1 \end{vmatrix} \\ \text{if } map_{i,5} = 0 \\ \begin{vmatrix} k \leftarrow C_T(e_{c_i,0}, e_{c_i,1}, e_{c_i,2}, e_{c_i,3}, e_{c_i,4}, r', D, v)^T \cdot C_{T\_d}(e_{c_i,0}, e_{c_i,1}, e_{c_i,2}, r', D, v) + k \\ F \leftarrow C_T(e_{c_i,0}, e_{c_i,1}, e_{c_i,2}, e_{c_i,3}, e_{c_i,4}, r', D, v)^T \cdot C_{T\_p}(e_{c_i,0}, e_{c_i,1}, e_{c_i,2}, r', D, v, p_z) + F \end{vmatrix} \\ F \leftarrow C_T(e_{c_i,0}, e_{c_i,1}, e_{c_i,2}, e_{c_i,3}, e_{c_i,4}, r', D, v)^T \cdot (-T_e^{<e>}) + F \text{ if } map_{i,5} = 1 \\ \text{augment}(F, k) \end{cases}$$

Augmented matrix:

| | | | | | | | | | | | | | | | | |
|---|---|---|---|---|---|---|---|---|---|---|---|---|---|---|---|---|
| −1.406 | 0 | 0 | 0 | 0 | 0 | 0 | 909.664 | 2728.992 | 0 | 227.416 | 227.416 | 909.664 | −909.664 | 75.805 | −50.537 | 252.684 | −379.027 |
| −0.156 | 0 | 0 | 0 | −0.032 | −0.032 | 322.931 | 102.716 | 146.683 | 80.733 | 7.328 | 34.239 | 83.133 | −83.133 | 4.991 | −3.327 | 31.586 | −47.378 |
| −0.078 | 0 | 0 | 0 | −0.032 | −0.032 | 322.931 | 102.716 | 146.683 | −146.683 | −8.97 | 8.97 | 83.133 | −83.133 | 3.327 | −3.327 | 31.586 | −31.586 |
| −0.003 | 0 | 322.931 | 322.931 | 0 | −0.005 | 53.822 | 8.423 | 16.298 | −7.328 | −4.485 | 1.495 | 14.129 | −3.664 | −0.154 | 0.154 | 5.956 | −3.215 |
| −0.02 | 0 | 322.931 | −0.032 | 0.005 | 0 | 63.676 | 18.488 | −34.239 | 19.583 | −2.99 | 5.98 | −3.538 | −8.423 | −0.583 | 0.154 | 2.218 | −6.556 |
| 111.328 | 0 | −0.032 | −0.032 | −0.005 | −0.015 | −0.015 | −0.001 | 16.298 | −41.567 | −4.654 | −2.411 | 14.403 | −2.443 | −0.154 | −0.244 | 6.205 | −1.709 |
| −0.001 | 0 | −0.01 | −0.015 | 2.443 | 0.547 | 20.931 | 2.548 | −2.776 × 10⁻¹⁵ | 1.769 | −0.988 | 0.507 | 1.053 | −0.06 | 0.242 | 0.122 | 0.813 | −0.452 |
| 33.681 | −0.091 | −0.008 | −0.01 | −0.002 | −0.003 | −0.002 | 0 | −4.211 | −5.127 | −1.209 | 0.68 | 2.7 | 1.051 | −0.163 | 0.055 | 1.217 | 0.048 |
| −0.001 | −0.273 | −0.015 | −0.015 | −0.002 | −0.007 | −0.001 | 0.547 | −18.951 | 0.821 | −1.562 | −3.045 | −0.055 | −0.036 | 0.132 | −0.012 | −0.743 |
| 24.056 | −0.008 | −0.008 | 146.683 | −0.002 | −0.003 | −0.001 | 0 | −6.317 | −6.317 | −0.87 | −0.571 | 1.434 | −0.251 | 0.007 | −0.042 | 0.958 | −0.019 |
| 0.335 | −0.023 | −0.001 | 8.97 | 0 | 0 | 2.822 | 0.367 | −0.964 | 0.381 | −0.242 | 0.091 | −0.037 | 0.103 | −0.052 | 0.034 | 0.111 | −0.052 |
| 7.98 | −0.023 | −0.003 | −0.001 | 0 | −0.001 | 0 | 0 | −1.413 | −1.114 | −0.242 | −0.142 | 0.399 | 0.248 | −0.008 | 0.007 | 0.215 | 0.066 |
| −0.001 | −0.091 | −0.008 | −0.008 | −0.001 | −0.001 | −0.001 | 0 | −3.912 | −0.006 | 0.111 | 0.048 | −1.682 | −0.306 | −0.036 | −0.029 | −0.57 | −0.061 |
| −0.001 | 909.664 | 83.133 | 83.133 | 12.634 | 13.856 | 7.875 | 1.268 | 2.228 | 0.617 | 0.571 | 0.052 | −0.848 | −0.885 | 0.061 | −0.075 | −0.429 | −0.062 |
| −0 | −0.008 | −0 | −0 | −0 | −0 | 0.152 | 0.063 | −0.197 | 0.105 | −0.022 | 0.022 | −0.081 | 0.001 | −0.01 | 0.005 | −0.015 | −0.012 |
| 0.414 | 50.537 | 3.327 | 3.327 | 0.244 | 0.244 | 0 | 0 | 0.034 | −0.141 | 0.005 | −0.023 | 0.031 | −0.016 | 0.005 | −0.005 | 0.007 | 0.01 |
| −0 | −0.025 | −0.003 | −0.003 | 0 | 0 | 0 | 0 | −0.819 | −0.458 | 0.05 | −0.054 | −0.266 | −0.065 | 0.008 | −0.019 | −0.132 | 0.009 |
| −0.001 | 379.027 | 47.378 | 31.586 | 5.208 | 8.072 | 4.72 | 1.151 | 0.785 | 1.375 | 0.788 | 0.233 | 0.115 | −0.342 | −0.366 | 0.015 | −0.017 | −0.174 | −0.082 |

Rigid Body Motions

Observing the $U_m$ array (from Eq. A-51) portion of the output for Sus. B-6 and B-7, the upper left portion has zeros for the first three diagonal positions. This makes the summed $U_m$ array unstable for matrix inversion at this point. The zeros occur because the optimization is strain based and nothing is done to address rigid body motion. (This is also discussed near the end of the New Method section of Section A.) To address the rigid body motion for this example, further equations are defined to set the average element displacements equal to the average external displacements for each edge (where an external displacement is defined).

$$\begin{array}{cc} \text{Average} & \text{Average} \\ \text{element} & \text{external} \\ \text{edge} & \text{edge} \\ \text{displacement} & \text{displacement} \end{array}$$

$$\frac{\int_{s_0}^{s_1} w_s(a)\, ds_x}{\int_{s_0}^{s_1} 1\, ds_x} = \frac{\int_{s_0}^{s_1} w_s\, ds_x}{\int_{s_0}^{s_1} 1\, ds_x} \quad \text{or} \quad \int_{s_0}^{s_1} w_s(a)\, ds_x = \int_{s_0}^{s_1} w_s\, ds_x$$

Considering Eq. B-31 and that the left side of the above equation is based on element displacement while the right side is based on external displacement, the following substitutions may be made.

$$\int_{s_0}^{s_1} (C_{w\_a} \cdot a + C_{w\_p})^T \cdot \begin{pmatrix} 1 \\ s_x \\ s_x^2 \\ s_x^3 \\ s_x^4 \\ s_x^5 \end{pmatrix} ds_x = \int_{s_0}^{s_1} \begin{pmatrix} w_{s0} \\ w_{s1} \\ w_{s2} \\ w_{s3} \\ w_{s4} \\ w_{s5} \end{pmatrix}^T \begin{pmatrix} 1 \\ s_x \\ s_x^2 \\ s_x^3 \\ s_x^4 \\ s_x^5 \end{pmatrix} ds_x$$

Rearranging the left side equation in the integral:

$$(C_{w\_a} \cdot a + C_{w\_p})^T \cdot \begin{pmatrix} 1 \\ s_x \\ s_x^2 \\ s_x^3 \\ s_x^4 \\ s_x^5 \end{pmatrix} =$$

$$(C_{w\_a} \cdot a)^T \cdot \begin{pmatrix} 1 \\ s_x \\ s_x^2 \\ s_x^3 \\ s_x^4 \\ s_x^5 \end{pmatrix} + C_{w\_p}^T \cdot \begin{pmatrix} 1 \\ s_x \\ s_x^2 \\ s_x^3 \\ s_x^4 \\ s_x^5 \end{pmatrix} = \begin{bmatrix} \begin{pmatrix} 1 \\ s_x \\ s_x^2 \\ s_x^3 \\ s_x^4 \\ s_x^5 \end{pmatrix}^T \cdot \begin{pmatrix} 1 \\ s_x \\ s_x^2 \\ s_x^3 \\ s_x^4 \\ s_x^5 \end{pmatrix} \cdot C_{w\_a} \end{bmatrix} \cdot a + \begin{pmatrix} 1 \\ s_x \\ s_x^2 \\ s_x^3 \\ s_x^4 \\ s_x^5 \end{pmatrix}^T \cdot C_{w\_p}$$

Which can be used to put the equated integrals into the form shown in Eq. B-43(a).

$$\begin{bmatrix} \int_{s_0}^{s_1} \begin{pmatrix} 1 \\ s_x \\ s_x^2 \\ s_x^3 \\ s_x^4 \\ s_x^5 \end{pmatrix} ds_x \end{bmatrix}^T \cdot C_{w\_a} \cdot a + \begin{bmatrix} \int_{s_0}^{s_1} \begin{pmatrix} 1 \\ s_x \\ s_x^2 \\ s_x^3 \\ s_x^4 \\ s_x^5 \end{pmatrix} ds_x \end{bmatrix}^T \cdot C_{w\_p} = \begin{bmatrix} \int_{s_0}^{s_1} \begin{pmatrix} 1 \\ s_x \\ s_x^2 \\ s_x^3 \\ s_x^4 \\ s_x^5 \end{pmatrix} ds_x \end{bmatrix}^T \cdot \begin{pmatrix} w_{s0} \\ w_{s1} \\ w_{s2} \\ w_{s3} \\ w_{s4} \\ w_{s5} \end{pmatrix} \quad \text{Eq. B-43(a)}$$

Using the same approach for the rotations, Eqs. B-43(b) and B-43(c) can be developed.

$$\begin{array}{cc} \text{Average} & \text{Average} \\ \text{element} & \text{external} \\ \text{edge bending} & \text{edge bending} \\ \text{rotation} & \text{rotation} \end{array} \quad \text{Eq. B-43(b)}$$

$$\frac{\int_{s_0}^{s_1} \theta_s(a)\, ds_x}{\int_{s_0}^{s_1} 1\, ds_x} = \frac{\int_{s_0}^{s_1} \theta_s\, ds_x}{\int_{s_0}^{s_1} 1\, ds_x} \quad \text{or}$$

$$\int_{s_0}^{s_1} \theta_s(a)\, ds_x = \int_{s_0}^{s_1} \theta_s\, ds_x$$

Which leads to:

$$\begin{bmatrix} \int_{s_0}^{s_1} \begin{pmatrix} 1 \\ s_x \\ s_x^2 \\ s_x^3 \\ s_x^4 \end{pmatrix} ds_x \end{bmatrix}^T \cdot C_{\theta\_a} \cdot a +$$

$$\begin{bmatrix} \int_{s_0}^{s_1} \begin{pmatrix} 1 \\ s_x \\ s_x^2 \\ s_x^3 \\ s_x^4 \end{pmatrix} ds_x \end{bmatrix}^T \cdot C_{\theta\_p} = \begin{bmatrix} \int_{s_0}^{s_1} \begin{pmatrix} 1 \\ s_x \\ s_x^2 \\ s_x^3 \\ s_x^4 \end{pmatrix} ds_x \end{bmatrix}^T \cdot \begin{pmatrix} \theta_{s0} \\ \theta_{s1} \\ \theta_{s2} \\ \theta_{s3} \\ \theta_{s4} \end{pmatrix}$$

$$\begin{array}{cc} \text{Average} & \text{Average} \\ \text{element} & \text{external} \\ \text{edge torsional} & \text{edge torsional} \\ \text{rotation} & \text{rotation} \end{array}$$

$$\frac{\int_{s_0}^{s_1} \phi_s(a)\, ds_x}{\int_{s_0}^{s_1} 1\, ds_x} = \frac{\int_{s_0}^{s_1} \phi_s\, ds_x}{\int_{s_0}^{s_1} 1\, ds_x} \quad \text{or}$$

$$\int_{s_0}^{s_1} \phi_s(a)\, ds_x = \int_{s_0}^{s_1} \phi_s\, ds_x$$

Which leads to:

$$\left[\int_{s_0}^{s_1} \begin{pmatrix} 1 \\ s_x \\ s_x^2 \\ s_x^3 \\ s_x^4 \end{pmatrix} ds_x \right]^T \cdot C_{\phi\_a} \cdot a + \left[\int_{s_0}^{s_1} \begin{pmatrix} 1 \\ s_x \\ s_x^2 \\ s_x^3 \\ s_x^4 \end{pmatrix} ds_x \right]^T \cdot C_{\phi\_p} =$$

$$\left[\int_{s_0}^{s_1} \begin{pmatrix} 1 \\ s_x \\ s_x^2 \\ s_x^3 \\ s_x^4 \end{pmatrix} ds_x \right]^T \cdot \begin{pmatrix} \phi_{s0} \\ \phi_{s1} \\ \phi_{s2} \\ \phi_{s3} \\ \phi_{s4} \end{pmatrix}$$

Eq. B-43(c)

The integral in Eq. B-43 is the same as that in Eq. B-29 except the vector being integrated has less rows. Consequently, the function in Eq. B-44 is defined to take advantage of the integration function defined in Eq. B-30.

$$S_{BC\_0\_1}(s_0, s_1, \text{no}) := \text{submatrix}(S_{0\_1}(s_0, s_1), 0, \text{no}, 0, 0)$$
Integration function    Eq. B-44

Considering the Eqs. B-43 and B-44 for the edge integrals, Su. B-8 produces an array which includes all of the edge integration data (where external displacements are known) for the element in the example problem. This subroutine calculates the algebraic form of the rigid body edge integrals for each row of the edge mapping array (where external displacements are known). The boundary conditions mapping array is used to establish if a given edge has a defined external displacement.

For this example, Su. B-8 produces five linear equations where only three are necessary for stable matrix inversion. Su. B-9 sums these into three linear equations in a manner where the nonzero value for the lowest numbered degree of freedom determines which equations are summed. Also, rows of zeros are added to the array as needed so that it can be summed with the area integral and edge integral arrays.

Su. B-8

$$U'_{BCl\_r} := \begin{vmatrix} k_T \leftarrow 0 \\ F \leftarrow 0 \\ q \leftarrow 0 \\ \text{for } i \in 0 \ldots \text{rows}(e_{map}) - 1 \\ \quad \text{if } e_{map_{i,0}} = 0 \\ \quad \quad \text{if } map_{i,0} = 1 \\ \quad \quad \quad k_T^{\langle q \rangle} \leftarrow (S_{BC\_0\_1}(e_{c_{i,3}}, e_{c_{i,4}}, 5)^T \cdot C_{w\_a}(e_{c_{i,0}}, e_{c_{i,1}}, e_{c_{i,2}}, r', D, v))^T \\ \quad \quad \quad F_q \leftarrow -S_{BC\_0\_1}(e_{c_{i,3}}, e_{c_{i,4}}, 5)^T \cdot C_{w\_p}(e_{c_{i,0}}, e_{c_{i,1}}, e_{c_{i,2}}, r', D, v, p_z)) \ldots + \\ \quad \quad \quad S_{BC\_0\_1}(e_{c_{i,3}}, e_{c_{i,4}}, 5)^T \cdot w_e^{\langle i \rangle} \\ \quad \quad \quad q \leftarrow q + 1 \\ \quad \quad \text{if } map_{i,1} = 1 \\ \quad \quad \quad k_T^{\langle q \rangle} \leftarrow (S_{BC\_0\_1}(e_{c_{i,3}}, e_{c_{i,4}}, 4)^T \cdot C_{\theta\_a}(e_{c_{i,0}}, e_{c_{i,1}}, e_{c_{i,2}}, r', D, v))^T \\ \quad \quad \quad F_q \leftarrow -S_{BC\_0\_1}(e_{c_{i,3}}, e_{c_{i,4}}, 4)^T \cdot C_{\theta\_p}(e_{c_{i,0}}, e_{c_{i,1}}, e_{c_{i,2}}, r', D, v, p_z)) \ldots + \\ \quad \quad \quad S_{BC\_0\_1}(e_{c_{i,3}}, e_{c_{i,4}}, 4)^T \cdot \theta_e^{\langle i \rangle} \\ \quad \quad \quad q \leftarrow q + 1 \\ \quad \quad \text{if } map_{i,2} = 1 \\ \quad \quad \quad k_T^{\langle q \rangle} \leftarrow (S_{BC\_0\_1}(e_{c_{i,3}}, e_{c_{i,4}}, 4)^T \cdot C_{\phi\_a}(e_{c_{i,0}}, e_{c_{i,1}}, e_{c_{i,2}}, r', D, v))^T \\ \quad \quad \quad F_q \leftarrow -S_{BC\_0\_1}(e_{c_{i,3}}, e_{c_{i,4}}, 4)^T \cdot C_{\phi\_p}(e_{c_{i,0}}, e_{c_{i,1}}, e_{c_{i,2}}, r', D, v, p_z)) \ldots + \\ \quad \quad \quad S_{BC\_0\_1}(e_{c_{i,3}}, e_{c_{i,4}}, 4)^T \cdot \phi_e^{\langle i \rangle} \\ \quad \quad \quad q \leftarrow q + 1 \\ \text{augment } F, k_T^T \end{vmatrix}$$

$$U'_{BCl\_r} = \begin{pmatrix} 0 & 0 & -2.5 & 2.5 & 0 & -0.42 & 0.42 & -0.02 & 0.02 & -0.07 & 0.07 & -0.01 & 0.01 & -0.01 & 0.01 & -0 & 0 & 0 & 0 \\ 0.45 & 37.5 & 6.25 & 3.13 & 0.52 & 1.04 & 0.35 & 0.09 & 0.06 & 0.17 & 0.04 & 0.01 & 0.01 & 0 & -0.02 & 0 & -0 & -0 & -0.01 \\ 0.36 & 0 & 2.5 & 0 & 0.21 & 0.83 & 0 & 0.07 & 0.02 & 0.21 & 0 & 0.02 & 0 & 0.02 & -0.02 & 0 & -0 & 0 & -0 \\ -0.54 & 0 & 0 & -2.5 & -0.42 & 0 & -0.42 & -0.07 & -0.07 & 0 & -0.07 & -0.01 & -0.01 & 0.03 & 0.02 & 0 & 0 & 0.01 & 0.01 \\ 0 & 0 & 0 & -2.5 & -0.21 & 0 & 0 & 0.02 & 0 & 0 & 0 & -0 & 0 & 0 & 0 & -0 & 0 & 0 & 0 \end{pmatrix}$$

Su. B-9

$$U'_{BCl\_rb} := \begin{vmatrix} out_{T_{18,17}} \leftarrow 0 \\ out_T^{\langle 0 \rangle} \leftarrow U'_{BCl\_r}^{T \langle 1 \rangle} \\ out_T^{\langle 1 \rangle} \leftarrow U'_{BCl\_r}^{T \langle 2 \rangle} - U'_{BCl\_r}^{T \langle 0 \rangle} \\ out_T^{\langle 2 \rangle} \leftarrow U'_{BCl\_r}^{T \langle 3 \rangle} - U'_{BCl\_r}^{T \langle 4 \rangle} \\ out_T^T \end{vmatrix}$$

$$U'_{BCl\_rb} = \begin{pmatrix} 0.45 & 37.5 & 6.25 & 3.13 & 0.52 & 1.04 & 0.35 & 0.09 & 0.06 & 0.17 & 0.04 & 0.01 & 0.01 & 0 & -0.02 & 0 & -0 & -0 & -0.01 \\ 0.36 & 0 & 5 & -2.5 & 0.21 & 1.25 & -0.42 & 0.09 & 0 & 0.28 & -0.07 & 0.02 & -0 & 0.03 & -0.03 & 0 & -0 & 0 & -0 \\ 0.54 & 0 & 0 & 5 & 0.63 & 0 & 0.42 & 0.09 & 0.07 & 0 & 0.07 & 0.01 & 0.01 & -0.03 & -0.02 & 0 & 0 & -0.01 & -0.01 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 & 0 & 0 & 0 & 0 \end{pmatrix}$$

Degrees of Freedom and Results Plots

Having the array that is the portion of the $U_b$ vector (in Eq. A-51) related to the rigid body edge integrals augmented to the portion of the $U_m$ array (in Eq. A-51) related to the rigid body edge integrals, the $U_m$ array and $U_b$ vector can be defined.

Array constant for Eq. A-51

$$U_m := \text{submatrix}(U'_{o\_el}, 0, \text{rows}(U'_{o\_el}) - 1, 1, \text{cols}(U'_{o\_el}) - 1) \ldots +$$
$$\text{submatrix}(U'_{el}, 0, \text{rows}(U'_{el}) - 1, 1, \text{cols}(U'_{el}) - 1) \ldots +$$
$$\text{submatrix}(U'_{BCl\_rb}, 0, \text{rows}(U'_{BCl\_rb}) - 1, 1, \text{cols}(U'_{BCl\_rb}) - 1)$$

Vector constant for Eq. A-51

$$U_b := U'^{(0)}_{o\_el} + U'^{(0)}_{el} + U'^{(0)}_{BCl\_rb}$$

Because the example model only has one element, $U_M = U_m$ and $U_B = U_b$ as shown below $U_M := U_m$ Array constant summed for all of the elements in the model for Eq. A-52

$U_B := U_b$ Vector constant summed for all of the elements in the model for Eq. A-52

Solving Eq. A-52 produces the degrees of freedom vector for this example problem. The degree of freedom vector makes it possible to find optimized solution results for displacements, loads, stresses, strains or any other value addressed by the governing equation. The simplest to evaluate is displacement as it can be evaluated using the base equation (Eq. B-7) with no other derivation.

Figure 15:
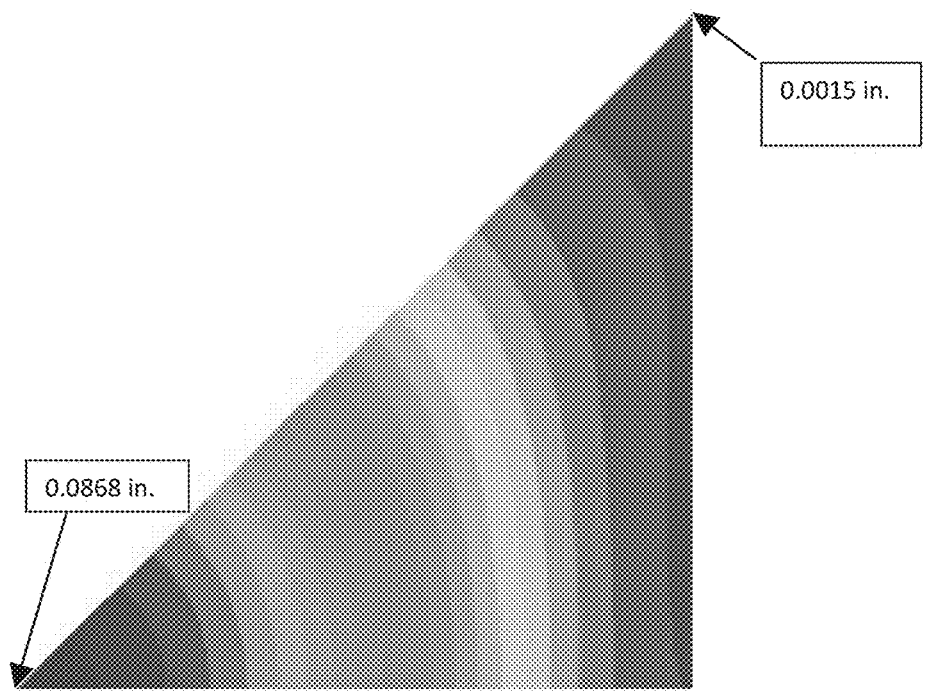
FIG. 15 is a displacement plot for the element of FIG. 14 evaluated according to the principles of the present disclosure.

FIG. 15 shows a gradient plot of the resulting displacement. The contours range from the most positive value (0.0015 in.) of the displacement at the lower left vertex of the triangle to the most negative value (−0.0868 in.) of the displacement at the upper right vertex of the triangle. The most positive value would ideally be zero as the boundary condition fixes the edge and the pressure causes a deformation in a negative direction. It is allowed to not exactly meet the boundary condition in the interest of making the overall solution the most accurate it can be. The theoretical exact solution for this problem is for the maximum displacement to be −0.0866 in. Consequently, with only one element, the new method has come very close to the correct maximum displacement value.

$$a := U_M^{-1} \cdot (-U_B)$$

$$U_B^T = (0.45 \ 0.36 \ 0.54 \ -69.34 \ -130.21 \ -37.76 \ -39.39 \ -10.85 \ -32.55 \ -14.16 \ -9.85 \ -1.18 \ 14.21 \ 10.44 \ -0.98 \ 1.04 \ 8.5 \ 0.63)$$

$$U_M = \begin{pmatrix} 37.5 & 6.3 & 3.1 & 0.5 & 1 & 0.3 & 0.1 & 909.7 & 2729.2 & 0 & 227.4 & 227.4 & 909.7 & -909.7 & 75.8 & -50.5 & 252.7 & -379 \\ 0 & 5 & -2.5 & -322.7 & -321.7 & 322.5 & -80.6 & 102.7 & 147 & 80.7 & 7.4 & 34.2 & 83.2 & -83.2 & s & -3.3 & 31.6 & -47.4 \\ 0 & 0 & 5 & 0.6 & -322.9 & 322.5 & -102.6 & 102.8 & 146.7 & -146.6 & -9 & 9 & 83.1 & -83.2 & 3.3 & -3.3 & 31.6 & -31.6 \\ 0 & 322.9 & 0 & 53.8 & 0 & 53.8 & -2.4 & 20.4 & 16.3 & -7.3 & 0 & 3 & 5.2 & -12.6 & 0.2 & -0.2 & 3 & -5.2 \\ 0 & 322.9 & 322.9 & 0 & 151.6 & 151.6 & -0.5 & 28.3 & 66.8 & 34.2 & 3.3 & 7.8 & 13.9 & -13.9 & 0.7 & -0.2 & 4.2 & -8.1 \\ 0 & -322.9 & -322.9 & -53.8 & -63.7 & 151.6 & -20.9 & 22.3 & 13 & 9 & -2.8 & 3.9 & 7.9 & -7.9 & -0.2 & 0.2 & 4.2 & -4.7 \\ 0 & 80.7 & 102.7 & 26.4 & 17.4 & 25.8 & 3.7 & 6.1 & 6.3 & 3 & 0.8 & 1.1 & -0.3 & -2.9 & 0.1 & 0 & 0 & -1.2 \\ -909.7 & -102.7 & -102.7 & -8.4 & -18.5 & 11.4 & -2.5 & 3.1 & -0.5 & 1.2 & -0.4 & 0.7 & 0.2 & -1.3 & -0.1 & 0 & 0.4 & -0.8 \\ -2729 & -146.7 & -146.7 & -16.3 & 34.2 & 16.3 & 0 & 4.2 & 19 & 6.3 & 1 & 1.4 & 3.9 & -2.2 & 0.2 & 0 & 0.8 & -1.4 \\ 0 & -80.7 & 146.7 & 7.3 & -19.6 & 41.6 & -1.8 & 5.1 & -0.8 & 6.3 & -0.4 & 1.1 & 0 & -0.6 & -0.1 & 0.1 & 0.5 & -0.8 \\ -227.4 & -7.3 & 9 & 4.5 & 3 & 4.7 & 1 & 1.2 & 1.6 & 0.9 & 0.2 & 0.2 & -0.1 & -0.6 & 0 & 0 & 0 & -0.2 \\ -227.4 & -34.2 & -9 & -1.5 & -6 & 2.4 & -0.5 & 0.5 & -0.7 & 0.6 & -0.1 & 0.1 & 0 & -0.1 & 0 & 0 & 0.1 & -0.1 \\ -909.7 & -83.1 & -83.1 & -14.1 & 3.5 & -14.4 & -1.1 & -2.7 & 3 & -1.4 & 0 & -0.4 & 1.7 & 0.8 & 0.1 & 0 & 0.3 & 0.3 \\ 909.7 & 83.1 & 83.1 & 3.7 & 8.4 & 2.4 & 0.1 & -1.1 & 0.1 & 0.3 & -0.1 & -0.2 & 0.3 & 0.9 & 0 & 0 & 0.1 & 0.4 \\ -75.8 & -5 & -3.3 & 0.2 & 0.6 & -0.2 & 0.2 & 0 & 0.3 & 0 & 0.1 & 0 & 0 & -0.1 & 0 & 0 & 0 & 0 \\ 50.5 & 3.3 & 3.3 & -0.2 & -0.2 & 0.2 & -0.1 & -0.1 & -0.1 & 0 & 0 & 0 & 0 & 0.1 & 0 & 0 & 0 & 0 \\ -252.7 & -31.6 & -31.6 & -6 & -2.2 & -6.2 & -0.8 & -1.2 & 0 & -1 & -0.1 & -0.2 & 0.6 & 0.4 & 0 & 0 & 0.1 & 0.2 \\ 379 & 47.4 & 31.6 & 3.2 & 6.6 & 1.7 & 0.5 & 0 & 0.7 & 0 & 0.1 & -0.1 & 0.1 & 0.1 & 0 & 0 & 0 & 0.1 \end{pmatrix}$$

$$a = \begin{pmatrix} -0.00579 \\ 0.00051 \\ 0.00177 \\ -0.13783 \\ 0.30742 \\ 0.35994 \\ 3.70675 \\ -0.1374 \\ 0.33852 \\ 0.04234 \\ -36.36436 \\ 0.99672 \\ 0.21519 \\ -6.15058 \\ 114.12614 \\ 77.43345 \\ -36.02243 \\ -15.34699 \end{pmatrix} \text{Degrees of Freedom}$$

A common stress result that is plotted in finite element analysis is von Mises stress. For this, the normal and shear stresses are first defined using Eqs. B-7, A-3, and A-5. The von Mises stress derivation is shown in Eqs. B-45 to B-48.

Normal Stress in the X-Direction

Eq. B-45
$$\sigma_x(x, y, a) = \left[ -D \cdot r'^{-4} \cdot \begin{bmatrix} 0 \\ 0 \\ 0 \\ 0 \\ 2 \cdot r'^3 \\ 2 \cdot r'^3 \cdot v \\ 2 \cdot r'^2 \cdot y \\ 2 \cdot r'^2 \cdot v \cdot x \\ 6 \cdot r'^2 \cdot x \\ 6 \cdot r'^2 \cdot v \cdot y \\ 6 \cdot r' \cdot x \cdot y \\ 6 \cdot r' \cdot v \cdot x \cdot y \\ -6 \cdot r' \cdot (v \cdot x^2 - 2 \cdot x^2 + y^2) \\ -6 \cdot r' \cdot (v \cdot x^2 - 2 \cdot x^2 + y^2) \\ -2 \cdot y \cdot (3 \cdot v \cdot x^2 - 6 \cdot x^2 + y^2) \\ 12 \cdot v \cdot x \cdot y^2 - 6 \cdot x \cdot y^2 - 2 \cdot v \cdot x^3 \\ 20 \cdot x^3 - 30 \cdot x \cdot y^2 - 10 \cdot v \cdot x^3 \\ 20 \cdot v \cdot y^3 - 10 \cdot y^3 - 30 \cdot v \cdot x^2 \cdot y \end{bmatrix}^T \cdot a - \frac{p_z \cdot (v \cdot x^2 + y^2)}{4} \right] \cdot \frac{6}{t^2}$$

$$\sigma_y(x, y, a) = \left[ -D \cdot r'^{-4} \cdot \begin{bmatrix} 0 \\ 0 \\ 0 \\ 0 \\ 2 \cdot r'^3 \cdot v \\ 2 \cdot r'^3 \\ 2 \cdot r'^2 \cdot v \cdot y \\ 2 \cdot r'^2 \cdot x \\ 6 \cdot r'^2 \cdot v \cdot x \\ 6 \cdot r'^2 \cdot y \\ 6 \cdot r' \cdot v \cdot x \cdot y \\ 6 \cdot r' \cdot x \cdot y \\ -6 \cdot r' \cdot (v \cdot y^2 - 2 \cdot v \cdot x^2 + x^2) \\ -6 \cdot r' \cdot (v \cdot y^2 + x^2 - 2 \cdot y^2) \\ 12 \cdot v \cdot x^2 \cdot y - 6 \cdot x^2 \cdot y - 2 \cdot v \cdot y^3 \\ -2 \cdot x \cdot (3 \cdot v \cdot y^2 + x^2 - 6 \cdot y^2) \\ 20 \cdot v \cdot x^3 - 10 \cdot x^2 - 30 \cdot v \cdot x \cdot y^2 \\ 20 \cdot y^3 - 30 \cdot x^2 \cdot y - 10 \cdot v \cdot y^3 \end{bmatrix}^T \cdot a - \frac{p_z \cdot (x^2 + v \cdot y^2)}{4} \right] \cdot \frac{6}{t^2}$$

Eq. B-46

$$T_{xy}(x, y, a) = (1 - v) \cdot \left[ -D \cdot r'^{-4} \cdot \begin{bmatrix} 0 \\ 0 \\ 0 \\ r'^3 \\ 0 \\ 0 \\ 2 \cdot r'^2 \cdot x \\ 2 \cdot r'^2 \cdot y \\ 0 \\ 0 \\ 3 \cdot r' \cdot x^2 \\ 3 \cdot r' \cdot y^2 \\ -12 \cdot r' \cdot x \cdot y \\ -12 \cdot r' \cdot x \cdot y \\ 4 \cdot x^3 - 6 \cdot x \cdot y^2 \\ 4 \cdot y^3 - 6 \cdot x^2 \cdot y \\ -30 \cdot x^2 \cdot y \\ -30 \cdot x \cdot y^2 \end{bmatrix}^T \cdot a - \frac{p_z \cdot x \cdot y}{2} \right] \cdot \frac{6}{t^2} \quad \text{Shear stress}$$

Eq. B-47

$$\sigma_{von}(x, y, a) = \frac{\sqrt{2}}{2} \cdot \sqrt{\sigma_x(x, y, a)^2 + (\sigma_x(x, y, a) - \sigma_y(x, y, a))^2 \ldots + \sigma_y(x, y, a)^2 + 6 \cdot T_{xy}(x, y, a)^2} \quad \text{Von Mises stress}$$

Eq. B-48

Normal Stress in the Y-Direction

Figure 16:
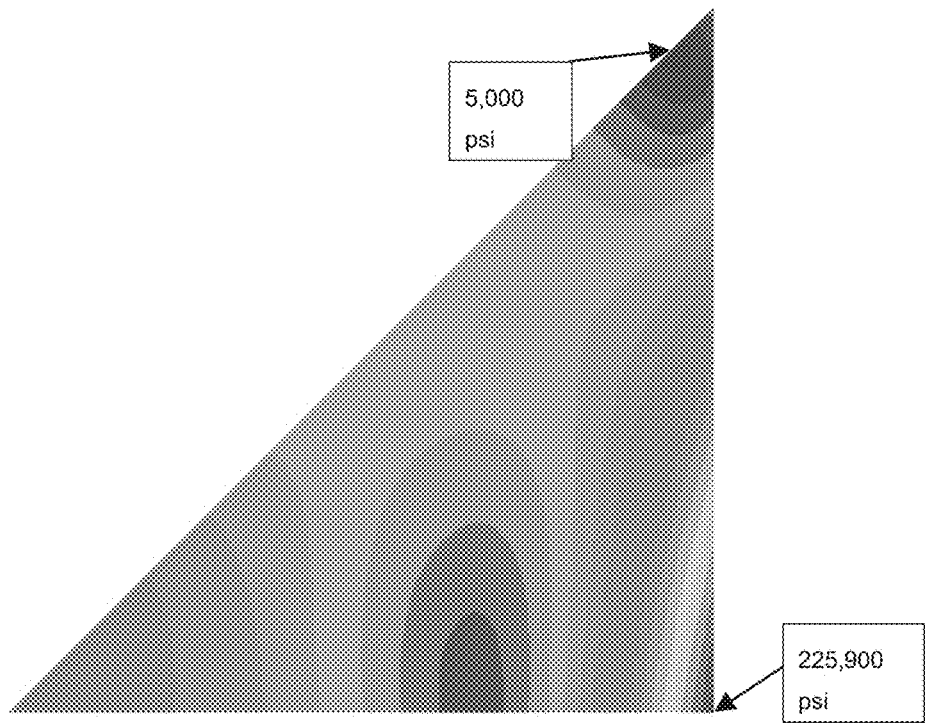
FIG. 16 is a Von Mises stress plot for the element of FIG. 14 evaluated according to the principles of the present disclosure.

FIG. 16 shows a gradient plot of the resulting von Mises stress. The contours range from the highest values of the von Mises stress (225,900 psi) at the lower right vertex of the triangle to the lowest values of the von Mises stress (5,000 psi) at the upper right vertex of the triangle. The theoretical exact solution for this problem is for the maximum von Mises stress to be 205,700 psi. Consequently with only one element, the new method has come within 10% of the true maximum displacement value.

Comparison with Traditional Finite Element Analysis

For comparison, the results of the new method are compared to four test models that were run using traditional finite element analysis. The shell elements used for comparison are based on a similar governing equation to that considered for the governing equation and theoretical value (as evidenced by the convergence toward the theoretical solution in the high degree of freedom models). For example, Abaqus finite element analysis software from Dassault Systemes (such as Abaqus version 6.9-2) considers additional governing equation components such as shear deformation in some shell elements. The elements used for this figure comparison are STRI65 for the parabolic triangular shell elements and S4 for the linear quadrilateral elements.

Given the 18 degree of freedom new method triangular shell developed for this example, parabolic triangular shell elements make appropriate comparison elements. By itself, a parabolic triangular shell element has 6 nodes with three translations and three rotations per node. This results in 36 degrees of freedom. Restraints are added to the model to remove degrees of freedom that allow in plane displacement and out of plane rotation (which are not considered for the example new method triangular element). This reduces the degrees of freedom to 3 degrees of freedom per node giving the element 18 degrees of freedom.

It is difficult to make an exact comparison between the new method and traditional finite element analysis due to the new method having degrees of freedom on the element where the traditional finite element analysis has degrees of freedom on the nodes. When the 6-node parabolic triangular is put into a mesh, the degrees of freedom in traditional finite element analysis are reduced on a per element basis because nodes are shared between elements. Consequently, comparisons will be made based on degrees of freedom in the model. This is found as 18 degrees of freedom multiplied by 8 elements for the new method model. It is found as three degrees of freedoms multiplied by the number of nodes for the traditional finite element analysis models.

FIGS. 17A-21A show von Mises stress when performing finite element analysis using the five models used for comparison purposes. The units are in psi (pounds per square inch). FIGS. 17B-21B show displacement magnified by 10× for each of the five models. The units are in inches.

Figure 17A:
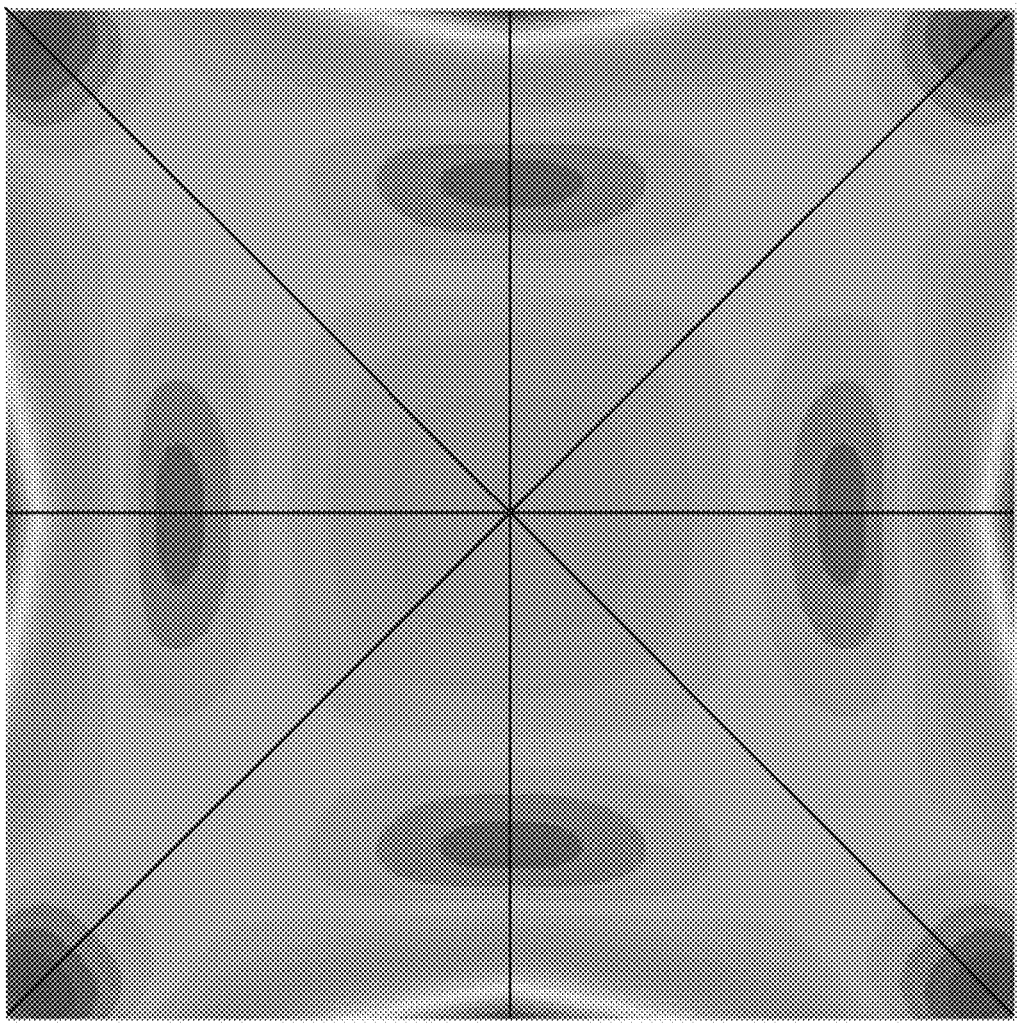
FIGS. 17A and 17B are Von Mises stress and displacement plots, respectively, for a triangular element according to the principles of the present disclosure.
Figure 17B:
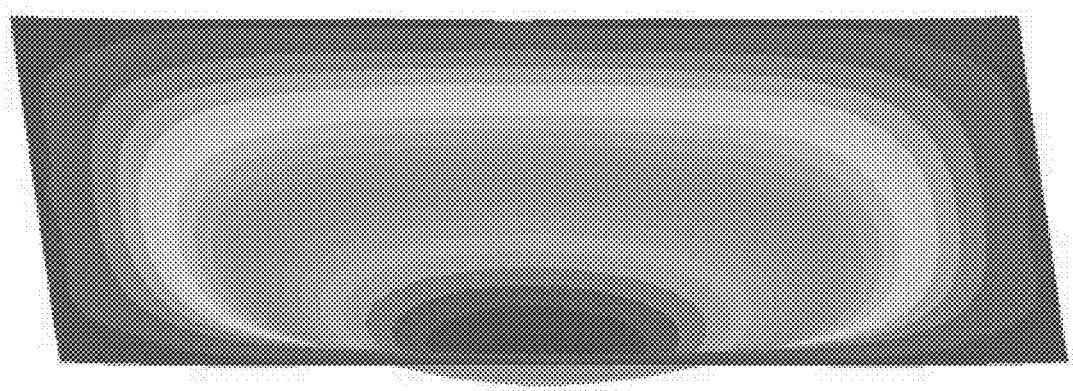

FIGS. 17A-17B correspond to the new method triangular element. As discussed earlier, the new method triangular element is modeled with symmetric restraints so it is appropriate to mirror it and present it as an eight element model with each element having 18 degrees of freedom. The center edge von Mises stress is 225,900 psi and the center displacement is −0.0868 in.

Figure 18A:
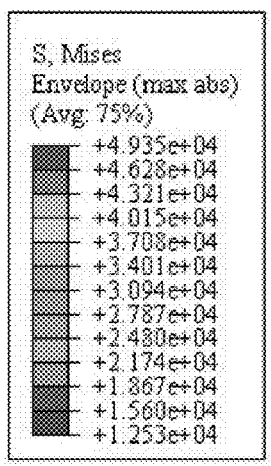
FIGS. 18A and 18B are Von Mises stress and displacement plots, respectively, for a traditional finite element analysis with 8 parabolic triangular elements.
Figure 18A:
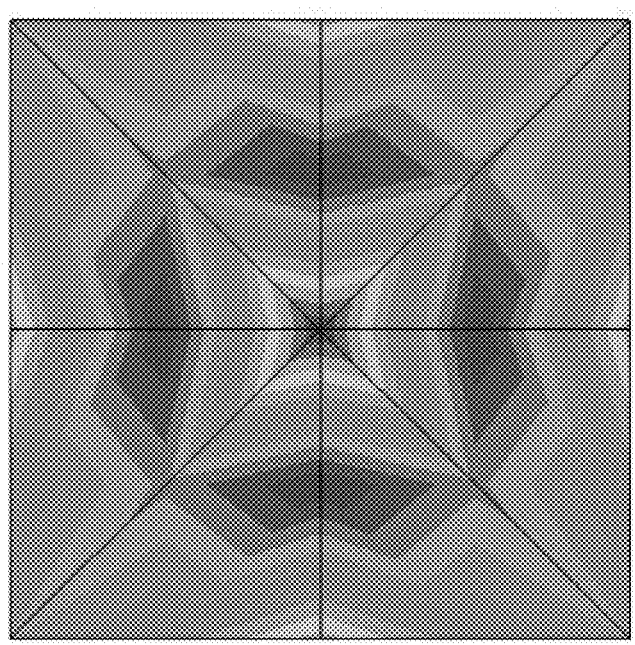
Figure 18B:
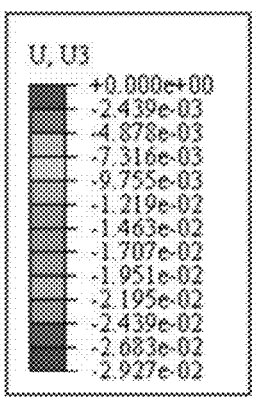
Figure 18B:
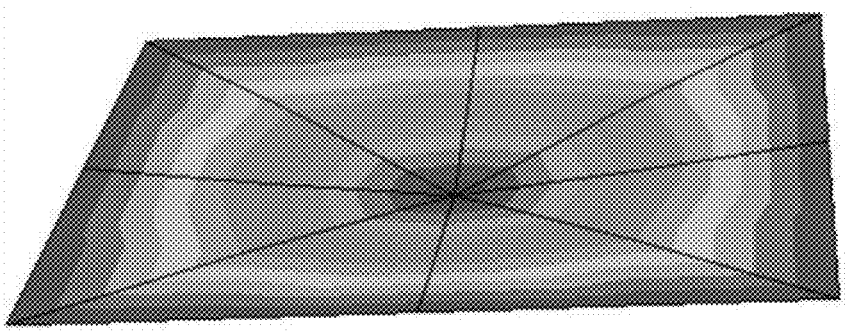
Figure 19A:
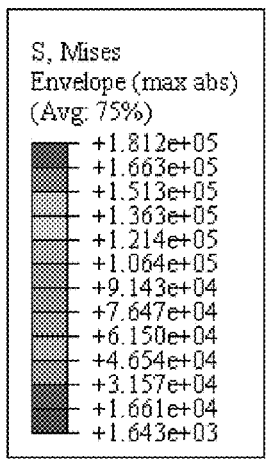
FIGS. 19A and 19B are Von Mises stress and displacement plots, respectively, for a traditional finite element analysis with 64 parabolic triangular elements.
Figure 19A:
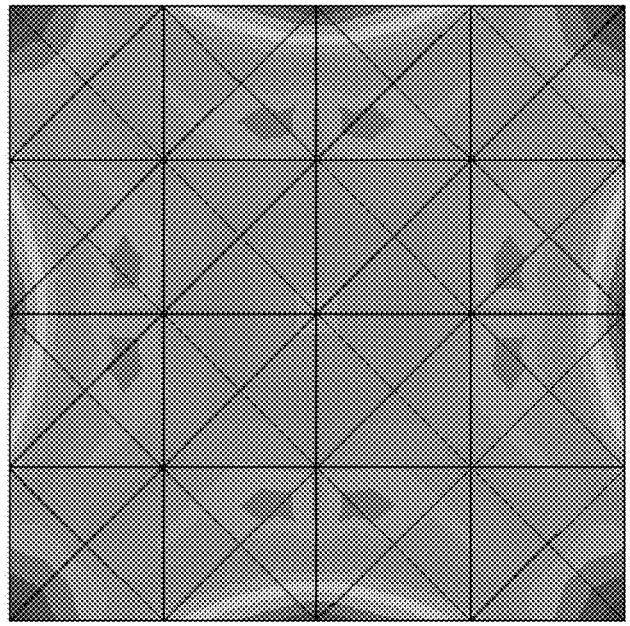
Figure 19B:
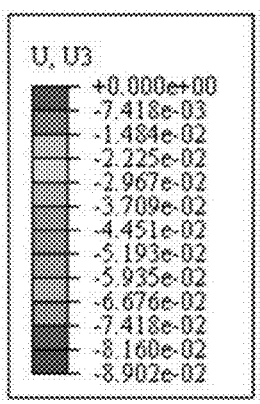
Figure 19B:
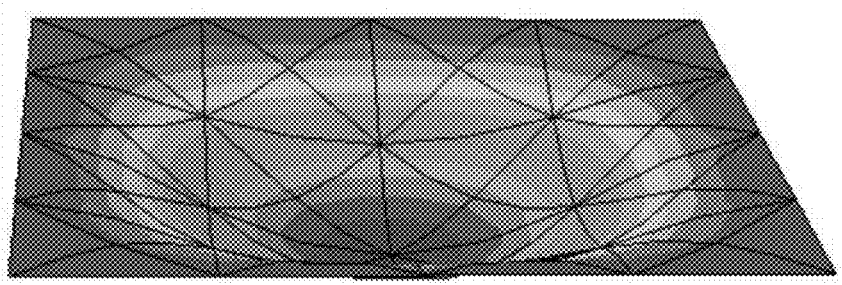
Figure 20A:
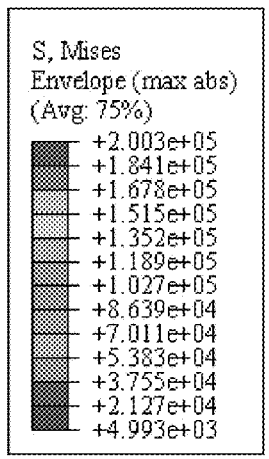
FIGS. 20A and 20B are Von Mises stress and displacement plots, respectively, for a traditional finite element analysis with 256 parabolic triangular elements.
Figure 20A:
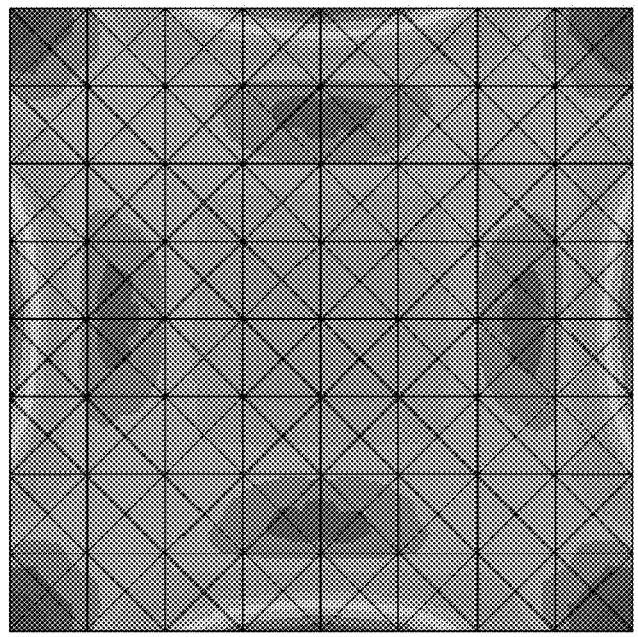
Figure 20B:
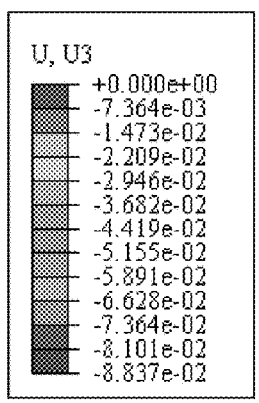
Figure 20B:
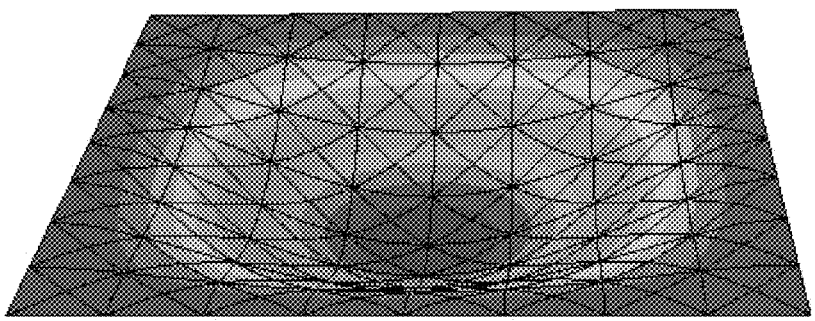
Figure 21A:
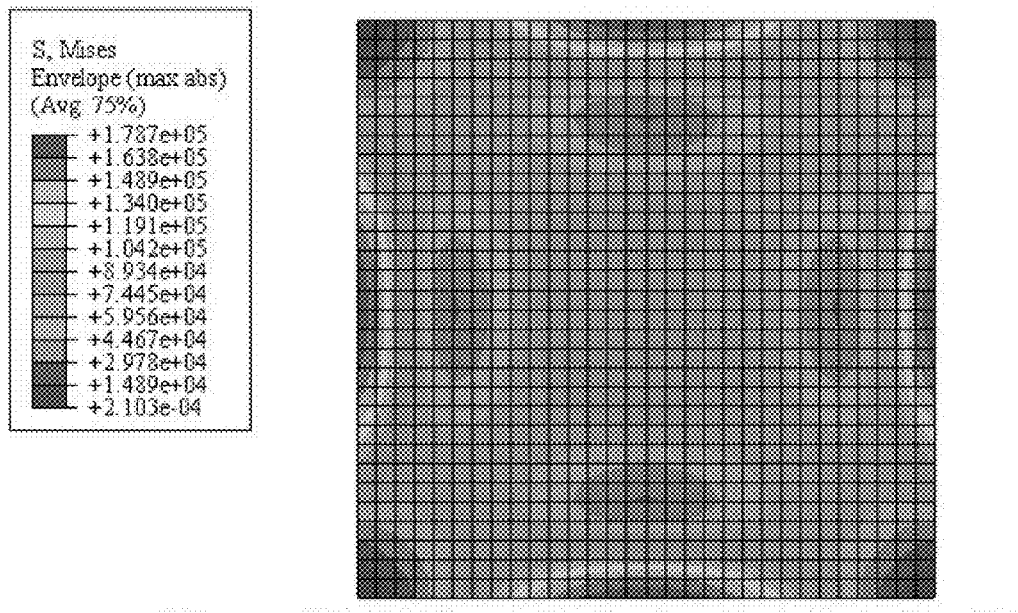
FIGS. 21A and 21B are Von Mises stress and displacement plots, respectively, for a traditional finite element analysis with 900 linear quadrilateral elements.
Figure 21B:
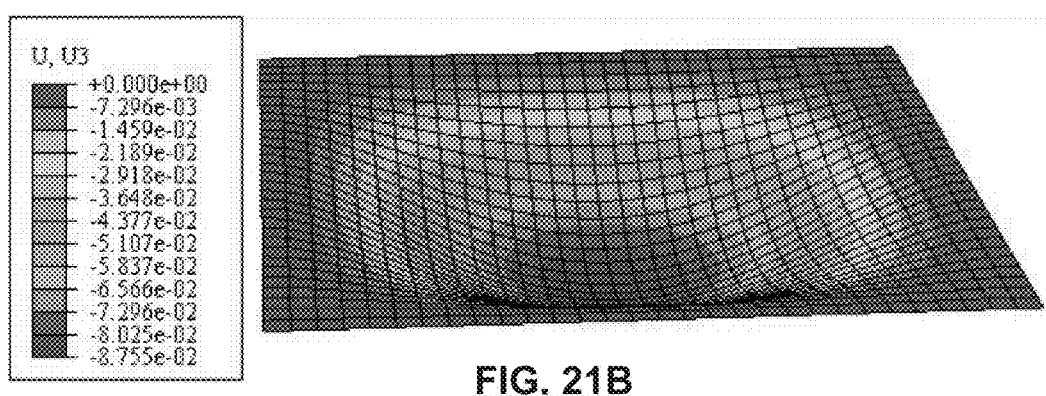

FIGS. 18A-18B correspond to a traditional finite element analysis with 8 parabolic triangular elements. This is intended to show the closest comparison between traditional finite element analysis and the new method. In this case, the traditional analysis is at some disadvantage as it has less degrees of freedom (as discussed above). FIGS. 19A-19B correspond to a traditional finite element analysis with 64 parabolic triangular elements. This is similar to the model in FIGS. 18A-18B except there are many more degrees of freedom. This is to help establish the relative accuracy of the new method. FIGS. 20A-20B correspond to a traditional finite element analysis with 256 parabolic triangular elements. This is to help demonstrate if this traditional finite element shell formulation is converging closely to the theoretical solution. (This is motivated by the possibility that the governing equation for this traditional finite element shell formulation could be different enough to make the comparison not appropriate.) FIGS. 21A-21B correspond to a traditional finite element analysis with 900 linear quadrilateral elements. This is shown for information given that this is probably the most commonly used element to solve this problem in a traditional finite element analysis.

Table B-2 shows a summary of results for stress and displacement (with percent error from theoretical).

Considering Table B-2, the new method performed very well relative to the traditional finite element analysis when comparing percent error and degrees of freedom. Comparing stresses between the new model and the parabolic triangular 64 element model, the new method has less than ⅓ the degrees of freedom yet it still produces a significantly more accurate result. Considering the parabolic triangular 256 element model, the stress results do appear to be converging close to the theoretical value so the comparison with the new method is appropriate. Additionally, the stress results show how the traditional finite element analysis produces relatively stiff results that tend to underestimate stress. Comparing stresses between the new method and the linear quadrilateral 900 element model, the new method produces a significantly more accurate result with considerably less degrees of freedom. The displacements in the traditional finite element analysis appear less predictable than the stresses. The parabolic triangular 256 element appears to be converging to a higher displacement value than the theoretical value (which could be explained with saying that the parabolic triangles are formulated to a slightly different governing equation). Even if this is accepted as accurate, the expectation would be that, like stress, the displacements should tend to under predict the theoretical displacements but get more accurate as the mesh is refined. This is true of all the results except the parabolic triangular 64 element model which predicts a higher displacement than the parabolic triangular 256 element model.

As discussed in Section A, the boundary conditions (at the nodes) being exactly met in traditional finite element analysis reduces the ability of the shape functions to accurately predict stresses/strains in the element. The result is a relatively stiff response that tends to under predict the stresses/strains. In the new method, neither boundary conditions nor stresses/strains in the element are enforced to be exactly met. Consequently, energy optimization can better utilize the degrees of freedom to predict both boundary conditions and stresses/strains.

Discussion

This example showed the formulation for a simple single element problem with straight edges. The example problem element only had three edges, but this same formulation could be used on an element with any number of straight edges.

The biggest negative shown in the example problem was that the value of the length constant (from Eq. B-7) could be chosen to make the matrix inversion unstable (though matrix inversion was stable over a large range of values). The most likely solution to this is just to make a wise choice relative

|  | Theoretical values[1] | New model[2] | Parabolic triangular 8 element[3] | Parabolic triangular 64 element | Parabolic triangular 256 element | Linear quadrilateral 900 element |
| --- | --- | --- | --- | --- | --- | --- |
| Maximum von Mises stress [ksi] | 205.7 | 225.9 (+9.8%) | 41.6 (−79.8%) | 181.2 (−11.9%) | 200.3 (−2.6%) | 178.7 (−13.1%) |
| Maximum displacement [in] | 0.0866 | 0.0868 (+0.3%) | 0.02927 (−66.2%) | 0.08902 (+2.8%) | 0.08837 (+2.1%) | 0.08755 (+1.1%) |
| Degrees of freedom | N/A | 144 | 75 | 435 | 1635 | 2883 |

[1]The theoretical value is 230.8 ksi, but this is only in one direction. Converting it to von Mises stress produces the 205.7 ksi value.
[2]The test model was run with one 18 degree of freedom element and symmetry. The number of degrees of freedom for the test model is shown as 144 to reflect the degrees of freedom as if it were an 8 element model. This is the relevant number of degrees of freedom for comparison with the other models.
[3]The high stress should occur in the center of an edge. The 8 parabolic triangle element model showed the high stress in the center of the plate. The table value is from the center of an edge.

to length constant. More study will be done on this and how well conditioned the matrix is for inversion in general.

The biggest positive shown in this example was the superior accuracy of the new method when compared to traditional finite element analysis. Also, all of the traditional finite element results underestimated the actual stress. This is to be expected based on the formulation of traditional finite element analysis. In typical stress analysis, underestimating the stress is problematic because the error reduces the safety factor of the evaluation. The new method tends to overestimate the actual stress which tends to increase the safety factor. In both cases the error can be reduced with mesh refinement. In the linear quadrilateral element solution with 900 elements, the stress was still significantly underestimated (and this is a commonly used element for stress analysis). Consequently, this example tends to show that much more mesh refinement is needed with traditional finite element analysis than the new method for two reasons. First, the new method is demonstrating much better accuracy so it would require less mesh refinement. Second, the error in traditional finite element analysis tends to not be conservative. Consequently, greater mesh refinement should be done in traditional finite element analysis to manage the non-conservative nature of the results.

The evaluation is described in several portions. The first portion (Displacement Equation) shows the displacement equation in a form useful for this example problem. The second portion (Area Integrals for a Circular Edge) shows an approach to convert the area integrals (from Section A, Eqs. A-38 and A-40) into an algebraic form. The third portion (Edge Integrals for a Circular Edge) shows an approach to convert the edge integrals (from Section A, Eq. A-47) into an algebraic form. The fourth portion (Model Formulation) defines values for material properties, element geometry, boundary conditions, and the algebraic forms of the area and edge integrals. The fifth portion (Rigid Body Motions) defines an approach to address rigid body motions. The approach used in the example uses springs to enforce element edge displacements with the displacements defined by the boundary conditions. The sixth portion (Degrees of Freedom and Results Plots) solves the energy optimization (from Section A, Eq. A-51) and uses the results to plot element displacement and stress. The seventh portion (Comparison with Traditional Finite Element Analysis) compares the new method displacement and stress results with the exact solution and four traditional finite element models. The evaluation results are discussed in an eighth portion (Discussion).

The test model for the example problem is a thin plate that is 2.5 inches in diameter by 0.1 inches thick. All of the edges are fixed and there is a 300 psi pressure applied evenly over the surface. The material properties include a Young's modulus of 3.0e7 psi and a Poisson's ratio of 0.3. Table C-1 provides a comparison summary of the theoretical, new model, and traditional finite element results (showing percent error with respect to theoretical).

|  | Theoretical values[1] | New model[2] | Parabolic triangular 8 element[3] | Parabolic triangular 48 element[3] | Parabolic triangular 462 element[3] | Linear quadrilateral 950 element[3] |
| --- | --- | --- | --- | --- | --- | --- |
| Maximum von Mises stress [ksi] | 31.25 | 31.25 (+0.0%) | 28.26 (−9.6%) | 31.19 (−0.2%) | 31.16 (−0.3%) | 28.49 (−8.8%) |
| Maximum displacement [in] | 0.004166 | 0.004166 (+0.0%) | 0.005563 (+33.5%) | 0.004462 (+7.1%) | 0.004322 (+3.8%) | 0.004282 (+2.8%) |
| Degrees of freedom | N/A | 144 | 75 | 339 | 2919 | 2997 |

[1]The theoretical value is 35.16 ksi, but this is only in one direction. Converting it to von Mises stress produces the 31.25 ksi value.
[2]The test model was run with one 18 degree of freedom element and symmetry. The degrees of freedom for the test model is shown as 144 to reflect the degrees of freedom as if it were an 8 element model. This is the relevant number of degrees of freedom for comparison with the other models.
[3]Because the high stress should occur continuously along the edge, the maximum von Mises stress reported is the average along the model edge.

Section C
Outline

In this Section, the algebraic equations for evaluating an element with circular sides are developed (and the straight side evaluation developed in Section B will also be used). Second, a simple pie shaped element is evaluated to find displacement and stress results. As validation, the element is defined with geometry, loading, and boundary conditions to match a well-known problem that has an exact solution. Third, the results are compared with the exact solution and traditional finite element results.

Displacement Equation

The displacement equation used for this evaluation is the same as that shown in Section B (Eq. B-7) except it is converted to polar coordinates with a Cartesian coordinates offset (as shown in Eq. C-1).

Defining: $x = r \cdot \cos(\theta) + x_o$  $y = r \cdot \sin(\theta) + y_o$

Where:

$r$—A radial position $\theta$—A radial position $x_o$—Offset in the x-direction for the circle center
$y_o$—Offset in the y-direction for the circle center $$w_r = \begin{Bmatrix} a_0 \\ a_1 \\ a_2 \\ a_3 \\ a_4 \\ a_5 \\ a_6 \\ a_7 \\ a_8 \\ a_9 \\ a_{10} \\ a_{11} \\ a_{12} \\ a_{13} \\ a_{14} \\ a_{15} \\ a_{16} \\ a_{17} \end{Bmatrix}^T \cdot \begin{Bmatrix} 1 \cdot r' \\ (r \cdot \cos(\theta) + x_o) \\ (r \cdot \sin(\theta) + y_o) \\ (r \cdot \cos(\theta) + x_o) \cdot (r \cdot \sin(\theta) + y_o) \cdot r'^{-1} \\ (r \cdot \cos(\theta) + x_o)^2 \cdot r'^{-1} \\ (r \cdot \sin(\theta) + y_o)^2 \cdot r'^{-1} \\ (r \cdot \cos(\theta) + x_o)^2 \cdot (r \cdot \sin(\theta) + y_o) \cdot r'^{-2} \\ (r \cdot \cos(\theta) + x_o) \cdot (r \cdot \sin(\theta) + y_o) \cdot r'^{-2} \\ (r \cdot \cos(\theta) + x_o)^3 \cdot r'^{-2} \\ (r \cdot \sin(\theta) + y_o)^3 \cdot r'^{-2} \\ (r \cdot \cos(\theta) + x_o)^3 \cdot (r \cdot \sin(\theta) + y_o) \cdot r'^{-3} \\ (r \cdot \cos(\theta) + x_o) \cdot (r \cdot \sin(\theta) + y_o)^3 \cdot r'^{-3} \\ [(r \cdot \cos(\theta) + x_o)^4 - 3 \cdot (r \cdot \cos(\theta) + x_o)^2 \cdot (r \cdot \sin(\theta) + y_o)2] \cdot r'^{-3} \\ [(r \cdot \sin(\theta) + y_o)^4 - 3 \cdot (r \cdot \cos(\theta) + x_o)^2 \cdot (r \cdot \sin(\theta) + y_o)^2] \cdot r'^{-3} \\ [(r \cdot \cos(\theta) + x_o)^4 \cdot (r \cdot \sin(\theta) + y_o) - (r \cdot \cos(\theta) + x_o)^2 \cdot (r \cdot \sin(\theta) + y_o)^3] \cdot r'^{-4} \\ [(r \cdot \cos(\theta) + x_o) \cdot (r \cdot \sin(\theta) + y_o)^4 - (r \cdot \cos(\theta) + x_o)^3 \cdot (r \cdot \sin(\theta) + y_o)^2] \cdot r'^{-4} \\ [(r \cdot \cos(\theta) + x_o)^5 - 5 \cdot (r \cdot \cos(\theta) + x_o)^3 \cdot (r \cdot \sin(\theta) + y_o)^2] \cdot r'^{-4} \\ [(r \cdot \sin(\theta) + y_o)^5 - 5 \cdot (r \cdot \cos(\theta) + x_o)^2 \cdot (r \cdot \sin(\theta) + y_o)^3] \cdot r'^{-4} \end{Bmatrix} \ldots +$$

$$+ \frac{p_z}{8 \cdot D} \cdot (r \cdot \cos(\theta) + x_O)^2 \cdot (r \cdot \sin(\theta) + y_o)^2 \quad \text{Eq. C-1}$$

Displacement equation for a circular edge

Use of Eq. C-1 ensures consistency with the straight edge evaluation so that a single element may include both straight and circular edges without consequence. Also, this ensures that the governing equation (Eq. B-2) is still being met. (It should be noted that when processing results for plotting, either coordinate system may be used at any point in the element.)

The other displacement and load equations are shown below in polar coordinates (Eqs. C-2 and C-3). These are similar to those shown in Section A (Eqs. A-45 and A-46). (A more thorough discussion of Eqs. C-2 and C-3 can be found in Ugural, 1999.)

$$\theta_r = \frac{\partial}{\partial r} w_r \quad \text{Eq. C-2}$$

Bending rotation in polar coordinates $$\phi_r = \frac{1}{r} \cdot \frac{\partial}{\partial \theta} w_r$$

Torsional rotation in polar coordinates $$P_r = -D \cdot \frac{\partial}{\partial r} \left( \frac{\partial^2}{\partial r^2} w_r + \frac{1}{r} \cdot \frac{\partial}{\partial r} w_r + \frac{1}{r^2} \cdot \frac{\partial^2}{\partial \theta^2} w_r \right) \quad \text{Eq. C-3}$$

Shear force in polar coordinates $$M_r = -D \cdot \left[ \frac{d^2}{dr^2} w_r + v \cdot \left( \frac{1}{r} \cdot \frac{\partial}{\partial r} w_r + \frac{1}{r^2} \cdot \frac{d^2}{d\theta^2} w_r \right) \right]$$

Bending moment in polar coordinates $$T_r = -D \cdot (1-v) \cdot \left( \frac{1}{r} \cdot \frac{\partial}{\partial r} \frac{\partial}{\partial \theta} w_r - \frac{1}{r^2} \cdot \frac{\partial}{\partial \theta} w_r \right)$$

Torsional moment in polar coordinates

Area integrals equivalent to those in Section A (Eqs. A-38 and A-40) can also be shown in polar coordinates as in Eqs. C-4 and C-5.

$$U_c = \frac{D}{2} \cdot \int_{\theta_0}^{\theta_1} \int_0^r \begin{bmatrix} \left( \frac{d^2}{dr^2} w_r + \frac{1}{r} \cdot \frac{\partial}{\partial r} w_r + \frac{1}{r^2} \cdot \frac{d^2}{d\theta^2} w_r \right)^2 \ldots + - \\ 2 \cdot (1-v) \cdot \frac{d^2}{dr^2} w_r \cdot \\ \left( \frac{1}{r} \cdot \frac{\partial}{\partial r} w_r + \frac{1}{r^2} \cdot \frac{d^2}{d\theta^2} w_r \right) \ldots + \\ 2 \cdot (1-v) \cdot \left( \frac{1}{r} \frac{\partial}{\partial r} \frac{\partial}{\partial \theta} w_r - \frac{1}{r^2} \cdot \frac{\partial}{\partial \theta} w_r \right)^2 \end{bmatrix} \cdot r dr d\theta \quad \text{Eq. C-4}$$

Strain energy for a circular, pie shaped element $$W_{cp} = \int_{\theta_0}^{\theta_1} \int_0^r w_r \cdot p_z \cdot r dr d\theta \quad \text{Eq. C-5}$$

External work generated by the pressure load for a circular, pie shaped element

Where: $\theta_0$ – Starting angle $\theta_1$ – Ending angle

Area Integrals for a Circular Edge

The strain energy for the element is given in Eq. C-4 and the external work due to the pressure load is given in Eq. C-5. Given these equations, there are two area integrals to be addressed in the total energy equation for the element (Eq. A-48 or A-49) and the energy optimization (Eq. A-49). The energy optimization lends itself to be broken into pieces, evaluated to form algebraic solutions, and then summed back together. This process for a circular edge is very similar to that for a straight edge. (Consequently, much of the process will be abbreviated.) When broken out the of the energy optimization, the strain energy and the external work due to the pressure load appear as in Eqs. C-6 and C-7.

$$U_{c_i} = \frac{\partial}{\partial a_i}$$

Eq. C-6

$$\left[\frac{D}{2} \cdot \int_{\theta_0}^{\theta_1} \int_0^r \begin{bmatrix} \left(\frac{d^2}{dr^2} w_r + \frac{1}{r} \cdot \frac{\partial}{\partial r} w_r + \frac{1}{r^2} \cdot \frac{d^2}{d\theta^2} w_r\right)^2 \ldots + - \\ 2 \cdot (1-v) \cdot \frac{d^2}{dr^2} w_r \cdot \\ \left(\frac{1}{r} \cdot \frac{\partial}{\partial r} w_r + \frac{1}{r^2} \cdot \frac{d^2}{d\theta^2} w_r\right) \ldots + \\ 2 \cdot (1-v) \cdot \left(\frac{1}{r} \frac{\partial}{\partial r} \frac{\partial}{\partial \theta} w_r - \frac{1}{r^2} \cdot \frac{\partial}{\partial \theta} w_r\right)^2 \end{bmatrix} \cdot rdrd\theta \right]$$

Strain energy for a circular, pie shaped element $$W_{cp_i} = \frac{\partial}{\partial a_i}\left(\int_{\theta_0}^{\theta_1} \int_0^r w_r \cdot p_z \cdot rdrd\theta\right)$$

Eq. C-7

External work generated by the pressure load for a circular, pie shaped element

Considering the strain energy (Eq. C-6) can produce a very large and complex algebraic form, it is desirable to find ways to make this process as easy and efficient as possible. It is clear that the strain energy equation will result in a symmetric array multiplied by the degree of freedom vector plus a vector related to the external pressure terms in the displacement equation. Also apparent is that once the partial derivative is applied, all of the degrees of freedom will have a power of 1. These observations are useful in simplifying the strain enemy integral (as shown in Eqs. C-8 to C-10).

Defining $d_1 = \frac{\partial^2}{\partial r^2} w_r + \frac{1}{r} \cdot \frac{\partial}{\partial r} w_r + \frac{1}{r^2} \cdot \frac{\partial^2}{\partial \theta^2} w_r,$ Eq. C-8

$d_2 = \frac{\partial^2}{\partial r^2} w_r, d_3 = \frac{1}{r} \cdot \frac{\partial}{\partial r} w_r + \frac{1}{r^2} \cdot \frac{\partial^2}{\partial \theta^2} w_r,$ and $d_4 = \frac{1}{r} \cdot \frac{\partial}{\partial r} \frac{\partial}{\partial \theta} w_r - \frac{1}{r^2} \cdot \frac{\partial}{\partial \theta} w_r$ Introducing Eq. C-8 into Eq. C-7 and Rearranging:

$$U_{c_i} = \frac{\partial}{\partial a_i}\left[\frac{D}{2} \cdot \int_{\theta_0}^{\theta_1} \int_0^r [d_1^2 - 2 \cdot (1-v) \cdot d_2 \cdot d_3 + 2 \cdot (1-v) \cdot d_4^2] \cdot rdrd\theta\right]$$

Eq. C-9

$$U_{c_i} = \frac{D}{2} \cdot \int_{\theta_0}^{\theta_1} \int_0^r \frac{\partial}{\partial a_i}[d_1^2 - 2 \cdot (1-v) \cdot d_2 \cdot d_3 + 2 \cdot (1-v) \cdot d_4^2] \cdot rdrd\theta$$

$$U_{c_i} = \frac{D}{2} \cdot \int_{\theta_0}^{\theta_1} \int_0^r \begin{bmatrix} 2 \cdot d_1 \cdot \frac{\partial}{\partial a_i} d_1 - 2 \cdot (1-v) \cdot \\ \left(d_2 \cdot \frac{\partial}{\partial a_i} d_3 + d_3 \cdot \frac{\partial}{\partial a_i} d_2\right) \ldots + \\ 2 \cdot (1-v) \cdot \left(2 \cdot d_4 \cdot \frac{\partial}{\partial a_i} d_4\right) \end{bmatrix} \cdot rdrd\theta$$

The integral in Eq. C-9 represents one row that is to be summed into the $U_m$ array (in Eq. A-51) and one position that is to be summed into the $U_b$ vector (in Eq. A-51). Considering the portion that is to be summed into the $U_m$ array (in Eq. A-51), a further definition can be made to identify each position in the array (as shown in Eq. C-10).

$$U_{c_{i,j}} =$$

Eq. C-10

$$\frac{D}{2} \cdot \int_{\theta_0}^{\theta_1} \int_0^r \begin{bmatrix} 2 \cdot d_{1_j} \cdot \frac{\partial}{\partial a_i} d_1 - 2 \cdot (1-v) \cdot \\ \left(d_{2_j} \cdot \frac{\partial}{\partial a_i} d_3 + d_{3_j} \cdot \frac{\partial}{\partial a_i} d_2\right) \ldots + \\ 2 \cdot (1-v) \cdot \left(2 \cdot d_{4_j} \cdot \frac{\partial}{\partial a_i} d_4\right) \end{bmatrix} \cdot rdrd\theta$$

Equation to find array terms

Eq. C-10 identifies the term in the array on the ith row and jth column. Definitions are made for all of the array positions using Eq. C-10. Considering that there is a limited number of possible polynomial expressions (given Eqs. C-8 and C-10), a generalized representation can be defined (as shown in Eqs. C-11 and C-12).

Eq. C-11

$$d_{1_j} \text{ or } d_{2_j} \text{ or } d_{3_j} \text{ or } d_{4_j} = \begin{pmatrix} \alpha_0 \\ \alpha_1 \\ \alpha_2 \\ \alpha_3 \\ \alpha_4 \\ \alpha_5 \\ \alpha_6 \\ \alpha_7 \\ \alpha_8 \\ \alpha_9 \\ \alpha_{10} \\ \alpha_{11} \\ \alpha_{12} \\ \alpha_{13} \\ \alpha_{14} \\ \alpha_{15} \\ \alpha_{16} \\ \alpha_{17} \\ \alpha_{18} \\ \alpha_{19} \\ \alpha_{20} \end{pmatrix}^T \cdot \begin{bmatrix} 1 \\ r \cdot \sin(\theta) \\ r \cdot \cos(\theta) \\ (r \cdot \sin(\theta))^2 \\ r \cdot \sin(\theta) \cdot (r \cdot \cos(\theta)) \\ (r \cdot \cos(\theta))^2 \\ (r \cdot \sin(\theta))^3 \\ (r \cdot \sin(\theta))^2 \cdot (r \cdot \cos(\theta)) \\ ((r \cdot \sin(\theta) \cdot (r \cdot \cos(\theta)))^2 \\ (r \cdot \cos(\theta))^3 \\ (r \cdot \sin(\theta))^4 \\ (r \cdot \sin(\theta))^3 \cdot (r \cdot \cos(\theta)) \\ (r \cdot \sin(\theta))^2 \cdot (r \cdot \cos(\theta))^2 \\ r \cdot \sin(\theta) \cdot (r \cdot \cos(\theta))^3 \\ (r \cdot \cos(\theta))^4 \\ (r \cdot \sin(\theta))^5 \\ (r \cdot \sin(\theta))^4 \cdot (r \cdot \cos(\theta)) \\ (r \cdot \sin(\theta))^3 \cdot (r \cdot \cos(\theta))^2 \\ (r \cdot \sin(\theta))^2 \cdot (r \cdot \cos(\theta))^3 \\ r \cdot \sin(\theta) \cdot (r \cdot \cos(\theta))^4 \\ (r \cdot \cos(\theta))^5 \end{bmatrix}$$

and $$\frac{\partial}{\partial a_i} d_1 \text{ or } \frac{\partial}{\partial a_i} d_2 \text{ or } \frac{\partial}{\partial a_i} d_3 \text{ or } \frac{\partial}{\partial a_i} d_4 = \begin{pmatrix} \beta_0 \\ \beta_1 \\ \beta_2 \\ \beta_3 \\ \beta_4 \\ \beta_5 \\ \beta_6 \\ \beta_7 \\ \beta_8 \\ \beta_9 \\ \beta_{10} \\ \beta_{11} \\ \beta_{12} \\ \beta_{13} \\ \beta_{14} \\ \beta_{15} \\ \beta_{16} \\ \beta_{17} \\ \beta_{18} \\ \beta_{19} \\ \beta_{20} \end{pmatrix}^T \cdot \begin{bmatrix} 1 \\ r \cdot \sin(\theta) \\ r \cdot \cos(\theta) \\ (r \cdot \sin(\theta))^2 \\ r \cdot \sin(\theta) \cdot (r \cdot \cos(\theta)) \\ (r \cdot \cos(\theta))^2 \\ (r \cdot \sin(\theta))^3 \\ (r \cdot \sin(\theta))^2 \cdot (r \cdot \cos(\theta)) \\ r \cdot \sin(\theta) \cdot (r \cdot \cos(\theta))^2 \\ (r \cdot \cos(\theta))^3 \\ (r \cdot \sin(\theta))^4 \\ (r \cdot \sin(\theta))^3 \cdot (r \cdot \cos(\theta)) \\ (r \cdot \sin(\theta))^2 \cdot (r \cdot \cos(\theta))^2 \\ r \cdot \sin(\theta) \cdot (r \cdot \cos(\theta))^3 \\ (r \cdot \cos(\theta))^4 \\ (r \cdot \sin(\theta))^5 \\ (r \cdot \sin(\theta))^4 \cdot (r \cdot \cos(\theta)) \\ (r \cdot \sin(\theta))^3 \cdot (r \cdot \cos(\theta))^2 \\ (r \cdot \sin(\theta))^2 \cdot (r \cdot \cos(\theta))^3 \\ r \cdot \sin(\theta) \cdot (r \cdot \cos(\theta))^4 \\ (r \cdot \cos(\theta))^5 \end{bmatrix}$$

Where $\alpha_0$-$\alpha_{20}$ and $\beta_0$-$\beta_{20}$ represent possible definitions for the constants in Eq. C-10.

Since Eq. C-10 can represent all possible outcomes for Eq. C-10, all of the terms can be evaluated with a single generalized integration (Eq. C-12).

Eq. C-12

$$Int_c = \int_{\theta_0}^{\theta_1} \int_0^r \left( \begin{pmatrix} \alpha_0 \\ \alpha_1 \\ \alpha_2 \\ \alpha_3 \\ \alpha_4 \\ \alpha_5 \\ \alpha_6 \\ \alpha_7 \\ \alpha_8 \\ \alpha_9 \\ \alpha_{10} \\ \alpha_{11} \\ \alpha_{12} \\ \alpha_{13} \\ \alpha_{14} \\ \alpha_{15} \\ \alpha_{16} \\ \alpha_{17} \\ \alpha_{18} \\ \alpha_{19} \\ \alpha_{20} \end{pmatrix}^T \cdot \begin{bmatrix} 1 \\ r \cdot \sin(\theta) \\ r \cdot \cos(\theta) \\ (r \cdot \sin(\theta))^2 \\ r \cdot \sin(\theta) \cdot (r \cdot \cos(\theta)) \\ (r \cdot \cos(\theta))^2 \\ (r \cdot \sin(\theta))^3 \\ (r \cdot \sin(\theta))^2 \cdot (r \cdot \cos(\theta)) \\ r \cdot \sin(\theta) \cdot (r \cdot \cos(\theta))^2 \\ (r \cdot \cos(\theta))^3 \\ (r \cdot \sin(\theta))^4 \\ (r \cdot \sin(\theta))^3 \cdot (r \cdot \cos(\theta)) \\ (r \cdot \sin(\theta))^2 \cdot (r \cdot \cos(\theta))^2 \\ r \cdot \sin(\theta) \cdot (r \cdot \cos(\theta))^3 \\ (r \cdot \cos(\theta))^4 \\ (r \cdot \sin(\theta))^5 \\ (r \cdot \sin(\theta))^4 \cdot (r \cdot \cos(\theta)) \\ (r \cdot \sin(\theta))^3 \cdot (r \cdot \cos(\theta))^2 \\ (r \cdot \sin(\theta))^2 \cdot (r \cdot \cos(\theta))^3 \\ r \cdot \sin(\theta) \cdot (r \cdot \cos(\theta))^4 \\ (r \cdot \cos(\theta))^5 \end{bmatrix} \cdot \begin{pmatrix} \beta_0 \\ \beta_1 \\ \beta_2 \\ \beta_3 \\ \beta_4 \\ \beta_5 \\ \beta_6 \\ \beta_7 \\ \beta_8 \\ \beta_9 \\ \beta_{10} \\ \beta_{11} \\ \beta_{12} \\ \beta_{13} \\ \beta_{14} \\ \beta_{15} \\ \beta_{16} \\ \beta_{17} \\ \beta_{18} \\ \beta_{19} \\ \beta_{20} \end{pmatrix}^T \cdot \begin{bmatrix} 1 \\ r \cdot \sin(\theta) \\ r \cdot \cos(\theta) \\ (r \cdot \sin(\theta))^2 \\ r \cdot \sin(\theta) \cdot (r \cdot \cos(\theta)) \\ (r \cdot \cos(\theta))^2 \\ (r \cdot \sin(\theta))^3 \\ (r \cdot \sin(\theta))^2 \cdot (r \cdot \cos(\theta)) \\ r \cdot \sin(\theta) \cdot (r \cdot \cos(\theta))^2 \\ (r \cdot \cos(\theta))^3 \\ (r \cdot \sin(\theta))^4 \\ (r \cdot \sin(\theta))^3 \cdot (r \cdot \cos(\theta)) \\ (r \cdot \sin(\theta))^2 \cdot (r \cdot \cos(\theta))^2 \\ r \cdot \sin(\theta) \cdot (r \cdot \cos(\theta))^3 \\ (r \cdot \cos(\theta))^4 \\ (r \cdot \sin(\theta))^5 \\ (r \cdot \sin(\theta))^4 \cdot (r \cdot \cos(\theta)) \\ (r \cdot \sin(\theta))^3 \cdot (r \cdot \cos(\theta))^2 \\ (r \cdot \sin(\theta))^2 \cdot (r \cdot \cos(\theta))^3 \\ r \cdot \sin(\theta) \cdot (r \cdot \cos(\theta))^4 \\ (r \cdot \cos(\theta))^5 \end{bmatrix} \right) \cdot r \, dr \, d\theta$$

or $$Int_c = Cvtc \cdot \int_{\theta_0}^{\theta_1} Sc_{0\_1\_1} \cdot \left( \int_0^r R_{o\_1} \cdot r \, dr \right) d\theta$$

Where: (Note: The "stack" command means that the three vectors stack into one.)

$$Sc_{0\_1\_1} = \text{stack}\left(\begin{bmatrix}1\\\sin(\theta)\\\cos(\theta)\\\sin(\theta)^2\\\sin(\theta)\cdot\cos(\theta)\\\cos(\theta)^2\\\sin(\theta)^3\\\sin(\theta)^2\cdot\cos(\theta)\\\sin(\theta)\cdot\cos(\theta)^2\\\cos(\theta)^3\\\sin(\theta)^4\\\sin(\theta)^3\cdot\cos(\theta)\\\sin(\theta)^2\cdot\cos(\theta)^2\\\sin(\theta)\cdot\cos(\theta)^3\\\cos(\theta)^4\\\sin(\theta)^5\\\sin(\theta)^4\cdot\cos(\theta)\\\sin(\theta)^3\cdot\cos(\theta)^2\\\sin(\theta)^2\cdot\cos(\theta)^3\\\sin(\theta)\cdot\cos(\theta)^4\\\cos(\theta)^5\\\sin(\theta)^6\end{bmatrix},\begin{bmatrix}\sin(\theta)^5\cdot\cos(\theta)\\\sin(\theta)^4\cdot\cos(\theta)^2\\\sin(\theta)^3\cdot\cos(\theta)^3\\\sin(\theta)^2\cdot\cos(\theta)^4\\\sin(\theta)\cdot\cos(\theta)^5\\\cos(\theta)^6\\\sin(\theta)^7\\\sin(\theta)^6\cdot\cos(\theta)\\\sin(\theta)^5\cdot\cos(\theta)^2\\\sin(\theta)^4\cdot\cos(\theta)^3\\\sin(\theta)^3\cdot\cos(\theta)^4\\\sin(\theta)^2\cdot\cos(\theta)^5\\\sin(\theta)\cdot\cos(\theta)^6\\\cos(\theta)^7\\\sin(\theta)^8\\\sin(\theta)^7\cdot\cos(\theta)\\\sin(\theta)^6\cdot\cos(\theta)^2\\\sin(\theta)^5\cdot\cos(\theta)^3\\\sin(\theta)^4\cdot\cos(\theta)^4\\\sin(\theta)^3\cdot\cos(\theta)^5\\\sin(\theta)^2\cdot\cos(\theta)^6\\\sin(\theta)\cdot\cos(\theta)^7\end{bmatrix},\begin{bmatrix}\cos(\theta)^8\\\sin(\theta)^9\\\sin(\theta)^8\cdot\cos(\theta)\\\sin(\theta)^7\cdot\cos(\theta)^2\\\sin(\theta)^6\cdot\cos(\theta)^3\\\sin(\theta)^5\cdot\cos(\theta)^4\\\sin(\theta)^4\cdot\cos(\theta)^5\\\sin(\theta)^3\cdot\cos(\theta)^6\\\sin(\theta)^2\cdot\cos(\theta)^7\\\sin(\theta)\cdot\cos(\theta)^8\\\cos(\theta)^9\\\sin(\theta)^{10}\\\sin(\theta)^9\cdot\cos(\theta)\\\sin(\theta)^8\cdot\cos(\theta)^2\\\sin(\theta)^7\cdot\cos(\theta)^3\\\sin(\theta)^6\cdot\cos(\theta)^4\\\sin(\theta)^5\cdot\cos(\theta)^5\\\sin(\theta)^4\cdot\cos(\theta)^6\\\sin(\theta)^3\cdot\cos(\theta)^7\\\sin(\theta)^2\cdot\cos(\theta)^8\\\sin(\theta)\cdot\cos(\theta)^9\\\cos(\theta)^{10}\end{bmatrix}\right)$$

and (Note: The vector presented below is actually the diagonal of a square array that otherwise all zeros.)

$$R_{o\_1} = \text{stack}\left(\begin{bmatrix}0\\0\\0\\0\\0\\0\\0\\0\\0\\0\\1\\1\\1\\1\\1\\r\\r\\r\\r\\r\\r\\r^2\end{bmatrix},\begin{bmatrix}r^2\\r^2\\r^2\\r^2\\r^2\\r^2\\r^3\\r^3\\r^3\\r^3\\r^3\\r^3\\r^3\\r^3\\r^4\\r^4\\r^4\\r^4\\r^4\\r^4\\r^4\\r^4\end{bmatrix},\begin{bmatrix}r^4\\r^5\\r^5\\r^5\\r^5\\r^5\\r^5\\r^5\\r^5\\r^5\\r^5\\r^6\\r^6\\r^6\\r^6\\r^6\\r^6\\r^6\\r^6\\r^6\\r^6\\r^6\end{bmatrix}\right)$$

and "Cvtc" is defined with Eq. C-13

Integrating Eq. C-12 results in Eq. C-13.

$$\text{Int}_c = Cvtc(\alpha,\beta) \cdot R_o(r) \cdot Sc_{0\_1}(\theta_0,\theta_1) \qquad \text{Eq. C-13}$$

(Note: $R_o(r)$ is presented as a vector. Actually the vector is the diagonal of a square array that is otherwise all zeros.)

Where:

$$Cvtc(\alpha, \beta) = \begin{pmatrix} \beta_0 \cdot \alpha_0 \\ \beta_0 \cdot \alpha_1 + \beta_1 \cdot \alpha_0 \\ \beta_0 \cdot \alpha_2 + \beta_0 \cdot \alpha_2 \\ \beta_1 \cdot \alpha_1 + \beta_0 \cdot \alpha_3 + \beta_3 \cdot \alpha_0 \\ \beta_1 \cdot \alpha_2 + \beta_2 \cdot \alpha_1 + \beta_0 \cdot \alpha_4 + \beta_4 \cdot \alpha_0 \\ \beta_2 \cdot \alpha_2 + \beta_0 \cdot \alpha_5 + \beta_5 \cdot \alpha_0 \\ \beta_1 \cdot \alpha_3 + \beta_3 \cdot \alpha_1 + \beta_0 \cdot \alpha_6 + \beta_6 \cdot \alpha_0 \\ \beta_1 \cdot \alpha_4 + \beta_2 \cdot \alpha_3 + \beta_3 \cdot \alpha_2 + \beta_4 \cdot \alpha_1 + \beta_0 \cdot \alpha_7 + \beta_7 \cdot \alpha_0 \\ \beta_1 \cdot \alpha_5 + \beta_2 \cdot \alpha_4 + \beta_4 \cdot \alpha_2 + \beta_5 \cdot \alpha_1 + \beta_0 \cdot \alpha_8 + \beta_8 \cdot \alpha_0 \\ \beta_2 \cdot \alpha_5 + \beta_5 \cdot \alpha_2 + \beta_0 \cdot \alpha_9 + \beta_9 \cdot \alpha_0 \\ \beta_3 \cdot \alpha_3 + \beta_1 \cdot \alpha_6 + \beta_6 \cdot \alpha_1 + \beta_0 \cdot \alpha_{10} + \beta_{10} \cdot \alpha_0 \\ \beta_3 \cdot \alpha_4 + \beta_4 \cdot \alpha_3 + \beta_1 \cdot \alpha_7 + \beta_2 \cdot \alpha_6 + \beta_6 \cdot \alpha_2 + \beta_7 \cdot \alpha_1 + \beta_0 \cdot \alpha_{11} + \beta_{11} \cdot \alpha_0 \\ \beta_3 \cdot \alpha_5 + \beta_4 \cdot \alpha_4 + \beta_5 \cdot \alpha_3 + \beta_1 \cdot \alpha_8 + \beta_2 \cdot \alpha_7 + \beta_7 \cdot \alpha_2 + \beta_8 \cdot \alpha_1 + \beta_0 \cdot \alpha_{12} + \beta_{12} \cdot \alpha_0 \\ \beta_4 \cdot \alpha_5 + \beta_5 \cdot \alpha_4 + \beta_1 \cdot \alpha_9 + \beta_2 \cdot \alpha_8 + \beta_8 \cdot \alpha_2 + \beta_9 \cdot \alpha_1 + \beta_0 \cdot \alpha_{13} + \beta_{13} \cdot \alpha_0 \\ \beta_5 \cdot \alpha_5 + \beta_2 \cdot \alpha_9 + \beta_9 \cdot \alpha_2 + \beta_0 \cdot \alpha_{14} + \beta_{14} \cdot \alpha_0 \\ \vdots \end{pmatrix}$$

$$R_o(r) = \begin{pmatrix} 0 \\ 0 \\ 0 \\ 0 \\ 0 \\ 0 \\ 0 \\ 0 \\ 0 \\ 0 \\ r^2 \cdot 2^{-1} \\ r^2 \cdot 2^{-1} \\ r^2 \cdot 2^{-1} \\ r^2 \cdot 2^{-1} \\ r^2 \cdot 2^{-1} \\ r^3 \cdot 3^{-1} \\ r^3 \cdot 3^{-1} \\ \vdots \end{pmatrix}$$

and $$Sc_{0\_1}(\theta_1, \theta_1) = \begin{pmatrix} \theta_0 - \theta_0 \\ \cos(\theta_0) - \cos(\theta_1) \\ \sin(\theta_1) - \sin(\theta_0) \\ \dfrac{\theta_1}{2} - \dfrac{\theta_0}{2} + \dfrac{\sin(2 \cdot \theta_0)}{4} - \dfrac{\sin(2 \cdot \theta_1)}{4} \\ \dfrac{\cos(\theta_0)^2}{2} - \dfrac{\cos(\theta_1)^2}{2} \\ \dfrac{\theta_1}{2} - \dfrac{\theta_0}{2} - \dfrac{\sin(2 \cdot \theta_0)}{4} + \dfrac{\sin(2 \cdot \theta_1)}{4} \\ \cos(\theta_0) - \dfrac{\cos(\theta_0)^3}{3} + \dfrac{\cos(\theta_1)^3}{3} - \cos(\theta_1) \\ \dfrac{\sin(\theta_1)^3}{3} - \dfrac{\sin(\theta_0)^3}{3} \\ \dfrac{\cos(\theta_0)^3}{3} - \dfrac{\cos(\theta_1)^3}{3} \\ \dfrac{\sin(\theta_0)^3}{3} - \sin(\theta_0) - \dfrac{\sin(\theta_1)^3}{3} + \sin(\theta_1) \end{pmatrix}$$

-continued $$\left| \begin{array}{c} \frac{3 \cdot \theta_1}{8} - \frac{3 \cdot \theta_0}{8} + \frac{\sin(2 \cdot \theta_0)}{4} - \frac{\sin(2 \cdot \theta_1)}{4} - \frac{\sin(4 \cdot \theta_0)}{32} + \frac{\sin(4 \cdot \theta_1)}{32} \\ \\ \frac{\sin(\theta_1)^4}{4} - \frac{\sin(\theta_0)^4}{4} \\ \\ \frac{\theta_1}{8} - \frac{\theta_0}{8} + \frac{\sin(4 \cdot \theta_0)}{32} - \frac{\sin(4 \cdot \theta_1)}{32} \\ \\ \frac{\cos(\theta_0)^4}{4} - \frac{\cos(\theta_1)^4}{4} \\ \\ \frac{3 \cdot \theta_1}{8} - \frac{3 \cdot \theta_0}{8} - \frac{\sin(2 \cdot \theta_0)}{4} + \frac{\sin(2 \cdot \theta_1)}{4} - \frac{\sin(4 \cdot \theta_0)}{32} + \frac{\sin(4 \cdot \theta_1)}{32} \end{array} \right|$$

$$\vdots$$

An equation similar to Eq. C-10 can be written for the portion of the strain energy relative to the external pressure. This is shown in Eq. C-14. Eq. C-14 represents one position that is to be summed into the $U_b$ vector (in Eq. A-51).

$$U_{c_i,p} = \frac{D}{2} \cdot \int_{\theta_0}^{\theta_1} \int_0^r \left[ \begin{array}{c} 2 \cdot d_{1_p} \cdot \frac{\partial}{\partial a_i} d_1 - 2 \cdot (1-v) \cdot \\ \left( d_{2_p} \cdot \frac{\partial}{\partial a_i} d_3 + d_{3_p} \cdot \frac{\partial}{\partial a_i} d_2 \right) \ldots + \\ 2 \cdot (1-v) \cdot \left( 2 \cdot d_{4_p} \cdot \frac{\partial}{\partial a_i} d_4 \right) \end{array} \right] \cdot r \, dr \, d\theta \quad \text{Eq. C-14}$$

It is clear that the approach used to evaluate Eq. C-10 will work for Eq. C-14 also. Eqs. C-15 to C-18 are the arrays for defining the constant vectors defined in Eq. C-11. One vector is assigned for each degree of freedom and then a vector is defined relative to the pressure load.

Eq. C-15

$$Uc_{1p}(x_o, y_o, D, p_z) := \frac{p_z}{8 \cdot D} \cdot \begin{pmatrix} 0 \\ 0 \\ 0 \\ 2 \cdot x_o^2 + 2 \cdot y_o^2 \\ 0 \\ 2 \cdot x_o^2 + 2 \cdot y_o^2 \\ 4 \cdot y_o \\ 4 \cdot x_o \\ 4 \cdot y_o \\ 4 \cdot x_o \\ 2 \\ 0 \\ 4 \\ 0 \\ 2 \\ 0 \\ 0 \\ 0 \\ 0 \\ 0 \\ 0 \end{pmatrix} \quad Uc_{1p}(x_o, y_o, r') := \frac{1}{r'^4} \cdot \begin{pmatrix} 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 2 \cdot r'^3 & 2 \cdot r'^3 & 2 \cdot r'^2 \cdot y_o & 2 \cdot r'^2 \cdot x_o \\ 0 & 0 & 0 & 0 & 0 & 0 & 0 & 0 \\ 0 & 0 & 0 & 0 & 2 \cdot r'^3 & 2 \cdot r'^3 & 2 \cdot r'^2 \cdot y_o & 2 \cdot r'^2 \cdot x_o \\ 0 & 0 & 0 & 0 & 0 & 0 & 2 \cdot r'^2 & 0 \\ 0 & 0 & 0 & 0 & 0 & 0 & 0 & 2 \cdot r'^2 \\ 0 & 0 & 0 & 0 & 0 & 0 & 2 \cdot r'^2 & 0 \\ 0 & 0 & 0 & 0 & 0 & 0 & 0 & 2 \cdot r'^2 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \end{pmatrix} \cdots$$

Eq. C-16

$$Uc_{2p}(x_o, y_o, D, p_z) := \frac{p_z}{8 \cdot D} \cdot \begin{pmatrix} 0 \\ 0 \\ 0 \\ 2 \cdot x_o^2 \\ 8 \cdot x_o \cdot y_o \\ 2 \cdot y_o^2 \\ 0 \\ 12 \cdot x_o \\ 12 \cdot y_o \\ 0 \\ 0 \\ 12 \\ 0 \\ 0 \\ 0 \\ 0 \\ 0 \\ 0 \\ 0 \end{pmatrix} \quad Uc_2(x_o, y_o, r') := \frac{1}{r'^4} \cdot \begin{pmatrix} 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 2 \cdot r'^3 & 0 & 2 \cdot r'^2 \cdot x_o \\ 0 & 0 & 0 & 2 \cdot r'^3 & 0 & 0 & 4 \cdot r'^2 \cdot x_o & 4 \cdot r'^2 \cdot y_o \\ 0 & 0 & 0 & 0 & 2 \cdot r'^3 & 0 & 2 \cdot r'^2 \cdot y_o & 0 \\ 0 & 0 & 0 & 0 & 0 & 0 & 0 & 0 \\ 0 & 0 & 0 & 0 & 0 & 0 & 0 & 6 \cdot r'^2 \\ 0 & 0 & 0 & 0 & 0 & 0 & 6 \cdot r'^2 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \end{pmatrix} \cdots$$

Eq. C-17

$$Uc_{3p}(x_o, y_o, D, p_z) := \frac{p_z}{8 \cdot D} \cdot \begin{pmatrix} 0 \\ 0 \\ 0 \\ 2 \cdot y_o^2 \\ -8 \cdot x_o \cdot y_o \\ 2 \cdot x_o^2 \\ 4 \cdot y_o \\ -8 \cdot x_o \\ -8 \cdot y_o \\ 4 \cdot x_o \\ 2 \\ 0 \\ -8 \\ 0 \\ 2 \\ 0 \\ 0 \\ 0 \\ 0 \\ 0 \end{pmatrix} \quad Uc_3(x_o, y_o, r') := \frac{1}{r'^4} \cdot \begin{pmatrix} 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 2 \cdot r'^3 & 0 & 2 \cdot r'^2 \cdot y_o \\ 0 & 0 & 0 & -2 \cdot r'^3 & 0 & 0 & -4 \cdot r'^2 \cdot x_o \\ 0 & 0 & 0 & 0 & 0 & 2 \cdot r'^3 & 0 \\ 0 & 0 & 0 & 0 & 0 & 0 & 2 \cdot r'^2 \\ 0 & 0 & 0 & 0 & 0 & 0 & 0 \\ 0 & 0 & 0 & 0 & 0 & 0 & -4 \cdot r'^2 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \end{pmatrix} \cdots$$

-continued $$Uc_{4p}(x_o, y_o, D, p_z) := \frac{p_z}{8 \cdot D} \cdot \begin{Bmatrix} 0 \\ 0 \\ 0 \\ -4 \cdot x_o \cdot y_o \\ 2 \cdot x_o^2 - 2 \cdot y_o^2 \\ 4 \cdot x_o \cdot y_o \\ -4 \cdot x_o \\ -8 \cdot y_o \\ 8 \cdot x_o \\ 4 \cdot y_o \\ 0 \\ -6 \\ 0 \\ 6 \\ 0 \\ 0 \\ 0 \\ 0 \\ 0 \\ 0 \\ 0 \end{Bmatrix}$$

$$Uc_4(x_o, y_o, r') := \frac{1}{r'^4} \cdot \begin{bmatrix} 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & -r'^3 & 0 & 0 & -2 \cdot r'^2 \cdot x_o \\ 0 & 0 & 0 & 0 & -2 \cdot r'^3 & 2 \cdot r'^3 & -2 \cdot r'^2 \cdot y_o \\ 0 & 0 & 0 & r'^3 & 0 & 0 & 2 \cdot r'^2 \cdot x_o \\ 0 & 0 & 0 & 0 & 0 & 0 & 0 \\ 0 & 0 & 0 & 0 & 0 & 0 & -4 \cdot r'^2 \\ 0 & 0 & 0 & 0 & 0 & 0 & 0 \\ 0 & 0 & 0 & 0 & 0 & 0 & 2 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \\ 0 & 0 & 0 & 0 & 0 & 0 & 0 \end{bmatrix} \cdots$$

Eq. C-18

At this point, all of the definitions necessary for an algebraic form of Eq. C-6 have been defined. Now these equations are used to generate array constants and vector constants consistent with Eq. A-50. This is performed with the subroutines below. (These subroutines are defined in a Mathcad format.) Su. C-1 assembles an array relative to the degrees of freedom based on Eq. C-11 and using Eq. C-13. Su. C-2 performs a similar role except it is relative to the pressure term.

$Int_{cU}(A_{a1}, A_{a2}, A_{a3}, A_{a4}, s_{01}, r_o, D, v) :=$  Su. C-1

$$\begin{vmatrix} out_{cols(A_{a1})-1, cols(A_{a1})-1} \leftarrow 0 \\ \text{for } i \in 0 \ldots \text{last}(r_o) \\ \quad s_{01r_i} \leftarrow s_{01_i} \cdot r_{o_i} \\ \text{for } j \in 0 \ldots cols(A_{a1}) - 1 \\ \quad \text{for } i \in j \ldots cols(A_{a1}) - 1 \\ \quad \quad d_{11} \leftarrow \left( Cvtc\left(A_{a1}^{\langle i \rangle}, A_{a1}^{\langle j \rangle}\right)^T + Cvtc\left(A_{a1}^{\langle j \rangle}, A_{a1}^{\langle i \rangle}\right)^T \right) \cdot s_{01r} \\ \quad \quad d_{23} \leftarrow \left( Cvtc\left(A_{a2}^{\langle i \rangle}, A_{a3}^{\langle j \rangle}\right)^T + Cvtc\left(A_{a2}^{\langle j \rangle}, A_{a3}^{\langle i \rangle}\right)^T \right) \cdot s_{01r} \\ \quad \quad d_{44} \leftarrow \left( Cvtc\left(A_{a4}^{\langle i \rangle}, A_{a4}^{\langle j \rangle}\right)^T + Cvtc\left(A_{a4}^{\langle j \rangle}, A_{a4}^{\langle i \rangle}\right)^T \right) \cdot s_{01r} \\ \quad \quad out_{i,j} \leftarrow \frac{D}{2} \cdot [d_{11} - 2 \cdot (1-v) \cdot d_{23} + 2 \cdot (1-v) \cdot d_{44}] \\ \quad \quad out_{j,i} \leftarrow out_{i,j} \\ out \end{vmatrix}$ -continued $Int_{cUpz}(A_{a1}, A_{a2}, A_{a3}, A_{a4},$  Su. C-2
$A_{pa1}, A_{pa2}, A_{pa3}, A_{pa4}, s_{01}, r_o, D, v) :=$ $$\begin{vmatrix} out_{cols(A_{a1})-1} \leftarrow 0 \\ \text{for } i \in 0 \ldots \text{last}(r_o) \\ \quad s_{01r_i} \leftarrow s_{01_i} \cdot r_{o_i} \\ \text{for } i \in 0 \ldots cols(A_{a1}) - 1 \\ \quad d_{11} \leftarrow \left( Cvtc\left(A_{a1}^{\langle i \rangle}, A_{pa1}\right)^T \ldots + Cvtc\left(A_{pa1}, A_{a1}^{\langle i \rangle}\right)^T \right) \cdot s_{01r} \\ \quad d_{23} \leftarrow \left( Cvtc\left(A_{a2}^{\langle i \rangle}, A_{pa3}\right)^T \ldots + Cvtc\left(A_{pa2}, A_{a3}^{\langle i \rangle}\right)^T \right) \cdot s_{01r} \\ \quad d_{44} \leftarrow \left( Cvtc\left(A_{a4}^{\langle i \rangle}, A_{pa4}\right)^T \ldots + Cvtc\left(A_{pa4}, A_{a4}^{\langle i \rangle}\right)^T \right) \cdot s_{01r} \\ \quad out_i \leftarrow \frac{D}{2} \cdot [d_{11} - 2 \cdot (1-v) \cdot d_{23} + 2 \cdot (1-v) \cdot d_{44}] \\ out \end{vmatrix}$ Eq. C-19 defines the functions for the generation of the strain energy constants array and constants vector respectively.

$Uc_o(\theta_0, \theta_1, x_o, y_o, r', D, v) := Int_{cU}(Uc_1(x_o, y_o, r'), Uc_2(x_o, y_o, r'), Uc_3(x_o, y_o, r'), Uc_4(x_o, y_o, r'), Sc_{0\_1}(\theta_0, \theta_1), R_o(r), D, v)$ $Uc_{pz}(\theta_0, \theta_1, x_o, y_o, r', D, v, p_z) := Int_{cUpz}(Uc_1(x_o, y_o, r'),$
$Uc_2(x_o, y_o, r'), Uc_3(x_o, y_o, r'), Uc_4(x_o, y_o, r'), Uc_{1p}(x_o, y_o, D, p_z), Uc_{2p}(x_o, y_o, D, p_z), Uc_{3p}(x_o, y_o, D, p_z), Uc_{4p}(x_o, y_o, D, p_z), Sc_{0\_1}(\theta_0, \theta_1), R_o(r), D, v)$   Eq. C-19

The other area integral to be addressed is Eq. C-7 for the pressure load. This is evaluated by introducing Eq. C-1 into Eq. C-7 as shown in Eq. C-20.

$$w_{cp_i} = \int_{\theta_0}^{\theta_1} \int_0^T \frac{d}{da_i} \begin{bmatrix} a_0 \\ a_1 \\ a_2 \\ a_3 \\ a_4 \\ a_5 \\ a_6 \\ a_7 \\ a_8 \\ a_9 \\ a_{10} \\ a_{11} \\ a_{12} \\ \vdots \\ a_{13} \\ a_{14} \\ a_{15} \\ a_{16} \\ a_{17} \end{bmatrix}^T \cdot \begin{bmatrix} 1 \cdot r' \\ (r \cdot \cos(\theta) + x_O) \\ (r \cdot \sin(\theta) + y_O) \\ (r \cdot \cos(\theta) + x_O) \cdot (r \cdot \sin(\theta) + y_O) \cdot r'^{-1} \\ (r \cdot \cos(\theta) + x_O)^2 \cdot r'^{-1} \\ (r \cdot \sin(\theta) + y_O)^2 \cdot r'^{-1} \\ (r \cdot \cos(\theta) + x_O)^2 \cdot (r \cdot \sin(\theta) + y_O)^2 \cdot r'^{-2} \\ (r \cdot \cos(\theta) + x_O) \cdot (r \cdot \sin(\theta) + y_O)^2 \cdot r'^{-2} \\ (r \cdot \cos(\theta) + x_O)^3 \cdot r'^{-2} \\ (r \cdot \sin(\theta) + y_O)^3 \cdot r'^{-2} \\ (r \cdot \cos(\theta) + x_O)^3 \cdot (r \cdot \sin(\theta) + y_O) \cdot r'^{-3} \\ (r \cdot \cos(\theta) + x_O) \cdot (r \cdot \sin(\theta) + y_O)^3 \cdot r'^{-3} \\ [(r \cdot \cos(\theta) + x_O)^4 - 3 \cdot (r \cdot \cos(\theta) + x_O)^2 \cdot (r \cdot \sin(\theta) + y_O)^2] \cdot r'^{-3} \\ [(r \cdot \sin(\theta) + y_O)^4 - 3 \cdot (r \cdot \cos(\theta) + x_O)^2 \cdot (r \cdot \sin(\theta) + y_O)^2] \cdot r'^{-3} \\ [(r \cdot \cos(\theta) + x_O)^4 \cdot (r \cdot \sin(\theta) + y_O) - (r \cdot \cos(\theta) + x_0)^2 \cdot (r \cdot \sin(\theta) + y_O)^3] \cdot r'^{-4} \\ [(r \cdot \cos(\theta) + x_O) \cdot (r \cdot \sin(\theta) + y_O)^4 - (r \cdot \cos(\theta) + x_0)^3 \cdot (r \cdot \sin(\theta) + y_O)^2] \cdot r'^{-4} \\ [(r \cdot \cos(\theta) + x_O)^5 - 5 \cdot (r \cdot \cos(\theta) + x_O)^3 \cdot (r \cdot \sin(\theta) + y_O)^2] \cdot r'^{-4} \\ [(r \cdot \sin(\theta) + y_O)^5 - 5 \cdot (r \cdot \cos(\theta) + x_O)^3 \cdot (r \cdot \sin(\theta) + y_O)^3] \cdot r'^{-4} \\ \frac{p_Z}{8 \cdot D} \cdot (r \cdot \cos(\theta) + x_O)^2 \cdot (r \cdot \sin(\theta) + y_O)^2 \end{bmatrix} \cdots + \begin{bmatrix} \cdot p_Z \cdot r \end{bmatrix} dr d\theta$$

Eq. C-20

Following the same logic used with the development of Eq. C-12, Eq. C-20 can be solved with the generalized integration shown in Eq. C-21.

$$Int_{cp} = \int_{\theta_0}^{\theta_1} \begin{bmatrix} \alpha_0 \\ \alpha_1 \\ \alpha_2 \\ \alpha_3 \\ \alpha_4 \\ \alpha_5 \\ \alpha_6 \\ \alpha_7 \\ \alpha_8 \\ \alpha_9 \\ \alpha_{10} \\ \alpha_{11} \\ \alpha_{12} \\ \vdots \end{bmatrix}^T \cdot \begin{bmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \vdots \end{bmatrix} \cdot \begin{bmatrix} 1 \\ r \\ r \\ r^2 \\ r^2 \\ r^2 \\ r^3 \\ r^3 \\ r^3 \\ r^3 \\ r^4 \\ r^4 \\ r^4 \\ \vdots \end{bmatrix}^T \cdot r dr d\theta \qquad \text{Generalized integration}$$

Eq. C-21

$$\begin{Bmatrix} \alpha_{13} \\ \alpha_{14} \\ \alpha_{15} \\ \alpha_{16} \\ \alpha_{17} \\ \alpha_{18} \\ \alpha_{19} \\ \alpha_{20} \end{Bmatrix}_{\theta_0} \begin{Bmatrix} \sin(\theta)^2 \cdot \cos(\theta)^2 \\ \sin(\theta) \cdot \cos(\theta)^3 \\ \cos(\theta)^4 \\ \sin(\theta)^5 \\ \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{Bmatrix}_{\theta_0} \begin{Bmatrix} r'^4 \\ r'^4 \\ r'^5 \\ r'^5 \\ r'^5 \\ r'^5 \\ r'^5 \\ r'^5 \\ r'^5 \end{Bmatrix}_0$$

Where $\alpha_0$-$\alpha_{20}$ represent possible definitions for the constants in Eq. C-20 and the vector of "r" terms represents the diagonal terms in a square array that is otherwise zeros.

Eq. C-21 is organized similar to Eq. C-12. Arranging Eq. C-21 in this manner makes it possible to take advantage of a portion of the integration performed in Eq. C-13 as shown in Eq. C-22.

$$\text{Int}_{cp} = Uc_{pzp}(x_o, y_o, r', D, p_z)^{(i)} \cdot R_{op}(r) \cdot Sc_{0\_1}(\theta_0, \theta_1) \qquad \text{Eq. C-22}$$

Where the "i" in brackets means that one column (for the ith degree of freedom) from the array of constants '$Uc_{pzp}(x_0, y_0, r', D, p_z)$' is being used in each integration.

(Note: $R_{op}(r)$ is presented as a vector. Actually the vector is the diagonal of a square array that is otherwise all zeros. Also, $Sc_{0\_1}(\theta_0, \theta_1)$ is defined for equation C-13 and only the first 21 rows are used in Eq. C-22.)

$$R_{op}(r) := \begin{Bmatrix} r^2 \cdot 2^{-1} \\ r^3 \cdot 3^{-1} \\ r^3 \cdot 3^{-1} \\ r^4 \cdot 4^{-1} \\ r^4 \cdot 4^{-1} \\ r^4 \cdot 4^{-1} \\ r^5 \cdot 5^{-1} \\ r^5 \cdot 5^{-1} \\ r^5 \cdot 5^{-1} \\ r^5 \cdot 5^{-1} \\ r^6 \cdot 6^{-1} \\ r^6 \cdot 6^{-1} \\ r^6 \cdot 6^{-1} \\ r^6 \cdot 6^{-1} \\ r^6 \cdot 6^{-1} \\ r^7 \cdot 7^{-1} \\ r^7 \cdot 7^{-1} \\ r^7 \cdot 7^{-1} \\ r^7 \cdot 7^{-1} \\ r^7 \cdot 7^{-1} \\ r^7 \cdot 7^{-1} \end{Bmatrix}$$

$$Uc_{pzp}(x_0, y_0, r', D, p_z) := \frac{p_z}{r'^4} \cdot$$

-continued $$\begin{bmatrix} r'^5 & r'^4 \cdot x_0 & r'^4 \cdot y_0 & r'^3 \cdot x_0 \cdot y_0 & r'^3 \cdot x_0^2 & r'^3 \cdot y_0^2 \\ 0 & 0 & r'^4 & r'^3 \cdot x_0 & 0 & 2 \cdot r'^3 \cdot y_0 \\ 0 & r'^4 & 0 & r'^3 \cdot y_0 & 2 \cdot r'^3 \cdot x_0 & 0 \\ 0 & 0 & 0 & 0 & 0 & r'^3 \\ 0 & 0 & 0 & r'^3 & 0 & 0 \\ 0 & 0 & 0 & 0 & r'^3 & 0 \\ 0 & 0 & 0 & 0 & 0 & 0 \\ 0 & 0 & 0 & 0 & 0 & \cdots \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix}$$

With an algebraic form established, Su. C-3 assembles an array relative to the degrees of freedom based on Eq. C-22 and Eq. C-23 defines the function for the constants vector to address the pressure load.

$$\text{Int}_{cUp}(A_\alpha, s_{01}, r_o, D, v) := \begin{vmatrix} out_{cols(A_\alpha)-1} \leftarrow 0 \\ \text{for } i \in 0 \ldots \text{last}(r_o) \\ s_{01r_i} \leftarrow s_{01_i} \cdot r_{o_i} \\ A_\alpha^T \cdot s_{01r} \end{vmatrix} \qquad \text{Su. C-3}$$

$$Uc_p(\theta_0, \theta_1, r, x_o, y_o, r', D, v, p_z) := \qquad \text{Ep. C-22}$$
$$\text{Int}_{cUp}(Uc_{pzp}(x_o, y_o, r', D, p_z), Sc_{0\_1}(\theta_0, \theta_1), R_{op}(r), D, v)$$

Edge Integrals for a Circular Edge

Recalling the edge energy integral (Eq. A-47), there are three edge loads and three edge displacements to be addressed in the total energy equation for the element (Eq. A-48 or A-49) and the energy optimization (Eq. A-49). For a circular edge, the displacement and loads are put in polar coordinates (Eqs. C-1 to C-3). The energy optimization lends itself to be broken into pieces, evaluated to form algebraic solutions, and then summed back together. All of the integrals will be addressed in this manner. When broken out the of the energy optimization, the edge energies appear as in Eq. C-23.

$$W_{ceP_i} = \frac{d}{da_i} \int_{\theta_1}^{\theta_0} P_r \cdot w_r(a) \cdot r\, d\theta = \int_{\theta_1}^{\theta_0} P_r \cdot \frac{d}{da_i} w_r(a) \cdot r\, d\theta \quad \text{Eq. C-23(a)}$$

Edge energy considering an external shear load $$W_{ceM_i} = \frac{d}{da_i} \int_{\theta_1}^{\theta_0} M_r \cdot \theta_r(a) \cdot r\, d\theta = \int_{\theta_1}^{\theta_0} M_r \cdot \frac{d}{da_i} \theta_r(a) \cdot r\, d\theta \quad \text{Eq. C-23(b)}$$

Edge energy considering an external moment $$W_{ceT_i} = \frac{d}{da_i} \int_{\theta_1}^{\theta_0} T_r \cdot \phi_r(a) \cdot r\, d\theta = \int_{\theta_1}^{\theta_0} T_r \cdot \frac{d}{da_i} \phi_r(a) \cdot r\, d\theta \quad \text{Eq. C-23(c)}$$

Edge energy considering an external torsion $$W_{cew_i} = \frac{d}{da_i} \int_{\theta_1}^{\theta_0} P_r(a) \cdot w_r \cdot r\, d\theta = \int_{\theta_1}^{\theta_0} w_r \cdot \frac{d}{da_i} P_r(a) \cdot r\, d\theta \quad \text{Eq. C-23(d)}$$

Edge energy considering an external shear displacement $$W_{ce\theta_i} = \frac{d}{da_i} \int_{\theta_1}^{\theta_0} M_r(a) \cdot \theta_r \cdot r\, d\theta = \int_{\theta_1}^{\theta_0} \theta_r \cdot \frac{d}{da_i} M_r(a) \cdot r\, d\theta \quad \text{Eq. C-23(e)}$$

Edge energy considering an external bending rotation $$W_{ce\phi_i} = \frac{d}{da_i} \int_{\theta_1}^{\theta_0} T_r(a) \cdot \phi_r \cdot r\, d\theta = \int_{\theta_1}^{\theta_0} \phi_r \cdot \frac{d}{da_i} T_r(a) \cdot r\, d\theta \quad \text{Eq. C-23(f)}$$

Edge energy considering an external torsional rotation

In general, the equations in Eq. C-23 represent one position that is to be summed into the $U_b$ vector (in Eq. A-51) for the element or one row to be summed into the $U_m$ array (in Eq. A-51) for a neighboring element. (In the case where a boundary condition is not known, this can represent one row to be summed into the $U_m$ array (in Eq. A-51) for the element but this is a special case that is discussed more later.)

The external loads and displacements may have any function as long as it can be expressed in terms of the local direction along the curve. It is very common for boundary conditions to just be constant (which is easily addressed). Neighboring elements will cause external loads and displacements based on their displacement equation. For this example, the external loads will be based on a sine and cosine vector similar to that in Eq. C-11. (Consequently, neighboring elements could have the same number or less degrees of freedom and a similar displacement equation and this formulation would not need to be modified.) Considering this approach, Eqs. C-1 to C-3 are rearranged into Eq. C-24.

Eq. C-24(a)

$$w_r = \begin{Bmatrix} w_{r_0} \\ w_{r_1} \\ w_{r_2} \\ w_{r_3} \\ w_{r_4} \\ w_{r_5} \\ w_{r_6} \\ w_{r_7} \\ w_{r_8} \\ w_{r_9} \\ w_{r_{10}} \\ w_{r_{11}} \\ w_{r_{12}} \\ w_{r_{13}} \\ w_{r_{14}} \\ w_{r_{15}} \\ w_{r_{16}} \\ w_{r_{17}} \\ w_{r_{18}} \\ w_{r_{19}} \\ w_{r_{20}} \end{Bmatrix}^T \cdot \begin{Bmatrix} 1 \\ \sin(\theta) \\ \cos(\theta) \\ \sin(\theta)^2 \\ \sin(\theta)\cdot\cos(\theta) \\ \cos(\theta)^2 \\ \sin(\theta)^3 \\ \sin(\theta)^2\cdot\cos(\theta) \\ \sin(\theta)\cdot\cos(\theta)^2 \\ \cos(\theta)^3 \\ \sin(\theta)^4 \\ \sin(\theta)^3\cdot\cos(\theta) \\ \sin(\theta)^2\cdot\cos(\theta)^2 \\ \sin(\theta)\cdot\cos(\theta)^3 \\ \cos(\theta)^4 \\ \sin(\theta)^5 \\ \sin(\theta)^4\cdot\cos(\theta) \\ \sin(\theta)^3\cdot\cos(\theta)^2 \\ \sin(\theta)^2\cdot\cos(\theta)^3 \\ \sin(\theta)\cdot\cos(\theta)^4 \\ \cos(\theta)^5 \end{Bmatrix}$$

Where $\begin{Bmatrix} w_{r_0} \\ w_{r_1} \\ w_{r_2} \\ w_{r_3} \\ w_{r_4} \\ w_{r_5} \\ w_{r_6} \\ w_{r_7} \\ w_{r_8} \\ w_{r_9} \\ w_{r_{10}} \\ w_{r_{11}} \\ w_{r_{12}} \\ w_{r_{13}} \\ w_{r_{14}} \\ w_{r_{15}} \\ w_{r_{16}} \\ w_{r_{17}} \\ w_{r_{18}} \\ w_{r_{19}} \\ w_{r_{20}} \end{Bmatrix} = Cc_{w\_a} \cdot a + Cc_{w\_p}$ and $$Cc_{w\_p}(r, x_o, y_o, r', D, v, p_z) := \frac{p_z}{8 \cdot D} \cdot \begin{pmatrix} x_o^2 \cdot y_o^2 \\ 2 \cdot r \cdot x_o^2 \cdot y_o \\ 2 \cdot r \cdot x_o \cdot y_o^2 \\ r^2 \cdot x_o^2 \\ 4 \cdot r^2 \cdot x_o \cdot y_o \\ r^2 \cdot y_o^2 \\ 0 \\ 2 \cdot r^3 \cdot x_o \\ 2 \cdot r^3 \cdot y_o \\ 0 \\ 0 \\ 0 \\ r^4 \\ 0 \\ 0 \\ 0 \\ 0 \\ 0 \\ 0 \\ 0 \\ 0 \end{pmatrix}$$

$$Cc_{w\_a}(r, x_o, y_o, r', D, v) := \frac{1}{r'^4} \cdot \begin{pmatrix} r'^5 & r'^4 \cdot x_o & r'^4 \cdot y_o & r'^3 \cdot x_o \cdot y_o \\ 0 & 0 & r \cdot r'^4 & r \cdot r'^3 \cdot x_o \\ 0 & r \cdot r'^4 & 0 & r \cdot r'^3 \cdot y_o \\ 0 & 0 & 0 & 0 \\ 0 & 0 & 0 & r^2 \cdot r'^3 \\ 0 & 0 & 0 & 0 \\ 0 & 0 & 0 & 0 \\ 0 & 0 & 0 & 0 \\ 0 & 0 & 0 & 0 \\ 0 & 0 & 0 & \cdots \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \end{pmatrix}$$

Eq. C-24(b)

$$\theta_r = \frac{d}{dr} w_r = \begin{pmatrix} \theta_{r_0} \\ \theta_{r_1} \\ \theta_{r_2} \\ \theta_{r_3} \\ \theta_{r_4} \\ \theta_{r_5} \\ \theta_{r_6} \\ \theta_{r_7} \\ \theta_{r_8} \\ \theta_{r_9} \\ \theta_{r_{10}} \\ \theta_{r_{11}} \\ \theta_{r_{12}} \\ \theta_{r_{13}} \\ \theta_{r_{14}} \end{pmatrix}^T \cdot \begin{pmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \end{pmatrix}$$

$$\begin{pmatrix} \theta_{r_{15}} \\ \theta_{r_{16}} \\ \theta_{r_{17}} \\ \theta_{r_{18}} \\ \theta_{r_{19}} \\ \theta_{r_{20}} \end{pmatrix} \begin{pmatrix} \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{pmatrix}$$

Where $\begin{pmatrix} \theta_{r_0} \\ \theta_{r_1} \\ \theta_{r_2} \\ \theta_{r_3} \\ \theta_{r_4} \\ \theta_{r_5} \\ \theta_{r_6} \\ \theta_{r_7} \\ \theta_{r_8} \\ \theta_{r_9} \\ \theta_{r_{10}} \\ \theta_{r_{11}} \\ \theta_{r_{12}} \\ \theta_{r_{13}} \\ \theta_{r_{14}} \\ \theta_{r_{15}} \\ \theta_{r_{16}} \\ \theta_{r_{17}} \\ \theta_{r_{18}} \\ \theta_{r_{19}} \\ \theta_{r_{20}} \end{pmatrix} = Cc_{\phi\_a} \cdot a + Cc_{\phi\_p}$ and $$Cc_{\theta\_p}(r, x_o, y_o, r', D, v, p_z) := \frac{p_z}{8 \cdot D} \cdot \begin{pmatrix} 0 \\ 2 \cdot x_o^2 \cdot y_o \\ 2 \cdot x_o \cdot y_o^2 \\ 2 \cdot r \cdot x_o^2 \\ 8 \cdot r \cdot x_o \cdot y_o \\ 2 \cdot r \cdot y_o^2 \\ 0 \\ 6 \cdot r^2 \cdot x_o \\ 6 \cdot r^2 \cdot y_o \\ 0 \\ 0 \\ 0 \\ 4 \cdot r^3 \\ 0 \\ 0 \\ 0 \\ 0 \\ 0 \\ 0 \\ 0 \\ 0 \end{pmatrix}$$

-continued $$Cc_{\theta\_a}(r, x_o, y_o, r', D, v) := \frac{1}{r'^4} \cdot \begin{pmatrix} 0 & 0 & 0 & 0 & 0 \\ 0 & 0 & r'^4 & r'^3 \cdot x_o & 0 \\ 0 & r'^4 & 0 & r'^3 \cdot y_o & 2 \cdot r'^3 \cdot x_o \\ 0 & 0 & 0 & 0 & 0 \\ 0 & 0 & 0 & 2 \cdot r \cdot r'^3 & 0 \\ 0 & 0 & 0 & 0 & 2 \cdot r \cdot r'^3 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 0 \end{pmatrix} \cdots$$

$$\phi_r = \frac{1}{r} \cdot \frac{d}{d\theta} \, w_r = \begin{pmatrix} \phi_{r_0} \\ \phi_{r_1} \\ \phi_{r_2} \\ \phi_{r_3} \\ \phi_{r_4} \\ \phi_{r_5} \\ \phi_{r_6} \\ \phi_{r_7} \\ \phi_{r_8} \\ \phi_{r_9} \\ \phi_{r_{10}} \\ \phi_{r_{11}} \\ \phi_{r_{12}} \\ \phi_{r_{13}} \\ \phi_{r_{14}} \end{pmatrix}^T \cdot \begin{pmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \end{pmatrix}$$

$$\begin{pmatrix} \phi_{r_{15}} \\ \phi_{r_{16}} \\ \phi_{r_{17}} \\ \phi_{r_{18}} \\ \phi_{r_{19}} \\ \phi_{r_{20}} \end{pmatrix} \quad \begin{pmatrix} \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{pmatrix}$$

-continued

Where $\begin{pmatrix} \phi_{r_0} \\ \phi_{r_1} \\ \phi_{r_2} \\ \phi_{r_3} \\ \phi_{r_4} \\ \phi_{r_5} \\ \phi_{r_6} \\ \phi_{r_7} \\ \phi_{r_8} \\ \phi_{r_9} \\ \phi_{r_{10}} \\ \phi_{r_{11}} \\ \phi_{r_{12}} \\ \phi_{r_{13}} \\ \phi_{r_{14}} \end{pmatrix} = Cc_{\phi\_a} \cdot a + Cc_{\phi\_p}$ and $$\begin{pmatrix} \phi_{r_{15}} \\ \phi_{r_{16}} \\ \phi_{r_{17}} \\ \phi_{r_{18}} \\ \phi_{r_{19}} \\ \phi_{r_{20}} \end{pmatrix}$$

$$\begin{pmatrix} \phi_{r_{18}} \\ \phi_{r_{19}} \\ \phi_{r_{20}} \end{pmatrix}$$

$$Cc_{\phi\_p}(r, x_o, y_o, r', D, v, p_z) := \frac{p_z}{8 \cdot D} \cdot \begin{pmatrix} 0 \\ -2 \cdot x_o \cdot y_o^2 \\ 2 \cdot x_o^2 \cdot y_o \\ -4 \cdot r_o \cdot y_o \\ 2 \cdot r \cdot (x_o^2 \cdot y_o^2) \\ 4 \cdot r \cdot x_o \cdot y_o \\ -2 \cdot r^2 \cdot x_o \\ -4 \cdot r^2 \cdot y_o \\ 4 \cdot r^2 \cdot x_o \\ 2 \cdot r^2 \cdot y_o \\ 0 \\ -2 \cdot r^3 \\ 0 \\ 2 \cdot r^3 \\ 0 \\ 0 \\ 0 \\ 0 \\ 0 \\ 0 \\ 0 \end{pmatrix}$$

$$Cc_{\phi\_a}(r, x_o, y_o, r', D, v) := \frac{1}{r'^4} \cdot \begin{bmatrix} 0 & 0 & 0 & 0 \\ 0 & -r'^4 & 0 & -r'^3 \cdot y_o \\ 0 & 0 & r'^4 & r'^3 \cdot x_o \\ 0 & 0 & 0 & -r \cdot r'^3 \\ 0 & 0 & 0 & 0 \\ 0 & 0 & 0 & r \cdot r'^3 \\ 0 & 0 & 0 & 0 \\ 0 & 0 & 0 & 0 \\ 0 & 0 & 0 & 0 \\ 0 & 0 & 0 & \ldots \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \end{bmatrix}$$

$$P_r = -D \cdot \left\{ \begin{bmatrix} \frac{d}{dr} \\ \frac{d^2}{dr^2} \\ \frac{1}{r} \cdot \frac{d}{dr} \\ \frac{1}{r^2} \cdot \frac{d^2}{d\theta^2} \end{bmatrix} w_r \ldots + \right\} = \begin{bmatrix} P_{r_0} \\ P_{r_1} \\ P_{r_2} \\ P_{r_3} \\ P_{r_4} \\ P_{r_5} \\ P_{r_6} \\ P_{r_7} \\ P_{r_8} \\ P_{r_9} \\ P_{r_{10}} \\ P_{r_{11}} \\ P_{r_{12}} \\ P_{r_{13}} \\ P_{r_{14}} \\ P_{r_{15}} \\ P_{r_{16}} \\ P_{r_{17}} \\ P_{r_{18}} \\ P_{r_{19}} \\ P_{r_{20}} \end{bmatrix}^T \cdot \begin{bmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \\ \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{bmatrix}$$

Where $\begin{bmatrix} P_{r_0} \\ P_{r_1} \\ \vdots \\ P_{r_{20}} \end{bmatrix} = Cc_{P\_a} \cdot a \ldots + Cc_{P\_p}$ and $$Cc_{P\_p}(r, x_o, y_o, r', D, v, p_z) := \frac{p_z}{8} \cdot \begin{bmatrix} -4 \cdot r \\ -4 \cdot y_o \\ -4 \cdot x_o \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{bmatrix}$$

-continued $$Cc_{P\_a}(r, x_o, y_o, r', D, v) := \frac{D}{r'^4} \cdot \begin{pmatrix} 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & -2 \cdot r'^2 & 0 \\ 0 & 0 & 0 & 0 & 0 & 0 & 0 & -2 \cdot r'^2 \\ 0 & 0 & 0 & 0 & 0 & 0 & -2 \cdot r'^2 & 0 \\ 0 & 0 & 0 & 0 & 0 & 0 & 0 & -2 \cdot r'^2 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \\ 0 & 0 & 0 & 0 & 0 & 0 & 0 & 0 \end{pmatrix} \cdots$$

Eq. C-24(e)

$$M_r = -D \cdot \left\{ \frac{d^2}{dr^2} w_r \cdots + v \cdot \left( \frac{1}{r} \cdot \frac{d}{dr} w_r \cdots + \frac{1}{r^2} \cdot \frac{d^2}{d\theta^2} w_r \right) \right\} = \begin{pmatrix} M_{r\,0} \\ M_{r\,1} \\ M_{r\,2} \\ M_{r\,3} \\ M_{r\,4} \\ M_{r\,5} \\ M_{r\,6} \\ M_{r\,7} \\ M_{r\,8} \\ M_{r\,9} \\ M_{r\,10} \\ M_{r\,11} \\ M_{r\,12} \\ M_{r\,13} \\ M_{r\,14} \\ M_{r\,15} \\ M_{r\,16} \\ M_{r\,17} \\ M_{r\,18} \\ M_{r\,19} \\ M_{r\,20} \end{pmatrix}^T \cdot \begin{pmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \\ \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{pmatrix}$$

-continued

Where $\begin{pmatrix} M_{r\,0} \\ M_{r\,1} \\ M_{r\,2} \\ M_{r\,3} \\ M_{r\,4} \\ M_{r\,5} \\ M_{r\,6} \\ M_{r\,7} \\ M_{r\,8} \\ M_{r\,9} \\ M_{r\,10} \\ M_{r\,11} \\ M_{r\,12} \\ M_{r\,13} \\ M_{r\,14} \\ M_{r\,15} \\ M_{r\,16} \\ M_{r\,17} \\ M_{r\,18} \\ M_{r\,19} \\ M_{r\,20} \end{pmatrix} = Cc_{M\_a} \cdot a \ldots + Cc_{M\_p}$ and $$Cc_{M\_p}(r, x_o, y_o, r', D, v, p_z) := \frac{p_z}{8} \cdot \begin{pmatrix} 0 \\ 0 \\ 0 \\ -2 \cdot x_o^2 - 2 \cdot v \cdot y_o^2 \\ 8 \cdot x_o \cdot y_o \cdot (v-1) \\ -2 \cdot v \cdot x_o^2 - 2 \cdot y_o^2 \\ -4 \cdot r \cdot v \cdot y_o \\ 4 \cdot r \cdot x_o \cdot (2 \cdot v - 3) \\ 4 \cdot r \cdot y_o \cdot (2 \cdot v - 3) \\ -4 \cdot r \cdot v \cdot x_o \\ -2 \cdot r^2 \cdot v \\ 0 \\ 4 \cdot r^2 \cdot (2 \cdot v - 3) \\ 0 \\ -2 \cdot r^2 \cdot v \\ 0 \\ 0 \\ 0 \\ 0 \\ 0 \\ 0 \end{pmatrix}$$

$$Cc_{M\_a}(r, x_o, y_o, r', D, v) := \frac{D}{r'^4} \cdot \begin{pmatrix} 0 & 0 & 0 & 0 \\ 0 & 0 & 0 & 0 \\ 0 & 0 & 0 & 0 \\ 0 & 0 & 0 & 2 \cdot r'^3 \cdot (v-1) \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \end{pmatrix} \cdots$$

Eq. C-24(f)

$$T_r = -D \cdot (1-v) \cdot \left( \begin{matrix} \frac{1}{r} \cdot \frac{d}{dr}\frac{d}{d\theta} w_r \cdots + \\ \frac{-1}{r^2} \cdot \frac{d}{d\theta} w_r \end{matrix} \right) = \begin{pmatrix} T_{r_0} \\ T_{r_1} \\ T_{r_2} \\ T_{r_3} \\ T_{r_4} \\ T_{r_5} \\ T_{r_6} \\ T_{r_7} \\ T_{r_8} \\ T_{r_9} \\ T_{r_{10}} \\ T_{r_{11}} \\ T_{r_{12}} \\ T_{r_{13}} \\ T_{r_{14}} \\ T_{r_{15}} \\ T_{r_{16}} \\ T_{r_{17}} \\ T_{r_{18}} \\ T_{r_{19}} \\ T_{r_{20}} \end{pmatrix}^T \cdot \begin{pmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \\ \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{pmatrix}$$

Where $\begin{pmatrix} T_{r_0} \\ T_{r_1} \\ T_{r_2} \\ T_{r_3} \\ T_{r_4} \\ T_{r_5} \\ T_{r_6} \\ T_{r_7} \\ T_{r_8} \\ T_{r_9} \\ T_{r_{10}} \\ T_{r_{11}} \\ T_{r_{12}} \\ T_{r_{13}} \\ T_{r_{14}} \\ T_{r_{15}} \\ T_{r_{16}} \\ T_{r_{17}} \\ T_{r_{18}} \\ T_{r_{19}} \\ T_{r_{20}} \end{pmatrix} = Cc_{T\_a} \cdot a \ldots + Cc_{T\_p}$ and $$Cc_{T\_p}(r, x_o, y_o, r', D, v, p_z) := \frac{p_z \cdot (1-v)}{8} \cdot \begin{pmatrix} 0 \\ 0 \\ 0 \\ 4 \cdot x_o \cdot y_o \\ 2 \cdot y_o^2 - 2 \cdot x_o^2 \\ -4 \cdot x_o \cdot y_o \\ 4 \cdot r \cdot x_o \\ 8 \cdot r \cdot y_o \\ -8 \cdot r \cdot x_o \\ -4 \cdot r \cdot y_o \\ 0 \\ 6 \cdot r^2 \\ 0 \\ -6 \cdot r^2 \\ 0 \\ 0 \\ 0 \\ 0 \\ 0 \\ 0 \\ 0 \end{pmatrix}$$

$$Cc_{T\_a}(r, x_o, y_o, r', D, v) := \frac{D \cdot (1-v)}{r'^4} \cdot \begin{pmatrix} 0 & 0 & 0 & 0 \\ 0 & 0 & 0 & 0 \\ 0 & 0 & 0 & 0 \\ 0 & 0 & 0 & r'^3 \\ 0 & 0 & 0 & 0 \\ 0 & 0 & 0 & -r'^3 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \\ 0 & 0 & 0 & 0 \end{pmatrix} \cdots$$

Similar to the area integrals addressed earlier, the edge integrals (Eq. C-23) can produce a very large and complex algebraic form. Consequently, it is desirable to find ways to make this process as easy and efficient as possible. To this end, another generalized integration is defined (as shown in Eq. C-25) that addresses possible integrals considering Eq. C-24.

Eq. C-24

$$\text{Int}'_c = \int_{\theta_0}^{\theta_1} \begin{pmatrix} \alpha'_0 \\ \alpha'_1 \\ \alpha'_2 \\ \alpha'_3 \\ \alpha'_4 \\ \alpha'_5 \\ \alpha'_6 \\ \alpha'_7 \\ \alpha'_8 \\ \alpha'_9 \\ \alpha'_{10} \\ \alpha'_{11} \\ \alpha'_{12} \\ \alpha'_{13} \\ \alpha'_{14} \\ \alpha'_{15} \\ \alpha'_{16} \\ \alpha'_{17} \\ \alpha'_{18} \\ \alpha'_{19} \\ \alpha'_{20} \end{pmatrix}^T \cdot \begin{pmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \\ \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{pmatrix} \cdot \left[ \begin{pmatrix} \beta'_0 \\ \beta'_1 \\ \beta'_2 \\ \beta'_3 \\ \beta'_4 \\ \beta'_5 \\ \beta'_6 \\ \beta'_7 \\ \beta'_8 \\ \beta'_9 \\ \beta'_{10} \\ \beta'_{11} \\ \beta'_{12} \\ \beta'_{13} \\ \beta'_{14} \\ \beta'_{15} \\ \beta'_{16} \\ \beta'_{17} \\ \beta'_{18} \\ \beta'_{19} \\ \beta'_{20} \end{pmatrix}^T \cdot \begin{pmatrix} 1 \\ \sin(\theta) \\ \cos(\theta) \\ \sin(\theta)^2 \\ \sin(\theta) \cdot \cos(\theta) \\ \cos(\theta)^2 \\ \sin(\theta)^3 \\ \sin(\theta)^2 \cdot \cos(\theta) \\ \sin(\theta) \cdot \cos(\theta)^2 \\ \cos(\theta)^3 \\ \sin(\theta)^4 \\ \sin(\theta)^3 \cdot \cos(\theta) \\ \sin(\theta)^2 \cdot \cos(\theta)^2 \\ \sin(\theta) \cdot \cos(\theta)^3 \\ \cos(\theta)^4 \\ \sin(\theta)^5 \\ \sin(\theta)^4 \cdot \cos(\theta) \\ \sin(\theta)^3 \cdot \cos(\theta)^2 \\ \sin(\theta)^2 \cdot \cos(\theta)^3 \\ \sin(\theta) \cdot \cos(\theta)^4 \\ \cos(\theta)^5 \end{pmatrix} \right] \cdot r \, d\theta \quad \text{Generalized integration}$$

Comparing Eq. C-24 to Eq. C-12, it can be seen that there are important similarities. The primary difference is Eq. C-12 has an additional integral relative to "dr" (that is independent of the integral relative to "dθ"). Consequently, Eq. C-24 can be expressed in functions defined for the area integrals (as shown in Eq. C-25).

$$\text{Int}'_c = Cvtc(\alpha, \beta) \cdot Sc_{0\_1}(\theta_0, \theta_1) \cdot r \quad \text{Eq. C-25}$$

At this point, most of the derivation needed for the edge energy has been completed. Similar to the formulation of the area integrals, the formulation from here forward uses a strategy to aid in simplicity of discussion rather than trying to be most efficient. (This strategy generates sparse arrays and coding it into an actual finite element solver could be done much more efficiently by reducing the calculation down to where adding or multiplying by zero does not occur.)

The subroutines and functions for the algebraic form of the edge integrals follows the same strategy as that discussed in Section B except, for ease of derivation, only constant displacements/loads will be considered. (It is not difficult to include the entire edge function but it is not needed for this example.) Consequently, three subroutines are included which are Sus. C-4 to C-6. Su. C-4 is similar to Su. B-3.

$$\text{Int}_{vco}(A_\alpha, V_\beta, s_{01}) := \begin{vmatrix} no \leftarrow 5 \\ A_{\alpha_{no,0}} \leftarrow 0 \text{ if } rows(A_\alpha) - 1 < no \\ V_{\beta_{no,0}} \leftarrow 0 \text{ if } rows(V_\beta) - 1 < no \\ out_{cols(A_\alpha)-1, cols(V_\beta)-1} \leftarrow 0 \\ \text{for } j \in 0 \ldots cols(V_\beta) - 1 \\ \text{for } i \in 0 \ldots cols(A_\alpha) - 1 \\ out_{i,j} \leftarrow Cvtc\left(A_\alpha^{(i)}, V_\beta^{(j)}\right)^T \cdot s_{01} \\ out \end{vmatrix} \quad \text{Su. C-4}$$

Sus. C-5 and C-6 perform the array and vector integration respectively for when a displacement/load is not known.

$$\text{Int}_c(A_\alpha, A_\beta, s_{01}) := \begin{vmatrix} out_{cols(A_\alpha)-1, cols(V_\beta)-1} \leftarrow 0 \\ \text{for } j \in 0 \ldots cols(A_\alpha) - 1 \\ \text{for } i \in 0 \ldots cols(A_\alpha) - 1 \\ out_{i,j} \leftarrow Cvtc\left(A_\alpha^{(i)}, A_\beta^{(j)}\right)^T \cdot s_{01} \\ out \end{vmatrix} \quad \text{Su. C-5}$$

$$\text{Int}_{cp}(A_\alpha, V_\beta, s_{01}) := \begin{vmatrix} out_{cols(A_\alpha)-1, cols(V_\beta)-1} \leftarrow 0 \\ \text{for } j \in 0 \ldots cols(V_\beta) - 1 \\ \text{for } i \in 0 \ldots cols(A_\alpha) - 1 \\ out_{i,j} \leftarrow Cvtc\left(A_\alpha^{(i)}, V_\beta^{(j)}\right)^T \cdot s_{01} \\ out \end{vmatrix} \quad \text{Su. C-6}$$

Eq. C-26 defines the algebraic functions for each of the edge energies. There are three functions (one for each subroutine) for each edge energy. The first is equivalent to that defined in Eq. B-39 except there is a vector rather than an identity matrix (because only a constant displacement/load is being considered). The second and third functions are array and vector definitions respectively for the situation where a displacement/load is not known.

$$Ccp_e(\theta_0, \theta_1, r, x_o, y_o, r', D, v) := \text{Int}_{vco}\left[Cc_{w\_a}(r, x_o, y_o, r', D, v), \begin{bmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{bmatrix}^T, Sc_{0\_1}(\theta_0, \theta_1)\right] \cdot r \quad \text{Eq. C-26(a)}$$

$$Ccp(\theta_0, \theta_1, r, x_o, y_o, r', D, v) := \text{Int}_c(Cc_{w\_a}(r, x_o, y_o, r', D, v), Cc_{P\_a}(r, x_o, y_o, r', D, v), Sc_{0\_1}(\theta_0, \theta_1)) \cdot r$$

$$Ccp_{pz}(\theta_0, \theta_1, r, x_o, y_o, r', D, v, p_z) := \text{Int}_{cp}(Cc_{w\_a}(r, x_o, y_o, r', D, v), Cc_{P\_p}(r, x_o, y_o, r', D, v, p_z), Sc_{0\_1}(\theta_0, \theta_1)) \cdot r$$

Eq. C-26(b)

$$Cc_{Me}(\theta_0, \theta_1, r, x_o, y_o, r', D, v) := Int_{vco}\left[Cc_{\theta\_a}(r, x_o, y_o, r', D, v), \begin{pmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{pmatrix}, Sc_{0\_1}(\theta_0, \theta_1)\right]^T \cdot r$$

$Cc_M(\theta_0, \theta_1, r, x_o, y_o, r', D, v) := -Int_c(Cc_{\theta\_a}(r, x_o, y_o, r', D, v), Cc_{M\_a}(r, x_o, y_o, r', D, v), Sc_{0\_1}(\theta_0, \theta_1)) \cdot r$ $Cc_{Mpz}(\theta_0, \theta_1, r, x_o, y_o, r', D, v, p_z) := -Int_{cp}(Cc_{\theta\_a}(r, x_o, y_o, r', D, v), Cc_{M\_p}(r, x_o, y_o, r', D, v, p_z), Sc_{0\_1}(\theta_0, \theta_1)) \cdot r$ Eq. C-26(c)

$$Cc_{Te}(\theta_0, \theta_1, r, x_o, y_o, r', D, v) := Int_{vco}\left[Cc_{\phi\_a}(r, x_o, y_o, r', D, v), \begin{pmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{pmatrix}, Sc_{0\_1}(\theta_0, \theta_1)\right]^T \cdot r$$

$Cc_T(\theta_0, \theta_1, r, x_o, y_o, r', D, v) := -Int_c(Cc_{\phi\_a}(r, x_o, y_o, r', D, v), Cc_{T\_a}(r, x_o, y_o, r', D, v), Sc_{0\_1}(\theta_0, \theta_1)) \cdot r$ $Cc_{Tpz}(\theta_0, \theta_1, r, x_o, y_o, r', D, v, p_z) := -Int_{cp}(Cc_{\phi\_a}(r, x_o, y_o, r', D, v), Cc_{T\_p}(r, x_o, y_o, r', D, v, p_z), Sc_{0\_1}(\theta_0, \theta_1)) \cdot r$ $$Cc_{we}(\theta_0, \theta_1, r, x_o, y_o, r', D, v) := Int_{vco}\left[Cc_{P\_a}(r, x_o, y_o, r', D, v), \begin{pmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{pmatrix}, Sc_{0\_1}(\theta_0, \theta_1)\right]^T \cdot r$$

Eq. C-26(d)

$Cc_w(\theta_0, \theta_1, r, x_o, y_o, r', D, v) := Int_c(Cc_{P\_a}(r, x_o, y_o, r', D, v), Cc_{w\_a}(r, x_o, y_o, r', D, v), Sc_{0\_1}(\theta_0, \theta_1)) \cdot r$ $Cc_{wpz}(\theta_0, \theta_1, r, x_o, y_o, r', D, v, p_z) := Int_{cp}(Cc_{P\_a}(r, x_o, y_o, r', D, v), Cc_{w\_p}(r, x_o, y_o, r', D, v, p_z), Sc_{0\_1}(\theta_0, \theta_1)) \cdot r$ $$Cc_{\theta e}(\theta_0, \theta_1, r, x_o, y_o, r', D, v) := Int_{vco}\left[Cc_{M\_a}(r, x_o, y_o, r', D, v), \begin{pmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{pmatrix}, Sc_{0\_1}(\theta_0, \theta_1)\right]^T \cdot r$$

Eq. C-26(e)

$Cc_\theta(\theta_0, \theta_1, r, x_o, y_o, r', D, v) := -Int_c(Cc_{M\_a}(r, x_o, y_o, r', D, v), Cc_{\theta\_a}(r, x_o, y_o, r', D, v), Sc_{0\_1}(\theta_0, \theta_1)) \cdot r$ $Cc_{\theta pz}(\theta_0, \theta_1, r, x_o, y_o, r', D, v, p_z) := -Int_{cp}(Cc_{M\_a}(r, x_o, y_o, r', D, v), Cc_{\theta\_p}(r, x_o, y_o, r', D, v, p_z), Sc_{0\_1}(\theta_0, \theta_1)) \cdot r$ $$Cc_{\phi e}(\theta_0, \theta_1, r, x_o, y_o, r', D, v) := Int_{vco}\left[Cc_{T\_a}(r, x_o, y_o, r', D, v), \begin{bmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{bmatrix}^T, Sc_{0\_1}(\theta_0, \theta_1)\right] \cdot r$$

Eq. C-26(f)

$Cc_\phi(\theta_0, \theta_1, r, x_o, y_o, r', D, v) := -Int_c(Cc_{T\_a}(r, x_o, y_o, r', D, v), Cc_{\phi\_a}(r, x_o, y_o, r', D, v), Sc_{0\_1}(\theta_0, \theta_1)) \cdot r$ $Cc_{\phi pz}(\theta_0, \theta_1, r, x_o, y_o, r', D, v, p_z) := -Int_{cp}(Cc_{T\_a}(r, x_o, y_o, r', D, v), Cc_{\phi\_p}(r, x_o, y_o, r', D, v, p_z), Sc_{0\_1}(\theta_0, \theta_1)) \cdot r$ At this point, all of the definitions necessary for an algebraic form of Eq. C-23 have been defined. These equations are now used to generate array constants and vector constants consistent with Eq. A-50. This occurs under the same strategy as that discussed in Section B (Eq. B-40) for a straight edge. However, a modified version of Eq. C-26 may be used if there were interactions with a neighboring element.

Model Formulation

Figure 22:
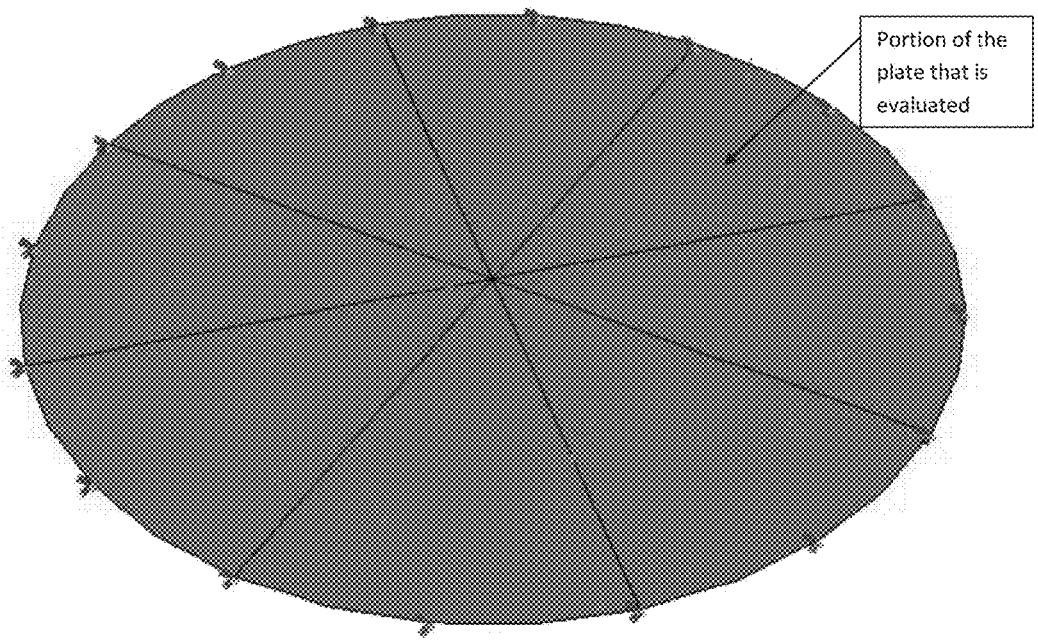
FIG. 22 is a perspective view of an example thin plate divided into eight elements and having a fixed edge and distributed pressure load.
Figure 23:
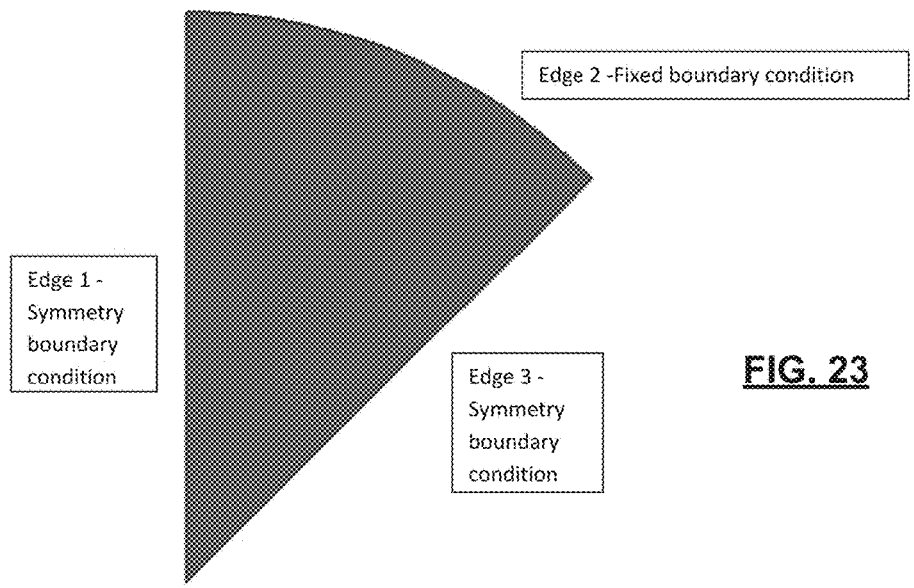
FIG. 23 is a top view of one of the elements of the plate of FIG. 22.

The test model (as shown in FIG. 22) is a thin plate that is 2.5 inches in diameter by 0.1 inches thick. All of the edges are fixed and there is a 300 psi pressure applied evenly over the surface. Considering symmetry, a single pie shaped element with symmetry restraints can be used to evaluate the whole plate. The evaluated portion of the plate is identified in FIG. 22 and shown with boundary conditions identified in FIG. 23. This problem is selected because a single, simple element can be used to solve it. Also, the exact solution is well known and can be used for comparison.

The material properties and element geometry are listed below.

E:=30·10$^6$ Modulus of elasticity
v:=0.3 Poisson's ratio
t:=0.1 Thickness $$D := \frac{E \cdot t^3}{12 \cdot (1 - v^2)}$$ Flexural rigidity D=2747.253
x$^T$=(0 0 0.884) Endpoints in the x-direction for the triangular element
y$^T$=(0 1.25 0.884) Endpoints in the y-direction for the triangular element
r':=6.4 Length dimension used to make the degrees of freedom unitless. (The value of 6.4 is arbitrarily selected as a good value relative to matrix inversion. This is the integer value that makes the matrix determinant and matrix inverse determinant closest to one.)

Element Definitions and Boundary Conditions

The equations derived for this example are for circular edges. Equations for straight edges are also included in this model. The element definition variables are organized to accept both shapes.

For the element definitions, three simple arrays are defined to guide the process of formulating an element. The first is an area mapping array as shown below. The area mapping array guides the area integral solutions for each edge. Each row represents an edge. The first column represents the edge shape. A zero indicates that the edge is linear where a one (as is the case here) indicates a circular edge. For both edge types, the next two columns are the indices for the start and end edge endpoints. For a circular edge, the third column is the circle center point and the fourth column is a one for a solid circle and a zero for a hole. The circle algorithms are set up to define a pie shaped area (or full circle) and the points are always in a clockwise manner. Given that the whole element for this example is a pie shape, one circular definition defines the whole element area.

$a_{map}$:=(1 1 2 0 1)   Area mapping array

The second array is an edge mapping array as shown below. The edge mapping array guides the edge integral solutions for each edge. Each row represents an edge. The first column represents the edge shape. A zero indicates that the edge is linear (as is the case for the first and third edges) where a one indicates a circular edge (as is the case for the second edge). For both edge types, the next two columns are the indices for the start and end edge endpoints. For a circular edge, the third column is the circle center point and the fourth column is a one for a solid circle and a zero for a hole. As in the area integrals, the circle algorithms are set up to define a pie shaped area (or full circle) and the points are defined in a clockwise manner.

$$e_{map} := \begin{pmatrix} 0 & 0 & 1 & 0 & 0 \\ 1 & 1 & 2 & 0 & 1 \\ 0 & 2 & 0 & 0 & 0 \end{pmatrix}$$

Edge mapping array

The third array (as shown below) is a boundary conditions mapping array that corresponds to the edge mapping array. Each row of this array identifies active boundary conditions for the corresponding row in the edge mapping array. A zero indicates that the external displacement/load is unknown. A one indicates that the external displacement/load is known. Each column represents a displacement/load as identified below. Considering that this is a single element problem, all of the boundary conditions consist of a known displacement/load and the corresponding load/displacement is not known. For this element, the first and third edges have symmetry boundary conditions and the second edge is fixed in displacement.

$$\text{map} := \begin{matrix} w & \theta & \phi & P & M & T \\ \begin{pmatrix} 0 & 1 & 0 & 1 & 0 & 1 \\ 1 & 1 & 1 & 0 & 0 & 0 \\ 0 & 1 & 0 & 1 & 0 & 1 \end{pmatrix} \end{matrix}$$

Boundary conditions mapping array

The boundary conditions are defined as arrays where each column corresponds with an edge defined in the edge mapping array. In the definitions, each row corresponds to a displacement/load constant defined in Eq. B-38 for the linear edges and (for this example) the circular edge is just defined as having constant displacement/load. The pressure loading is defined as a scalar value.

$$P_e = \begin{pmatrix} 0 & 0 & 0 \\ 0 & 0 & 0 \\ 0 & 0 & 0 \\ 0 & 0 & 0 \end{pmatrix} \text{Shear load} \quad M_e = \begin{pmatrix} 0 & 0 & 0 \\ 0 & 0 & 0 \\ 0 & 0 & 0 \\ 0 & 0 & 0 \end{pmatrix} \text{Bending moment}$$

$$T_e = \begin{pmatrix} 0 & 0 & 0 \\ 0 & 0 & 0 \\ 0 & 0 & 0 \\ 0 & 0 & 0 \end{pmatrix} \text{Torsional moment} \quad w_e = \begin{pmatrix} 0 & 0 & 0 \\ 0 & 0 & 0 \\ 0 & 0 & 0 \\ 0 & 0 & 0 \\ 0 & 0 & 0 \\ 0 & 0 & 0 \end{pmatrix} \text{Displacement}$$

$$\theta_e = \begin{pmatrix} 0 & 0 & 0 \\ 0 & 0 & 0 \\ 0 & 0 & 0 \\ 0 & 0 & 0 \\ 0 & 0 & 0 \end{pmatrix} \text{Bending rotation} \quad \phi_e = \begin{pmatrix} 0 & 0 & 0 \\ 0 & 0 & 0 \\ 0 & 0 & 0 \\ 0 & 0 & 0 \\ 0 & 0 & 0 \end{pmatrix} \text{Torsional rotation}$$

Circular Edges:

$$Pc_e = (0 \ 0 \ 0) \ \text{Shear load} \quad Mc_e = (0 \ 0 \ 0) \ \text{Bending moment}$$

$$Tc_e = (0 \ 0 \ 0) \ \text{Torsional moment} \quad wc_e = (0 \ 0 \ 0) \ \text{Displacement}$$

$$\theta c_e = (0 \ 0 \ 0) \ \text{Bending rotation} \quad \phi c_e = (0 \ 0 \ 0) \ \text{Torsional rotation}$$

Area Loading:

$p_z := -300$ Distributed pressure

Continuing with the element definition, functions defined in Section B (Eq. B-41) are used which establish edge slope and edge y-intercept. These are for the area integrals and the equations were defined in Eq. A-37. More functions defined in Section B (Eq. B-42) are used here and are relevant to the edge integrals. These equations were defined in Eqs. A-41 to A-43.

For the circular edges, Su. C-7 is defined to covert mapping data along with the endpoint data into a vector containing staring angle, ending angle, radius, and x- and y-direction center position.

$$\text{tr\_ro}(v) := \begin{vmatrix} v0 \leftarrow (x_{v_1} \ -x_{v_3} \ y_{v_1} \ -y_{v_3})^T \\ v1 \leftarrow (x_{v_2} \ -x_{v_3} \ y_{v_2} \ -y_{v_3})^T \\ \theta_0 \leftarrow \text{acos}\left[\frac{v0 \cdot (1 \ 0)^T}{|v0|}\right] \\ \theta_0 \leftarrow 2 \cdot \pi - \theta_0 \ \text{if} \ v0 \cdot (0 \ 1)^T \leq 0 \\ \theta_1 \leftarrow \text{acos}\left[\frac{v1 \cdot (1 \ 0)^T}{|v1|}\right] \\ \theta_1 \leftarrow 2 \cdot \pi - \theta_1 \ \text{if} \ v1 \cdot (0 \ 1)^T < 0 \\ \theta_1 \leftarrow \theta_1 - 2 \cdot \pi \ \text{if} \ \theta_1 > \theta_0 \\ (\theta_0 \ \theta_1 \ |v0| \ x_{v_3} \ y_{v_3})^T \end{vmatrix} \quad \text{Su. C-7}$$

The area mapping array and edge mapping array are defined in simple terms to make input logical and simple. Eqs. B-41 and B-42 and Su. C-7 can be used to put these arrays in a form that is more convenient for use in subroutines. Sus. C-8 and C-9 perform this function. These subroutines are used as a way to automate the process and as a way to ensure that division by zero doesn't occur (as it could if $x_0=x_1$ in Eq. B-41). (In Section B, Sus. B-4 and B-5 are the same as Sus. C-8 and C-9 except Sus. C-8 and C-9 include Su. C-7 for the circular edge definition.)

$$a_c := \begin{vmatrix} \\ \\ \\ \\ \\ \\ \\ \\ \\ \\ \\ \\ \\ \\ \end{vmatrix}$$

Su. C-8

$$\begin{vmatrix} out_{T_{4,\text{rows}(a_{map})-1}} \leftarrow 0 \\ \text{for } i \in 0 \ldots \text{rows}(a_{map}) - 1 \\ \quad \begin{vmatrix} out_{T_{0,i}} \leftarrow x_{a_{map_{i,1}}} \\ out_{T_{1,i}} \leftarrow x_{a_{map_{i,2}}} \\ \text{if } x_{a_{map_{i,1}}} \neq x_{a_{map_{i,2}}} \wedge a_{map_{i,0}} = 0 \\ \quad \begin{vmatrix} out_{T_{2,i}} \leftarrow m_{ofunc}(x_{a_{map_{i,1}}}, x_{a_{map_{i,2}}}, y_{a_{map_{i,1}}}, y_{a_{map_{i,2}}}) \\ out_{T_{3,i}} \leftarrow b_{ofunc}(x_{a_{map_{i,1}}}, x_{a_{map_{i,2}}}, y_{a_{map_{i,1}}}, y_{a_{map_{i,2}}}) \end{vmatrix} \\ out_T^{\langle i \rangle} \leftarrow \text{tr\_ro}\left[(a_{map}^T)^{\langle i \rangle}\right] \text{ if } a_{map_{i,0}} = 1 \end{vmatrix} \\ out_T^T \end{vmatrix}$$

$a_c := (\, 1.571 \quad 0.785 \quad 1.25 \quad 0 \quad 0 \,)$
Area mapping array for calculation $$e_c := \begin{vmatrix} out_{T_{4,\text{rows}(e_{map})-1}} \leftarrow 0 \\ \text{for } i \in 0 \ldots \text{rows}(e_{map}) - 1 \\ \quad \begin{vmatrix} \text{if } e_{map_{i,0}} = 0 \\ \quad \begin{vmatrix} p \leftarrow e_{map_{i,1}} \\ q \leftarrow e_{map_{i,2}} \\ out_T^{\langle i \rangle} \leftarrow \begin{pmatrix} \theta_{xfunc}(x_p, x_q, y_p, y_q) \\ \theta_{yfunc}(x_p, x_q, y_p, y_q) \\ s_{yfunc}(x_p, x_q, y_p, y_q) \\ s_{x0func}(x_p, x_q, y_p, y_q) \\ s_{x1func}(x_p, x_q, y_p, y_q) \end{pmatrix} \end{vmatrix} \\ out_T^{\langle i \rangle} \leftarrow \text{tr\_ro}\left[(e_{map}^T)^{\langle i \rangle}\right] \text{ if } e_{map_{i,0}} = 1 \end{vmatrix} \\ out_T^T \end{vmatrix}$$

Su. C-9

$$e_c = \begin{pmatrix} 0 & 1 & 0 & 0 & 1.25 \\ 1.571 & 0.785 & 1.25 & 0 & 0 \\ -0.707 & -0.707 & 0 & -1.25 & 0 \end{pmatrix}$$

Edge mapping array for calculation

Considering the equations for the area integrals, Su. B-6(defined in Section B) along with Su. C-10 produce arrays which include all of the area integration data for the element in the example problem. These arrays are the portion of the $U_b$ vector (in Eq. A-51) related to the area integrals augmented to the portion of the $U_m$ array (in Eq. A-51) related to the area integrals. These subroutines start by populating the output array and vector with zeros. They then calculate the algebraic form of the strain energy and work of the pressure load for each row of the area mapping array. The factor of 2 on the strain energy array and vector is from Eq. A-48.

$$U'_{o\_ec} := \begin{vmatrix} k_{17,17} \leftarrow 0 \\ F_{17} \leftarrow 0 \\ \text{for } i \in 0 \ldots \text{rows}(a_{map}) - 1 \\ \quad \begin{vmatrix} \text{if } a_{map_{i,0}} = 1 \\ \quad \begin{vmatrix} k \leftarrow -2 \cdot Uc_o(a_{c_{i,0}}, a_{c_{i,1}}, a_{c_{i,2}}, a_{c_{i,3}}, a_{c_{i,4}}, r', D, v) \cdot \\ a_{map_{i,4}} + k \\ F \leftarrow -2 \cdot Uc_{pz}(a_{c_{i,0}}, a_{c_{i,1}}, a_{c_{i,2}}, a_{c_{i,3}}, a_{c_{i,4}}, r', D, v, p_z) \cdot \\ a_{map_{i,4}} + F \\ F \leftarrow Uc_p(a_{c_{i,0}}, a_{c_{i,1}}, a_{c_{i,2}}, a_{c_{i,3}}, a_{c_{i,4}}, r', D, v, p_z) \cdot \\ a_{map_{i,4}} + F \\ \text{augment}(F, k) \end{vmatrix} \end{vmatrix} \end{vmatrix}$$

Su. C-10

Considering the equations for the edge integrals, Su. B-7(defined in Section B) along with Su. C-11 produce arrays which includes all of the edge integration data for the element in the example problem. These arrays are the portion of the $U_b$ vector (in Eq. A-51) related to the edge integrals augmented to the portion of the $U_m$ array (in Eq. A-51) related to the edge integrals. These subroutines start by populating the output array and vector with zeros. They then calculate the algebraic form of the edge integrals for each row of the edge mapping array. The boundary conditions mapping array uses the logic discussed with Eq. B-40 to determine the correct algorithm for addressing the displacement/load situation.

Su. C-11

$$U'_{ec} := \begin{vmatrix} k_{17,17} \leftarrow 0 \\ F_{17} \leftarrow 0 \\ \text{for } i \in 0 \ldots \text{rows}(e_{map}) - 1 \\ \text{if } e_{map_{i,0}} = 1 \\ \quad \begin{vmatrix} \text{if } \text{map}_{i,0} = 1 \\ \quad \begin{vmatrix} k \leftarrow Cc_w(e_{c_{i,0}}, e_{c_{i,1}}, e_{c_{i,2}}, e_{c_{i,3}}, e_{c_{i,4}}, r', D, v) \cdot e_{map_{i,4}} + k \\ F \leftarrow Cc_{wpz}(e_{c_{i,0}}, e_{c_{i,1}}, e_{c_{i,2}}, e_{c_{i,3}}, e_{c_{i,4}}, r', D, v, p_z) \cdot e_{map_{i,4}} + F \end{vmatrix} \\ F \leftarrow -Cc_{we}(e_{c_{i,0}}, e_{c_{i,1}}, e_{c_{i,2}}, e_{c_{i,3}}, e_{c_{i,4}}, r', D, v)^T \cdot (-wc_{e_{0,i}}) + F \text{ if } \text{map}_{i,0} = 1 \\ \text{if } \text{map}_{i,1} = 0 \\ \quad \begin{vmatrix} k \leftarrow Cc_\theta(e_{c_{i,0}}, e_{c_{i,1}}, e_{c_{i,2}}, e_{c_{i,3}}, e_{c_{i,4}}, r', D, v) \cdot e_{map_{i,4}} + k \\ F \leftarrow Cc_{\theta pz}(e_{c_{i,0}}, e_{c_{i,1}}, e_{c_{i,2}}, e_{c_{i,3}}, e_{c_{i,4}}, r', D, v, p_z) \cdot e_{map_{i,4}} + F \end{vmatrix} \\ F \leftarrow -Cc_{\theta e}(e_{c_{i,0}}, e_{c_{i,1}}, e_{c_{i,2}}, e_{c_{i,3}}, e_{c_{i,4}}, r', D, v)^T \cdot (\theta c_{e_{0,i}}) + F \text{ if } \text{map}_{i,1} = 1 \\ \text{if } \text{map}_{i,2} = 0 \\ \quad \begin{vmatrix} k \leftarrow Cc_\phi(e_{c_{i,0}}, e_{c_{i,1}}, e_{c_{i,2}}, e_{c_{i,3}}, e_{c_{i,4}}, r', D, v) \cdot e_{map_{i,4}} + k \\ F \leftarrow Cc_{\phi pz}(e_{c_{i,0}}, e_{c_{i,1}}, e_{c_{i,2}}, e_{c_{i,3}}, e_{c_{i,4}}, r', D, v, p_z) \cdot e_{map_{i,4}} + F \end{vmatrix} \\ F \leftarrow -Cc_{\phi e}(e_{c_{i,0}}, e_{c_{i,1}}, e_{c_{i,2}}, e_{c_{i,3}}, e_{c_{i,4}}, r', D, v)^T \cdot (\phi c_{e_{0,i}}) + F \text{ if } \text{map}_{i,2} = 1 \\ \text{if } \text{map}_{i,3} = 0 \\ \quad \begin{vmatrix} k \leftarrow Cc_P(e_{c_{i,0}}, e_{c_{i,1}}, e_{c_{i,2}}, e_{c_{i,3}}, e_{c_{i,4}}, r', D, v) \cdot e_{map_{i,4}} + k \\ F \leftarrow Cc_{Ppz}(e_{c_{i,0}}, e_{c_{i,1}}, e_{c_{i,2}}, e_{c_{i,3}}, e_{c_{i,4}}, r', D, v, p_z) \cdot e_{map_{i,4}} + F \end{vmatrix} \\ F \leftarrow -Cc_{Pe}(e_{c_{i,0}}, e_{c_{i,1}}, e_{c_{i,2}}, e_{c_{i,3}}, e_{c_{i,4}}, r', D, v)^T \cdot (Pc_{e_{0,i}}) + F \text{ if } \text{map}_{i,3} = 1 \\ \text{if } \text{map}_{i,4} = 0 \\ \quad \begin{vmatrix} k \leftarrow Cc_M(e_{c_{i,0}}, e_{c_{i,1}}, e_{c_{i,2}}, e_{c_{i,3}}, e_{c_{i,4}}, r', D, v) \cdot e_{map_{i,4}} + k \\ F \leftarrow Cc_{Mpz}(e_{c_{i,0}}, e_{c_{i,1}}, e_{c_{i,2}}, e_{c_{i,3}}, e_{c_{i,4}}, r', D, v, p_z) \cdot e_{map_{i,4}} + F \end{vmatrix} \\ F \leftarrow -Cc_{Me}(e_{c_{i,0}}, e_{c_{i,1}}, e_{c_{i,2}}, e_{c_{i,3}}, e_{c_{i,4}}, r', D, v)^T \cdot (Mc_{e_{0,i}}) + F \text{ if } \text{map}_{i,4} = 1 \\ \text{if } \text{map}_{i,5} = 0 \\ \quad \begin{vmatrix} k \leftarrow Cc_T(e_{c_{i,0}}, e_{c_{i,1}}, e_{c_{i,2}}, e_{c_{i,3}}, e_{c_{i,4}}, r', D, v) \cdot e_{map_{i,4}} + k \\ F \leftarrow Cc_{Tpz}(e_{c_{i,0}}, e_{c_{i,1}}, e_{c_{i,2}}, e_{c_{i,3}}, e_{c_{i,4}}, r', D, v, p_z) \cdot e_{map_{i,4}} + F \end{vmatrix} \\ F \leftarrow -Cc_{Te}(e_{c_{i,0}}, e_{c_{i,1}}, e_{c_{i,2}}, e_{c_{i,3}}, e_{c_{i,4}}, r', D, v)^T \cdot (Tc_{e_{0,i}}) + F \text{ if } \text{map}_{i,5} = 1 \end{vmatrix} \\ \text{augment}(F, k) \end{vmatrix}$$

Rigid Body Motions

In Section B, the rigid body motions were addressed by equating average external displacements to average element edge displacements. In this example, the rigid body motions will be addressed by including springs between the external displacement and the element displacement. One interesting aspect of including springs is it offers some control over how rigidly the external displacements will be met. Checking the results with soft springs versus stiff springs, as a minimum, provides insight as to the accuracy of the solution. Possibly this could be used to improve the solution.

Eq. C-27 defines the energy associated with the springs. This is defined in the linear edge notation, but it is applicable to all edges.

$$U_{spr\_w_i} = \frac{\partial}{\partial a_i}\left[\frac{1}{2} \cdot k_w \cdot \int (w_s(a) - w_s)^2 ds\right] \quad \text{Eq. C-27(a)}$$

$$U_{spr\_w_i} = k_w \cdot \left(\int w_s(a) \cdot \frac{\partial}{\partial a_i} w_s(a) ds - \int w_s \cdot \frac{\partial}{\partial a_i} w_s(a) ds\right)$$

$$U_{spr\_w_i} = k_w \cdot (C_{wr\_a} \cdot a + C_{wr\_p} + C_{wr\_w}^T \cdot w_s)$$

Where $C_{wr\_w}^T \cdot w_s = C_{wr\_w}^T \cdot \begin{Bmatrix} w_{s0} \\ w_{s1} \\ w_{s2} \\ w_{s3} \\ w_{s4} \\ w_{s5} \end{Bmatrix}$ -continued $$U_{spr\_\theta_i} = \frac{\partial}{\partial a_i}\left[\frac{1}{2} \cdot k_\theta \cdot \int (\theta_s(a) - \theta_s)^2 ds\right]$$ Eq. C-27(b)

$$U_{spr\_\theta_i} = k_\theta \cdot \left(\int \theta_s(a) \cdot \frac{\partial}{\partial a_i}\theta_s(a)ds - \int \theta_s \cdot \frac{\partial}{\partial a_i}\theta_s(a)ds\right)$$

$$U_{spr\_\theta_i} = k_\theta \cdot (C_{\theta r\_a} \cdot a + C_{\theta r\_p} + C_{\theta r\_\theta}^T \cdot \theta_s)$$

Where $C_{\theta r\_\theta}^T \cdot \theta_s = C_{\theta r\_\theta}^T \cdot \begin{pmatrix} \theta_{s0} \\ \theta_{s1} \\ \theta_{s2} \\ \theta_{s3} \\ \theta_{s4} \\ \theta_{s5} \end{pmatrix}$ $$U_{spr\_\phi_i} = \frac{\partial}{\partial a_i}\left[\frac{1}{2} \cdot k_\phi \cdot \int (\phi_s(a) - \phi_s)^2 ds\right]$$ Eq. C-27(c)

$$U_{spr\_\phi_i} = k_\phi \cdot \left(\int \phi_s(a) \cdot \frac{\partial}{\partial a_i}\phi_s(a)ds - \int \phi_s \cdot \frac{\partial}{\partial a_i}\phi_s(a)ds\right)$$

$$U_{spr\_\phi_i} = k_\phi \cdot (C_{\phi r\_a} \cdot a + C_{\phi r\_p} + C_{\phi r\_\phi}^T \cdot \phi_s)$$

Where $C_{\phi r\_\phi}^T \cdot \phi_s = C_{\phi r\_\phi}^T \cdot \begin{pmatrix} \phi_{s0} \\ \phi_{s1} \\ \phi_{s2} \\ \phi_{s3} \\ \phi_{s4} \\ \phi_{s5} \end{pmatrix}$ Sus. C-12 and C-13 use these definitions to assemble arrays for linear and circular edges respectively. The results of these arrays can be summed into the $U_b$ vector (in Eq. A-51) and the $U_m$ array (in Eq. A-51).

$$Int(A_\alpha, A_\beta, s_{01}) := \begin{vmatrix} no \leftarrow 5 \\ A_{\alpha_{no,0}} \leftarrow 0 \text{ if } rows(A_\alpha) - 1 < no \\ A_{\beta_{no,0}} \leftarrow 0 \text{ if } rows(A_\beta) - 1 < no \\ out_{cols(A_\alpha)-1,cols(A_\beta)-1} \leftarrow 0 \\ \text{for } j \in 0 \ldots cols(A_\beta) - 1 \\ \quad \text{for } i \in j \ldots cols(A_\alpha) - 1 \\ \quad\quad out_{i,j} \leftarrow Cvt\left(A_\alpha^{(i)}, A_\beta^{(j)}\right)^T \cdot s_{01} \\ \quad\quad out_{j,i} \leftarrow out_{i,j} \\ out \end{vmatrix}$$ Su. C-12

$$Int_{co}(A_\alpha, A_\beta, s_{01}) := \begin{vmatrix} no \leftarrow 5 \\ A_{\alpha_{no,0}} \leftarrow 0 \text{ if } rows(A_\alpha) - 1 < no \\ A_{\beta_{no,0}} \leftarrow 0 \text{ if } rows(A_\beta) - 1 < no \\ out_{cols(A_\alpha)-1,cols(A_\beta)-1} \leftarrow 0 \\ \text{for } j \in 0 \ldots cols(A_\beta) - 1 \\ \quad \text{for } i \in j \ldots cols(A_\alpha) - 1 \\ \quad\quad out_{i,j} \leftarrow Cvtc\left(A_\alpha^{(i)}, A_\beta^{(j)}\right)^T \cdot s_{01} \\ \quad\quad out_{j,i} \leftarrow out_{i,j} \\ out \end{vmatrix}$$ Su. C-13

Using Su. C-12 and Su. B-3, Eq. C-28 can be used as a way of putting the linear edge spring energy integrals into an algebraic form.

$$C_{wr\_a}(\theta_x, \theta_y, s_y, s_0, s_1, r', D, v) :=$$ Eq. C-28(a)
$$Int(C_{w\_a}(\theta_x, \theta_y, s_y, r', D, v),$$
$$\quad C_{w\_a}(\theta_x, \theta_y, s_y, r', D, v), S_{0\_1}(s_0, s_1))$$

$$C_{wr\_p}(\theta_x, \theta_y, s_y, s_0, s_1, r', D, v, p_z) :=$$
$$Int_v(C_{w\_a}(\theta_x, \theta_y, s_y, r', D, v),$$
$$\quad C_{w\_p}(\theta_x, \theta_y, s_y, r', D, v, p_z), S_{0\_1}(s_0, s_1))$$

$$C_{wr\_w}(\theta_x, \theta_y, s_y, s_0, s_1, r', D, v) :=$$

$$Int_v\left[C_{w\_a}(\theta_x, \theta_y, s_y, r', D, v),\right.$$

$$\left.\begin{pmatrix} -1 & 0 & 0 & 0 & 0 & 0 \\ 0 & -1 & 0 & 0 & 0 & 0 \\ 0 & 0 & -1 & 0 & 0 & 0 \\ 0 & 0 & 0 & -1 & 0 & 0 \\ 0 & 0 & 0 & 0 & -1 & 0 \\ 0 & 0 & 0 & 0 & 0 & -1 \end{pmatrix}^T, S_{0\_1}(s_0, s_1)\right]$$

$$C_{\theta r\_a}(\theta_x, \theta_y, s_y, s_0, s_1, r', D, v) :=$$ Eq. C-28(b)
$$Int(C_{\theta\_a}(\theta_x, \theta_y, s_y, r', D, v),$$
$$\quad C_{\theta\_a}(\theta_x, \theta_y, s_y, r', D, v), S_{0\_1}(s_0, s_1))$$

$$C_{\theta r\_p}(\theta_x, \theta_y, s_y, s_0, s_1, r', D, v, p_z) :=$$
$$Int_v(C_{\theta\_a}(\theta_x, \theta_y, s_y, r', D, v),$$
$$\quad C_{\theta\_p}(\theta_x, \theta_y, s_y, r', D, v, p_z), S_{0\_1}(s_0, s_1))$$

$$C_{\theta r\_\theta}(\theta_x, \theta_y, s_y, s_0, s_1, r', D, v) :=$$

$$Int_v\left[C_{\theta\_a}(\theta_x, \theta_y, s_y, r', D, v),\right.$$

$$\left.\begin{pmatrix} -1 & 0 & 0 & 0 & 0 \\ 0 & -1 & 0 & 0 & 0 \\ 0 & 0 & -1 & 0 & 0 \\ 0 & 0 & 0 & -1 & 0 \\ 0 & 0 & 0 & 0 & -1 \end{pmatrix}^T, S_{0\_1}(s_0, s_1)\right]$$

-continued $$C_{\phi r\_a}(\theta_x, \theta_y, s_y, s_0, s_1, r', D, v) := \qquad \text{Eq. C-28(c)}$$
$$Int_v(C_{\phi\_a}(\theta_x, \theta_y, s_y, r', D, v),$$
$$C_{\phi\_a}(\theta_x, \theta_y, s_y, r', D, v), S_{0\_1}(s_0, s_1))$$
$$C_{\phi r\_p}(\theta_x, \theta_y, s_y, s_0, s_1, r', D, v, p_z) :=$$
$$Int_v(C_{\phi\_a}(\theta_x, \theta_y, s_y, r', D, v),$$
$$C_{\phi\_p}(\theta_x, \theta_y, s_y, r', D, v, p_z), S_{0\_1}(s_0, s_1))$$
$$C_{\phi r\_\phi}(\theta_x, \theta_y, s_y, s_0, s_1, r', D, v) :=$$

$$Int_v\left[C_{\phi\_a}(\theta_x, \theta_y, s_y, r', D, v), \begin{pmatrix} -1 & 0 & 0 & 0 & 0 \\ 0 & -1 & 0 & 0 & 0 \\ 0 & 0 & -1 & 0 & 0 \\ 0 & 0 & 0 & -1 & 0 \\ 0 & 0 & 0 & 0 & -1 \end{pmatrix}, S_{0\_1}(s_0, s_1)\right]^T$$

Likewise, using Su. C-13 and Su. C-4, Eq. C-29 can be used as a way of putting the circular edge spring energy integrals into an algebraic form.

$$\text{Eq. C-29(a)}$$
$$Cc_{wr\_a}(\theta_0, \theta_1, r, x_o, y_o, r', D, v) := Int_c(Cc_{w\_a}(r, x_o, y_o, r', D, v), Cc_{w\_a}(r, x_o, y_o, r', D, v), Sc_{0\_1}(\theta_0, \theta_1)) \cdot r$$
$$Cc_{wr\_p}(\theta_0, \theta_1, r, x_o, y_o, r', D, v, p_z) := Int_{cp}(Cc_{w\_a}(r, x_o, y_o, r', D, v), Cc_{w\_p}(r, x_o, y_o, r', D, v, p_z), Sc_{0\_1}(\theta_0, \theta_1)) \cdot r$$

$$Cc_{wr\_w}(\theta_0, \theta_1, r, x_o, y_o, r', D, v) := Int_{vco}\left[Cc_{w\_a}(r, x_o, y_o, r', D, v), \begin{pmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{pmatrix}, Sc_{0\_1}(\theta_0, \theta_1)\right]^T \cdot r$$

-continued

Eq. C-29(b)

$Cc_{\theta r\_a}(\theta_0, \theta_1, r, x_o, y_o, r', D, v) := Int_{co}(Cc_{\theta\_a}(r, x_o, y_o, r', D, v), Cc_{\theta\_a}(r, x_o, y_o, r', D, v), Sc_{0\_1}(\theta_0, \theta_1)) \cdot r$ $Cc_{\theta r\_p}(\theta_0, \theta_1, r, x_o, y_o, r', D, v, p_z) := Int_{vco}(Cc_{\theta\_a}(r, x_o, y_o, r', D, v), Cc_{\theta\_p}(r, x_o, y_o, r', D, v, p_z), Sc_{0\_1}(\theta_0, \theta_1)) \cdot r$ $$Cc_{\theta r\_\theta}(\theta_0, \theta_1, r, x_o, y_o, r', D, v) := Int_{vco}\left[Cc_{\theta\_a}(r, x_o, y_o, r', D, v), \begin{bmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{bmatrix}^T, Sc_{0\_1}(\theta_0, \theta_1)\right] \cdot r$$

Eq. C-29(c)

$Cc_{\phi r\_a}(\theta_0, \theta_1, r, x_o, y_o, r', D, v) := Int_{co}(Cc_{\phi\_a}(r, x_o, y_o, r', D, v), Cc_{\phi\_a}(r, x_o, y_o, r', D, v), Sc_{0\_1}(\theta_0, \theta_1)) \cdot r$ $Cc_{\phi r\_p}(\theta_0, \theta_1, r, x_o, y_o, r', D, v, p_z) := Int_{vco}(Cc_{\phi\_a}(r, x_o, y_o, r', D, v), Cc_{\phi\_p}(r, x_o, y_o, r', D, v, p_z), Sc_{0\_1}(\theta_0, \theta_1)) \cdot r$ $$Cc_{\phi r\_\phi}(\theta_0, \theta_1, r, x_o, y_o, r', D, v) := Int_{vco}\left[Cc_{\phi\_a}(r, x_o, y_o, r', D, v), \begin{bmatrix} -1 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \\ 0 \end{bmatrix}^T, Sc_{0\_1}(\theta_0, \theta_1)\right] \cdot r$$

Considering the Eqs. C-28 and C-29 for the edge integrals, Sus. C-14 and C-15 produce arrays for linear and circular edges respectively which include all of the edge integration data for the element in the example problem. These subroutines calculate the algebraic form of the spring energy integrals for each row of the edge mapping array (where external displacements are known). The boundary conditions mapping array is used to establish if a given edge has a defined external displacement.

Su. C-14

$$U'_{sprl} := \begin{vmatrix} k_{17,17} \leftarrow 0 \\ F_{17} \leftarrow 0 \\ \text{for } i \in 0 .. \text{rows}(e_{map}) - 1 \\ \quad \text{if } e_{map_{i,0}} = 0 \\ \quad \quad \begin{vmatrix} \text{if map}_{i,0} = 1 \\ \quad \begin{vmatrix} k \leftarrow C_{wr\_a}(e_{c_{i,0}}, e_{c_{i,1}}, e_{c_{i,2}}, e_{c_{i,3}}, e_{c_{i,4}}, r', D, v) + k \\ F \leftarrow C_{wr\_p}(e_{c_{i,0}}, e_{c_{i,1}}, e_{c_{i,2}}, e_{c_{i,3}}, e_{c_{i,4}}, r', D, v, p_z) \ldots \\ \quad + C_{wr\_w}(e_{c_{i,0}}, e_{c_{i,1}}, e_{c_{i,2}}, e_{c_{i,3}}, e_{c_{i,4}}, r', D, v)^T \cdot w_e^{<i>} + F \end{vmatrix} \\ \\ \text{if map}_{i,1} = 1 \\ \quad \begin{vmatrix} k \leftarrow C_{\theta r\_a}(e_{c_{i,0}}, e_{c_{i,1}}, e_{c_{i,2}}, e_{c_{i,3}}, e_{c_{i,4}}, r', D, v) + k \\ F \leftarrow C_{\theta r\_p}(e_{c_{i,0}}, e_{c_{i,1}}, e_{c_{i,2}}, e_{c_{i,3}}, e_{c_{i,4}}, r', D, v, p_z) \ldots \\ \quad + C_{\theta r\_\theta}(e_{c_{i,0}}, e_{c_{i,1}}, e_{c_{i,2}}, e_{c_{i,3}}, e_{c_{i,4}}, r', D, v)^T \cdot \theta_e^{<i>} + F \end{vmatrix} \\ \text{if map}_{i,2} = 1 \\ \quad \begin{vmatrix} k \leftarrow C_{\phi r\_a}(e_{c_{i,0}}, e_{c_{i,1}}, e_{c_{i,2}}, e_{c_{i,3}}, e_{c_{i,4}}, r', D, v) + k \\ F \leftarrow C_{\phi r\_p}(e_{c_{i,0}}, e_{c_{i,1}}, e_{c_{i,2}}, e_{c_{i,3}}, e_{c_{i,4}}, r', D, v, p_z) \ldots \\ \quad + C_{\phi r\_\phi}(e_{c_{i,0}}, e_{c_{i,1}}, e_{c_{i,2}}, e_{c_{i,3}}, e_{c_{i,4}}, r', D, v)^T \cdot \phi_e^{<i>} + F \end{vmatrix} \end{vmatrix} \\ \text{augment}(F, k) \end{vmatrix}$$

Su. C-15

$$U'_{sprc} := \begin{vmatrix} k_{17,17} \leftarrow 0 \\ F_{17} \leftarrow 0 \\ \text{for } i \in 0 .. \text{rows}(e_{map}) - 1 \\ \quad \text{if } e_{map_{i,0}} = 0 \\ \quad \quad \begin{vmatrix} \text{if map}_{i,0} = 1 \\ \quad \begin{vmatrix} k \leftarrow Cc_{wr\_a}(e_{c_{i,0}}, e_{c_{i,1}}, e_{c_{i,2}}, e_{c_{i,3}}, e_{c_{i,4}}, r', D, v) + k \\ F \leftarrow Cc_{wr\_p}(e_{c_{i,0}}, e_{c_{i,1}}, e_{c_{i,2}}, e_{c_{i,3}}, e_{c_{i,4}}, r', D, v, p_z) \ldots \\ \quad + Cc_{wr\_w}(e_{c_{i,0}}, e_{c_{i,1}}, e_{c_{i,2}}, e_{c_{i,3}}, e_{c_{i,4}}, r', D, v)^T \cdot wc_{e_{0,i}} + F \end{vmatrix} \\ \\ \text{if map}_{i,1} = 1 \\ \quad \begin{vmatrix} k \leftarrow Cc_{\theta r\_a}(e_{c_{i,0}}, e_{c_{i,1}}, e_{c_{i,2}}, e_{c_{i,3}}, e_{c_{i,4}}, r', D, v) + k \\ F \leftarrow Cc_{\theta r\_p}(e_{c_{i,0}}, e_{c_{i,1}}, e_{c_{i,2}}, e_{c_{i,3}}, e_{c_{i,4}}, r', D, v, p_z) \ldots \\ \quad + Cc_{\theta r\_\theta}(e_{c_{i,0}}, e_{c_{i,1}}, e_{c_{i,2}}, e_{c_{i,3}}, e_{c_{i,4}}, r', D, v)^T \cdot \theta c_{e_{0,i}} + F \end{vmatrix} \\ \text{if map}_{i,2} = 1 \\ \quad \begin{vmatrix} k \leftarrow Cc_{\phi r\_a}(e_{c_{i,0}}, e_{c_{i,1}}, e_{c_{i,2}}, e_{c_{i,3}}, e_{c_{i,4}}, r', D, v) + k \\ F \leftarrow Cc_{\phi r\_p}(e_{c_{i,0}}, e_{c_{i,1}}, e_{c_{i,2}}, e_{c_{i,3}}, e_{c_{i,4}}, r', D, v, p_z) \ldots \\ \quad + Cc_{\phi r\_\phi}(e_{c_{i,0}}, e_{c_{i,1}}, e_{c_{i,2}}, e_{c_{i,3}}, e_{c_{i,4}}, r', D, v)^T \cdot \phi c_{e_{0,i}} + F \end{vmatrix} \end{vmatrix} \\ \text{-augment}(F, k) \end{vmatrix}$$

The stiffness "k" is included as a multiplier on the arrays resulting from Sus. C-14 and C-15. For this example, the stiffness will be defined as unity.

$k := 1$    Spring stiffness for the edge springs added to remove rigid body motions Degrees of Freedom and Results Plots Having the array that is the portion of the $U_b$ vector (in Eq. A-51) related to the rigid body edge integrals augmented to the portion of the $U_m$ array (in Eq. A-51) related to the rigid body edge integrals, the $U_m$ array and $U_b$ vector can be defined.

$U_m :=$    Array constant for Eq. A-51
$submatrix(U'_{o\_el}, 0, rows(U'_{o\_el}) - 1, 1, cols(U'_{o\_el}) - 1) \ldots +$
$submatrix(U'_{el}, 0, rows(U'_{el}) - 1, 1, cols(U'_{el}) - 1) \ldots +$
$submatrix(U'_{o\_ec}, 0, rows(U'_{o\_ec}) - 1, 1, cols(U'_{o\_ec}) - 1) \ldots +$
$submatrix(U'_{ec}, 0, rows(U'_{ec}) - 1, 1, cols(U'_{ec}) - 1) \ldots +$
$k \cdot \begin{pmatrix} submatrix(U'_{sprl}, 0, rows(U'_{sprl}) - 1, 1, cols(U'_{sprl}) - 1) \ldots + \\ submatrix(U'_{sprc}, 0, rows(U'_{sprc}) - 1, 1, cols(U'_{sprc}) - 1) \end{pmatrix}$ $U_b := U'^{(0)}_{o\_el} + U'^{(0)}_{el} + U'^{(0)}_{o\_ec} + U'^{(0)}_{ec} + k \cdot (U'^{(0)}_{sprl} + U'^{(0)}_{sprc})$    Vector constant for Eq. A-51

Because the example model only has one element, $U_M = U_m$ and $U_B = U_b$ as shown below:

$U_M := U_m$ Array constant summed for all of the elements in the model for Eq. A-52

$U_B := U_b$ Vector constant summed for all of the elements in the model for Eq. A-52

Solving Eq. A-52 produces the degrees of freedom vector for this example problem.

Figure 24:
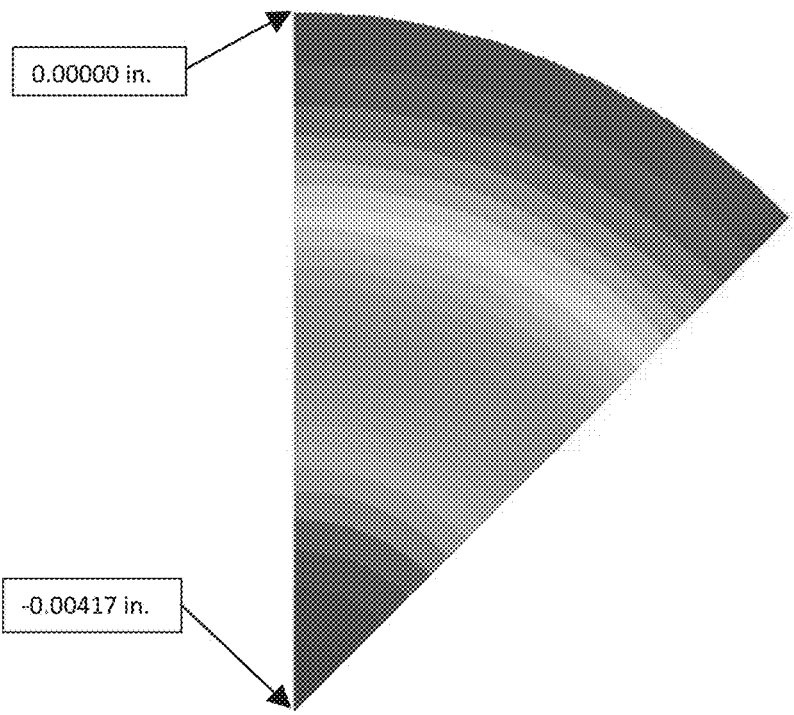
FIG. 24 is a displacement plot for the element of FIG. 23 evaluated according to the principles of the present disclosure.

$a := U_M^{-1} \cdot (-U_B)$    $a = \begin{pmatrix} -0.00065 \\ 0 \\ 0 \\ -0 \\ 0.03412 \\ 0.03413 \\ 0 \\ 0 \\ -0 \\ -0 \\ 0 \\ -0.44728 \\ -0.44728 \\ -0 \\ -0 \\ -0 \\ -0 \end{pmatrix}$    Degrees of Freedom The degree of freedom vector makes it possible to find optimized solution results for displacements, loads, stresses, strains or any other value addressed by the governing equation. The simplest to evaluate is displacement as it can be evaluated using the base equation (Eq. B-7) with no other derivation. FIG. 24 shows a gradient plot of the resulting displacement. The contours range from the most positive values of the displacement 0.0000 in.) at the outer edge of the wedge to the most negative values of the displacement (−0.00417 in.) at the tip of the wedge. This exactly matches the theoretical exact solution for this problem. This occurs in this problem because the geometry and selected degrees of freedom are capable of an exact solution. The energy optimization ensures that the exact solution is found.

Figure 25:
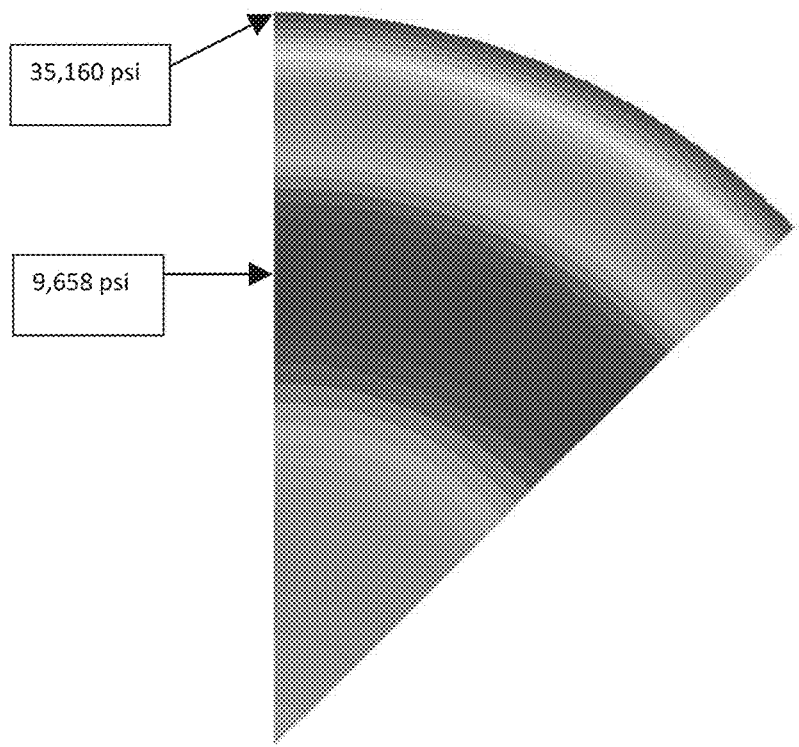
FIG. 25 is a Von Mises stress plot for the element of FIG. 23 evaluated according to the principles of the present disclosure.

A common stress result that is plotted in finite element analysis is von Mises stress. FIG. 25 shows a gradient plot of the resulting von Mises stress (using Eq. B-48). The contours range from the highest value of the von Mises stress (35,160 psi) at the outer edge of the wedge to the lowest value of the von Mises stress (9,658 psi) at the center $U_B^T = (-0.03\ -0.02\ -0.01\ -5.01\ -7.31\ -7.31\ -1.66\ -2.14\ -1.36\ -2.21\ -0.23\ -0.51\ 0.98\ 0.82\ 0.05\ -0.05\ 0.19\ 0.37)$ $U_M = \begin{pmatrix}
40.2 & 2.9 & 7.1 & 0.5 & 0.3 & 1.3 & 758.9 & 314.4 & 943 & 2276.7 & 314.4 & 314.4 & -628.8 & 628.8 & -28.9 & 69.9 & -349.4 & 1 \\
2.9 & 3.1 & -0.1 & 0.3 & 265.8 & -265.6 & 70.8 & -70.7 & -102.1 & 102.2 & 5.1 & -5.1 & -47.8 & 47.7 & -1.6 & 1.6 & -15 & \\
7.1 & -0.1 & 2.9 & -375.4 & 265.5 & -264.9 & 70.7 & -39.3 & 212.2 & 102.3 & 46 & 21.6 & -47.8 & 47.8 & -1.6 & 4.8 & -45 & \\
0.5 & 0.3 & 375.8 & 57.7 & 36.7 & 36.7 & 13.8 & 5.3 & -4.3 & 18.7 & 1.6 & 1.7 & -8.1 & 2.5 & -0.2 & 0.4 & -2.4 & \\
0.3 & -265.3 & -265.6 & -36.7 & 164.7 & -24 & 22.4 & -10.9 & 14.6 & 16.6 & 3.3 & -0.8 & -7.3 & 1.7 & -0 & -0.2 & -2.9 & \\
1.3 & 265.6 & 266.2 & -36.6 & 122.7 & 164.8 & 19.1 & -0.6 & 48.9 & 67.3 & 8.6 & 4.5 & -8.3 & 13.9 & -0.2 & 0.7 & -7.4 & \\
-758.8 & -70.7 & -70.7 & -2.6 & 16.2 & -7.5 & 3.4 & -0.3 & 2 & 1.2 & 0.5 & 0.1 & -1.4 & -0.5 & -0 & -0 & -0.5 & . \\
-314.2 & 70.8 & 39.3 & 21.7 & 15.7 & 16.6 & 3.7 & 4.2 & 1.6 & 6.1 & 0.5 & 1 & -1.9 & 0 & -0.1 & 0.1 & -0.5 & . \\
-942.9 & 102.2 & -212.2 & 4.3 & 33.4 & -34.5 & 3.9 & -0.6 & 5.1 & -3.4 & 0.8 & -0 & -0.7 & -1.1 & 0.1 & -0.1 & -0.5 & . \\
-2276.3 & -102.2 & -102 & -18.7 & 18.1 & 48.5 & 3.4 & -0.1 & 8.8 & 23.1 & 1.5 & 1.1 & -1.7 & 5.2 & -0.1 & 0.2 & -1.3 & \\
-314.4 & -5.1 & -46 & -0.4 & 2.6 & -6.8 & 0.5 & -0.1 & 0.6 & -0.8 & 0.1 & (i & -0.1 & -0.2 & 0 & -0 & -0.1 & \\
-314.4 & 5.1 & -21.5 & 3.7 & 2.6 & 1.6 & 0.7 & 1 & 0.4 & 1.4 & 0.1 & 0.3 & -0.4 & 0 & -0 & 0 & -0.1 & \\
628.8 & 47.8 & 47.8 & -0.3 & -2.3 & 2.3 & -1.3 & -0.7 & -0.3 & -0.8 & -0.2 & -0.2 & 0.9 & 0.4 & 0 & -0 & 0.2 & \\
-628.8 & -47.8 & -47.7 & -10.9 & -8.9 & 8.9 & -1.7 & -1.2 & -0.1 & 4.8 & -0.1 & -0 & 0.6 & 2.1 & -0 & 0 & 0.1 & \\
28.9 & 1.6 & 1.6 & -0.2 & 0 & -0.2 & -0 & -0.1 & 0 & -0.1 & -0 & -0 & 0.1 & 0 & 0 & -0 & 0 & \\
-69.9 & -1.6 & -4.8 & 0.3 & -0.2 & 0.6 & 0 & 0.2 & -0 & 0.3 & 0 & 0.1 & -0 & 0.1 & -0 & 0 & -0 & \\
349.4 & 15 & 45 & 0.9 & -0.3 & 6 & -0.2 & -0 & -0.2 & 0.7 & -0.1 & -0 & 0.1 & 0.2 & 0 & 0 & 0.1 & \\
-144.7 & -15 & -15 & -3.6 & -3.1 & 0.8 & -0.6 & -0.6 & -0.3 & 0.8 & -0.1 & -0.1 & 0.3 & 0.6 & 0 & 0 & 0.1 & \\
\end{pmatrix}$ of the wedge. The minimum occurs along an edge and the minimum value reported is the minimum value plotted. As noted in the displacement discussion, the plotted results match the theoretical exact solution for this problem.

Comparison with Traditional Finite Element Analysis

For comparison, the results of the new method are compared to four test models that were run using traditional finite element analysis. The Abaqus shell elements are based on a similar governing equation to that considered for the governing equation and theoretical value (as evidenced by the convergence toward the theoretical solution in the high degree of freedom models). Abaqus considers additional governing equation components such as shear deformation in some shell elements. The elements used for this comparison are STRI65 for the parabolic triangular shell elements and S4 for the linear quadrilateral elements.

help demonstrate if this traditional finite element shell formulation is converging closely to the theoretical solution. (This is motivated by the possibility that the governing equation for this traditional finite element shell formulation could be different enough to make the comparison not appropriate.) The average edge von Mises stress is 31,162 psi.

Figure 30A:
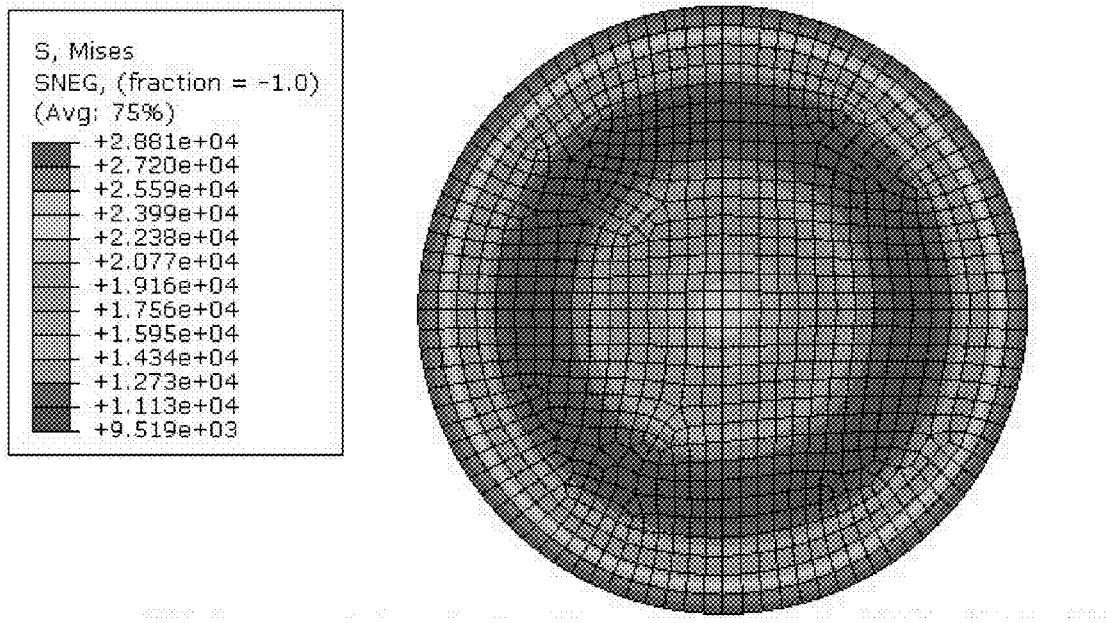
FIGS. 30A and 30B are Von Mises stress and displacement plots, respectively, for a traditional finite element analysis with 950 linear quadrilateral elements.
Figure 30B:
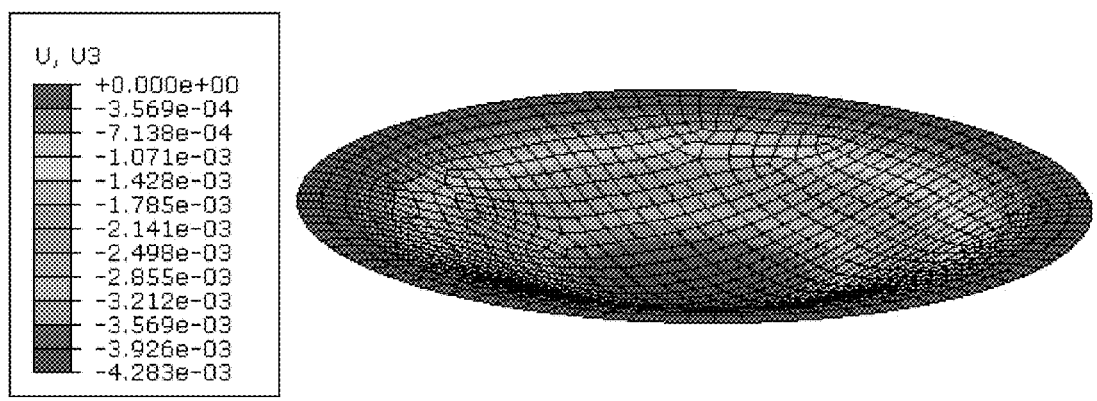

FIGS. 30A-30B correspond to a traditional finite element analysis with 950 linear quadrilateral elements. This is shown for information given that this is probably the most commonly used element to solve this problem in a traditional finite element analysis. The average edge von Mises stress is 28,488 psi.

Table C-2 presents a summary of results for stress and displacement (with percent error being relative to the theoretical solution):

|  | Theoretical values[1] | New model[2] | Parabolic triangular 8 element[3] | Parabolic triangular 48 element[3] | Parabolic triangular 462 element[3] | Linear quadrilateral 950 element[3] |
|---|---|---|---|---|---|---|
| Maximum von Mises stress [ksi] | 31.25 | 31.25 (+0.0%) | 28.26 (−9.6%) | 31.19 (−0.2%) | 31.16 (−0.3%) | 28.49 (−8.8%) |
| Maximum displacement [in] | 0.004166 | 0.004166 (+0.0%) | 0.005563 (+33.5%) | 0.004462 (+7.1%) | 0.004322 (+3.8%) | 0.004282 (+2.8%) |
| Degrees of freedom | N/A | 144 | 75 | 339 | 2919 | 2997 |

[1] The theoretical value is 35.16 ksi, but this is only in one direction. Converting it to von Mises stress produces the 31.25 ksi value.
[2] The test model was run with one 18 degree of freedom element and symmetry. The degrees of freedom for the test model is shown as 144 to reflect the degrees of freedom as if it were an 8 element model. This is the relevant number of degrees of freedom for comparison with the other models.
[3] Because the high stress should occur continuously along the edge, the maximum von Mises stress reported is the average along the model edge.

Figure 26A:
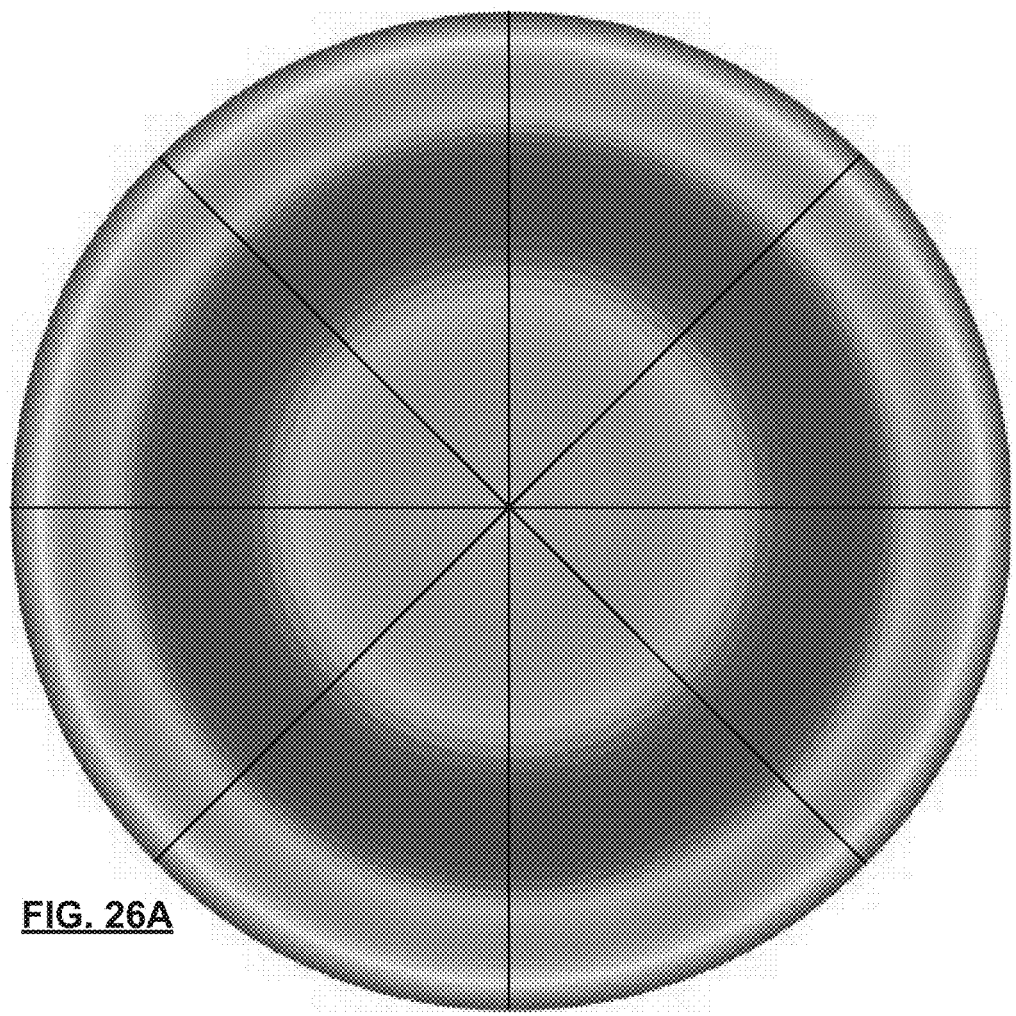
FIGS. 26A and 26B are Von Mises stress and displacement plots, respectively, for finite element analysis of a curved element according to the principles of the present disclosure.
Figure 26B:
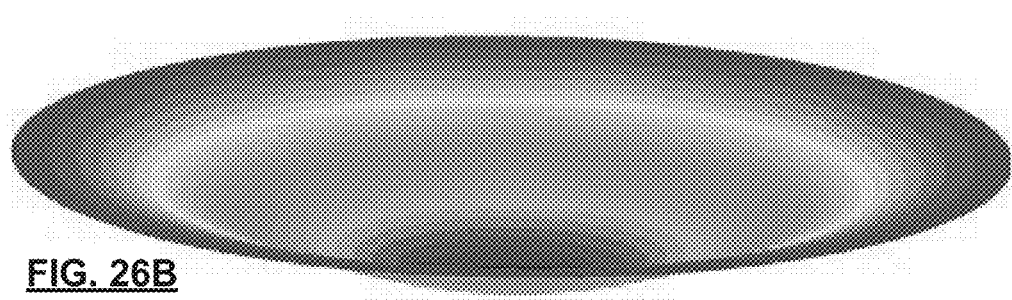
Figure 26C:
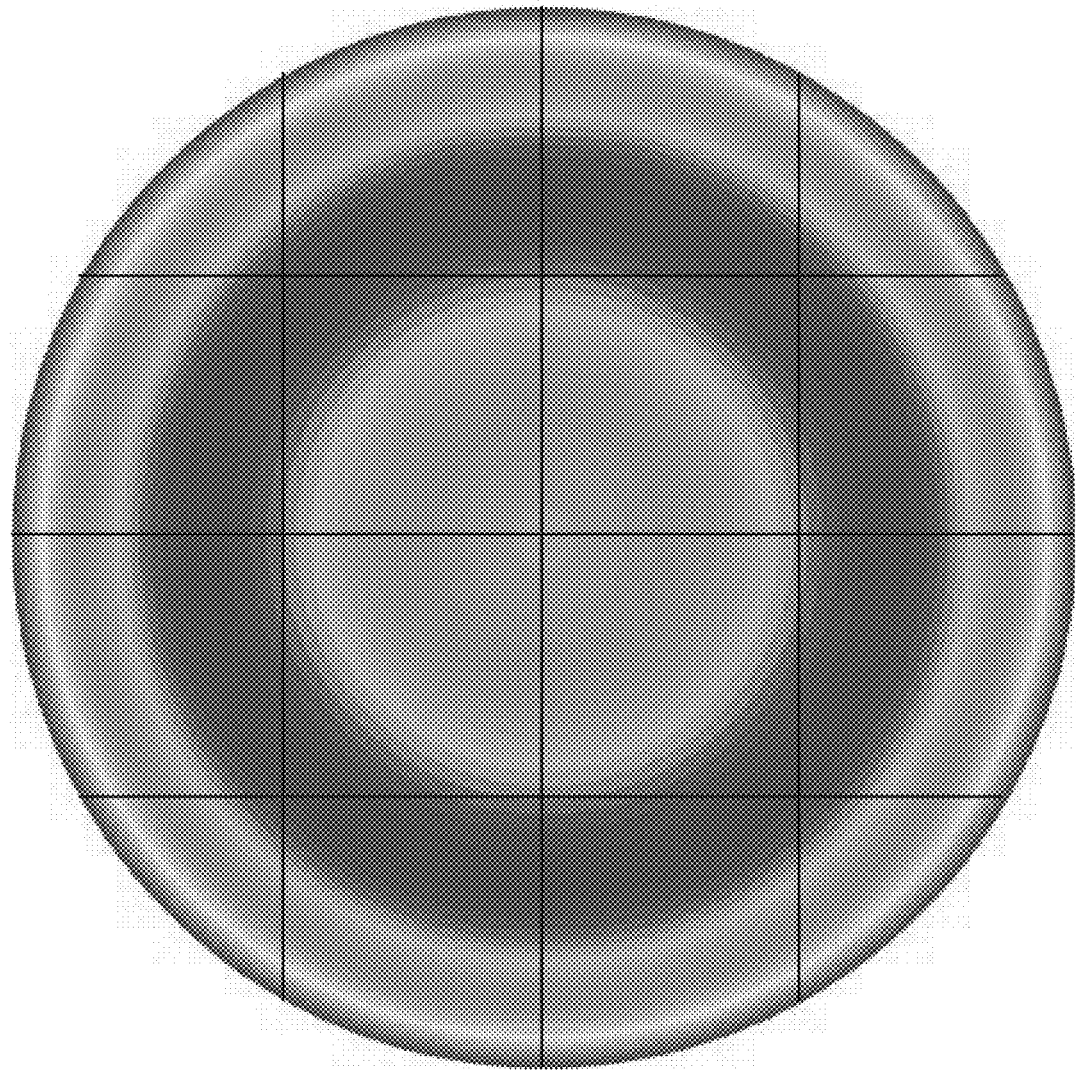
FIG. 26C is a Von Mises stress plot demonstrating an alternative mesh construction using a rectangular grid.

FIGS. 26A-30A and FIGS. 26B-30B show von Mises stress and displacement magnified 75x, respectively, for the five models used for comparison. FIGS. 26A-26B correspond to the new method with a pie shaped element. As discussed earlier, the new method element is modeled with symmetric restraints so it is appropriate to mirror it and present it as an eight element model with each element having 18 degrees of freedom. The average edge von Mises stress is 35,160 psi and the center displacement is 0.00417 in.

Note that the example objects being studied in this disclosure possess radial symmetry. As a result, the mesh for the new method can be generated by overlaying a radial grid on the object, as shown in FIG. 26A. In various circumstances, such as for shapes that do not have radial symmetry, another form of grid may be overlaid on part or all of the object. For example only, in FIG. 26C a rectangular grid is shown overlaid on the object of FIG. 22.

Figure 27A:
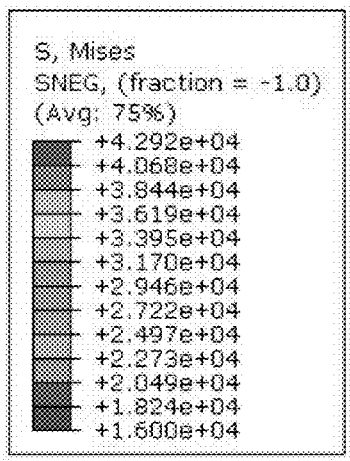
FIGS. 27A and 27B are Von Mises stress and displacement plots, respectively, for a traditional finite element analysis with 8 parabolic triangular elements.
Figure 27A:
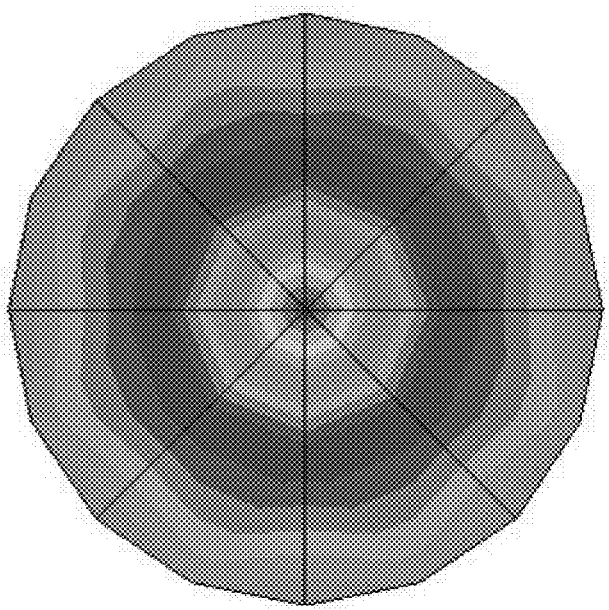
Figure 27B:
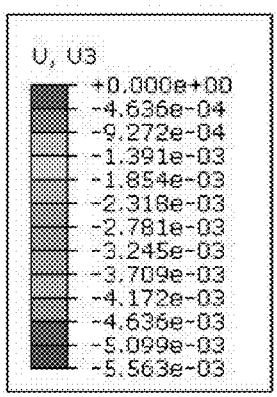
Figure 27B:
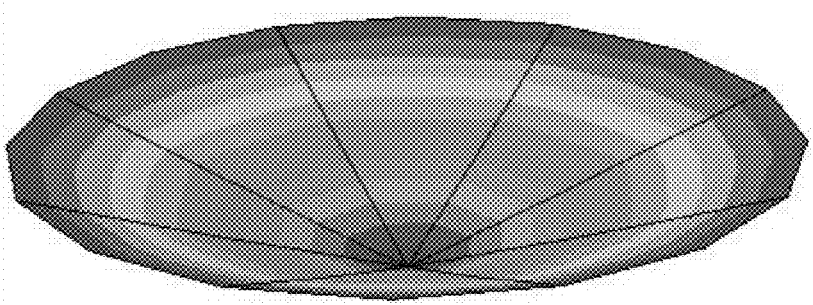

FIGS. 27A-27B correspond to a traditional finite element analysis with 8 parabolic triangular elements. This is intended to show the closest comparison between traditional finite element analysis and the new method. In this case, the traditional analysis is at some disadvantage as it has fewer degrees of freedom. The average edge von Mises stress is 28,255 psi.

Figure 28A:
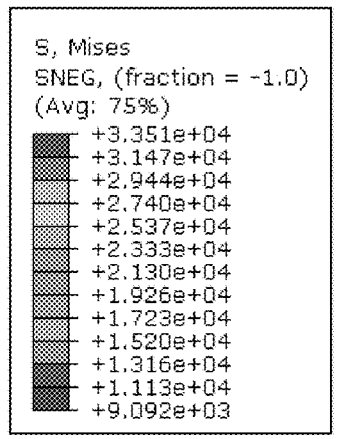
FIGS. 28A and 28B are Von Mises stress and displacement plots, respectively, for a traditional finite element analysis with 48 parabolic triangular elements.
Figure 28A:
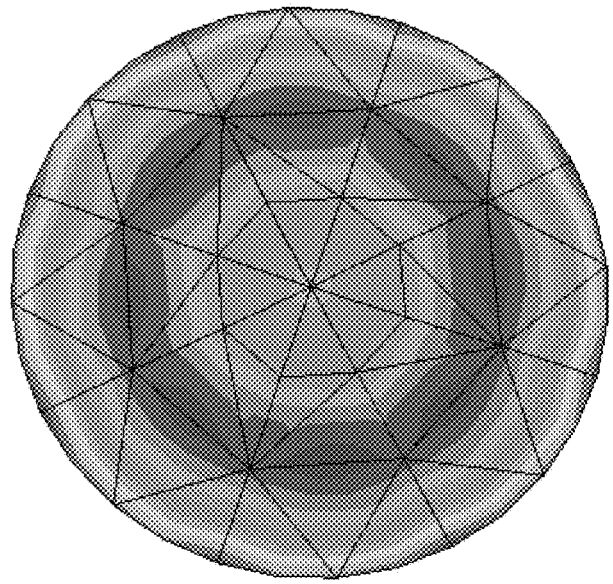
Figure 28B:
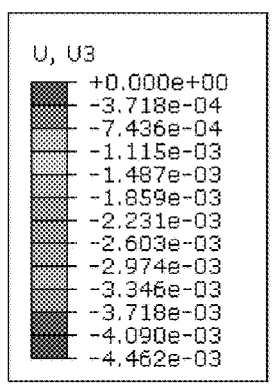
Figure 28B:
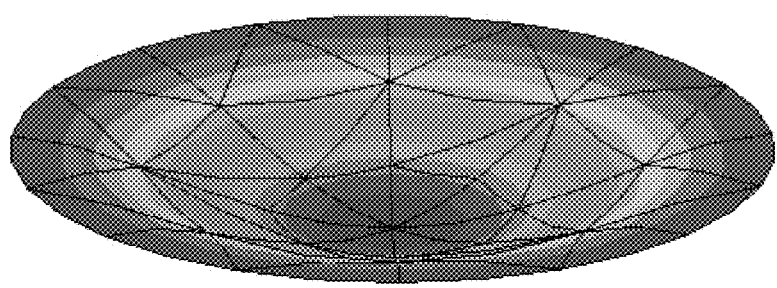

FIGS. 28A-28B correspond to a traditional finite element analysis with 48 parabolic triangular elements. This is similar to the model in FIGS. 27A-27B except there are many more degrees of freedom. The average edge von Mises stress is 31,194 psi.

Figure 29A:
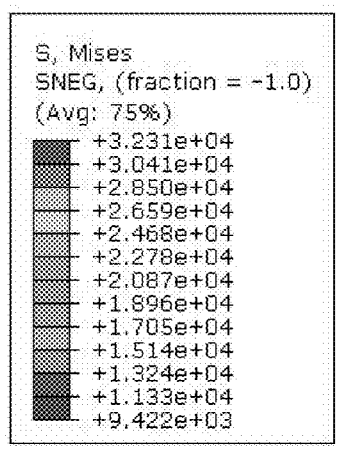
FIGS. 29A and 29B are Von Mises stress and displacement plots, respectively, for a traditional finite element analysis with 462 parabolic triangular elements.
Figure 29A:
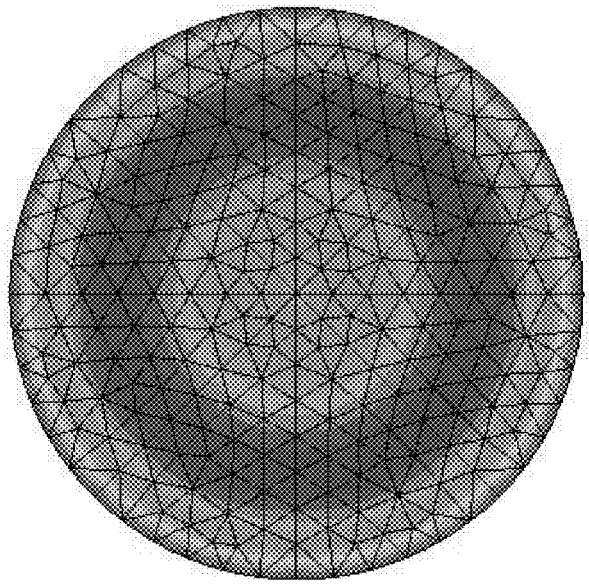
Figure 29B:
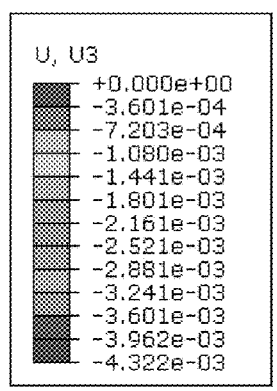
Figure 29B:
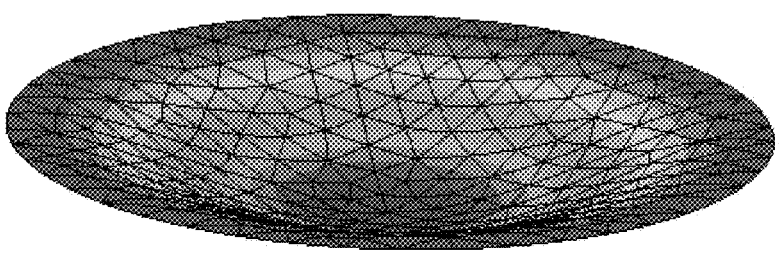

FIGS. 29A-29B correspond to a traditional finite element analysis with 462 parabolic triangular elements. This is to Considering Table C-2, the new method and the traditional finite element method performed better than in Section B. The new method produced an exact solution. The traditional finite element method performed well, but it's not possible for it to produce an exact solution because the circular edge must be represented with a series of straight edges.

As discussed in Section A, the boundary conditions (at the nodes) being exactly met in traditional finite element method reduces the ability of the shape functions to accurately predict stresses/strains in the element. The result is a relatively stiff response that tends to under predict the stresses/strains. In this example, the inability of traditional finite element method to exactly follow the shape of the model further reduces its ability to produce accurate stresses/strains. In this example model, the inability of traditional finite element method to follow the circular edge tends to cause the stress to be higher due to less material being represented (which counteracts some of the stiffening from the boundary conditions being exactly met). However, the stress contour accuracy is compromised.

Discussion

This example showed the formulation for a simple single element problem with two straight edges and a circular edge. The example problem element only had three edges, but this same formulation could be used on an element with any number of edges.

The biggest positive shown in this example was that the new method produced and exact solution where it is not possible for the traditional finite element method to produce an exact solution. The traditional finite element method cannot produce an exact solution for this example (without and infinite number of elements) because it cannot exactly match the geometry (i.e. the edges between nodes in traditional finite element analysis must be straight, not circular).

Section D

Outline

In this Section, algebraic equations for evaluating an element with general curved sides are developed (and the straight side evaluation developed in Section B will also be used). Second, a simple pie shaped element is evaluated to find displacement and stress results. As validation, the element is defined with geometry, loading, and boundary conditions to match a well-known problem that has an exact solution. Third, the results are compared with the exact solution results.

The evaluation is described in several portions. The first portion (Edge Equation and Local Load/Displacement Definitions) discusses how the general curve is defined and derives relationships necessary for its evaluation. The second portion (Numerical Integration) discusses the numerical integration approach used to evaluate the general curve. The third portion (Area Integrals for a General Curved Edge) shows an approach to convert the area integrals (from Section A, Eqs. A-38 and A-40) into a form that can be numerically integrated. The fourth portion (Edge Integrals for a General Curved Edge) shows an approach to convert the edge integrals (from Section A, Eq. A-47) into form that can be numerically integrated. The fifth portion (Model Formulation) defines values for material properties, element geometry, boundary conditions, and the algebraic forms of the area and edge integrals. The sixth portion (Rigid Body Motions) defines an approach to address rigid body motions. The approach used in the example uses springs to enforce element edge displacements with the displacements defined by the boundary conditions. The seventh portion (Degrees of Freedom and Results Plots) solves the energy optimization (from Section A, Eq. A-51) and uses the results to plot element displacement and stress. The evaluation results are discussed in an eighth portion (Discussion).

The test model for the example problem is a thin plate that is 2.5 inches in diameter by 0.1 inches thick. All of the edges are fixed and there is a 300 psi pressure applied evenly over the surface. The material properties include a Young's modulus of 3.0e7 psi and a Poisson's ratio of 0.3.

Edge Equation and Local Load/Displacement Definitions

Figure 31A:
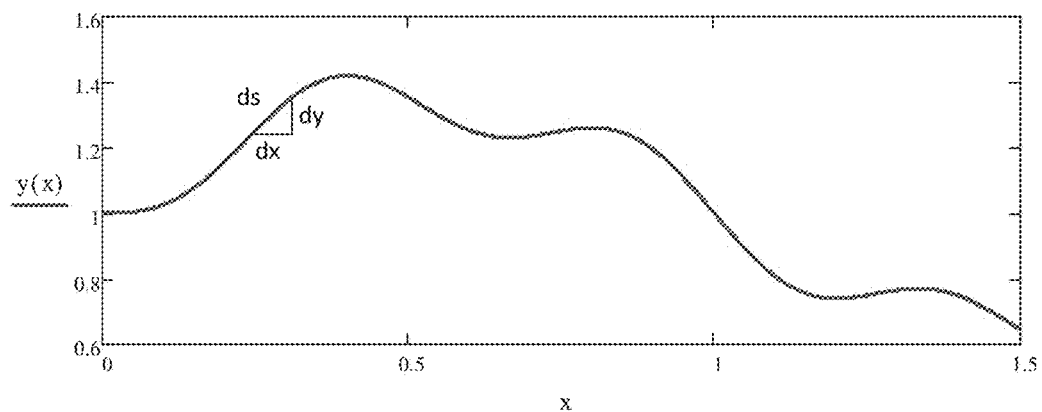
FIG. 31A is a plot of a function providing an example edge shape.
Figure 31B:
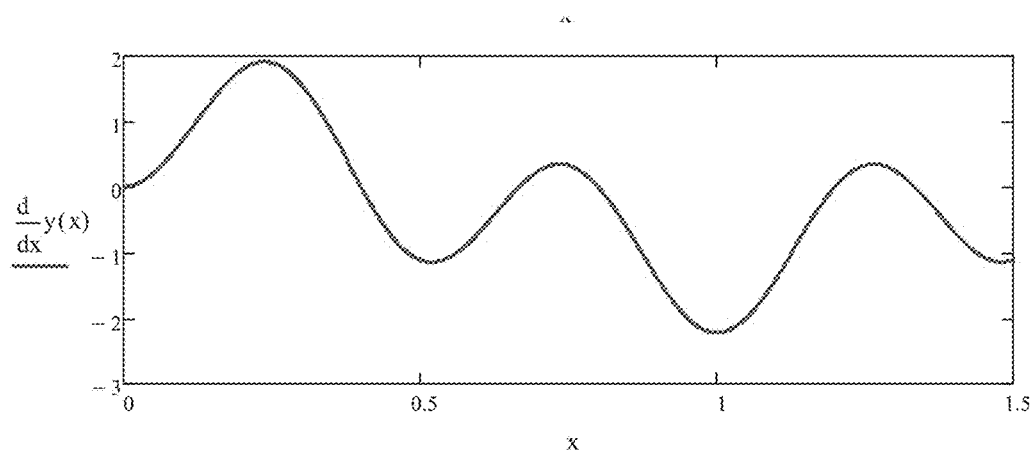
FIG. 31B is a plot of the first derivative of the function of FIG. 31A, which provides an example edge slope.

The displacement equation used for this evaluation is the same as that shown in Section B (Eq. B-7). The focus of this Section is to establish a method to evaluate a curve with a generalized shape (as in Eq. D-1) and associated slope (as in Eq. D-2). FIGS. 31A-31B shows a possible edge shape and edge slope and helps identify variables. (It should be noted that though the edge shape function plotted in FIGS. 31A-31B is possible, the edge shape function used for the example problem in this Section a circular shape is so that it can be compared to an exact solution.)

$$y(x)\text{-Edge shape function} \qquad \text{Eq. D-1}$$

$$\frac{d}{dx}y(x)\text{-Edge slope function} \qquad \text{Eq. D-2}$$

For the Eq. D-1 and D-2 and Figure D-1: dx—Differential distance the in x-direction
dy—Differential distance the in y-direction ds—Differential curve length For this derivation, the edge shape function (Eq. D-1) and its slope (Eq. D-2), though arbitrary, are continuous over the portion of the element that the edge represents. Also as plotted in the coordinate system of the element, the slope cannot go to or pass through positive or negative infinity.

(The limitations defined for this strategy do not prevent evaluation of discontinuous edges and slopes passing through positive or negative infinity. Discontinuous edges and slopes passing through positive or negative infinity can both be addressed similar to that in the example by breaking the given edge into multiple edges. In the case of the discontinuity, the edge break would occur at the discontinuity. In the case of the curve passing through positive or negative infinity, the natural break would occur when the slope is close to one. Given that an infinite slope is a slope of zero when viewed from the other axis, each edge could be evaluated with respect to the axis where the slope passes through zero.)

To evaluate the general curve, the loads/displacements local to a point on the curve are defined. The desire is to perform the area and edge integrals with respect to the element x-direction. Consequently, loads/displacements need to be defined relative to the s-face (shown as the ds segment in FIGS. 31A-31B) in a way that facilitates integration along the x-axis of the element. This process uses the slope of the curve to facilitate orientation of a load/displacement onto the s-face at a point on the curve.

Considering FIGS. 31A-31B, Eqs. D-3 to D-5 can be defined. These provide a way to orient loads/displacements relative to the s-face at a point on the edge curve.

$$ds^2 = dx^2 + dy^2 \text{ or} \qquad \text{Eq. D-3}$$

$$ds = \sqrt{dx^2 + dy^2} = \sqrt{1+\left(\frac{dy}{dx}\right)^2}\cdot dx$$

$$\frac{dx}{ds} = \frac{dx}{\sqrt{dx^2+dy^2}} = \frac{1}{\sqrt{1+\left(\frac{dy}{dx}\right)^2}} \qquad \text{Eq. D-4}$$

$$\frac{dy}{ds} = \frac{dy}{\sqrt{dx^2+dy^2}} = \frac{\frac{dy}{dx}}{\sqrt{1+\left(\frac{dy}{dx}\right)^2}} \qquad \text{Eq. D-5}$$

The first load to address is the shear load on the s-face. Considering Eq. A-4 along with FIGS. 31A-31B, Eq. D-6 can be defined. For the example problem, only the shear force on the s-face with respect to the x-axis will be used.

$$P_{sx} = P_x \cdot \frac{dx}{ds} - P_y \cdot \frac{dy}{ds} \qquad \text{Eq. D-6}$$

Shear force on the s-face with respect to the x-axis $$P_{sy} = P_x \cdot \frac{dy}{ds} + P_y \cdot \frac{dx}{ds}$$

Shear force on the s-face with respect to the y-axis

However, it is useful to define the shear force on the s-face with respect to the y-axis also to help establish the orthogonal tensor in Eq. D-7. (The orthogonal tensor's usefulness will be clear when the moments are addressed.)

Rearranging Eq. D-6:

$$\begin{pmatrix} P_{sx} \\ P_{sx} \end{pmatrix} = \begin{pmatrix} \dfrac{dx}{ds} & -\dfrac{dy}{ds} \\ \dfrac{dy}{ds} & \dfrac{dx}{ds} \end{pmatrix} \cdot \begin{pmatrix} P_x \\ P_y \end{pmatrix} = Q_o \cdot \begin{pmatrix} P_x \\ P_y \end{pmatrix} \quad \text{Eq. D-7}$$

Where:

$$Q_o = \begin{pmatrix} \dfrac{dx}{ds} & -\dfrac{dy}{ds} \\ \dfrac{dy}{ds} & \dfrac{dx}{ds} \end{pmatrix}$$

The shear loads are relatively straightforward to transform with the orthogonal tensor given that they are in vector form. Transforming the moments is a little more complex given that they exist in tensor form. The moment transformation occurs (as follows) to produce Eq. D-8.

$$\begin{pmatrix} M_{sx} & T_{sxy} \\ T_{sxy} & M_{sy} \end{pmatrix} = Q_o \cdot \begin{pmatrix} M_x & T_{xy} \\ T_{xy} & M_y \end{pmatrix} \cdot Q_o = \quad \text{Eq. D-8}$$

$$\begin{pmatrix} \dfrac{dx}{ds} & -\dfrac{dy}{ds} \\ \dfrac{dy}{ds} & \dfrac{dx}{ds} \end{pmatrix} \cdot \begin{pmatrix} M_x & T_{xy} \\ T_{xy} & M_y \end{pmatrix} \cdot \begin{pmatrix} \dfrac{dx}{ds} & -\dfrac{dy}{ds} \\ \dfrac{dy}{ds} & \dfrac{dx}{ds} \end{pmatrix}^T$$

Solving $$\begin{pmatrix} M_{sx} & T_{sxy} \\ T_{sxy} & M_{sy} \end{pmatrix} = \left[ \begin{array}{cc} M_x \cdot \left(\dfrac{dx}{ds}\right)^2 - 2 \cdot T_{xy} \cdot \dfrac{dx}{ds} \cdot \dfrac{dy}{ds} + M_y \cdot \left(\dfrac{dy}{ds}\right)^2 & T_{xy} \cdot \left(\dfrac{dx}{ds}\right)^2 - T_{xy} \cdot \left(\dfrac{dy}{ds}\right)^2 \ldots + \\ & M_x \cdot \dfrac{dx}{ds} \cdot \dfrac{dy}{ds} - M_y \cdot \dfrac{dx}{ds} \cdot \dfrac{dy}{ds} \\ T_{xy} \cdot \left(\dfrac{dx}{ds}\right)^2 - T_{xy} \cdot \left(\dfrac{dy}{ds}\right)^2 \ldots + & M_y \cdot \left(\dfrac{dx}{ds}\right)^2 - 2 \cdot T_{xy} \cdot \\ M_x \cdot \dfrac{dx}{ds} \cdot \dfrac{dy}{ds} - M_y \cdot \dfrac{dx}{ds} \cdot \dfrac{dy}{ds} & \dfrac{dx}{ds} \cdot \dfrac{dy}{ds} + M_x \cdot \left(\dfrac{dy}{ds}\right)^2 \end{array} \right]$$

or $$M_{sx} = M_x \cdot \left(\dfrac{dx}{ds}\right)^2 - 2 \cdot T_{xy} \cdot \dfrac{dx}{ds} \cdot \dfrac{dy}{ds} + M_y \cdot \left(\dfrac{dy}{ds}\right)^2$$

Bending moment on the s-face with respect to the x-axis $$T_{sxy} = T_{xy} \cdot \left(\dfrac{dx}{ds}\right)^2 - T_{xy} \cdot \left(\dfrac{dy}{ds}\right)^2 + M_x \cdot \dfrac{dx}{ds} \cdot \dfrac{dy}{ds} - M_y \cdot \dfrac{dx}{ds} \cdot \dfrac{dy}{ds}$$

Torsion on the s-face $$M_{sy} = M_y \cdot \left(\dfrac{dx}{ds}\right)^2 + 2 \cdot T_{xy} \cdot \dfrac{dx}{ds} \cdot \dfrac{dy}{ds} + M_x \cdot \left(\dfrac{dy}{ds}\right)^2$$

Bending moment on the s-face with respect to the y-axis

For the displacements (including rotations), the displacement requires no transformation as it is a scalar. The rotations can be transformed similar to the shear force (as shown in Eqs. D-9 and D-10).

$$\begin{pmatrix} \theta_{sx} \\ \theta_{sy} \end{pmatrix} = Q_o \cdot \begin{pmatrix} \theta_{wx} \\ \theta_{wy} \end{pmatrix} = \begin{pmatrix} \dfrac{dx}{ds} & -\dfrac{dy}{ds} \\ \dfrac{dy}{ds} & \dfrac{dx}{ds} \end{pmatrix} \cdot \begin{pmatrix} \theta_{wx} \\ \theta_{wy} \end{pmatrix} \quad \text{Eq. D-9}$$

$$\theta_{sx} = \theta_{wx} \cdot \dfrac{dx}{ds} - \theta_{wy} \cdot \dfrac{dy}{ds}$$

Bending rotation on the s-face with respect to the x-axis $$\theta_{sy} = \theta_{wx} \cdot \dfrac{dy}{ds} + \theta_{wy} \cdot \dfrac{dx}{ds}$$

Bending rotation on the s-face with respect to the y-axis
Where:

$$\phi_{wx} = \dfrac{\partial}{\partial y} w \text{ and } \phi_{wy} = \dfrac{\partial}{\partial x} w$$

$$\begin{pmatrix} \phi_{sx} \\ \phi_{sy} \end{pmatrix} = Q_o \cdot \begin{pmatrix} \phi_{wx} \\ \phi_{wy} \end{pmatrix} = \begin{pmatrix} \dfrac{dx}{ds} & -\dfrac{dy}{ds} \\ \dfrac{dy}{ds} & \dfrac{dx}{ds} \end{pmatrix} \cdot \begin{pmatrix} \phi_{wx} \\ \phi_{wy} \end{pmatrix} \quad \text{Eq. D-10}$$

$$\phi_{sx} = \phi_{wx} \cdot \dfrac{dy}{ds} - \phi_{wy} \cdot \dfrac{dx}{ds}$$

Torsional rotation on the s-face with respect to the x-axis $$\phi_{sy} = \phi_{wx} \cdot \dfrac{dy}{ds} + \phi_{wy} \cdot \dfrac{dx}{ds}$$

Torsional rotation on the s-face with respect to the y-axis
Where:

$$\phi_{wx} = \dfrac{\partial}{\partial x} w \text{ and } \phi_{wy} = \dfrac{\partial}{\partial y} w$$

There is redundancy in the rotations where the x-direction of one is the same as the y-direction for the other. This is done for simplicity but can be changed for coding a solver.

Numerical Integration

To simplify the integration process for this example, a numerical integration scheme will be employed for the area and edge integrals related to the curved edge. The selected numerical integration scheme is based on a 5-point Gaussian quadrature rule (as described in Chapra et al., 1998). This approach is attractive because it can address a very wide range of curve shapes with very good accuracy and minimal computation. Eqs. D-11 to D-13 show the general approach to this numerical integration.

$$U_g = \int_{x_0}^{x_1} F_f(x) dx \quad \text{Integral to be numerically evaluated} \quad \text{Eq. D-11}$$

Where $F_I(x)$ is the function of being integrated $$Gx := \frac{1}{3} \cdot \left( -\sqrt{5 + 2 \cdot \sqrt{\frac{10}{7}}} \quad -\sqrt{5 - 2 \cdot \sqrt{\frac{10}{7}}} \quad 0 \quad \sqrt{5 - 2 \cdot \sqrt{\frac{10}{7}}} \quad \sqrt{5 + 2 \cdot \sqrt{\frac{10}{7}}} \right)^T \quad \text{Eq. D-12}$$

$Gx^T = (\,-0.906 \quad -0.538 \quad 0 \quad 0.538 \quad 0.906\,)$

Gauss quadrature function arguments $$Gc := \left( \frac{322 - 13 \cdot \sqrt{70}}{900} \quad \frac{322 + 13 \cdot \sqrt{70}}{900} \quad \frac{128}{225} \quad \frac{322 + 13 \cdot \sqrt{70}}{900} \quad \frac{322 - 13 \cdot \sqrt{70}}{900} \right)^T$$

$Gc^T = (\,0.237 \quad 0.479 \quad 0.569 \quad 0.479 \quad 0.237\,)$

Gauss quadrature weighting factors $$x_{o_i} = \frac{1}{2} \cdot (Gx_i + 1) \cdot (x_1 - x_0) + x_0$$

Vector of points where the function being integrated must be evaluated

Where "i" is an index representing the rows of the Gauss quadrature function arguments $$U_g = \sum_{i=0}^{last(Gc)} \left[ Gc_i \cdot F_I(x_{o_i}) \cdot \left[ \frac{1}{2} \cdot (x_1 - x_0) \right] \right] \quad \text{Eq. D-13}$$

Numerical integration using Using a 5-point Gaussian quadrature rule

Area Integrals for a General Curved Edge

Recalling the strain energy for the element (Eq. A-36) and the external work due to the pressure load (Eq. A-39), there are two area integrals to be addressed in the total energy equation for the element (Eq. A-48 or A-49) and the energy optimization (Eq. A-49). The energy optimization lends itself to be broken into pieces, evaluated numerically, and then summed back together. All of the integrals will be addressed in this manner. When broken out the of the energy optimization, the strain energy and the external work due to the pressure load appear as in Eqs. D-14 and D-15.

$$U_{g_i} = \frac{\partial}{\partial a_i} \left[ \frac{D}{2} \cdot \int_{x_0}^{x_1} \int_{0}^{y_e} \left( \frac{d^2}{dx^2} w + \frac{d^2}{dy^2} w \right)^2 - \right. \quad \text{Eq. D-14}$$

$$\left. 2 \cdot (1 - v) \cdot \left[ \frac{d^2}{dx^2} w \cdot \frac{d^2}{dy^2} w - \left( \frac{\partial}{\partial x} \frac{\partial}{\partial y} w \right)^2 \right] dy dx \right]$$

Strain energy linear equations in the energy optimization $$W_{pg_i} = \frac{\partial}{\partial a_i} \left( \int_{x_0}^{x_1} \int_{0}^{y_e} w \cdot p_z \, dy dx \right) \quad \text{Eq. D-15}$$

External work due to the pressure load linear equations in the energy optimization Where: $y_e$—Curved edge function i—Degrees of freedom (from 0 to 17)

Noting the similarity between Eqs. D-14 and D-15 with Eqs. B-9 and B-10, much of the area integral derivation in Section B is applicable in this Section. Eq. B-11 is directly applicable. Eqs. D-16 and D-17 below represent the applicable equation for this Section as related to Eqs. B-13 and B-19.

$$U_{g_{i,j}} = \frac{D}{2} \cdot \int_{x_0}^{x_1} \int_{0}^{y_e} 2 \cdot (w_{xx} + w_{yy})_j \cdot \frac{\partial}{\partial a_i}(w_{xx} + w_{yy}) \ldots + \quad \text{Eq. D-16}$$

$$-2 \cdot (1 - v) \cdot \left( w_{xx_j} \cdot \frac{\partial}{\partial a_i} w_{yy} + \right.$$

$$\left. w_{yy_j} \cdot \frac{\partial}{\partial a_i} w_{xx} - 2 \cdot w_{xy_j} \cdot \frac{\partial}{\partial a_i} w_{xy} \right) dy dx$$

Equation to find array terms $$U_{g_{i,p}} = \frac{D}{2} \cdot \int_{x_0}^{x_1} \int_{0}^{y_e} 2 \cdot (w_{xx} + w_{yy})_p \cdot \frac{\partial}{\partial a_i}(w_{xx} + w_{yy}) \ldots + \quad \text{Eq. D-17}$$

$$-2 \cdot (1 - v) \cdot \left( w_{xx_p} \cdot \frac{\partial}{\partial a_i} w_{yy} + \right.$$

$$\left. w_{yy_p} \cdot \frac{\partial}{\partial a_i} w_{xx} - 2 \cdot w_{xy_p} \cdot \frac{\partial}{\partial a_i} w_{xy} \right) dy dx$$

Portion of the strain energy relative to the external pressure

Likewise, the generalized integration (Eq. B-16) can be rewritten to Eq. D-18 for this Section.

$$\int_{x_0}^{x_1}\int_{x_0}^{x_1}\left[\begin{pmatrix}\alpha_0\\\alpha_1\\\alpha_2\\\alpha_3\\\alpha_4\\\alpha_5\\\alpha_6\\\alpha_7\\\alpha_8\\\alpha_9\end{pmatrix}^T\cdot\begin{pmatrix}x^3\\x^2\\x\\1\\x^2\cdot y\\x\cdot y\\y\\x^2\cdot y\\y^2\\y^3\end{pmatrix}\right]\cdot\left[\begin{pmatrix}\beta_1\\\beta_2\\\beta_3\\\beta_4\\\beta_5\\\beta_6\\\beta_7\\\beta_8\\\beta_9\end{pmatrix}^T\cdot\begin{pmatrix}x^3\\x^2\\x\\1\\x^2\cdot y\\x\cdot y\\y\\x^2\cdot y\\y^2\\y^3\end{pmatrix}\right]dy\,dx \quad \text{Generalized ingration}$$

Eq. D-18

$$\text{or } Int_g = \int_{x_0}^{x_1}\int_0^{y_e}\begin{bmatrix}\alpha_9\cdot\beta_9\\\alpha_8\cdot\beta_9+\alpha_9\cdot\beta_8\\\alpha_7\cdot\beta_9+\alpha_9\cdot\beta_7\\\alpha_6\cdot\beta_9+\alpha_9\cdot\beta_6+\alpha_8\cdot\beta_8\\\alpha_5\cdot\beta_9+\alpha_9\cdot\beta_5+\alpha_7\cdot\beta_8+\alpha_8\cdot\beta_7\\\alpha_4\cdot\beta_9+\alpha_9\cdot\beta_4+\alpha_7\cdot\beta_7\\\alpha_3\cdot\beta_9+\alpha_9\cdot\beta_3+\alpha_6\cdot\beta_8+\alpha_8\cdot\beta_6\\\alpha_2\cdot\beta_9+\alpha_9\cdot\beta_2+\alpha_5\cdot\beta_8+\alpha_6\cdot\beta_7+\alpha_7\cdot\beta_6+\alpha_8\cdot\beta_5\\\alpha_1\cdot\beta_9+\alpha_9\cdot\beta_1+\alpha_4\cdot\beta_8+\alpha_5\cdot\beta_7+\alpha_7\cdot\beta_5+\alpha_8\cdot\beta_4\\\alpha_0\cdot\beta_9+\alpha_9\cdot\beta_0+\alpha_4\cdot\beta_7+\alpha_7\cdot\beta_4\\\alpha_3\cdot\beta_8+\alpha_8\cdot\beta_3+\alpha_6\cdot\beta_6\\\alpha_2\cdot\beta_8+\alpha_3\cdot\beta_7+\alpha_7\cdot\beta_3+\alpha_8\cdot\beta_2+\alpha_5\cdot\beta_6+\alpha_6\cdot\beta_5\\\alpha_1\cdot\beta_8+\alpha_2\cdot\beta_7+\alpha_7\cdot\beta_2+\alpha_8\cdot\beta_1+\alpha_4\cdot\beta_6+\alpha_5\cdot\beta_5+\alpha_6\cdot\beta_4\\\alpha_0\cdot\beta_8+\alpha_1\cdot\beta_7+\alpha_7\cdot\beta_1+\alpha_8\cdot\beta_0+\alpha_4\cdot\beta_5+\alpha_5\cdot\beta_4\\\alpha_0\cdot\beta_7+\alpha_7\cdot\beta_0+\alpha_4\cdot\beta_4\\\alpha_3\cdot\beta_6+\alpha_6\cdot\beta_3\\\alpha_2\cdot\beta_6+\alpha_3\cdot\beta_5+\alpha_5\cdot\beta_3+\alpha_6\cdot\beta_2\\\alpha_1\cdot\beta_6+\alpha_2\cdot\beta_5+\alpha_3\cdot\beta_4+\alpha_4\cdot\beta_3+\alpha_5\cdot\beta_2+\alpha_6\cdot\beta_1\\\alpha_0\cdot\beta_6+\alpha_1\cdot\beta_5+\alpha_2\cdot\beta_4+\alpha_4\cdot\beta_2+\alpha_5\cdot\beta_1+\alpha_6\cdot\beta_0\\\alpha_0\cdot\beta_5+\alpha_1\cdot\beta_4+\alpha_4\cdot\beta_1+\alpha_5\cdot\beta_0\\\alpha_0\cdot\beta_4+\alpha_4\cdot\beta_0\\\alpha_3\cdot\beta_3\\\alpha_2\cdot\beta_3+\alpha_3\cdot\beta_2\\\alpha_1\cdot\beta_3+\alpha_2\cdot\beta_2+\alpha_3\cdot\beta_1\\\alpha_0\cdot\beta_3+\alpha_1\cdot\beta_2+\alpha_2\cdot\beta_1+\alpha_3\cdot\beta_0\\\alpha_0\cdot\beta_2+\alpha_1\cdot\beta_1+\alpha_2\cdot\beta_0\\\alpha_0\cdot\beta_1+\alpha_1\cdot\beta_0\\\alpha_0\cdot\beta_0\end{bmatrix}^T\cdot\begin{pmatrix}y^6\\y^5\\x\cdot y^5\\y^4\\x\cdot y^4\\x^2\cdot y^4\\y^3\\x\cdot y^3\\x^2\cdot y^3\\x^3\cdot y^3\\y^2\\x\cdot y^2\\x^2\cdot y^2\\x^3\cdot y^2\\x^4\cdot y^2\\y\\x\cdot y\\x^2\cdot y\\x^3\cdot y\\x^4\cdot y\\x^5\cdot y\\1\\x\\x^2\\x^3\\x^4\\x^5\\x^6\end{pmatrix}dy\,dx$$

To put the generalized integral into a form that can be numerically evaluated (as in Eq. D-11), Eq. D-18 only needs to have the integration relative to "dy" performed. Consequently, Eq. D-19 can be written similar to Eq. B-23 to take advantage of derivation already performed. (It should be noted that Eq. D-19, in this situation, does not represent an algebraic solution to the Eq. D-14. Rather, Eq. D-19 is equivalent to the function being integrated in Eq. D-11.)

Eq. D-19

$Ug_o(x, y_e, r', D, v) := Int_U(U_{xx}(r'), U_{xy}(r'), SU_g(x, y_e), D, v)$
$Ug_{pz}(x, y_e, r', D, v, p_z) := Int_{Up}(U_{xx}(r'), U_{yy}(r'), U_{xy}(r'), U_{xxp}(D, p_z),$
$U_{yyp}(D, p_z), U_{xyp}(D, p_z), SU_g(x, y_e), D, v)$
Where $$SU_g(x, y_e) := \frac{1}{420}\cdot\text{stack}$$

-continued $$\begin{bmatrix}\begin{pmatrix}60\cdot y_e^7\\70\cdot y_e^6\\70\cdot x\cdot y_e^6\\84\cdot y_e^5\\84\cdot x\cdot y_e^5\\84\cdot x^2\cdot y_e^5\\105\cdot y_e^4\\105\cdot x\cdot y_e^4\\105\cdot x^2\cdot y_e^4\\105\cdot x^3\cdot y_e^4\\140\cdot y_e^3\\140\cdot x\cdot y_e^3\\140\cdot x^2\cdot y_e^3\\140\cdot x^3\cdot y_e^7\end{pmatrix}\cdot\begin{pmatrix}140\cdot x^4\cdot y_e^3\\210\cdot y_e^2\\210\cdot x\cdot y_e^2\\210\cdot x^2\cdot y_e^2\\210\cdot x^3\cdot y_e^2\\210\cdot x^4\cdot y_e^2\\210\cdot x^5\cdot y_e^2\\420\cdot y_e\\420\cdot x\cdot y_e\\420\cdot x^2\cdot y_e\\420\cdot x^3\cdot y_e\\420\cdot x^4\cdot y_e\\420\cdot x^5\cdot y_e\\420\cdot x^6\cdot y_e\end{pmatrix}\end{bmatrix}$$

The other area integral to be addressed is Eq. D-15 for the pressure load. This can be written similar to Eq. B-23 (as shown in Eq. D-20).

$$W_{pg} = p_z \int_{x_0}^{x_1} \int_{y_0}^{y_1} \begin{bmatrix} 1 \cdot r' \\ x \\ y \\ x \cdot y \cdot r'^{-1} \\ x^2 \cdot r'^{-1} \\ y^2 \cdot r'^{-1} \\ x^2 \cdot y \cdot r'^{-2} \\ x \cdot y^2 \cdot r'^{-2} \\ x^3 \cdot r'^{-2} \\ y^3 \cdot r'^{-2} \\ x^3 \cdot y \cdot r'^{-3} \\ x \cdot y^3 \cdot r'^{-3} \\ (x^4 \cdot 3 \cdot x^2 \cdot y^2) \cdot r'^{-3} \\ (y^4 \cdot 3 \cdot x^2 \cdot y^2) \cdot r'^{-3} \\ (x^4 \cdot y \cdot x^2 \cdot y^3) \cdot r'^{-4} \\ (x \cdot y^4 \cdot x^3 \cdot y^2) \cdot r'^{-4} \\ (x^5 \cdot 5 \cdot x^3 \cdot y^2) \cdot r'^{-4} \\ (y^5 \cdot 5 \cdot x^2 \cdot y^3) \cdot r'^{-4} \end{bmatrix} dy\, dx \quad \text{Eq. D-20}$$

External work due to the pressure load linear equations in the energy optimization To put the external work due to pressure into a form that can be numerically evaluated (as in Eq. D-11), Eq. D-20 only needs to have the integration relative to "dy" performed. Consequently, Eq. D-21 can be written similar to Eq. B-25 to take advantage of derivation already performed. (It should be noted that Eq. D-21, in this situation, does not represent an algebraic solution to the Eq. D-15. Rather, Eq. D-21 is equivalent to the function being integrated in Eq. D-11.)

Following the same logic used with the development of Eq. D-12, Eq. D-20 can be solved with the generalized integration shown in Eq. D-21.

$$Ug_p(x,y_e,r',D,v,p_z) := p_z \cdot CvtU'(SU_g(x,y_e),r') \quad \text{Eq. D-21}$$

Edge Integrals for a General Curved Edge

Recalling the edge energy integral (Eq. A-47), there are three edge loads and three edge displacements to be addressed in the total energy equation for the element (Eq. A-48 or A-49) and the energy optimization (Eq. A-49). For a general curved edge, the displacement and loads are put in a form so that they may be numerically integrated with respect to the x-axis of the element (similar to Eq. D-11). To achieve this form, Eqs. D-3 to D-10 are introduced into an edge integral similar to that in Eq. A-47. This results in Eq. D-22 which is the form of Eq. A-47 evaluated in this Section. (The derivation considers only the s-face variables with respect to the x-axis for all of the variables defined in Eqs. D-3 to D-10.)

Introducing Eq. D-6 and then Eqs. D-3 to D-5 into the First Term in Eq. A-47:

$$W_{gPw} = \int P_{sx} \cdot w_{sx} ds = \int \left(P_x \cdot \frac{dx}{ds} - P_y \cdot \frac{dy}{ds}\right) \cdot w\, ds \quad \text{Eq. D-22(a)}$$

-continued $$W_{gPw} = \int \left[P_x \cdot \frac{1}{\sqrt{1+\left(\frac{dy}{dx}\right)^2}} - P_y \cdot \frac{\frac{dy}{dx}}{\sqrt{1+\left(\frac{dy}{dx}\right)^2}}\right] \cdot$$

$$w \cdot \sqrt{1+\left(\frac{dy}{dx}\right)^2}\, dx$$

$$W_{gPw} = \int \frac{P_x - P_y \cdot \frac{dy}{dx}}{\sqrt{1+\left(\frac{dy}{dx}\right)^2}} \cdot w \cdot \sqrt{1+\left(\frac{dy}{dx}\right)^2}\, dx$$

or $$W_{gPw} = \int \left(P_x - P_y \cdot \frac{dy}{dx}\right) \cdot w\, dx$$

Edge energy considering shear load and displacement

Introducing Eqs. D-8 and D-9 then Eqs. D-3 to D-5 into the Second Term in Eq. A-47:

$$W_{gM\theta} = \int M_{sx} \cdot \theta_{sx} ds = \quad \text{Eq. D-22(b)}$$

$$\int \left[M_x \cdot \left(\frac{dx}{ds}\right)^2 - 2 \cdot T_{xy} \cdot \frac{dx}{ds} \cdot \frac{dy}{ds} + M_y \cdot \left(\frac{dy}{ds}\right)^2\right] \cdot$$

$$\left(\theta_{wx} \cdot \frac{dx}{ds} - \theta_{wy} \cdot \frac{dy}{ds}\right) ds$$

$$W_{gM\theta} = \int \begin{bmatrix} M_x \cdot \left[\frac{1}{\sqrt{1+\left(\frac{dy}{dx}\right)^2}}\right]^2 \ldots + \\ -2 \cdot T_{xy} \cdot \frac{1}{\sqrt{1+\left(\frac{dy}{dx}\right)^2}} \cdot \frac{\frac{dy}{dx}}{\sqrt{1+\left(\frac{dy}{dx}\right)^2}} \ldots + \\ M_y \cdot \left[\frac{\frac{dy}{dx}}{\sqrt{1+\left(\frac{dy}{dx}\right)^2}}\right]^2 \end{bmatrix} \cdot$$

$$\begin{bmatrix} \theta_{wx} \cdot \frac{1}{\sqrt{1+\left(\frac{dy}{dx}\right)^2}} \ldots + \\ -\theta_{wy} \cdot \frac{\frac{dy}{dx}}{\sqrt{1+\left(\frac{dy}{dx}\right)^2}} \end{bmatrix} \cdot \sqrt{1+\left(\frac{dy}{dx}\right)^2}\, dx$$

$$W_{gM\theta} = \int \frac{M_x - 2 \cdot T_{xy} \cdot \frac{dy}{dx} + M_y \cdot \left(\frac{dy}{dx}\right)^2}{1+\left(\frac{dy}{dx}\right)^2} \cdot$$

$$\frac{\theta_{wx} - \theta_{wy} \cdot \frac{dy}{dx}}{\sqrt{1+\left(\frac{dy}{dx}\right)^2}} \cdot \sqrt{1+\left(\frac{dy}{dx}\right)^2}\, dx$$

-continued or $$W_{gM\theta} = \int \frac{\left[M_x - 2 \cdot T_{xy} \cdot \frac{dy}{dx} + M_y \cdot \left(\frac{dy}{dx}\right)^2\right] \cdot \left(\theta_{wx} - \theta_{wy} \cdot \frac{dy}{dx}\right)}{1 + \left(\frac{dy}{dx}\right)^2} dx$$

Edge energy cosidering bending moment and bending rotation

Introducing Eqs. D-8 and D-10 then Eqs. D-3 to D-5 into the Third Term in Eq. A-47:

Eq. D-22(c)

$$W_{gT\phi} = \int T_{sxy} \cdot \phi_{sy} \, ds = \int \left\{ \begin{bmatrix} T_{xy} \cdot \left(\frac{dx}{ds}\right)^2 - T_{xy} \cdot \left(\frac{dy}{ds}\right)^2 \ldots + \\ M_x \cdot \frac{dx}{ds} \cdot \frac{dy}{ds} - M_y \cdot \frac{dx}{ds} \cdot \frac{dy}{ds} \end{bmatrix} \cdot \left(\phi_{wx} \cdot \frac{dx}{ds} + \phi_{wy} \cdot \frac{dy}{ds}\right) \right\} ds$$

$$W_{gT\phi} = \int \left\{ \begin{bmatrix} T_{xy} \cdot \left[\frac{1}{\sqrt{1+\left(\frac{dy}{dx}\right)^2}}\right]^2 \ldots + \\ -T_{xy} \cdot \left[\frac{\frac{dy}{dx}}{\sqrt{1+\left(\frac{dy}{dx}\right)^2}}\right]^2 \ldots + \\ M_x \cdot \frac{1}{\sqrt{1+\left(\frac{dy}{dx}\right)^2}} \cdot \frac{\frac{dy}{dx}}{\sqrt{1+\left(\frac{dy}{dx}\right)^2}} \ldots + \\ M_y \cdot \frac{1}{\sqrt{1+\left(\frac{dy}{dx}\right)^2}} \cdot \frac{\frac{dy}{dx}}{\sqrt{1+\left(\frac{dy}{dx}\right)^2}} \end{bmatrix} \cdot \left[\phi_{wx} \cdot \frac{1}{\sqrt{1+\left(\frac{dy}{dx}\right)^2}} \ldots + \phi_{wy} \cdot \frac{\frac{dy}{dx}}{\sqrt{1+\left(\frac{dy}{dx}\right)^2}} \right] \cdot \sqrt{1+\left(\frac{dy}{dx}\right)^2} \, dx \right.$$

$$W_{gT\phi} = \int \frac{T_{xy} \cdot \left[1 - \left(\frac{dy}{dx}\right)^2\right] + (M_x - M_y) \cdot \frac{dy}{dx}}{1 + \left(\frac{dy}{dx}\right)^2} \cdot \frac{\phi_{wx} + \phi_{wy} \cdot \frac{dy}{dx}}{\sqrt{1+\left(\frac{dy}{dx}\right)^2}} \cdot \sqrt{1+\left(\frac{dy}{dx}\right)^2} \, dx$$

or $$W_{gT\phi} = \int \frac{\left[T_{xy} \cdot \left[1 - \left(\frac{dy}{dx}\right)^2\right] + (M_x - M_y) \cdot \frac{dy}{dx}\right] \cdot \left(\phi_{wx} + \phi_{wy} \cdot \frac{dy}{dx}\right)}{1 + \left(\frac{dy}{dx}\right)^2} dx$$

Edge energy considering torsional moment and torsional rotation

Eq. D-22 establishes the form the edge energy equations. Eq. D-23 shows the form of the edge energy equations used for evaluation of the external loads and degrees of freedom.

$$W_{geP_i} = \frac{\partial}{\partial a_i} \int_{x_0}^{x_1} \left(P_x - P_y \cdot \frac{dy}{dx}\right) \cdot w(a)\, dx \qquad \text{Eq. D-23(a)}$$

or $$W_{geP_i} = \int_{x_0}^{x_1} \left(P_x - P_y \cdot \frac{dy}{dx}\right) \cdot \frac{\partial}{\partial a_i} w(a)\, dx$$

Edge energy considering an external shear load $$W_{geM_i} = \frac{\partial}{\partial a_i} \int_{x_0}^{x_1} \frac{M_x - 2\cdot T_{xy}\cdot\frac{dy}{dx} + M_y\cdot\left(\frac{dy}{dx}\right)^2}{1+\left(\frac{dy}{dx}\right)^2} \cdot \qquad \text{Eq. D-23(b)}$$

$$\left(\theta_{wx}(a) - \theta_{wy}(a)\cdot\frac{dy}{dx}\right) dx$$

or $$W_{geM_i} = \int_{x_0}^{x_1} \frac{M_x - 2\cdot T_{xy}\cdot\frac{dy}{dx} + M_y\cdot\left(\frac{dy}{dx}\right)^2}{1+\left(\frac{dy}{dx}\right)^2} \cdot$$

$$\left(\frac{\partial}{\partial a_i}\theta_{wx}(a) - \frac{\partial}{\partial a_i}\theta_{wy}(a)\cdot\frac{dy}{dx}\right) dx$$

Edge energy considering an external moment $$W_{geT_i} = \frac{\partial}{\partial a_i}\int_{x_0}^{x_1} \frac{T_{xy}\cdot\left[1-\left(\frac{dy}{dx}\right)^2\right] + (M_x - M_y)\cdot\frac{dy}{dx}}{1+\left(\frac{dy}{dx}\right)^2} \cdot \qquad \text{Eq. D-23(c)}$$

$$\left(\phi_{wx}(a) + \phi_{wy}(a)\cdot\frac{dy}{dx}\right) dx$$

or $$W_{geT_i} = \int_{x_0}^{x_1} \frac{T_{xy}\cdot\left[1-\left(\frac{dy}{dx}\right)^2\right] + (M_x - M_y)\cdot\frac{dy}{dx}}{1+\left(\frac{dy}{dx}\right)^2} \cdot$$

$$\left(\frac{\partial}{\partial a_i}\phi_{wx}(a) + \frac{\partial}{\partial a_i}\phi_{wy}(a)\cdot\frac{dy}{dx}\right) dx$$

Edge energy considering an external torsion $$W_{gew_i} = \frac{\partial}{\partial a_i}\int_{x_0}^{x_1}\left(P_x(a) - P_y(a)\cdot\frac{dy}{dx}\right)\cdot w\, dx \qquad \text{Eq. D-23(d)}$$

or $$W_{gew_i} = \int_{x_0}^{x_1} w\cdot\left(\frac{\partial}{\partial a_i}P_x(a) - \frac{\partial}{\partial a_i}P_y(a)\cdot\frac{dy}{dx}\right) dx$$

Edge energy considering an external shear displacement $$W_{ge\theta_i} = \frac{\partial}{\partial a_i}\int_{x_0}^{x_1}\left[M_x(a) - 2\cdot T_{xy}(a)\cdot\frac{dy}{dx} + M_y(a)\cdot\left(\frac{dy}{dx}\right)^2\right]\cdot \qquad \text{Eq. D-23(e)}$$

$$\frac{\theta_{wx} - \theta_{wy}\cdot\frac{dy}{dx}}{1+\left(\frac{dy}{dx}\right)^2} dx$$

or $$W_{ge\theta_i} =$$

$$\int_{x_0}^{x_1} \frac{\theta_{wx} - \theta_{wy}\cdot\frac{dy}{dx}}{1+\left(\frac{dy}{dx}\right)^2}\cdot\left[\frac{\partial}{\partial a_i}M_x(a) - 2\cdot\frac{\partial}{\partial a_i}T_{xy}(a)\cdot\frac{dy}{dx} + \right.$$

$$\left.\frac{\partial}{\partial a_i}M_y(a)\cdot\left(\frac{dy}{dx}\right)^2\right] dx$$

Edge energy considering an external bending rotation $$W_{ge\phi_i} = \qquad \text{Eq. D-23(f)}$$

$$\frac{\partial}{\partial a_i}\int_{x_0}^{x_1}\left[T_{xy}(a)\cdot\left[1-\left(\frac{dy}{dx}\right)^2\right] + (M_x(a) - M_y(a))\cdot\frac{dy}{dx}\right]\cdot$$

$$\frac{\phi_{wx} + \phi_{wy}\cdot\frac{dy}{dx}}{1+\left(\frac{dy}{dx}\right)^2} dx$$

or $$W_{ge\phi_i} = \int_{x_0}^{x_1} \frac{\phi_{wx} + \phi_{wy}\cdot\frac{dy}{dx}}{1+\left(\frac{dy}{dx}\right)^2}\cdot\left[\frac{\partial}{\partial a_i}T_{xy}(a)\cdot\left[1-\left(\frac{dy}{dx}\right)^2\right] + \right.$$

$$\left.\left(\frac{\partial}{\partial a_i}M_x(a) - \frac{\partial}{\partial a_i}M_y(a)\right)\cdot\frac{dy}{dx}\right] dx$$

Edge energy considering an external torsional rotation

In general, the equations in Eq. D-23 represent one position that is to be summed into the $U_b$ vector (in Eq. A-51) for the element or one row to be summed into the $U_m$ array (in Eq. A-51) for a neighboring element. In the case where a boundary condition is not known, this can represent one row to be summed into the $U_m$ array (in Eq. A-51) for the element.

The external loads and displacements may have any function as long as it can be expressed in terms of the local direction along the curve. It is very common for boundary conditions to just be constant (which is easily addressed). Neighboring elements will cause external loads and displacements based on their displacement equation. To accommodate a neighboring element, equation development (as in Eq. B-15) could be done for the x- and y-direction displacements/loads and then that could be incorporated into Eq. D-23. For this example, the external displacements/loads will be represented with a simple constant. However, the situation where a boundary condition is not known may still be accommodated. Eq. D-24 shows the form of these equations with D-23(a) being shown as an example.

$$W_{geP_{i,j}} = \int_{x_0}^{x_1} \left(P_{x_j} - P_{y_j} \cdot \frac{dy}{dx}\right) \cdot \frac{d}{da_i} w(a) \, dx \quad \text{Eq. D-24(a)}$$

Edge energy considering an external shear load $$W_{geP_{i,p}} = \int_{x_0}^{x_1} \left(P_{x_p} - P_{y_p} \cdot \frac{dy}{dx}\right) \cdot \frac{d}{da_i} w(a) \, dx \quad \text{Eq. D-24(b)}$$

Edge energy considering an external shear load

Where "i" and "j" represent degrees of freedom and "p" represents the portion of the function related to the external pressure.

Considering Eqs. D-23 and D-24, it is clear that both equations can be numerically integrated if equations for the displacements/loads are defined relative to each degree of freedom and relative to the portion of the function related to the pressure load. These definitions are made in Eq. D-25 (where the base displacement is defined in Eq. B-7).

$$w = a^T \cdot F_w(x, y, r', D, v) + F_{w\_pz}(x, y, r', D, v, p_z) \quad \text{Eq. D-25(a)}$$

$$\theta_x = \frac{d}{dy} w = a^T \cdot F_{\theta x}(x, y, r', D, v) + F_{\theta x\_pz}(x, y, r', D, v, p_z) \quad \text{Eq. D-25(b)}$$

$$\theta_y = \frac{d}{dx} w = a^T \cdot F_{\theta y}(x, y, r', D, v) + F_{\theta y\_pz}(x, y, r', D, v, p_z) \quad \text{Eq. D-25(c)}$$

$$\phi_x = \frac{d}{dx} w = a^T \cdot F_{\phi x}(x, y, r', D, v) + F_{\phi x\_pz}(x, y, r', D, v, p_z) \quad \text{Eq. D-25(d)}$$

$$\phi_y = \frac{d}{dy} w = a^T \cdot F_{\phi y}(x, y, r', D, v) + F_{\phi y\_pz}(x, y, r', D, v, p_z) \quad \text{Eq. D-25(e)}$$

$$P_x = -D \cdot \frac{d}{dy}\left(\frac{d^2}{dy^2} w + \frac{d^2}{dx^2} w\right) =$$
$$a^T \cdot F_{Px}(x, y, r', D, v) + F_{Px\_pz}(x, y, r', D, v, p_z) \quad \text{Eq. D-25(f)}$$

$$P_y = -D \cdot \frac{d}{dx}\left(\frac{d^2}{dx^2} w + \frac{d^2}{dy^2} w\right) =$$
$$a^T \cdot F_{Py}(x, y, r', D, v) + F_{Py\_pz}(x, y, r', D, v, p_z) \quad \text{Eq. D-25(g)}$$

$$M_x = -D \cdot \left(\frac{d^2}{dy^2} w + v \cdot \frac{d^2}{dx^2} w\right) =$$
$$a^T \cdot F_{Mx}(x, y, r', D, v) + F_{Mx\_pz}(x, y, r', D, v, p_z) \quad \text{Eq. D-25(h)}$$

$$M_y = -D \cdot \left(\frac{d^2}{dx^2} w + v \cdot \frac{d^2}{dy^2} w\right) =$$
$$a^T \cdot F_{My}(x, y, r', D, v) + F_{My\_pz}(x, y, r', D, v, p_z) \quad \text{Eq. D-25(i)}$$

$$T_{xy} = -D \cdot (1-v) \cdot \frac{d}{dx}\frac{d}{dy} w =$$
$$a^T \cdot F_{Txy}(x, y, r', D, v) + F_{Txy\_pz}(x, y, r', D, v, p_z) \quad \text{Eq. D-25(j)}$$

Where:

$$F_{W\_pz}(x, y, r', D, v, p_z) := \frac{p_z}{8 \cdot D} \cdot x^2 \cdot y^2$$

$$F_{\theta x\_pz}(x, y, r', D, v, p_z) := \frac{p_z \cdot x^2 \cdot y}{4 \cdot D}$$

$$F_{\theta y\_pz}(x, y, r', D, v, p_z) := \frac{p_z \cdot x \cdot y^2}{4 \cdot D}$$

$$F_{\phi x\_pz}(x, y, r', D, v, p_z) := \frac{p_z \cdot x \cdot y^2}{4 \cdot D}$$

$$F_{\phi y\_pz}(x, y, r', D, v, p_z) := \frac{p_z \cdot x^2 \cdot y}{4 \cdot D}$$

$$F_{Px\_pz}(x, y, r', D, v, p_z) := \frac{p_z \cdot y}{2}$$

$$F_{Py\_pz}(x, y, r', D, v, p_z) := \frac{p_z \cdot x}{2}$$

$$F_{Mx\_pz}(x, y, r', D, v, p_z) := \frac{-p_z \cdot (x^2 + v \cdot y^2)}{4}$$

$$F_{My\_pz}(x, y, r', D, v, p_z) := \frac{-p_z \cdot (v \cdot x^2 + y^2)}{4}$$

$$F_{Txy\_pz}(x, y, r', D, v, p_z) := \frac{-p_z \cdot (1-v) \cdot x \cdot y}{2}$$

$$F_w(x, y, r', D, v) := \begin{bmatrix} 1 \cdot r' \\ x \\ y \\ x \cdot y \cdot r'^{-1} \\ x^2 \cdot r'^{-1} \\ y^2 \cdot r'^{-1} \\ x^2 \cdot y \cdot r'^{-2} \\ x \cdot y^2 \cdot r'^{-2} \\ x^3 \cdot r'^{-2} \\ y^3 \cdot r'^{-2} \\ x^3 \cdot y \cdot r'^{-3} \\ x \cdot y^3 \cdot r'^{-3} \\ (x^4 - 3 \cdot x^2 \cdot y^2) \cdot r'^{-3} \\ (y^4 - 3 \cdot x^2 \cdot y^2) \cdot r'^{-3} \\ (x^4 \cdot y - x^2 \cdot y^3) \cdot r'^{-4} \\ (x \cdot y^4 - x^3 \cdot y^2) \cdot r'^{-4} \\ (x^5 - 5 \cdot x^3 \cdot y^2) \cdot r'^{-4} \\ (y^5 - 5 \cdot x^2 \cdot y^3) \cdot r'^{-4} \end{bmatrix}$$

$$F_{\theta x}(x, y, r', D, v) := \begin{bmatrix} 0 \\ 0 \\ 1 \\ x \cdot r'^{-1} \\ 0 \\ 2 \cdot y \cdot r'^{-1} \\ x^2 \cdot r'^{-2} \\ 2 \cdot x \cdot y \cdot r'^{-2} \\ 0 \\ 3 \cdot y^2 \cdot r'^{-2} \\ x^3 \cdot r'^{-3} \\ 3 \cdot x \cdot y^2 \cdot r'^{-3} \\ -6 \cdot x^2 \cdot y \cdot r'^{-3} \\ (4 \cdot y^3 - 6 \cdot x^2 \cdot y) \cdot r'^{-3} \\ x^2 \cdot (x^2 - 3 \cdot y^2) \cdot r'^{-4} \\ -2 \cdot x \cdot y \cdot (x^2 - 2 \cdot y^2) \cdot r'^{-4} \\ -10 \cdot x^3 \cdot y \cdot r'^{-4} \\ 5 \cdot y^2 \cdot (y^2 - 3 \cdot x^2) \cdot r'^{-4} \end{bmatrix}$$

-continued $$F_{\theta y}(x, y, r', D, v) := \begin{bmatrix} 0 \\ 1 \\ 0 \\ y \cdot r'^{-1} \\ 2 \cdot x \cdot r'^{-1} \\ 0 \\ 2 \cdot x \cdot y \cdot r'^{-2} \\ y^2 \cdot r'^{-2} \\ 3 \cdot x^2 \cdot r'^{-2} \\ 0 \\ 3 \cdot x^2 \cdot y \cdot r'^{-3} \\ y^3 \cdot r'^{-3} \\ 2 \cdot x \cdot (2 \cdot x^2 - 3 \cdot y^2) \cdot r'^{-3} \\ -6 \cdot x \cdot y^2 \cdot r'^{-3} \\ -2 \cdot x \cdot y \cdot (y^2 - 2 \cdot x^2) \cdot r'^{-4} \\ y^2 \cdot (y^2 - 3 \cdot x^2) \cdot r'^{-4} \\ 5 \cdot x^2 \cdot (x^2 - 3 \cdot y^2) \cdot r'^{-4} \\ -10 \cdot x \cdot y^3 \cdot r'^{-4} \end{bmatrix}$$

$$F_{\phi x}(x, y, r', D, v) := \begin{bmatrix} 0 \\ 1 \\ 0 \\ y \cdot r'^{-1} \\ 2 \cdot x \cdot r'^{-1} \\ 0 \\ 2 \cdot x \cdot y \cdot r'^{-2} \\ y^2 \cdot r'^{-2} \\ 3 \cdot x^2 \cdot r'^{-2} \\ 0 \\ 3 \cdot x^2 \cdot y \cdot r'^{-3} \\ y^3 \cdot r'^{-3} \\ 2 \cdot x \cdot (2 \cdot x^2 - 3 \cdot y^2) \cdot r'^{-3} \\ -6 \cdot x \cdot y^2 \cdot r'^{-3} \\ -2 \cdot x \cdot y \cdot (y^2 - 2 \cdot x^2) \cdot r'^{-4} \\ y^2 \cdot (y^2 - 3 \cdot x^2) \cdot r'^{-4} \\ 5 \cdot x^2 \cdot (x^2 - 3 \cdot y^2) \cdot r'^{-4} \\ -10 \cdot x \cdot y^3 \cdot r'^{-4} \end{bmatrix}$$

$$F_{\phi y}(x, y, r', D, v) := \begin{bmatrix} 0 \\ 0 \\ 1 \\ x \cdot r'^{-1} \\ 0 \\ 2 \cdot y \cdot r'^{-1} \\ x^2 \cdot r'^{-2} \\ 2 \cdot x \cdot y \cdot r'^{-2} \\ 0 \\ 3 \cdot y^2 \cdot r'^{-2} \\ x^3 \cdot r'^{-3} \\ 3 \cdot x \cdot y^2 \cdot r'^{-3} \\ -6 \cdot x^2 \cdot y \cdot r'^{-3} \\ (4 \cdot y^3 - 6 \cdot x^2 \cdot y) \cdot r'^{-3} \\ x^2 \cdot (x^2 - 3 \cdot y^2) \cdot r'^{-4} \\ -2 \cdot x \cdot y \cdot (x^2 - 2 \cdot y^2) \cdot r'^{-4} \\ -10 \cdot x^3 \cdot y \cdot r'^{-4} \\ 5 \cdot y^2 \cdot (y^2 - 3 \cdot x^2) \cdot r'^{-4} \end{bmatrix}$$

$$F_{Px}(x, y, r', D, v) := -D \cdot \begin{bmatrix} 0 \\ 0 \\ 0 \\ 0 \\ 0 \\ 0 \\ 2 \cdot r'^{-2} \\ 0 \\ 0 \\ 6 \cdot r'^{-2} \\ 6 \cdot x \cdot r'^{-3} \\ 6 \cdot x \cdot r'^{-3} \\ -12 \cdot y \cdot r'^{-3} \\ 12 \cdot y \cdot r'^{-3} \\ 6 \cdot (x^2 - y^2) \cdot r'^{-4} \\ 12 \cdot x \cdot y \cdot r'^{-4} \\ -60 \cdot x \cdot y \cdot r'^{-4} \\ -30 \cdot (x^2 - y^2) \cdot r'^{-4} \end{bmatrix}$$

$$F_{Py}(x, y, r', D, v) := -D \cdot \begin{bmatrix} 0 \\ 0 \\ 0 \\ 0 \\ 0 \\ 0 \\ 0 \\ 2 \cdot r'^{-2} \\ 6 \cdot r'^{-2} \\ 0 \\ 6 \cdot y \cdot r'^{-3} \\ 6 \cdot y \cdot r'^{-3} \\ 12 \cdot x \cdot r'^{-3} \\ -12 \cdot x \cdot r'^{-3} \\ 12 \cdot x \cdot y \cdot r'^{-4} \\ -6 \cdot (x^2 - y^2) \cdot r'^{-4} \\ 30 \cdot (x^2 - y^2) \cdot r'^{-4} \\ -60 \cdot x \cdot y \cdot r'^{-4} \end{bmatrix}$$

$$F_{Mx}(x, y, r', D, v) := -D \cdot \begin{bmatrix} 0 \\ 0 \\ 0 \\ 0 \\ 2 \cdot v \cdot r'^{-1} \\ 2 \cdot r'^{-1} \\ 2 \cdot v \cdot y \cdot r'^{-2} \\ 2 \cdot x \cdot r'^{-2} \\ 6 \cdot v \cdot x \cdot r'^{-2} \\ 6 \cdot y \cdot r'^{-2} \\ 6 \cdot v \cdot x \cdot y \cdot r'^{-3} \\ 6 \cdot x \cdot y \cdot r'^{-3} \\ -6 \cdot (v \cdot y^2 - 2 \cdot v \cdot x^2 + x^2) \cdot r'^{-3} \\ -6 \cdot (v \cdot y^2 + x^2 - 2 \cdot y^2) \cdot r'^{-3} \\ -2 \cdot y \cdot (v \cdot y^2 - 6 \cdot v \cdot x^2 + 3 \cdot x^2) \cdot r'^{-4} \\ -2 \cdot x \cdot (3 \cdot v \cdot y^2 + x^2 - 6 \cdot y^2) \cdot r'^{-4} \\ -10 \cdot x \cdot (3 \cdot v \cdot y^2 - 2 \cdot v \cdot x^2 + x^2) \cdot r'^{-4} \\ -10 \cdot y \cdot (v \cdot y^2 + 3 \cdot x^2 - 2 \cdot y^2) \cdot r'^{-4} \end{bmatrix}$$

-continued $$F_{My}(x, y, r', D, v) := -D \cdot \begin{bmatrix} 0 \\ 0 \\ 0 \\ 0 \\ 2 \cdot r'^{-1} \\ 2 \cdot v \cdot r'^{-1} \\ 2 \cdot y \cdot r'^{-2} \\ 2 \cdot v \cdot x \cdot r'^{-2} \\ 6 \cdot x \cdot r'^{-2} \\ 6 \cdot v \cdot x \cdot r'^{-2} \\ 6 \cdot x \cdot y \cdot r'^{-3} \\ 6 \cdot v \cdot x \cdot y \cdot r'^{-3} \\ -6 \cdot (v \cdot x^2 - 2 \cdot x^2 + y^2) \cdot r'^{-3} \\ -6 \cdot (v \cdot x^2 - 2 \cdot v \cdot y^2 + y^2) \cdot r'^{-3} \\ -2 \cdot y \cdot (3 \cdot v \cdot x^2 - 6 \cdot x^2 + y^2) \cdot r'^{-4} \\ -2 \cdot x \cdot (v \cdot x^2 - 6 \cdot v \cdot y^2 + 3 \cdot y^2) \cdot r'^{-4} \\ -10 \cdot x \cdot (v \cdot x^2 - 2 \cdot x^2 + 3 \cdot y^2) \cdot r'^{-4} \\ -10 \cdot y \cdot (3 \cdot v \cdot x^2 - 2 \cdot v \cdot y^2 + y^2) \cdot r'^{-4} \end{bmatrix}$$

$$F_{Txy}(x, y, r', D, v) := -D \cdot (1-v) \cdot \begin{bmatrix} 0 \\ 0 \\ 0 \\ 1 \cdot r'^{-1} \\ 0 \\ 0 \\ 2 \cdot x \cdot r'^{-2} \\ 2 \cdot y \cdot r'^{-2} \\ 0 \\ 0 \\ 3 \cdot x^2 \cdot r'^{-3} \\ 3 \cdot y^2 \cdot r'^{-3} \\ -12 \cdot x \cdot y \cdot r'^{-3} \\ -12 \cdot x \cdot y \cdot r'^{-3} \\ 2 \cdot x \cdot (2 \cdot x^2 - 3 \cdot y^2) \cdot r'^{-4} \\ (4 \cdot y^3 - 6 \cdot x^2 \cdot y) \cdot r'^{-4} \\ -30 \cdot x^2 \cdot y \cdot r'^{-4} \\ -30 \cdot x \cdot y^2 \cdot r'^{-4} \end{bmatrix}$$

At this point, the definitions necessary for a numerical integration of Eq. D-23 have been defined.

Model Formulation

Figure 32:
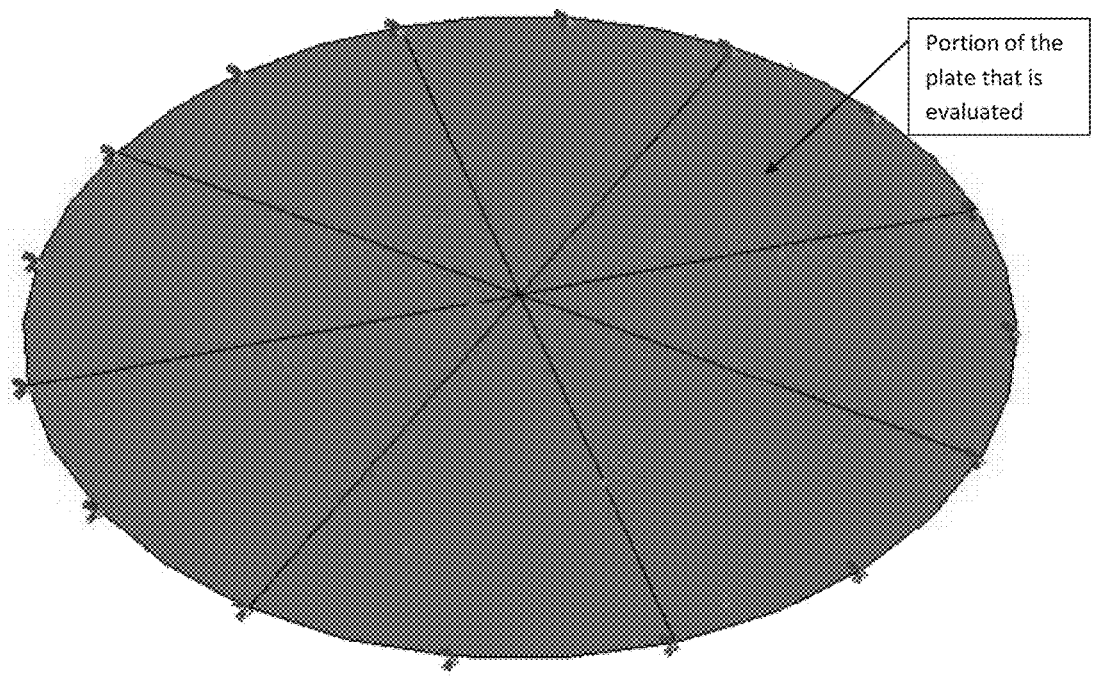
FIG. 32 is a perspective view of an example thin plate divided into eight elements and having a fixed edge and distributed pressure load.
Figure 33:
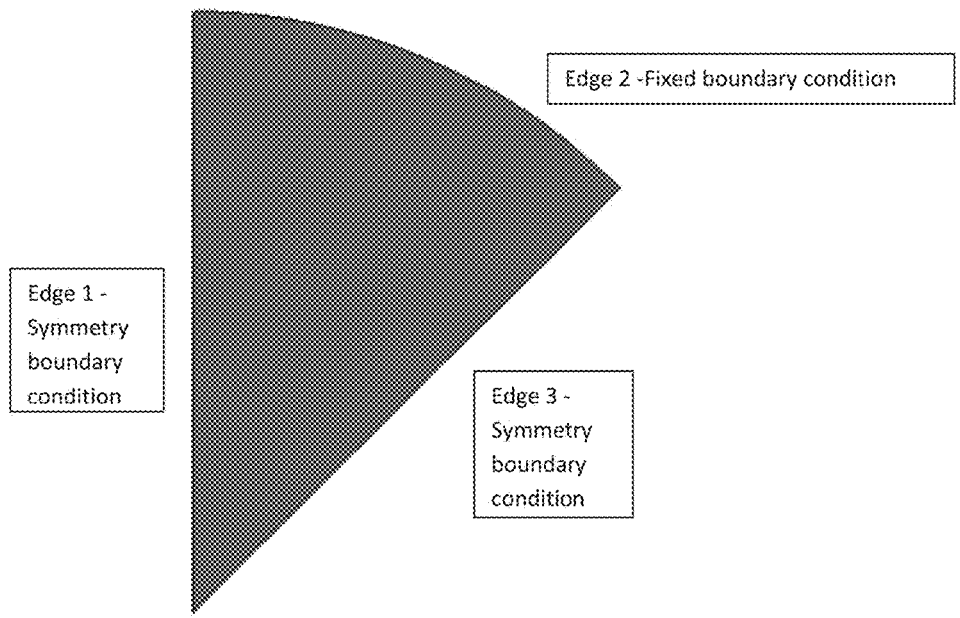
FIG. 33 is a top view of one of the elements of the plate of FIG. 32.

The test model (as shown in FIG. 32) is a thin plate that is 2.5 inches in diameter by 0.1 inches thick. (This is the same model as used in Section C.) All of the edges are fixed and there is a 300 psi pressure applied evenly over the surface. Considering symmetry, a single pie shaped element with symmetry restraints can be used to evaluate the whole plate. The evaluated portion of the plate is identified in FIG. 32 and shown with boundary conditions identified in FIG. 33. This problem is selected because a single, simple element can be used to solve it. Also, the exact solution is well known and can be used for comparison.

The material properties and element geometry are listed below.

E:=30·10$^6$ Modulus of elasticity
v:=0.3 Poisson's ratio
t:=0.1 Thickness $$D := \frac{E \cdot t^3}{12 \cdot (1-v^2)}$$ Flexural rigidity D=2747.253
x$^T$=(0 0 0.884) Endpoints in the x-direction for the triangular element
y$^T$=(0 1.25 0.884) Endpoints in the y-direction for the triangular element
r'=6.4 Length dimension used to make the degrees of freedom unitless. (The value of 6.4 is arbitrarily selected as a good value relative to matrix inversion. This is the integer value that makes the matrix determinant and matrix inverse determinant closest to one.)

$r_{fl} := 1.25$      Circle radius $y_e(x) := \sqrt{r_{fl}^2 - x^2}$      General edge curve $y'_e(x) := -\dfrac{x}{\sqrt{r_{fl}^2 - x^2}}$      General edge curve slope Element Definitions and Boundary Conditions The equations derived for this example are for general curved edges. Equations for straight edges are also included in this model. The element definition variables are organized to accept both shapes.

For the element definitions, three simple arrays are defined to guide the process of formulating an element. The first is an area mapping array as shown below. The area mapping array guides the area integral solutions for each edge. Each row represents an edge. The first column represents the edge shape. A zero indicates that the edge is linear, a one indicates a circular edge, and a two (as is the case here) indicates a general curved edge. For all three edge types, the next two columns are the indices for the start and end edge endpoints. For a circular edge, the third column is the circle center point and the fourth column is a one for a solid circle and a zero for a hole. The circle algorithms are set up to define a pie shaped area (or full circle) and the points are defined in a clockwise manner. For a general curved edge, the third column is the number of integration segments for the numerical integration. This is defined as 6 for this problem. With 6 segments, the accuracy of the results when compared to the exact solution are equivalent to that of the circular edge derivation (which itself should produce an exact solution) at a percent error near 10$^{-10}$%. (With one integration segment, the results match the exact solution to five digits. With two integration segments, this is increased to seven digits. Consequently, the Gaussian quadrature works very well for this example.)

For a general curved edge area, everything under the curve and bounded by the two endpoints is included. Consequently, a straight edge is defined from point 2 to point 0 to remove the excess area.

$$a_{map} := \begin{pmatrix} 2 & 1 & 2 & 6 & 0 \\ 0 & 2 & 0 & 0 & 0 \end{pmatrix}$$

Area mapping array

The second array is an edge mapping array as shown below. The edge mapping array guides the edge integral solutions for each edge. Each row represents an edge. The first column represents the edge shape. A zero indicates that the edge is linear, a one indicates a circular edge, and a two (as is the case here) indicates a general curved edge. For all three edge types, the next two columns are the indices for the start and end edge endpoints. For a circular edge, the third column is the circle center point and the fourth column is a one for a solid circle and a zero for a hole. As in the area integrals, the circle algorithms are set up to define a pie shaped area (or full circle) and the points are defined in a clockwise manner. For a general curved edge, the third column is the number of integration segments for the numerical integration.

$$e_{map} := \begin{pmatrix} 0 & 0 & 1 & 0 & 0 \\ 2 & 1 & 2 & 6 & 0 \\ 0 & 2 & 0 & 0 & 0 \end{pmatrix}$$

Edge mapping array

The third array (as shown below) is a boundary conditions mapping array that corresponds to the edge mapping array. Each row of this array identifies active boundary conditions for the corresponding row in the edge mapping array. A zero indicates that the external displacement/load is unknown. A one indicates that the external displacement/load is known. Each column represents a displacement/load as identified below. Considering that this is a single element problem, all of the boundary conditions consist of a known displacement/load and the corresponding load/displacement is not known. For this element, the first and third edges have symmetry boundary conditions and the second edge is fixed in displacement.

$$\text{map} := \begin{pmatrix} 0 & 1 & 0 & 1 & 0 & 1 \\ 1 & 1 & 1 & 0 & 0 & 0 \\ 0 & 1 & 0 & 1 & 0 & 1 \end{pmatrix}$$

Boundary conditions mapping array

The boundary conditions are defined as arrays where each column corresponds with an edge defined in the edge mapping array. In the definitions, each row corresponds to a displacement/load constant defined in Eq. B-38 for the linear edges and (for this example) the general curved edge is just defined as having constant displacement/load. The pressure loading is defined as a scalar value.

Linear Edges:

$$P_e = \begin{pmatrix} 0 & 0 & 0 \\ 0 & 0 & 0 \\ 0 & 0 & 0 \end{pmatrix} \text{ Shear load} \quad M_e = \begin{pmatrix} 0 & 0 & 0 \\ 0 & 0 & 0 \\ 0 & 0 & 0 \\ 0 & 0 & 0 \end{pmatrix} \text{ Bending moment}$$

$$T_e = \begin{pmatrix} 0 & 0 & 0 \\ 0 & 0 & 0 \\ 0 & 0 & 0 \\ 0 & 0 & 0 \end{pmatrix} \text{ Torsional moment} \quad w_e = \begin{pmatrix} 0 & 0 & 0 \\ 0 & 0 & 0 \\ 0 & 0 & 0 \\ 0 & 0 & 0 \\ 0 & 0 & 0 \\ 0 & 0 & 0 \end{pmatrix} \text{ Displacement}$$

-continued $$\theta_e = \begin{pmatrix} 0 & 0 & 0 \\ 0 & 0 & 0 \\ 0 & 0 & 0 \\ 0 & 0 & 0 \\ 0 & 0 & 0 \\ 0 & 0 & 0 \end{pmatrix} \text{ Bending rotation} \quad \phi_e = \begin{pmatrix} 0 & 0 & 0 \\ 0 & 0 & 0 \\ 0 & 0 & 0 \\ 0 & 0 & 0 \\ 0 & 0 & 0 \\ 0 & 0 & 0 \end{pmatrix} \text{ Torsional rotation}$$

General Curve Edges:

$$Pg_e = (0 \ 0 \ 0) \text{ Shear load} \quad Mg_e = (0 \ 0 \ 0) \text{ Bending moment}$$

$$Tg_e = (0 \ 0 \ 0) \text{ Torsional moment} \quad wg_e = (0 \ 0 \ 0) \text{ Displacement}$$

$$\theta g_e = (0 \ 0 \ 0) \text{ Bending rotation} \quad \phi g_e = (0 \ 0 \ 0) \text{ Torsional rotation}$$

Area Loading:

$$p_z = -300 \qquad \text{Distributed Pressure}$$

Continuing with the element definition, subroutines defined in Section C (Su. C-8 and C-9) are used to define the area mapping array for calculation and edge mapping array for calculation. In various implementations, no additional modification to the subroutines is necessary for the general curve edge.

$$a_c = \begin{pmatrix} 0 & 0.884 & 0 & 0 & 0 \\ 0.884 & 0 & 1 & 0 & 0 \end{pmatrix}$$

Area mapping array for calculation $$e_c = \begin{pmatrix} 0 & 1 & 0 & 0 & 1.25 \\ 0 & 0 & 0 & 0 & 0 \\ -0.707 & -0.707 & 0 & -1.25 & 0 \end{pmatrix}$$

Edge mapping array for calculation

Considering the equations for the area integrals, Su. B-6 (defined in Section B) along with Su. D-1 produce arrays which include all of the area integration data for the element in the example problem. These arrays are the portion of the $U_b$ vector (in Eq. A-51) related to the area integrals augmented to the portion of the $U_m$ array (in Eq. A-51) related to the area integrals. These subroutines start by populating the output array and vector with zeros. They then calculate the algebraic form of the strain energy and work of the pressure load for each row of the area mapping array. The factor of 2 on the strain energy array and vector is from Eq. A-48.

Su. D-1

$$U'_{o\_eg} := \begin{vmatrix} k_{17,17} \leftarrow 0 \\ F_{17} \leftarrow 0 \\ no \leftarrow 0 \\ \text{for } i \in 0 \ldots \text{rows}(a_{map}) - 1 \\ \quad (x_0 \, x_1 \, no) \leftarrow (x_{a_{map_{i,1}}} \, x_{a_{map_{i,2}}} \, a_{map_{i,3}}) \text{ if } a_{map_{i,0}} = 2 \\ \text{for } j \in 1 \ldots no \quad \quad \text{if } no > 0 \\ \quad \begin{vmatrix} x0 \leftarrow \frac{j-1}{no} \cdot (x_1 - x_0) + x_0 \\ x1 \leftarrow \frac{j}{no} \cdot (x_1 - x_0) + x_0 \\ \text{for } i \in 0 \ldots \text{last}(Gx) \\ \quad \begin{vmatrix} x_0 \leftarrow \frac{1}{2} \cdot (Gx_i + 1) \cdot (x1 - x0) + x0 \\ k \leftarrow k + 2 \cdot Gc_i \cdot Ug_o(x_o, y_e(x_o), r', D, v) \cdot \left[\frac{1}{2} \cdot (x1 - x0)\right] \\ F \leftarrow F - Gc_i \cdot Ug_p(x_o, y_e(x_o), r', D, v, p_z) \cdot \left[\frac{1}{2} \cdot (x1 - x0)\right] \\ F \leftarrow F + 2 \cdot Gc_i \cdot Ug_{pz}(x_o, y_e(x_o), r', D, v, p_z) \cdot \left[\frac{1}{2} \cdot (x1 - x0)\right] \end{vmatrix} \end{vmatrix} \\ \text{augment}(F, k) \end{vmatrix}$$

Considering the equations for the edge integrals, Su. B-7(defined in Section B) along with Sus. D-2 to D-4 produce arrays which includes all of the edge integration data for the element in the example problem. Eq. D-26 sums the results of Sus. D-2 to D-4. These arrays are the portion of the $U_b$ vector (in Eq. A-51) related to the edge integrals augmented to the portion of the $U_m$ array (in Eq. A-51) related to the edge integrals. These subroutines start by populating the output array and vector with zeros. They then calculate the algebraic or numerical integration form of the edge integrals for each row of the edge mapping array. The boundary conditions mapping array uses the logic discussed with Eq. B-40 to determine the correct algorithm for addressing the displacement/load situation.

$U'_{eg} := U'_{eg\_P\_w} + U'_{eg\_M\_\theta} + U'_{eg\_T\_\phi}$ General curve edge integral numerical solution  Eq. D-26

Where:

Su. D-2

$$U'_{eg\_P\_w} := \begin{vmatrix} k_{17,17} \leftarrow 0 \\ F_{17} \leftarrow 0 \\ no \leftarrow 0 \\ \text{for } i \in 0 \ldots \text{rows}(e_{map}) - 1 \\ \text{if } e_{map_{i,0}} = 2 \\ \quad \begin{vmatrix} 0 \\ (x_0 \, x_1 \, no \, i_{map}) \leftarrow \left(x_{e_{map_{i,1}}} \, x_{e_{map_{i,2}}} \, e_{map_{i,3}} \, i\right) \end{vmatrix} \\ \text{if } no > 0 \\ \quad \begin{vmatrix} 0 \\ \text{for } j \in 1 \ldots no \\ \quad \begin{vmatrix} x0 \leftarrow \frac{j-1}{no} \cdot (x_1 - x_0) + x_0 \\ x1 \leftarrow \frac{j}{no} \cdot (x_1 - x_0) + x_0 \\ \text{for } i \in 0 \ldots \text{last}(Gx) \\ \quad \begin{vmatrix} x_o \leftarrow \frac{1}{2} \cdot (Gx_i + 1) \cdot (x1 - x0) + x0 \\ IF'_w \leftarrow F_{Px}(x_o, y_e(x_o), r', D, v) - F_{Py}(x_o, y_e(x_o), r', D, v) \cdot y'_e(x_o) \\ IF'_P \leftarrow -F_w(x_o, y_e(x_o), r', D, v) \\ IF_w \leftarrow Gc_i \cdot IF'_w \cdot IF'^T_P \cdot \left[\frac{1}{2} \cdot (x1 - x0)\right] \\ \text{if } \leftarrow map_{i_{map},0} = 0 \\ \quad \begin{vmatrix} k \leftarrow IF_w + k \\ F \leftarrow F - Gc_i \cdot IF'_w \cdot F_{w\_pz}(x_o, y_e(x_o), r', D, v, p_z) \cdot \left[\frac{1}{2} \cdot (x1 - x0)\right] \end{vmatrix} \end{vmatrix} \end{vmatrix} \end{vmatrix}$$

-continued $$\left|\left|\left|\left|\left|\begin{array}{l}F \leftarrow -Gc_i \cdot IF'_w \cdot \left[\frac{1}{2} \cdot (x1-x0)\right] \cdot wg_{e_{0,i_{map}}} + F \text{ if } map_{i_{map},0} = 1\\ \text{if } map_{i_{map},3} = 0\\ \quad \left|\begin{array}{l}k \leftarrow IF_w^T + k\\ F \leftarrow F + Gc_i \cdot \begin{pmatrix}F_{Px\_pz}(x_o, y_e(x_o), r', D, v, p_z) \ldots + -\\ F_{Py\_pz}(x_o, y_e(x_o), r', D, v, p_z) \cdot y'_e(x_o)\end{pmatrix} \cdot IF'_p \cdot \left[\frac{1}{2} \cdot (x1-x0)\right]\end{array}\right.\\ F \leftarrow Gc_i \cdot IF'_P \cdot \left[\frac{1}{2} \cdot (x1-x0)\right] \cdot Pg_{e_{0,i_{map}}} + F \text{ if } map_{i_{map},3} = 1\end{array}\right.\right.\right.\right.\right.$$

$$augment(F,k)$$

Su. D-3

$$U''_{eg\_M\_\theta} := \left|\begin{array}{l}k_{17,17} \leftarrow 0\\ F_{17} \leftarrow 0\\ no \leftarrow 0\\ \text{for } i \in 0 \ldots \text{rows}(e_{map}) - 1\\ \text{if } e_{map_{i,0}} = 2\\ \quad \left|\begin{array}{l}(x_0 \; x_1 \; no \; i_{map}) \leftarrow \left(x_{e_{map_{i,1}}} \; x_{e_{map_{i,2}}} \; e_{map_{i,3}} \; i\right)\\ 0\end{array}\right.\\ \text{if } no > 0\\ \quad \left|\begin{array}{l}0\\ \text{for } j \in 1 \ldots no\\ \quad \left|\begin{array}{l}x0 \leftarrow \frac{j-1}{no} \cdot (x_1 - x_0) + x_0\\ x1 \leftarrow \frac{j}{no} \cdot (x_1 - x_0) + x_0\\ \text{for } i \in 0 \ldots \text{last}(Gx)\\ \quad \left|\begin{array}{l}x_o \leftarrow \frac{1}{2} \cdot (Gx_i + 1) \cdot (x1 - x0) + x0\\ IF'_\theta \leftarrow F_{Mx}(x_o, y_e(x_o), r', D, v) \ldots + -\\ \qquad 2 \cdot F_{Txy}(x_o, y_e(x_o), r', D, v) \cdot y'_e(x_o) \ldots +\\ \qquad F_{My}(x_o, y_e(x_o), r', D, v) \cdot y'_e(x_o)^2\\ IF'_M \leftarrow \frac{F_{\theta x}(x_o, y_e(x_o), r', D, v) - F_{\theta y}(x_o, y_e(x_o), r', D, v) \cdot y'_e(x_o)}{1 + y'_e(x_o)^2}\\ IF_\theta \leftarrow Gc_i \cdot IF'_\theta \cdot IF'^T_M \cdot \left[\frac{1}{2} \cdot (x1-x0)\right]\\ \text{if } \leftarrow map_{i_{map},1} = 0\\ \quad \left|\begin{array}{l}k \leftarrow IF_\theta + k\\ F \leftarrow F + Gc_i \cdot IF'_\theta \cdot \frac{F_{\theta x\_pz}(x_o, y_e(x_o), r', D, v, p_z) \ldots + -}{1 + \cdot y'_e(x_o)^2} \left[\frac{1}{2} \cdot (x1-x0)\right]\\ F \leftarrow -Gc_i \cdot \frac{IF'_\theta}{1 + y'_e(x_o)^2} \cdot \left[\frac{1}{2} \cdot (x1-x0)\right] \cdot \theta g_{e_{0,i_{map}}} + F \text{ if } map_{i_{map},1} = 1\\ \text{if } map_{i_{map},4} = 0\\ \quad \left|\begin{array}{l}k \leftarrow IF_\theta^T + k\\ F \leftarrow F + Gc_i \cdot \begin{pmatrix}F_{Mx\_pz}(x_o, y_e(x_o), r', D, v, p_z) \ldots + -\\ 2 \cdot F_{Txy\_pz}(x_o, y_e(x_o), r', D, v, p_z) \cdot y'_e(x_o) \ldots +\\ F_{My\_pz}(x_o, y_e(x_o), r', D, v, p_z) \cdot y'_e(x_o)^2\end{pmatrix} \cdot IF'_M \cdot \left[\frac{1}{2}(x1-x0)\right]\end{array}\right.\\ F \leftarrow -Gc_i \cdot IF'_M \cdot \left[\frac{1}{2} \cdot (x1-x0)\right] \cdot Mg_{e_{0,i_{map}}} + F \text{ if } map_{i_{map},4} = 1\end{array}\right.\end{array}\right.\end{array}\right.\end{array}\right.$$

$$augment(F,k)$$

Su. D-4

$$U''_{eg\_T\_\phi} := \left|\begin{array}{l}k_{17,17} \leftarrow 0\\ F_{17} \leftarrow 0\\ no \leftarrow 0\\ \text{for } i \in 0 \ldots \text{rows}(e_{map}) - 1\\ \text{if } e_{map_{i,0}} = 2\\ \quad \left|\begin{array}{l}(x_0 \; x_1 \; no \; i_{map}) \leftarrow \left(x_{e_{map_{i,1}}} \; x_{e_{map_{i,2}}} \; e_{map_{i,3}} \; i\right)\\ 0\end{array}\right.\\ \text{if } no > 0\end{array}\right.$$

$$\begin{vmatrix} 0 \\ \text{for } j \in 1 \ldots no \\ \quad \begin{vmatrix} x0 \leftarrow \dfrac{j-1}{no} \cdot (x_1 - x_0) + x_0 \\ x1 \leftarrow \dfrac{j}{no} \cdot (x_1 - x_0) + x_0 \\ \text{for } i \in 0 \ldots \text{last}(Gx) \\ \quad \begin{vmatrix} x_o \leftarrow \dfrac{1}{2} \cdot (Gx_i + 1) \cdot (x1 - x0) + x0 \\ IF'_\phi \leftarrow F_{Txy}(x_o, y_e(x_o), r', D, v) \cdot (1 - y'_e(x_o)^2) \ldots + \\ \qquad F_{Mx}(x_o, y_e(x_o), r', D, v) \cdot y'_e(x_o) \ldots + - \\ \qquad F_{My}(x_o, y_e(x_o), r', D, v) \cdot y'_e(x_o) \\ IF'_T \leftarrow \dfrac{F_{\phi x}(x_o, y_e(x_o), r', D, v) - F_{\phi y}(x_o, y_e(x_o), r', D, v) \cdot y'_e(x_o)}{1 + y'_e(x_o)^2} \\ IF_\phi \leftarrow Gc_i \cdot IF'_\phi \cdot IF'^T_T \cdot \left[\dfrac{1}{2}(x1-x0)\right] \\ \text{if} \leftarrow map_{i_{map},2} = 0 \\ \quad \begin{vmatrix} k \leftarrow IF_\phi + k \\ F \leftarrow F + Gc_i \cdot IF'_\phi \cdot \dfrac{F_{\phi x\_pz}(x_o, y_e(x_o), r', D, v, p_z) \ldots +}{1 + \cdot y'_e(x_o)^2} \left[\dfrac{1}{2} \cdot (x1-x0)\right] \\ F \leftarrow Gc_i \cdot \dfrac{IF'_\phi}{1 + y'_e(x_o)^2} \cdot \left[\dfrac{1}{2} \cdot (x1-x0)\right] \cdot \phi g_{e_{0,i_{map}}} + F \text{ if } map_{i_{map},2} = 1 \\ \text{if } map_{i_{map},5} = 0 \\ \quad \begin{vmatrix} k \leftarrow IF_\phi^T + k \\ F \leftarrow F + Gc_i \cdot \begin{bmatrix} F_{Txy\_pz}(x_o, y_e(x_o), r', D, v, p_z) \cdot (1 - y'_e(x_o)^2) \ldots + \\ F_{Mx\_pz}(x_o, y_e(x_o), r', D, v, p_z) \cdot y'_e(x_o) \ldots + - \\ F_{My\_pz}(x_o, y_e(x_o), r', D, v, p_z) \cdot y'_e(x_o) \end{bmatrix} \cdot IF'_T \cdot \left[\dfrac{1}{2} \cdot (x1-x0)\right] \\ F \leftarrow -Gc_i \cdot IF'_T \cdot \left[\dfrac{1}{2} \cdot (x1-x0)\right] \cdot Tg_{e_{0,i_{map}}} + F \text{ if } map_{i_{map},5} = 1 \end{vmatrix} \end{vmatrix} \end{vmatrix} \end{vmatrix} \\ \text{augment}(F, k) \end{vmatrix}$$

Rigid Body Motions

In this example, the rigid body motions will be addressed by including springs between the external displacement and the element displacement as in Section C. Eqs. D-27 to D-29 define the energy associated with the springs and these equations are similar to Eq. C-27. Eqs. D-27 to D-29 use functions defined with Eq. D-25.

$$Ug_{spr\_w_i} = \frac{\partial}{\partial a_i}\left[\frac{1}{2} \cdot k_w \cdot \int (w_s(a) - w_s)^2 ds\right] \quad \text{Eq. D-27(a)}$$

$$Ug_{spr\_w_i} = k_w \cdot \left(\int w_s(a) \cdot \frac{\partial}{\partial a_i} w_s(a) ds - \int w_s \cdot \frac{\partial}{\partial a_i} w_s(a) ds\right)$$

Introducing Eq. D-3;

$$Ug_{spr\_w_i} = k_w \cdot \left[\int_{x_0}^{x_1} w_s(a) \cdot \frac{\partial}{\partial a_i} w_s(a) \cdot \sqrt{1 + \left(\frac{dy}{dx}\right)^2}\, dx - \int_{x_0}^{x_1} w_s \cdot \frac{\partial}{\partial a_i} w_s(a) \cdot \sqrt{1 + \left(\frac{dy}{dx}\right)^2}\, dx\right]$$

For:

$$\int_{x_0}^{x_1} w_s(a) \cdot \frac{\partial}{\partial a_i} w_s(a) \cdot \sqrt{1 + \left(\frac{dy}{dx}\right)^2}\, dx = Cg_{wr\_a} \cdot a + Cg_{wr\_p}$$

Where:

$$Cg_{wr\_a}(x, y_e, y'_e, r', D, v) := \quad \text{Eq. D-27(b)}$$
$$F_w(x, y_e, r', D, v) \cdot F_w(x, y_e, r', D, v)^T \cdot \sqrt{1 + y'^2_e}$$

$$Cg_{wr\_p}(x, y_e, y'_e, r', D, v, p_z) := \quad \text{Eq. D-27(c)}$$
$$F_{w\_pz}(x, y_e, r', D, v, p_z) \cdot F_w(x, y_e, r', D, v)^T \cdot \sqrt{1 + y'^2_e}$$

For:

$$-\int_{x_0}^{x_1} w_s \cdot \frac{\partial}{\partial a_i} w_s(a) \cdot \sqrt{1 + \left(\frac{dy}{dx}\right)^2}\, dx = Cg_{wr\_w} \cdot w_s$$

Where:

$$Cg_{wr\_w}(x, y_e, y'_e, r', D, v) := \quad \text{Eq. D-27(d)}$$
$$-F_w(x, y_e, r', D, v)^T \cdot \sqrt{1 + y'^2_e}$$

$$Ug_{spr\_\theta_i} = \frac{\partial}{\partial a_i}\left[\frac{1}{2} \cdot k_\theta \cdot \int (\theta_s(a) - \theta_s)^2 ds\right] \quad \text{Eq. D-28(a)}$$

$$Ug_{spr\_\theta_i} = k_\theta \cdot \left(\int \theta_s(a) \cdot \frac{\partial}{\partial a_i} \theta_s(a) ds - \int \theta_s \cdot \frac{\partial}{\partial a_i} \theta_s(a) ds\right)$$

Introducing Eqs. D-3 and D-9:

$$Ug_{spr\_\theta_i} =$$

$$k_\theta \cdot \left[ \int_{x_0}^{x_1} \frac{\theta_{wx}(a) - \theta_{wy}(a) \cdot \frac{dy}{dx}}{\sqrt{1+\left(\frac{dy}{dx}\right)^2}} \cdot \frac{\partial}{\partial a_i} \frac{\theta_{wx}(a) - \theta_{wy}(a) \cdot \frac{dy}{dx}}{\sqrt{1+\left(\frac{dy}{dx}\right)^2}} \cdot \sqrt{1-\left(\frac{dy}{dx}\right)^2} \, dx \ldots + - \int_{x_0}^{x_1} \frac{\theta_{wx} - \theta_{wy} \cdot \frac{dy}{dx}}{\sqrt{1+\left(\frac{dy}{dx}\right)^2}} \cdot \frac{\partial}{\partial a_i} \frac{\theta_{wx}(a) - \theta_{wy}(a) \cdot \frac{dy}{dx}}{\sqrt{1+\left(\frac{dy}{dx}\right)^2}} \cdot \sqrt{1-\left(\frac{dy}{dx}\right)^2} \, dx \right]$$

For:

$$\int_{x_0}^{x_1} \frac{\theta_{wx}(a) - \theta_{wy}(a) \cdot \frac{dy}{dx}}{\sqrt{1+\left(\frac{dy}{dx}\right)^2}} \cdot \frac{\partial}{\partial a_i} \frac{\theta_{wx}(a) - \theta_{wy}(a) \cdot \frac{dy}{dx}}{\sqrt{1+\left(\frac{dy}{dx}\right)^2}} \cdot \sqrt{1-\left(\frac{dy}{dx}\right)^2} \, dx = Cg_{\theta r\_a} \cdot a + Cg_{\theta r\_p}$$

Where:

$$Cg_{\theta r\_a}(x, y_e, y'_e, r', D, v) := \frac{\begin{pmatrix} F_{\theta x}(x, y_e, r', D, v) \ldots + \\ -F_{\theta y}(x, y_e, r', D, v) \cdot y'_e \end{pmatrix} \begin{pmatrix} F_{\theta x}(x, y_e, r', D, v) \ldots + \\ -F_{\theta y}(x, y_e, r', D, v) \cdot y'_e \end{pmatrix}^T}{\sqrt{1+y'^2_e}}$$

Eq. D-28(b)

$$Cg_{\theta r\_p}(x, y_e, y'_e, r', D, v, p_z) :=$$ Eq. D-28(c)

$$\frac{\begin{pmatrix} F_{\theta x\_pz}(x, y_e, r', D, v, p_z) \ldots + \\ -F_{\theta y\_pz}(x, y_e, r', D, v, p_z) \cdot y'_e \end{pmatrix} \begin{pmatrix} F_{\theta x}(x, y_e, r', D, v) \ldots + \\ -F_{\theta y}(x, y_e, r', D, v) \cdot y'_e \end{pmatrix}}{\sqrt{1+y'^2_e}}$$

For:

$$-\int_{x_0}^{x_1} \frac{\theta_{wx} - \theta_{wy} \cdot \frac{dy}{dx}}{\sqrt{1+\left(\frac{dy}{dx}\right)^2}} \cdot \frac{\partial}{\partial a_i} \frac{\theta_{wx}(a) - \theta_{wy}(a) \cdot \frac{dy}{dx}}{\sqrt{1+\left(\frac{dy}{dx}\right)^2}} \cdot \sqrt{1-\left(\frac{dy}{dx}\right)^2} \, dx = Cg_{\theta r\_\theta} \cdot \frac{\theta_{wx} - \theta_{wy} \cdot \frac{dy}{dx}}{\sqrt{1+\left(\frac{dy}{dx}\right)^2}}$$

Where:

$$Cg_{\theta r\_\theta}(x, y_e, y'_e, r', D, v) := -(F_{\theta x}(x, y_e, r', D, v) - F_{\theta y}(x, y_e, r', D, v) \cdot y'_e)^T$$

Eq. D-28(d)

-continued $$Ug_{spr\_\phi_i} = \frac{\partial}{\partial a_i}\left[\frac{1}{2} \cdot k_\phi \cdot \int (\phi_s(a) - \phi_s)^2 ds\right]$$ Eq. D-29(a)

$$Ug_{spr\_\phi_i} = k_\phi \cdot \left( \int \phi_s(a) \cdot \frac{\partial}{\partial a_i} \phi_s(a) ds - \int \phi_s \cdot \frac{\partial}{\partial a_i} \phi_s(a) ds \right)$$

Introducing Eqs. D-3 and D-10:

$$Ug_{spr\_\phi_i} =$$

$$k_\phi \cdot \left[ \int_{x_0}^{x_1} \frac{\phi_{wx}(a) + \phi_{wy}(a) \cdot \frac{dy}{dx}}{\sqrt{1+\left(\frac{dy}{dx}\right)^2}} \cdot \frac{\partial}{\partial a_i} \frac{\phi_{wx}(a) + \phi_{wy}(a) \cdot \frac{dy}{dx}}{\sqrt{1+\left(\frac{dy}{dx}\right)^2}} \cdot \sqrt{1+\left(\frac{dy}{dx}\right)^2} \, dx \ldots + - \int_{x_0}^{x_1} \frac{\phi_{wx} + \phi_{wy} \cdot \frac{dy}{dx}}{\sqrt{1+\left(\frac{dy}{dx}\right)^2}} \cdot \frac{\partial}{\partial a_i} \frac{\phi_{wx}(a) + \phi_{wy}(a) \cdot \frac{dy}{dx}}{\sqrt{1+\left(\frac{dy}{dx}\right)^2}} \cdot \sqrt{1+\left(\frac{dy}{dx}\right)^2} \, dx \right]$$

For:

$$\int_{x_0}^{x_1} \frac{\phi_{wx}(a) + \phi_{wy}(a) \cdot \frac{dy}{dx}}{\sqrt{1+\left(\frac{dy}{dx}\right)^2}} \cdot \frac{\partial}{\partial a_i} \frac{\phi_{wx}(a) + \phi_{wy}(a) \cdot \frac{dy}{dx}}{\sqrt{1+\left(\frac{dy}{dx}\right)^2}} \cdot \sqrt{1+\left(\frac{dy}{dx}\right)^2} \, dx =$$

$$Cg_{\phi r\_a} \cdot a + Cg_{\phi r\_p}$$

Where:

$$Cg_{\phi r\_a}(x, y_e, y'_e, r', D, v) := \frac{\left(\begin{pmatrix} F_{\phi x}(x, y_e, r', D, v) \ldots + \\ -F_{\phi y}(x, y_e, r', D, v) \cdot y'_e \end{pmatrix}\right)\left(\begin{pmatrix} F_{\phi x}(x, y_e, r', D, v) \ldots + \\ -F_{\phi y}(x, y_e, r', D, v) \cdot y'_e \end{pmatrix}\right)^T}{\sqrt{1+y'^2_e}}$$

Eq. D-29(b)

$$Cg_{\phi r\_p}(x, y_e, y'_e, r', D, v, p_z) :=$$ Eq. D-29(c)

$$\frac{\begin{pmatrix} F_{\phi x\_pz}(x, y_e, r', D, v, p_z) \ldots + \\ -F_{\phi y\_pz}(x, y_e, r', D, v, p_z) \cdot y'_e \end{pmatrix} \begin{pmatrix} F_{\phi x}(x, y_e, r', D, v) \ldots + \\ -F_{\phi y}(x, y_e, r', D, v) \cdot y'_e \end{pmatrix}}{\sqrt{1+y'^2_e}}$$

187
-continued

For:

$$-\int_{x_0}^{x_1} \frac{\phi_{wx} + \phi_{wy} \cdot \frac{dy}{dx}}{\sqrt{1 + \left(\frac{dy}{dx}\right)^2}} \cdot \frac{\partial}{\partial a_i}$$

$$\frac{\phi_{wx}(a) + \phi_{wy}(a) \cdot \frac{dy}{dx}}{\sqrt{1 + \left(\frac{dy}{dx}\right)^2}} \cdot \sqrt{1 + \left(\frac{dy}{dx}\right)^2} \, dx =$$

$$Cg_{\phi r\_\phi} \cdot \frac{\phi_{wx} + \phi_{wy} \cdot \frac{dy}{dx}}{\sqrt{1 + \left(\frac{dy}{dx}\right)^2}}$$

188

Where:

$$Cg_{\phi r\_\phi}(x, y_e, y'_e, r', D, v) := -(F_{\phi x}(x, y_e, r', D, v) + F_{\phi y}(x, y_e, r', D, v))^T \quad \text{Eq. D-29(d)}$$

Su. D-5 uses these functions in Eqs. D-27 to D-29 to assemble arrays for the general curved edges. The results of these arrays can be summed into the $U_b$ vector (in Eq. A-51) and the $U_m$ array (in Eq. A-51). Su. D-5 produces an array for general curved edge which includes the edge integration data for the general curved edge portion of the example problem. (Though Eqs. D-27 to D-29 are written in more general terms, Su. D-5 is only written to accept a simple constant external displacement. This is consistent with Sus. D-2 to D-4.) The linear edge portion of the problem is evaluated with Su. C-14. These subroutines calculate the algebraic form of the spring energy integrals for each row of the edge mapping array (where external displacements are known). The boundary conditions mapping array is used to establish if a given edge has a defined external displacement.

Su. D-5

$$U'_{sprg} := \begin{vmatrix} k_{17,17} \leftarrow 0 \\ F_{17} \leftarrow 0 \\ \text{for } i \in 0 \ldots \text{rows}(e_{map}) - 1 \\ \text{if } e_{map_{i,0}} = 2 \\ \begin{vmatrix} (x_0 \ x_1 \ no) \leftarrow \left(x_{a_{map_{i,1}}} x_{a_{map_{i,2}}} e_{map_{i,3}}\right) \\ \text{for } q \in 1 \ldots no \\ \begin{vmatrix} (x0 \ x1) \leftarrow \left[\frac{q-1}{no} \cdot (x_1 - x_0) + x_0 \frac{q}{no} \cdot (x_1 - x_0) + x_0\right] \\ \text{for } p \in 0 \ldots \text{last}(Gx) \end{vmatrix} \end{vmatrix} \\ \begin{vmatrix} x_o \leftarrow \frac{1}{2} \cdot (Gx_p + 1) \cdot (x1 - x0) + x0 \\ k \leftarrow k + Gc_p \cdot Cg_{wr\_a}(x_o, y_e(x_o), y'_e(x_o), r', D, v) \cdot \left[\frac{1}{2} \cdot (x1 - x0)\right] \\ F \leftarrow F + \begin{pmatrix} Gc_p \cdot Cg_{wr\_p}(x_o, y_e(x_o), y'_e(x_o), r', D, v, p_z) \ldots + \\ Gc_p \cdot Cg_{wr\_w}(x_o, y_e(x_o), y'_e(x_o), r', D, v)^T \cdot wg_{e_{0,i}} \end{pmatrix} \cdot \left[\frac{1}{2} \cdot (x1 - x0)\right] \\ \text{for } p \in 0 \ldots \text{last}(Gx) \end{vmatrix} \\ \begin{vmatrix} x_o \leftarrow \frac{1}{2} \cdot (Gx_p + 1) \cdot (x1 - x0) + x0 \\ k \leftarrow k + Gc_p \cdot Cg_{\theta r\_a}(x_o, y_e(x_o), y'_e(x_o), r', D, v) \cdot \left[\frac{1}{2} \cdot (x1 - x0)\right] \\ F \leftarrow F + \left[Gc_p \cdot Cg_{\theta r\_p}(x_o, y_e(x_o), y'_e(x_o), r', D, v, p_z) \ldots + Gc_p \cdot Cg_{\theta r\_\theta}(x_o, y_e(x_o), y'_e(x_o), r', D, v)^T \cdot \left(\frac{\theta g_{e_{0,i}}}{\sqrt{1 + y'_e(x_o)^2}}\right)\right] \cdot \left[\frac{1}{2} \cdot (x1 - x0)\right] \\ \text{for } p \in 0 \ldots \text{last}(Gx) \end{vmatrix} \\ \begin{vmatrix} x_o \leftarrow \frac{1}{2} \cdot (Gx_p + 1) \cdot (x1 - x0) + x0 \\ k \leftarrow k + Gc_p \cdot Cg_{\phi r\_a}(x_o, y_e(x_o), y'_e(x_o), r', D, v) \cdot \left[\frac{1}{2} \cdot (x1 - x0)\right] \\ F \leftarrow F + \left[Gc_p \cdot Cg_{\phi r\_p}(x_o, y_e(x_o), y'_e(x_o), r', D, v, p_z) \ldots + Gc_p \cdot Cg_{\phi r\_\phi}(x_o, y_e(x_o), y'_e(x_o), r', D, v)^T \cdot \left(\frac{\phi g_{e_{0,i}}}{\sqrt{1 + y'_e(x_o)^2}}\right)\right] \cdot \left[\frac{1}{2} \cdot (x1 - x0)\right] \end{vmatrix} \\ \leftarrow \text{augment}(F, k) \end{vmatrix}$$

if $map_{i,0} = 1$ if $map_{i,1} = 1$ if $map_{i,2} = 1$

-continued

Su. D-5

$$U'_{sprg} := \begin{vmatrix} k_{17,17} \leftarrow 0 \\ F_{17} \leftarrow 0 \\ \text{for } i \in 0 \ldots \text{rows}(e_{map}) - 1 \\ \text{if } e_{map_{i,0}} = 2 \\ \quad \begin{vmatrix} (x_0 \; x_1 \; no) \leftarrow \left( x_{a_{map_{i,1}}}, x_{a_{map_{i,2}}}, e_{map_{i,3}} \right) \\ \text{for } q \in 1 \ldots no \\ \quad \begin{vmatrix} (x0 \; x1) \leftarrow \left[ \dfrac{q-1}{no} \cdot (x_1 - x_0) + x_0 \quad \dfrac{q}{no} \cdot (x_1 - x_0) + x_0 \right] \end{vmatrix} \\ \text{for } p \in 0 \ldots \text{last}(Gx) \end{vmatrix} \\ \quad \quad \begin{vmatrix} x_o \leftarrow \dfrac{1}{2} \cdot (Gx_p + 1) \cdot (x1 - x0) + x0 \\ k \leftarrow k + Gc_p \cdot Cg_{wr\_a}(x_o, y_e(x_o), y'_e(x_o), r', D, v) \cdot \left[ \dfrac{1}{2} \cdot (x1 - x0) \right] \\ F \leftarrow F + \left( \begin{array}{l} Gc_p \cdot Cg_{wr\_p}(x_o, y_e(x_o), y'_e(x_o), r', D, v, p_z) \ldots + \\ Gc_p \cdot Cg_{wr\_w}(x_o, y_e(x_o), y'_e(x_o), r', D, v)^T \cdot wg_{e_{0,i}} \end{array} \right) \cdot \left[ \dfrac{1}{2} \cdot (x1 - x0) \right] \end{vmatrix} \\ \text{for } p \in 0 \ldots \text{last}(Gx) \\ \quad \quad \begin{vmatrix} x_o \leftarrow \dfrac{1}{2} \cdot (Gx_p + 1) \cdot (x1 - x0) + x0 \\ k \leftarrow k + Gc_p \cdot Cg_{\theta r\_a}(x_o, y_e(x_o), y'_e(x_o), r', D, v) \cdot \left[ \dfrac{1}{2} \cdot (x1 - x0) \right] \\ F \leftarrow F + \left[ \begin{array}{l} Gc_p \cdot Cg_{\theta r\_p}(x_o, y_e(x_o), y'_e(x_o), r', D, v, p_z) \ldots + \\ Gc_p \cdot Cg_{\theta r\_\theta}(x_o, y_e(x_o), y'_e(x_o), r', D, v)^T \cdot \left( \dfrac{\theta g_{e_{0,i}}}{\sqrt{1 + y'_e(x_o)^2}} \right) \end{array} \right] \cdot \left[ \dfrac{1}{2} \cdot (x1 - x0) \right] \end{vmatrix} \\ \text{for } p \in 0 \ldots \text{last}(Gx) \\ \quad \quad \begin{vmatrix} x_o \leftarrow \dfrac{1}{2} \cdot (Gx_p + 1) \cdot (x1 - x0) + x0 \\ k \leftarrow k + Gc_p \cdot Cg_{\phi r\_a}(x_o, y_e(x_o), y'_e(x_o), r', D, v) \cdot \left[ \dfrac{1}{2} \cdot (x1 - x0) \right] \\ F \leftarrow F + \left[ \begin{array}{l} Gc_p \cdot Cg_{\phi r\_p}(x_o, y_e(x_o), y'_e(x_o), r', D, v, p_z) \ldots + \\ Gc_p \cdot Cg_{\phi r\_\phi}(x_o, y_e(x_o), y'_e(x_o), r', D, v)^T \cdot \left( \dfrac{\phi g_{e_{0,i}}}{\sqrt{1 + y'_e(x_o)^2}} \right) \end{array} \right] \cdot \left[ \dfrac{1}{2} \cdot (x1 - x0) \right] \end{vmatrix} \\ -\text{augment}(F, k) \end{vmatrix}$$

if $map_{i,0} = 1$ if $map_{i,1} = 1$ if $map_{i,2} = 1$

The stiffness "k" is included as a multiplier on the arrays resulting from Sus. D-5 and C-14. For this example, the stiffness will be defined as unity.

k:=1 Spring stiffness for the edge springs added to remove rigid body motions

Degrees of Freedom and Results Plots

Having the array that is the portion of the $U_b$ vector (in Eq. A-51) related to the rigid body edge integrals augmented to the portion of the $U_m$ array (in Eq. A-51) related to the rigid body edge integrals, the $U_m$ array and $U_b$ vector can be defined.

Array constant for Eq. A-51

$U_m := \text{submatrix}(U'_{o\_el}, 0, \text{rows}(U'_{o\_el}) - 1, 1, \text{cols}(U'_{o\_el}) - 1) \ldots +$ $\text{submatrix}(U'_{el}, 0, \text{rows}(U'_{el}) - 1, 1, \text{cols}(U'_{el}) - 1) \ldots +$ -continued $\text{submatrix}(U'_{o\_eg}, 0, \text{rows}(U'_{o\_eg}) - 1, 1, \text{cols}(U'_{o\_eg}) - 1) \ldots +$ $\text{submatrix}(U'_{eg}, 0, \text{rows}(U'_{eg}) - 1, 1, \text{cols}(U'_{eg}) - 1) \ldots +$ $k \cdot \left( \begin{array}{l} \text{submatrix}(U'_{sprl}, 0, \text{rows}(U'_{sprl}) - 1, 1, \text{cols}(U'_{sprl}) - 1) \ldots + \\ \text{submatrix}(U'_{sprg}, 0, \text{rows}(U'_{sprg}) - 1, 1, \text{cols}(U'_{sprg}) - 1) \end{array} \right)$ Vector constant for Eq. A-51

$U_b := U'^{(0)}_{o\_el} + U'^{(0)}_{el} + U'^{(0)}_{o\_eg} + U'^{(0)}_{eg} + k \cdot (U'^{(0)}_{sprl} + U'^{(0)}_{sprg})$ Because the example model only has one element, $U_M = U_m$ and $U_B = U_b$ as shown below:

$U_M := U_m$ Array constant summed for all of the elements in the model for Eq. A-52

$U_B := U_b$ Vector constant summed for all of the elements in the model for Eq. A-52

$U_B{}^T = (-0.03 \ -0.02 \ -0.01 \ -5.01 \ -7.31 \ -7.31 \ -1.66 \ -2.14 \ -1.36 \ -2.21 \ -0.23 \ -0.51 \ 0.98 \ 0.82 \ 0.05 \ -0.05 \ 0.19 \ 0.37)$ $U_M =$

| 40.2 | 2.9 | 7.1 | 0.5 | 0.3 | 1.3 | 758.9 | 314.4 | 943 | 2276.7 | 314.4 | 314.4 | -628.8 | 628.8 | -28.9 | 69.9 | -349.4 | 1 |
|---|---|---|---|---|---|---|---|---|---|---|---|---|---|---|---|---|---|
| 2.9 | 3.1 | -0.1 | 03 | 265.8 | -265.6 | 70.8 | -70.7 | -102.1 | 102.2 | 5.1 | -5.1 | -47.8 | 47.7 | -1.6 | 1.6 | -15 | |
| 7.1 | -0.1 | 2.9 | -375.4 | 265.5 | -264.9 | 70.7 | -39.3 | 212.2 | 102.3 | 46 | 21.6 | -47.8 | 47.8 | -1.6 | 4.8 | -45 | |
| 0.5 | 03 | 375.8 | 57.7 | 36.7 | 36.7 | 13.8 | 5.3 | -4.3 | 18.7 | 1.6 | 1.7 | -8.1 | 2.5 | -0.2 | 0.4 | -2.4 | |
| 0.3 | -265.3 | -265.6 | -36.7 | 164.7 | -24 | 22.4 | -10.9 | 14.6 | 16.6 | 3.3 | -0.8 | -7.3 | 1.7 | -0 | -0.2 | -2.9 | |
| 1.3 | 265.6 | 266.2 | -36.6 | 122.7 | 164.8 | 19.1 | -0.6 | 48.9 | 67.3 | 8.6 | 4.5 | -8.3 | 13.9 | -0.2 | 0.7 | -7.4 | |
| -758.8 | -70.7 | -70.7 | -2.6 | 16.2 | -7.5 | 3.4 | -0.3 | 2 | 1.2 | 0.5 | 0.1 | -1.4 | -0.5 | -0 | -0 | -0.5 | . |
| -314.2 | 70.8 | 39.3 | 21.7 | 15.7 | 16.6 | 3.7 | 4.2 | 1.6 | 6.1 | 0.5 | 1 | -1.9 | 0 | -0.1 | 0.1 | -0.5 | . |
| -942.9 | 102.2 | 212.2 | 4.3 | 33.4 | -34.5 | 3.9 | -0.6 | 5.1 | -3.4 | 0.8 | -0 | -0.7 | -1.1 | 0.1 | -0.1 | -0.5 | . |
| -2276.3 | -102.2 | -102 | -18.7 | 18.1 | 48.5 | 3.4 | -0.1 | 8.8 | 23.1 | 1.5 | 1.1 | -1.7 | 5.2 | -0.1 | 0.2 | -1.3 | |
| -314.4 | -5.1 | -46 | -0.4 | 2.6 | -6.8 | 0.5 | -0.1 | 0.6 | -0.8 | 0.1 | 0 | -0.1 | -0.2 | 0 | -0 | -0.1 | |
| -314.4 | 5.1 | -21.5 | 3.7 | 2.6 | 1.6 | 0.7 | 1 | 0.4 | 1.4 | 0.1 | 0.3 | -0.4 | 0 | -0 | 0 | -0.1 | |
| 628.8 | 47.8 | 47.8 | -0.3 | -2.3 | 2.3 | -1.3 | -0.7 | -0.3 | -0.8 | -0.2 | -0.2 | 0.9 | 0.4 | 0 | -0 | 0.2 | |
| -628.8 | -47.8 | -47.7 | -10.9 | -8.9 | 8.9 | -1.7 | -1.2 | -0.1 | 4.8 | -0.1 | -0 | 0.6 | 2.1 | -0 | 0 | 0.1 | |
| 28.9 | 1.6 | 1.6 | -0.2 | 0 | -0.2 | -0 | -0.1 | 0 | -0.1 | -0 | -0 | 0.1 | 0 | 0 | -0 | 0 | |
| -69.9 | -1.6 | -4.8 | 0.3 | -0.2 | 0.6 | 0 | 0.2 | -0 | 0.3 | 0 | 0.1 | -0 | 0.1 | -0 | 0 | -0 | |
| 349.4 | 15 | 45 | 0.9 | -0.3 | 6 | -0.2 | -0 | -0.2 | 0.7 | -0.1 | -0 | 0.1 | 0.2 | 0 | 0 | 0.1 | |
| -144.7 | -15 | -15 | -3.6 | -3.1 | 0.8 | -0.6 | -0.6 | -0.3 | 0.8 | -0.1 | -0.1 | 0.3 | 0.6 | 0 | 0 | 0.1 | |

Solving Eq. A-52 produces the degrees of freedom vector for this example problem.

$$a := U_M^{-1} \cdot (-U_B)$$

$$a = \begin{pmatrix} -0.00065 \\ 0 \\ -0 \\ -0 \\ 0.03412 \\ 0.03413 \\ 0 \\ 0 \\ -0 \\ -0 \\ 0 \\ -0 \\ -0.44728 \\ -0.44728 \\ -0 \\ -0 \\ 0 \\ -0 \end{pmatrix} \quad \text{Degrees of Freedom}$$

Figure 34:
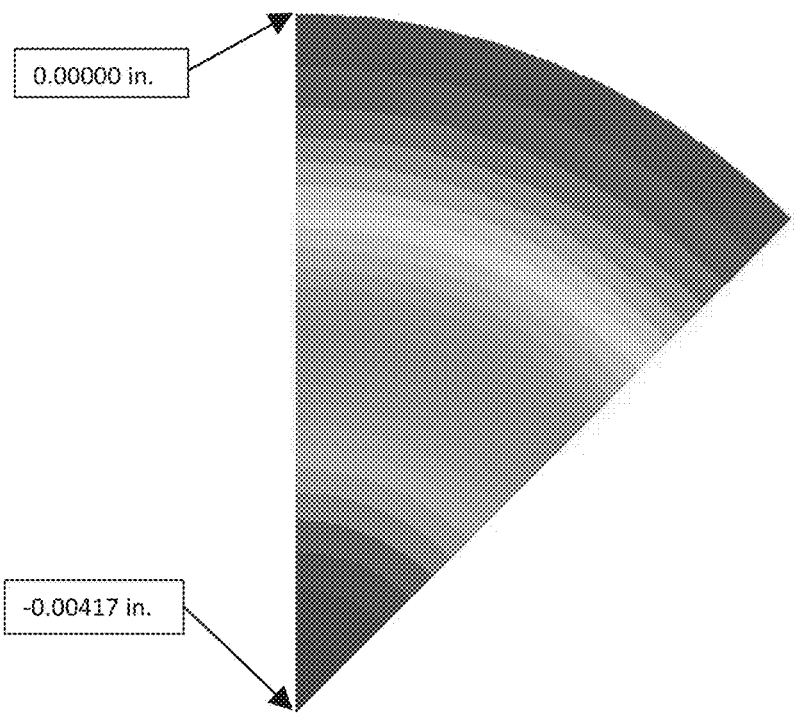
FIG. 34 is a displacement plot for the element of FIG. 33 evaluated according to the principles of the present disclosure.

The degree of freedom vector makes it possible to find optimized solution results for displacements, loads, stresses, strains or any other value addressed by the governing equation. The simplest to evaluate is displacement as it can be evaluated using the base equation (Eq. B-7) with no other derivation. FIG. 34 shows a gradient plot of the resulting displacement. The contours range from the most positive values of the displacement (0.0000 in.) at an outer edge of the wedge to the most negative values of the displacement (−0.00417 in.) at the tip of the wedge This matches the theoretical exact solution for this problem.

Figure 35:
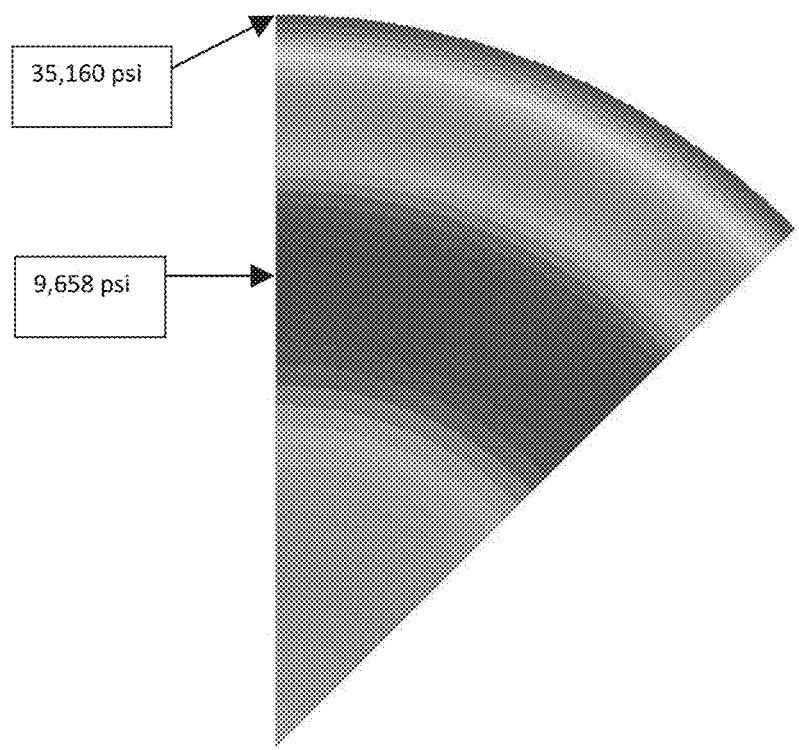
FIG. 35 is a Von Mises stress plot for the element of FIG. 33 evaluated according to the principles of the present disclosure.

A common stress result that is plotted in finite element analysis is von Mises stress. FIG. 35 shows a gradient plot of the resulting von Mises stress (using Eq. B-48). The contours range from the highest value of the von Mises stress (35,160 psi) at the outer edge of the wedge to the lowest value of the von Mises stress (9,658 psi) in a band at the center of the wedge. As noted in the displacement discussion, the plotted results match the exact theoretical solution for this problem.

Discussion

This example showed the formulation for a simple single element problem with two straight edges and a general curved edge. The example problem element only had three edges (including two straight edges and one circular edge), but this same formulation could be used on an element with any number of edges. Also, the general curved edge is not limited to being circular in shape.

The biggest positive shown in this example was that the new method produced results as accurate as the circular edge (which also is essentially an exact solution) using a general curve formulation and numerical integration. The numerical integration was performed using a 5-point Gaussian quadrature rule over six segments of the general curve.

Section E

Outline

In this Section, an example is described of the new method being used to accurately model complex geometry. The selected example problem highlights how the new method can outperform traditional finite element analysis.

The evaluation is described in several portions. The first portion (Model Description) describes the example problem and its boundary conditions. The second portion (Material Properties) shows the material properties used in the example model. The third portion (Element Definition) shows how the evaluated element can be defined in the new method using the derivations provided in Sections B and C. The fourth portion (Results and Comparison with Traditional Finite Element Analysis) compares the new method displacement and stress results with four traditional finite element models. The evaluation results are discussed in an eighth portion (Discussion).

The test model (shown in FIGS. 1-3) is a thin plate with boundary conditions including a fixed edge, a distributed pressure over the entire surface of the plate, and edge loads on all of the unrestrained edges. The shape of the plate includes straight edges and circular edges. The example model is evaluated with one set of results for the new method and four sets of results for the traditional finite element method.

A summary of the stress and displacement results is given in Table E-1 (with percent error calculated with respect to the finest mesh).

|  | New model[2] | Linear quadrilateral 164 element[3] | Parabolic triangular 168 element[3] | Linear quadrilateral 2,988 element[3] | Parabolic triangular 1,696 element[3] |
|---|---|---|---|---|---|
| Maximum von Mises stress [ksi[4]] | 41.83 (−4.1%) | 29.51 (−32.3%) | 26.84 (−38.5%) | 39.45 (−9.5%) | 43.61 |
| Maximum displacement [in] | 0.004765 (+3.7%) | 0.003955 (−13.9%) | 0.003740 (−18.6%) | 0.00457 (−0.5%) | 0.004593 |
| Degrees of freedom | 144 | 612 | 1,224 | 9,792 | 11,112 |

[1]A theoretical value is not readily available for this example. Consequently, the finest meshed model is considered to be sufficiently accurate. In Sections B and C, the finest meshed, parabolic triangular element model produced the most accurate traditional finite element model results. In this example, the parabolic triangular element model has by far the most degrees of freedom and is therefore considered the finest meshed model.
[2]The test model was run with one 18 degree of freedom element and symmetry. The degrees of freedom for the test model is shown as 144 to reflect the degrees of freedom as if it were an 8 element model. This is the relevant number of degrees of freedom for comparison with the other models.
[3]The traditional finite element models were run as a quarter model and symmetry. In the results plots, they are reflected to make a complete model and the degrees of freedom listed in Table E-2 represent a full model run.
[4]The results shown in FIGS. 4A-4B to FIGS. 6A-6B are given in psi.

Model Description

The example model (as shown in FIG. 1) is a 0.1 inches thick plate with circular and straight edges. It has a modulus of elasticity of $3.0 \cdot 10^7$ psi and a Poisson's ratio of 0.30. It has fixed boundary conditions on the center hole, a pressure load over the entire surface, and edge loading along the small circular holes, slots, and outer edge of the plate (as shown in FIGS. 2 and 3).

The shape and boundary conditions used for the example model are selected to highlight how the new method can excel over the traditional finite element method. Relative to the shape, having circular edges and holes puts traditional finite element analysis at a disadvantage. In traditional finite element analysis, the edge shape between nodes must be linear and the elements don't have holes. (Straight edged holes could be formulated into the traditional finite element method but it's not logical to do due to the added degrees of freedom.) Neither of these limitations applies to the new method. Relative to the boundary condition selection, having the high stress occur at a boundary condition puts traditional finite element analysis at a disadvantage. This is because the boundary conditions must be exactly met in traditional finite element analysis at the cost of reduced accuracy in the stress results. The new method optimizes to try to achieve the most accurate result relative to displacement and stress.

Figure 2:
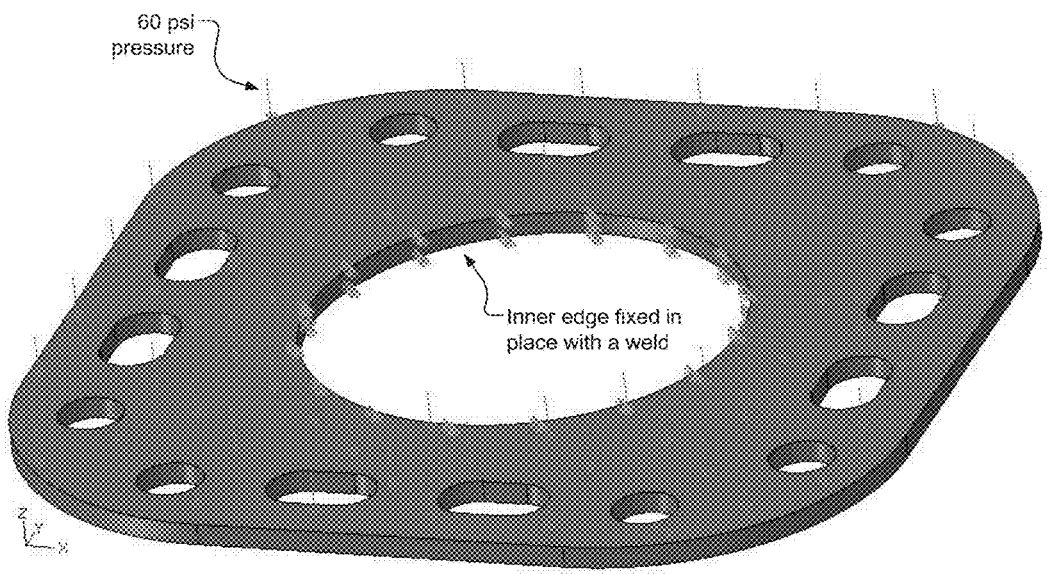
FIG. 2 is a perspective view of the plate of FIG. 1 showing applied loads and fixed edges.
Figure 3:
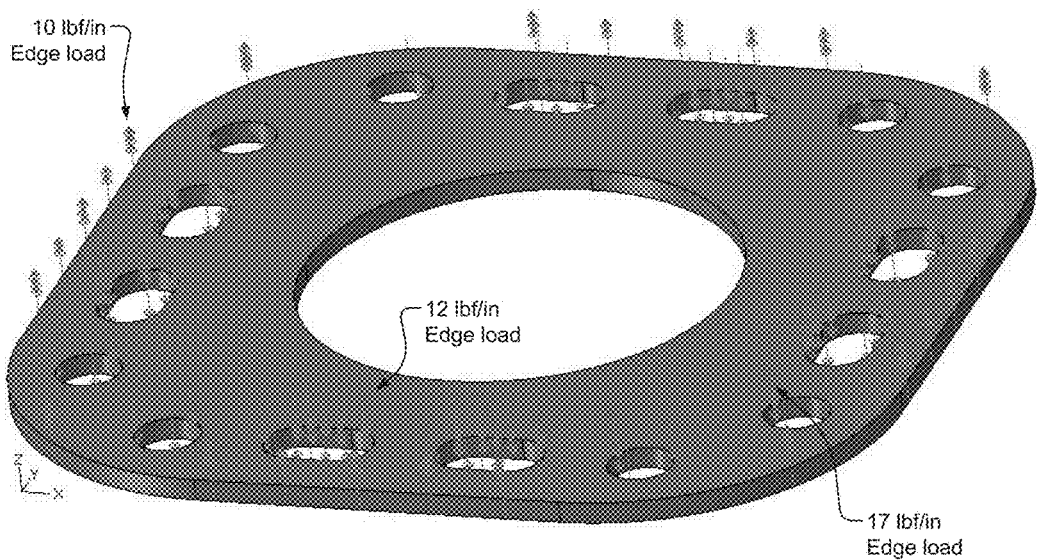
FIG. 3 is a perspective view of the plate of FIG. 1 showing additional applied loads.
Figure 4A:
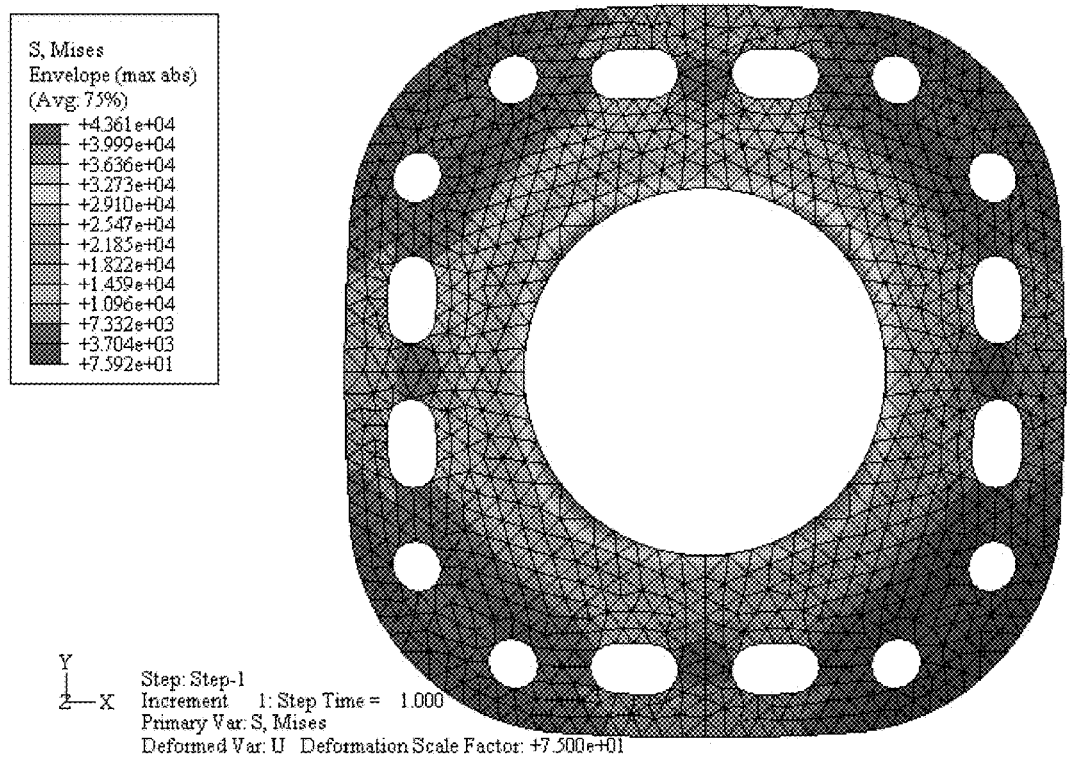
FIG. 4A is a stress plot of the plate of FIG. 1 under applied loads using traditional finite element analysis with a fine mesh.
Figure 4B:
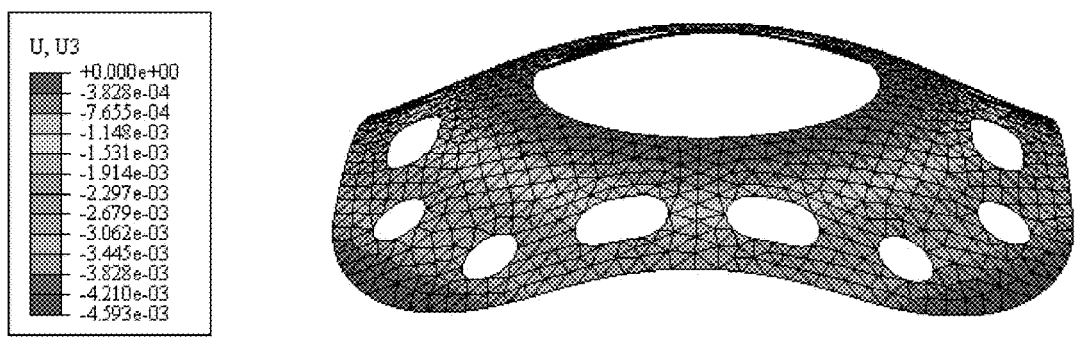
FIG. 4B is a displacement plot of the plate under applied loads with the fine mesh.

The boundary conditions shown in FIGS. 2 and 3 are applied to the plate simultaneously for the model solution. They are shown separately in two figures to make load identification easier.

While the edge loads are significant, the pressure load is purposely chosen to be dominant. This causes the largest displacement to occur on the outer edge of the plate which makes it easier for a relatively coarse mesh to perform well (in both the new method and traditional finite element analysis). Relatively coarse meshes are used in this example model to highlight the difference in performance between the new method and traditional finite element analysis.

Material Properties

The material properties for the example model are listed below.

$E := 30 \cdot 10^6$ Modulus of elasticity $v := 0.3$ Poisson's ratio $t := 0.05$ Thickness $$D: \frac{E \cdot t^3}{12 \cdot (1 - v^2)} \text{ Flexural rigidity}$$

D=343.407 r':=2.83 Length dimension used to make the degrees of freedom unitless. (The value of 2.83 is arbitrarily selected as a good value relative to matrix inversion. This is the integer value that makes the matrix determinant and matrix inverse determinant closest to one.)

k:=1 Spring stiffness for the edge springs added to remove rigid body motions.

The spring stiffness value of 1 is arbitrarily selected to represent a very soft spring stiffness for the example model. The primary reason for the spring is to remove rigid body motions. However, removing rigid body motions with a spring formulation provides an added ability to more rigidly enforce boundary conditions (similar to traditional finite element analysis) by defining a very stiff spring. With a value of 1, the stiffness is sufficiently low that it has a negligible effect relative to boundary condition enforcement yet it is significant enough for stable matrix inversion.

Element Definition

Figure 36:
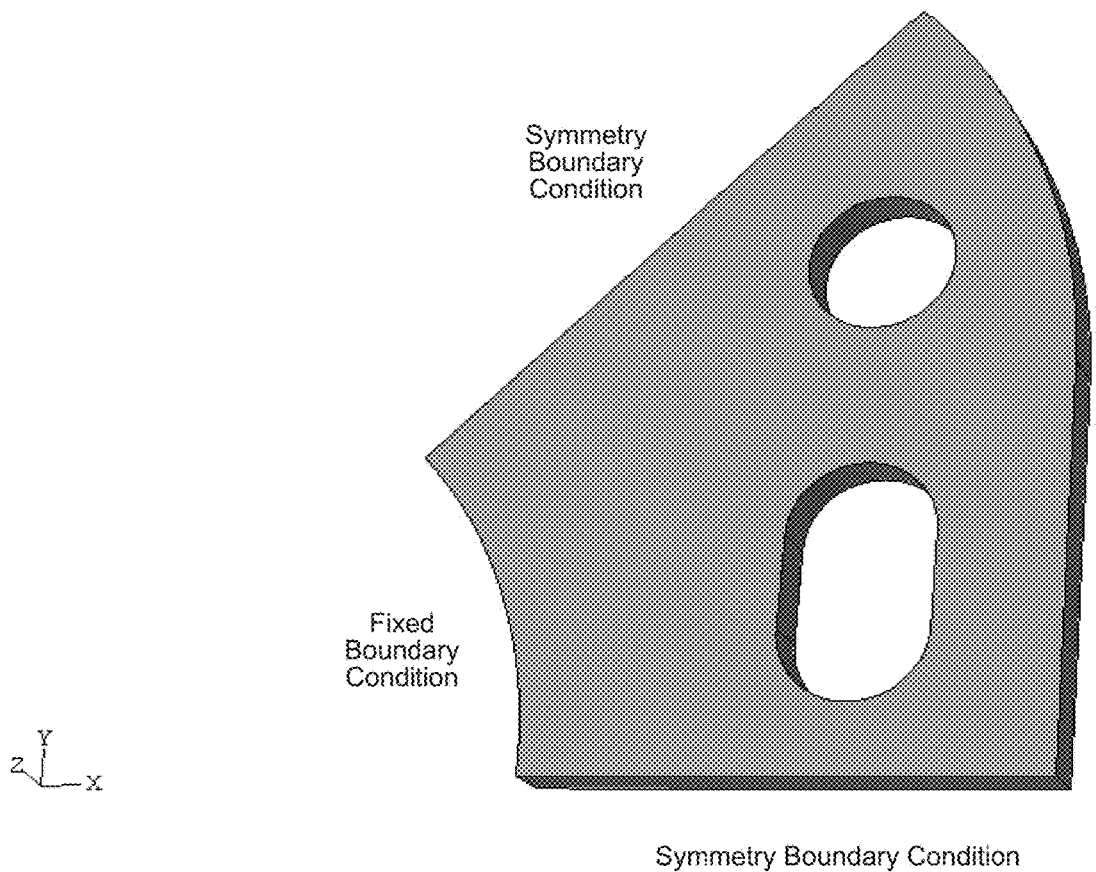
FIG. 36 is a perspective view of an example element of the mounting plate of FIG. 1 according to the principles of the present disclosure.

Observing the symmetry of the example model (shown in FIG. 1), one eighth of the model can be evaluated (as shown in FIG. 36). To demonstrate the versatility and accuracy of the new method, only one element will be used for the portion of the model shown in FIG. 36.

The fixed boundary condition in FIG. 36 is based on the fixed boundary condition identified in FIG. 2. The symmetry boundary conditions imply fixed bending rotation along the edge and no shear load or torsion along the edge. The pressure and edge loads shown in FIGS. 2 and 3 are also included for the model solution but are not shown in FIG. 36.

Figure 37:
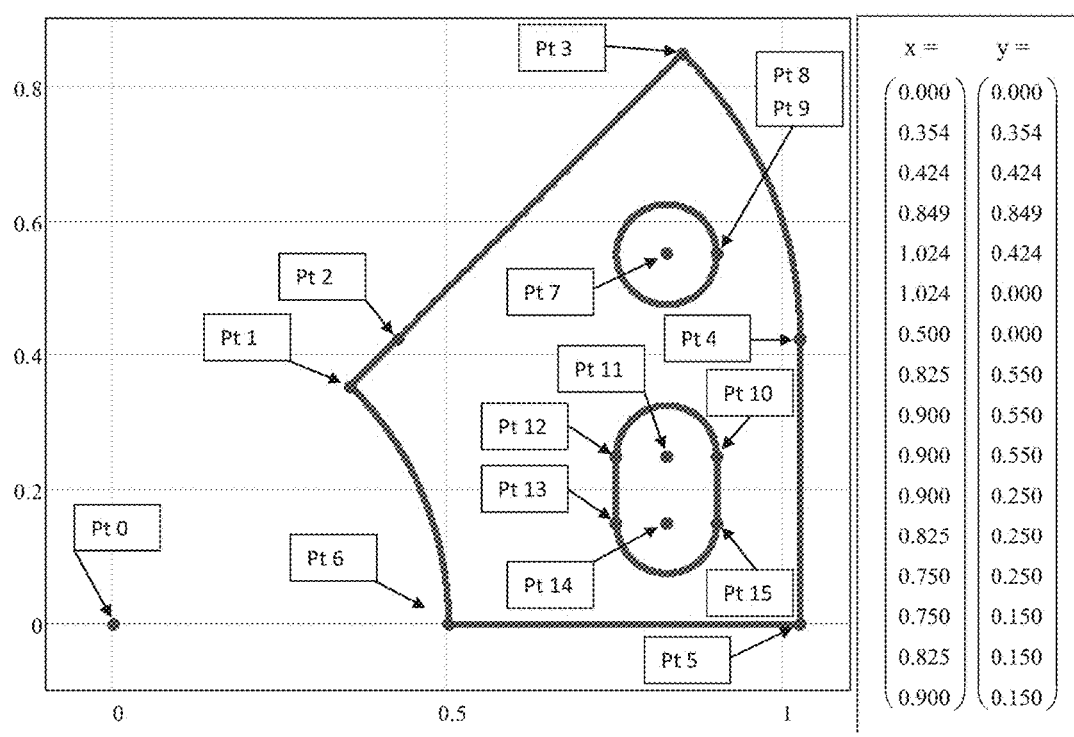
FIG. 37 is a graphical depiction of element points and dimensions used to define the element of FIG. 36.

The element points and dimensions used to define the element are shown in FIG. 37. The point numbers correspond to the rows in the x- and y-dimensions that are given on the right side of the figure (e.g. Pt 0 has an x-dimension of 0.000 in. and a y-dimension of 0.000 in. and Pt 7 has an x-dimension of 0.825 in. and a y-dimension of 0.550 in.).

The points shown in FIG. 37 are edge endpoints. These endpoints are used for mapping the element areas and edges. Points 8 and 9 occur at the same location to signify the start and end to the circular curve creating a 360-degree enclosed circle. The straight edges follow the derivation in Section B and the circular edges follow the derivation in Section C.

The area mapping array is shown below. Each row represents an edge that is a boundary to an area. The first column (or column 0) identifies the type of edge being identified. A zero indicates a linear edge, a one indicates a circular edge, and a two indicates a general curved edge. For all three edge types, the next two columns are the indices for the start and end edge endpoints (which correspond to the point numbers in FIG. 37). Columns beyond this are not applicable for a linear edge. For linear edges, the edges need to be defined in a clockwise manner for a solid area. Defining edges in a counterclockwise manner generates a hole. For a circular edge, the third column is the circle center point and the fourth column is a one for a solid area and a zero for a hole. The circle algorithms are set up to define a pie shaped area (or full circle) and the points are defined in a clockwise manner. For a general curved edge, the third column is the number of integration segments for the numerical integration and the last column is not applicable. Similar to the linear edge, the solid area is positioned on the right side of the definition direction.

$$a_{map} := \begin{pmatrix} 1 & 1 & 6 & 0 & -1 \\ 0 & 0 & 2 & 0 & 0 \\ 0 & 2 & 4 & 0 & 0 \\ 1 & 3 & 4 & 2 & 1 \\ 1 & 8 & 9 & 7 & -1 \\ 0 & 10 & 12 & 0 & 0 \\ 0 & 13 & 15 & 0 & 0 \\ 1 & 12 & 10 & 11 & -1 \\ 1 & 15 & 13 & 14 & -1 \end{pmatrix} \quad \text{Area mapping array}$$

Observing the definition of the area mapping array, the element areas are added and subtracted in a logical sequence to produce an area as shown in FIG. 36.

The edge mapping array is shown below. Each row represents a defined edge. The columns represent the same values as defined for the area mapping array. For linear edges, the edges need to be defined in a clockwise manner relative to the neighboring solid area (or in a counterclockwise manner relative to a neighboring hole). For a circular edge, the fourth column is a one for the edge being on the outside of a solid area and a zero for the edge being on the inside of a hole. The circle algorithms are defined in a clockwise manner. For a general curved edge, similar to the linear edge, the edge is defined so that the solid area is on the right side of the definition direction.

$$e_{map} := \begin{pmatrix} 1 & 1 & 6 & 0 & -1 \\ 0 & 1 & 2 & 0 & 0 \\ 0 & 2 & 3 & 0 & 0 \\ 1 & 3 & 4 & 2 & 1 \\ 0 & 4 & 5 & 0 & 0 \\ 0 & 5 & 6 & 0 & 0 \\ 1 & 8 & 9 & 7 & -1 \\ 1 & 12 & 10 & 11 & -1 \\ 1 & 15 & 13 & 14 & -1 \\ 0 & 15 & 10 & 0 & 0 \\ 0 & 12 & 13 & 0 & 0 \end{pmatrix} \quad \text{Edge mapping array}$$

To identify the boundary conditions on an edge, a boundary conditions mapping array is defined (as shown below) that corresponds to the edge mapping array. Each row of the boundary conditions mapping array identifies active boundary conditions for the corresponding row in the edge mapping array. A zero indicates that the external displacement/load is unknown. A one indicates that the external displacement/load is known. Each column represents a displacement/load as identified below (where the columns are displacement, bending rotation, torsional rotation, shear load, bending moment, and torsional moment respectively).

$$map := \begin{matrix} w & \theta & \phi & P & M & T \\ \begin{pmatrix} 1 & 1 & 1 & 0 & 0 & 0 \\ 0 & 1 & 0 & 1 & 0 & 1 \\ 0 & 1 & 0 & 1 & 0 & 1 \\ 0 & 0 & 0 & 1 & 1 & 1 \\ 0 & 0 & 0 & 1 & 1 & 1 \\ 0 & 1 & 0 & 1 & 0 & 1 \\ 0 & 0 & 0 & 1 & 1 & 1 \\ 0 & 0 & 0 & 1 & 1 & 1 \\ 0 & 0 & 0 & 1 & 1 & 1 \\ 0 & 0 & 0 & 1 & 1 & 1 \\ 0 & 0 & 0 & 1 & 1 & 1 \end{pmatrix} \end{matrix}$$

Boundary conditions mapping array

Considering that this is a single element problem, all of the boundary conditions consist of a known displacement/load and the corresponding load/displacement is not known. This element has one edge with known displacements and unknown loads, seven edges with unknown displacements and known loads, and three edges with symmetry boundary conditions.

The boundary condition values are defined as arrays where each column corresponds with an edge defined in the edge mapping array and each row corresponds with a displacement/load constant defined in Eq. E-38. (Only the rows corresponding to the constant displacements/loads are shown as these are the only rows where nonzero values occur.) The pressure loading is defined as a scalar value. These values correspond with the values shown in FIGS. 2 and 3.

Area loading $p_z = -60$

Distributed pressure

-continued

Linear edges:

$P_e^{T^{(0)T}} = (\ 0\ \ 0\ \ 0\ \ 0\ \ 10\ \ 0\ \ 0\ \ 0\ \ 0\ \ -12\ \ -12\ )$

Shear load $M_e^{T^{(0)T}} = (\ 0\ \ 0\ \ 0\ \ 0\ \ 0\ \ 0\ \ 0\ \ 0\ \ 0\ \ 0\ \ 0\ )$ Bending moment $T_e^{T^{(0)T}} = (\ 0\ \ 0\ \ 0\ \ 0\ \ 0\ \ 0\ \ 0\ \ 0\ \ 0\ \ 0\ \ 0\ )$ Torsional moment $w_e^{T^{(0)T}} = (\ 0\ \ 0\ \ 0\ \ 0\ \ 0\ \ 0\ \ 0\ \ 0\ \ 0\ \ 0\ \ 0\ )$ Displacement $\theta_e^{T^{(0)T}} = (\ 0\ \ 0\ \ 0\ \ 0\ \ 0\ \ 0\ \ 0\ \ 0\ \ 0\ \ 0\ \ 0\ )$ Bending rotation $\phi_e^{T^{(0)T}} = (\ 0\ \ 0\ \ 0\ \ 0\ \ 0\ \ 0\ \ 0\ \ 0\ \ 0\ \ 0\ \ 0\ )$ Torsional rotation Circular edges:

$Pc_e = (\ 0\ \ 0\ \ 0\ \ 10\ \ 0\ \ 0\ \ -17\ \ -12\ \ -12\ \ 0\ \ 0\ )$

Shear load $wc_e = (\ 0\ \ 0\ \ 0\ \ 0\ \ 0\ \ 0\ \ 0\ \ 0\ \ 0\ \ 0\ \ 0\ )$

-continued

Displacement $Mc_e = (\ 0\ \ 0\ \ 0\ \ 0\ \ 0\ \ 0\ \ 0\ \ 0\ \ 0\ \ 0\ \ 0\ )$

Bending moment $Tc_e = (\ 0\ \ 0\ \ 0\ \ 0\ \ 0\ \ 0\ \ 0\ \ 0\ \ 0\ \ 0\ \ 0\ )$ Torsional moment $\theta c_e = (\ 0\ \ 0\ \ 0\ \ 0\ \ 0\ \ 0\ \ 0\ \ 0\ \ 0\ \ 0\ \ 0\ )$ Bending rotation $\phi c_e = (\ 0\ \ 0\ \ 0\ \ 0\ \ 0\ \ 0\ \ 0\ \ 0\ \ 0\ \ 0\ \ 0\ )$ Torsional rotation Results and Comparison with Traditional Finite Element Analysis For comparison, the results of the new method are compared to four test models that were run using traditional finite element analysis. The Abaqus shell elements are based on a similar governing equation to that considered for the governing equation and theoretical value (as evidenced by the convergence toward the theoretical solution in the high degree of freedom models shown in Sections B and C). Abaqus considers additional governing equation components such as shear deformation in some shell elements. The elements used for this comparison are STRI65 for the parabolic triangular shell elements and S4 for the linear quadrilateral elements.

FIGS. 4A-4B to FIGS. 6A-6B show von Mises stress and displacement magnified 75 times for the five models used for comparison. FIGS. 6A-6B shows the results for the new method. As discussed earlier, the model for the new method is a ⅛ symmetry, single element model. Consequently, it is appropriate to mirror it three times and present it as full model. Likewise, the traditional finite element models (FIGS. 4A-4B to FIGS. 30A-30B) are modeled with quarter symmetry, mirrored twice, and presented full models.

Table E-2 provides a summary of results for stress and displacement (with percent error calculated with respect to the finest mesh):

|  | New model[2] | Linear quadrilateral 164 element[3] | Parabolic triangular 168 element[3] | Linear quadrilateral 2,988 element[3] | Parabolic triangular 1,696 element[3] |
| --- | --- | --- | --- | --- | --- |
| Maximum von Mises stress [ksi[4]] | 41.83 (−4.1%) | 29.51 (−32.3%) | 26.84 (−38.5%) | 39.45 (−9.5%) | 43.61 |
| Maximum displacement [in] | 0.004765 (+3.7%) | 0.003955 (−13.9%) | 0.003740 (−18.6%) | 0.00457 (−0.5%) | 0.004593 |
| Degrees of freedom | 144 | 612 | 1,224 | 9,792 | 11,112 |

[1] A theoretical value is not readily available for this example. Consequently, the finest meshed model is considered to be sufficiently accurate. In Sections B and C, the finest meshed, parabolic triangular element model produced the most accurate traditional finite element model results. In this example, the parabolic triangular element model has by far the most degrees of freedom and is therefore considered the finest meshed model.
[2] The test model was run with one 18 degree of freedom element and symmetry. The degrees of freedom for the test model is shown as 144 to reflect the degrees of freedom as if it were an 8 element model. This is the relevant number of degrees of freedom for comparison with the other models.
[3] The traditional finite element models were run as a quarter model and symmetry. In the results plots, they are reflected to make a complete model and the degrees of freedom listed in Table E-2 represent a full model run.
[4] The results shown in FIGS. 4A-4B to FIGS. 6A-6B are given in psi.

Considering Table E-2 and FIGS. 4A-4B to FIGS. 6A-6B, the new method performed very well relative to the traditional finite element method. FIGS. 5A-5B and FIGS. 30A-30B represent meshes that are about as coarse as is possible with traditional finite element analysis for this problem and still mesh the holes. From these meshes, it is clear that significant mesh refinement is required with traditional finite element analysis if circular geometry, as in this example, is to be accurately followed. The new method can exactly follow this geometry with any coarseness of mesh. Consequently, the geometry in this example does not contribute to inaccuracy of the results for the new method.

The stress and displacement results for the new method are very accurate even compared to the finely meshed, traditional finite element models. Though the new method results are generally more accurate than the traditional finite element model results, selection of boundary conditions and loading in this example contribute to how well the new method performs relative to the traditional finite element method.

Referring back to FIGS. 6A and 6B, Von Mises stress and displacement magnified 75× for the new method are shown. The maximum von Mises stress shown is 41,830 psi and the maximum negative displacement shown is −0.004765 in. The minimum von Mises stress shown is 1,750 psi and the maximum positive displacement shown is 0.000067 in.

Referring back to FIGS. 5A-5B, von Mises stress and displacement magnified 75× are shown for a course mesh having 168 parabolic triangular elements. Referring back to FIGS. 4A-4B, von Mises stress and displacement magnified 75× are shown for a finer mesh having 1696 parabolic triangular elements.

Figure 38A:
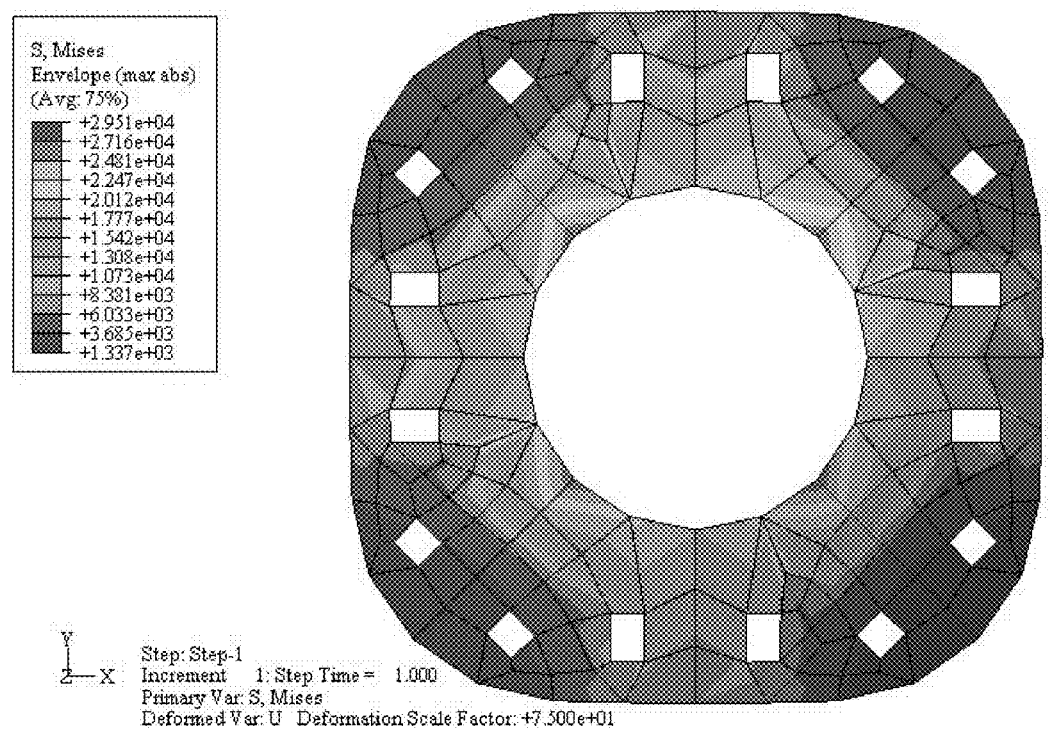
FIGS. 38A and 38B are Von Mises stress and displacement plots, respectively, for a traditional finite element analysis with 164 linear quadrilateral elements.
Figure 38B:
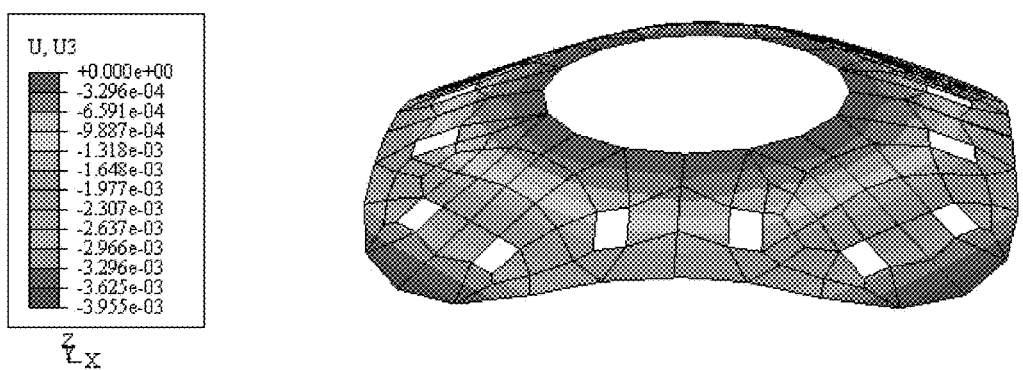
Figure 39A:
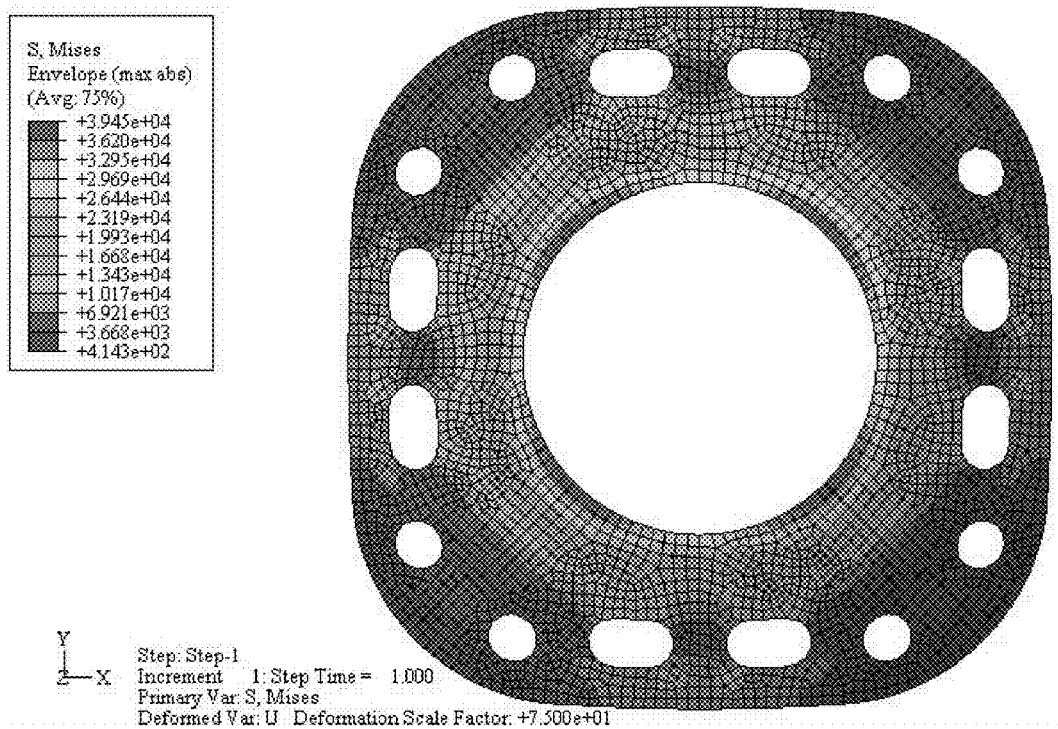
FIGS. 39A and 39B are Von Mises stress and displacement plots, respectively, for a traditional finite element analysis with 2988 linear quadrilateral elements.
Figure 39B:
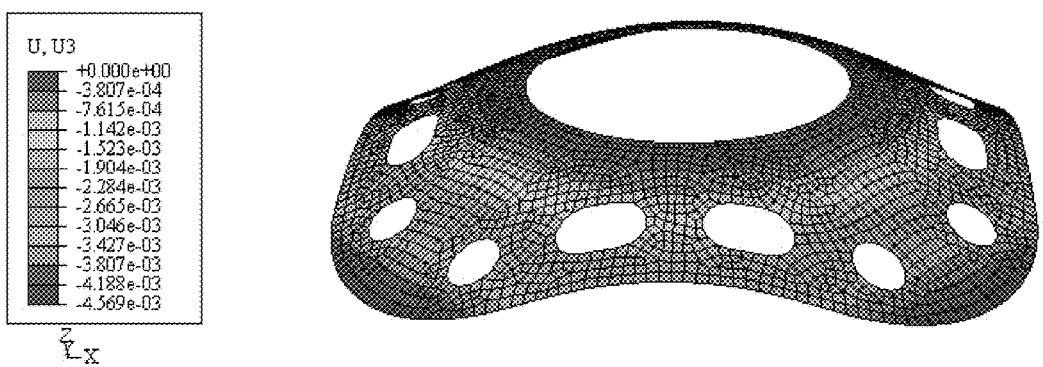

FIGS. 38A and 38B are Von Mises stress and displacement plots, respectively, for a traditional finite element analysis with 164 linear quadrilateral elements. FIGS. 39A and 39B are Von Mises stress and displacement plots, respectively, for a traditional finite element analysis with 2988 linear quadrilateral elements.

Discussion

This example showed the new method's ability to accurately address complex geometry. It showed how the traditional finite element method may require a much finer mesh to accurately follow a given geometry. This is undesirable due to the increase computational needs to accurately solve the problem.

The example problem results using the new method were very accurate even compared to the finely meshed traditional finite element models. However, the geometry and boundary conditions were selected to highlight the strengths of the new method. Consequently, more accurate results for the new method can be expected in general but not necessarily to this degree in general.

Section F

Outline

In this Section, a relatively simple theoretical description of a plane stress, stress analysis is shown using the new method. The example problem is a triangular shell element with in-plane normal and shear loading. The governing equation used for this example is based on an Airy stress function. For additional background on the Airy stress function, see Heinbockel, J. H., "Introduction to Tensor Calculus and Continuum Mechanics," 1996, Department of Mathematics and Statistics, Old Dominion University. Where previous Sections considered the z-direction displacement in the shell due to bending, this Section considers x- and y-direction displacement due to in-plane loading.

The comparison is described in several portions. The first portion (Plane Stress Equations) provides equations relevant to the example problem. These equations represent one possible plane strain formulation. The second portion (New Method Displacement Equations) defines body force, Airy stress function, and displacement equations for the plane stress example. The third portion (Plane Stress Strain Energy and Body Force Energy) derives the equations for the strain energy and body force energy. The fourth portion (Straight Edge Example Problem) shows the remaining derivation needed for a straight edged element. A summary of these points is discussed in the fifth portion (Discussion).

Plane Stress Equations

The shell equations presented here are for shell stresses and strains in the plane of the shell (unlike the other Sections where shell bending is addressed). The governing equation and more discussion on this topic can be found in Heinbockel, 1996.

Eqs. F-1 to F-3 define the governing equation and the corresponding stress and strain equations.

$$\frac{\partial^4}{\partial x^4}\Phi + 2 \cdot \frac{\partial^2}{\partial x^2}\frac{\partial^2}{\partial y^2}\Phi + \frac{\partial^4}{\partial y^4}\Phi + \frac{1-2\cdot v}{1-v}\cdot\left(\frac{\partial^2}{\partial x^2}V + \frac{\partial^2}{\partial y^2}V\right) = 0 \quad \text{Eq. F-1}$$

Governing equation

Where:

$\Phi$ - Airy stress function  Eq. F-2

$V$ - Body forces $v$ - Poisson's ratio $$\sigma_x = \frac{\partial^2}{\partial y^2}\phi + V$$

Stress in the x-direction $$\sigma_y = \frac{\partial^2}{\partial x^2}\phi + V$$

Stress in the y-direction $$T_{xy} = -\frac{\partial}{\partial x}\frac{\partial}{\partial y}\phi$$

Shear stress in the xy-plane $$\varepsilon_x = \frac{1}{E}\cdot\left(\frac{\partial^2}{\partial y^2}\phi - v\cdot\frac{\partial^2}{\partial x^2}\phi\right) = \frac{\partial}{\partial x}u \quad \text{Eq. F-3}$$

Strain in the x-direction $$\varepsilon_y = \frac{1}{E}\cdot\left(\frac{\partial^2}{\partial x^2}\phi - v\cdot\frac{\partial^2}{\partial y^2}\phi\right) = \frac{\partial}{\partial y}v$$

Strain in the y-direction $$Y_{xy} = -\frac{2\cdot(1+v)}{E}\cdot\frac{\partial}{\partial x}\frac{\partial}{\partial y}\phi = \frac{\partial}{\partial y}u + \frac{\partial}{\partial x}v$$

Shear Strain in the xy-plane

Where:

u—Displacement in the x-direction v—Displacement in the y-direction

E—Modulus of elasticity

New Method Displacement Equations

This section describes the new method displacement for the example problem. The first step is to define a reasonable body force equation (shown in Eq. F-4). Then the Airy stress function and displacement equations are defined (Eqs. F-5 to F-7). The definitions were developed similar to that in the Displacement Equation section of Section B. For brevity, the definitions are given without showing a detailed approach.

$$V = -\rho \cdot g_x \cdot x - \rho \cdot g_y \cdot y - c_{\rho g} \quad \text{Eq. F-4}$$

Where:

$g_x$—Gravitational acceleration in the x-direction $\rho$—Shell density $g_y$—Gravitational acceleration in the y-direction $c_{\rho g}$—Body force constant $$\Phi = E \cdot \begin{pmatrix} b_0 \\ b_1 \\ b_2 \\ b_3 \\ b_4 \\ b_5 \\ b_6 \\ b_7 \\ b_8 \\ b_9 \\ b_{10} \\ b_{11} \\ b_{12} \end{pmatrix}^T \cdot \begin{bmatrix} x \cdot r' \\ y \cdot r' \\ x \cdot y \\ x^2 \\ y^2 \\ x^2 \cdot y \cdot r'^{-1} \\ x \cdot y^2 \cdot r'^{-1} \\ x^3 \cdot r'^{-1} \\ y^3 \cdot r'^{-1} \\ x^3 \cdot y \cdot r'^{-2} \\ x \cdot y^3 \cdot r'^{-2} \\ (x^4 - 3 \cdot x^2 \cdot y^2) \cdot r'^{-2} \\ (y^4 - 3 \cdot x^2 \cdot y^2) \cdot r'^{-2} \end{bmatrix} \quad \text{Eq. F-5}$$

Airy stress function

Where:

$(b_0\ b_1\ b_2\ b_3\ b_4\ b_5\ b_6\ b_7\ b_8\ b_9\ b_{10}\ b_{11}\ b_{12})$—Degrees of freedom $r'$—Length constant used to make the degrees of freedom unitless $$u = \begin{pmatrix} b_0 \\ b_1 \\ b_2 \\ b_3 \\ b_4 \\ b_5 \\ b_6 \\ b_7 \\ b_8 \\ b_9 \\ b_{10} \\ b_{11} \\ b_{12} \end{pmatrix}^T \cdot \begin{bmatrix} -v \cdot r' \\ 0 \cdot r' \\ -y \cdot (1+v) \\ -2 \cdot v \cdot x \\ 2 \cdot x \\ -2 \cdot v \cdot x \cdot y \cdot r'^{-1} \\ (x^2 - 2 \cdot y^2 - v \cdot y^2) \cdot r'^{-1} \\ (-3 \cdot v \cdot x^2 - 3 \cdot y^2) \cdot r'^{-1} \\ 6 \cdot x \cdot y \cdot r'^{-1} \\ -y \cdot (3 \cdot v \cdot x^2 + y^2) \cdot r'^{-2} \\ y \cdot (3 \cdot x^2 - 2 \cdot y^2 - v \cdot y^2) \cdot r'^{-2} \\ -2 \cdot x \cdot (x^2 + 2 \cdot v \cdot x^2 - 3 \cdot v \cdot y^2) \cdot r'^{-2} \\ -2 \cdot x \cdot (-6 \cdot y^2 - 3 \cdot v \cdot y^2 + x^2) \cdot r'^{-2} \end{bmatrix} \cdots + \quad \text{Eq. F-6}$$

$$\frac{1-v}{2 \cdot E} \cdot \begin{pmatrix} c_{\rho g} \\ \rho \cdot g_x \\ \rho \cdot g_y \end{pmatrix}^T \cdot \begin{pmatrix} -2 \cdot x \\ -x^2 + y^2 \\ -2 \cdot x \cdot y \end{pmatrix}$$

Displacement in the x-direction $$v = \begin{pmatrix} b_0 \\ b_1 \\ b_2 \\ b_3 \\ b_4 \\ b_5 \\ b_6 \\ b_7 \\ b_8 \\ b_9 \\ b_{10} \\ b_{11} \\ b_{12} \end{pmatrix}^T \cdot \begin{bmatrix} 0 \cdot r' \\ -v \cdot r' \\ -x \cdot (1+v) \\ 2 \cdot y \\ -2 \cdot v \cdot y \\ (-2 \cdot x^2 - v \cdot x^2 + y^2) \cdot r'^{-1} \\ -2 \cdot v \cdot x \cdot y \cdot r'^{-1} \\ 6 \cdot x \cdot y \cdot r'^{-1} \\ (-3 \cdot x^2 - 3 \cdot v \cdot y^2) \cdot r'^{-1} \\ -x \cdot (-3 \cdot y^2 + 2 \cdot x^2 + v \cdot x^2) \cdot r'^{-2} \\ -x \cdot (3 \cdot v \cdot y^2 + x^2) \cdot r'^{-2} \\ 2 \cdot y \cdot (6 \cdot x^2 + 3 \cdot v \cdot x^2 - y) \cdot r'^{-2} \\ 2 \cdot y \cdot (-y^2 - 2 \cdot v \cdot y^2 + 3 \cdot v \cdot x^2) \cdot r'^{-2} \end{bmatrix} \cdots + \quad \text{Eq. F-7}$$

$$\frac{1-v}{2 \cdot E} \cdot \begin{pmatrix} c_{\rho g} \\ \rho \cdot g_x \\ \rho \cdot g_y \end{pmatrix}^T \cdot \begin{pmatrix} -2 \cdot y \\ -2 \cdot x \cdot y \\ x^2 - y^2 \end{pmatrix}$$

Displacement in the y-direction

Plane Stress Strain Energy and Body Force Energy

The strain energy for this problem can be derived considering the basic definition for strain energy (Eq. F-8) along with Hooke's law as applied to plane stress (Eq. F-9). The strain energy, in a form that is applicable to this example, is given in Eq. F-10.

$$U = \frac{1}{2} \cdot \iiint_V \sigma_x \cdot \varepsilon_x + \sigma_y \cdot \varepsilon_y + \quad \text{Eq. F-8}$$

$$\sigma_z \cdot \varepsilon_z + T_{xy} \cdot Y_{xy} + T_{xz} \cdot Y_{xz} + T_{yz} \cdot Y_{yz} dxdydz$$

Basic for of the strain energy equation

Where:

$\sigma_x$ - Stress in the x-direction $\sigma_y$ - Stress in the y-direction $\sigma_z$ - Stress in the z-direction $T_{xy}$ - Shear stress in the xy-direction $T_{xz}$ - Shear stress in the xz-direction $T_{yz}$ - Shear stress in the yz-direction $\varepsilon_x$ - Strain in the x-direction $\varepsilon_y$ - Strain in the y-direction $\varepsilon_z$ - Strain in the z-direction $Y_{xy}$ - Shear Stress in the xy-direction $Y_{xz}$ - Shear Stress in the xz-direction $Y_{yz}$ - Shear Stress in the yz-direction $$\sigma_z = T_{xz} = T_{yz} = 0 \quad \text{Eq. F-9}$$

Hooke's law as applied to plane stress $$\varepsilon_x = \frac{1}{E} \cdot \sigma_x - v \cdot (\sigma_y + \sigma_z) = \frac{1}{E} \cdot (\sigma_x - v \cdot \sigma_y)$$

$$\varepsilon_y = \frac{1}{E} \cdot \sigma_y - v \cdot (\sigma_x + \sigma_z) = \frac{1}{E} \cdot (\sigma_y - v \cdot \sigma_x)$$

$$Y_{xy} = \frac{2 \cdot (1+v) \cdot T_{xy}}{E}$$

Introducing Eq. F-9 into Eq. F-8 and making the strain energy be a function of stress:

$$U = \frac{1}{2} \cdot \iiint \frac{\sigma_x}{E} \cdot (\sigma_x - v \cdot \sigma_y) +$$

$$\frac{\sigma_y}{E} \cdot (\sigma_y - v \cdot \sigma_x) + T_{xy} \cdot \frac{2 \cdot (1+v) \cdot T_{xy}}{E} dxdydz$$

Considering that the stress is constant through the thickness, and introducing Eq. F-2:

$$U = \frac{t}{2 \cdot E} \cdot \iint_A \left(\frac{d^2}{dx^2}\Phi + V\right)^2 + \left(\frac{d^2}{dy^2}\Phi + V\right)^2 \ldots dydx + \quad \text{Eq. F-10}$$

$$-2 \cdot v \cdot \left(\frac{d^2}{dx^2}\Phi + V\right) \cdot \left(\frac{d^2}{dy^2}\Phi + V\right) \ldots +$$

$$2 \cdot (1+v) \cdot \left(\frac{d}{dx}\frac{d}{dy}\Phi\right)^2$$

Strain energy

Where:
t—Shell thickness

The body force energy can be derived similar to the strain energy with the resulting area integral shown in Eq. F-11.

$$W_b = t \cdot \iint_A V \cdot (\varepsilon_x + \varepsilon_y) dxdy \quad \text{Eq. F-11}$$

Body force energy

Straight Edge Example Problem

This section describes the new method for an example problem with straight edges. FIG. 12 shows the triangular finite element for the example problem with edges and edge ends identified.

To develop the energy optimization, there are area integrals and edge integrals to be addressed. The strain energy equation (Eq. F-10) and the energy equation for the body loads (Eq. F-11) are both area integrals. The rest of the energy equations are edge integrals. The integrals for both the area and edges are developed for a single edge. Then the same integration is performed on all of the edges in succession to address all of the energy associated with the element. To this end, as slightly different strategy is used for the area integrals versus the edge integral. The area integrals use the coordinate system of the element and are derived as shown below in Eqs. F-12 to F-15.

To generate an integral that can be performed along each successive edge, the curve representing the edge is derived and incorporated into integral. Below is the derivation for the straight edges of the triangle.

$$y(x) = m \cdot x + b \quad \text{Eq. F-12}$$
Edge function for area integration $$m = \frac{y_{end} - y_{start}}{x_{end} - x_{start}} \quad \text{Edge slope} \quad \text{Eq. F-13}$$

$$b = y_{start} - \frac{y_{end} - y_{start}}{x_{end} - x_{start}} \cdot x_{start} \quad \text{Edge y-intercept}$$

for: $x_{end} - x_{start} \neq 0$

Where:
The subscript "start" implies the starting point on a given edge
The subscript "end" implies the ending point on a given edge
Introducing Eq. F-13 into Eq. F-10 and incorporating the x-position of the curve end points:

$$U_e = \frac{t}{2 \cdot E} \cdot \int_{x_{start}}^{x_{end}} \int_0^{m \cdot x + b} \left(\frac{d^2}{dx^2}\Phi + V\right)^2 + \left(\frac{d^2}{dy^2}\Phi + V\right)^2 \ldots dydx + \quad \text{Eq. F-14}$$

$$-2 \cdot v \cdot \left(\frac{d^2}{dx^2}\Phi + V\right) \cdot \left(\frac{d^2}{dy^2}\Phi + V\right) \ldots + 2 \cdot (1+v) \cdot \left(\frac{d}{dx}\frac{d}{dy}\Phi\right)^2$$

If Eq. F-14 is performed on each successive edge, the summed values produce the area integral for the whole element. (Edges with no change in the x-direction are excluded from this summation as there is no change in energy for these edges in this formulation and they make Eq. F-37 unstable.)

Similar to that for strain energy, a derivation can be performed for the external work on the element applied by the body force.

Introducing Eq. F-13 into Eq. F-11 and incorporating the x-position of the curve end points:

$$W_b = t \cdot \int_{x_{start}}^{x_{end}} \int_0^{m \cdot x + b} V \cdot (\varepsilon_x + \varepsilon_y) dy\, dx \quad \text{Body force energy} \quad \text{Eq. F-15}$$

The edge integrals, similar to the area integral formulation, are formulated for a single edge. Then each successive edge is summed to account for all of the edge energy. For convenience, however, the edge integrals are formulated in local coordinates. The local coordinates (as shown in FIG. 12) are defined in Eqs. F-16 to F-18.

| | | |
|---|---|---|
| $\Delta x = x_{end} - x_{start}$ | Edge length in the x-direction | Eq. F-16 |
| $\Delta y = y_{end} - y_{start}$ | Edge length in the y-direction | |
| $\Delta r = \sqrt{\Delta x^2 + \Delta y^2}$ | Length of the edge | |
| $\theta_x = \frac{\Delta x}{\Delta r}$ | Component in the x-direction | Eq. F-17 |
| $\theta_y = \frac{\Delta y}{\Delta r}$ | Component in the y-direction | |

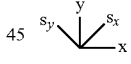

| | | |
|---|---|---|
| $s_x = \theta_x \cdot x + \theta_y \cdot y$ | Local x-direction in terms of the element coordinates | Eq. F-18 |
| $s_x = -\theta_y \cdot x + \theta_x \cdot y$ | Local y-direction in terms of the element coordinates | |
| or | | |
| $x = s_x \cdot \theta_x - s_y \cdot \theta_y$ | Element x-direction in terms of the local coordinates | |
| $y = s_x \cdot \theta_y + s_y \cdot \theta_x$ | Local y-direction in terms of the element coordinates | |

Given the local coordinates definition (Eq. F-18), edge displacements and loads can be defined in local coordinates (as shown in Eqs. F-19 and F-20). This is followed by the edge energy integral for external work also in local coordinates (Eq. F-21).

$$u_s = u(s_x \cdot \theta_x - s_y \cdot \theta_y, s_x \cdot \theta_y + s_y \cdot \theta_x) \quad \text{Eq. F-19}$$
Displacement in the local x-direction $$v_s = v(s_x \cdot \theta_x - s_y \cdot \theta_y, s_x \cdot \theta_y + s_y \cdot \theta_x)$$
Displacement in the local y-direction -continued $$P_{vs} = t \cdot \frac{d^2}{ds_x^2}\Phi_s \qquad \text{Eq. F-20}$$

Force in the local y-direction $$P_{us} = -t \cdot \frac{d}{ds_x}\frac{d}{ds_y}\Phi_s$$

Force in the local x-direction $$W_e = \int_{s_{x\_start}}^{s_{x\_end}} P_{vs} \cdot v_s + P_{us} \cdot u_s \, ds_x \qquad \text{Eq. F-21}$$

Edge energy integral for external work

When considering the external work for this method, the external influences could be external displacements or external loads. For the external displacements, the energy integral is established considering the external displacement and the element loads. For the external loads, the energy integral is established considering the external loads and the element displacements. This results in two sets of external work integrals that need to be considered. Consequently, the total energy for the element is found by doubling the internal strain energy and subtracting external displacement based work and external load based work (as shown in Eq. F-22).

$$\Pi = 2U - (\Sigma W_b + \Sigma W_e)_w - (\Sigma W_b + \Sigma W_e)_P \text{ Total energy for an element} \qquad \text{Eq. F-22}$$

Where:
$\Sigma$—Implies summing over all edges
The subscript "w" implies external work from external displacements
The subscript "P" implies external work from external loads Having the total energy equation for the element, the optimization is performed by minimizing based on the degrees of freedom (as shown in Eq. F-23).

$$\frac{\partial}{\partial a_0}\Pi = 0 \text{ Energy optimization} \qquad \text{Eq. F-23}$$

$$\frac{\partial}{\partial a_1}\Pi = 0$$

$$\frac{\partial}{\partial a_2}\Pi = 0$$

$$\vdots$$

$$\frac{\partial}{\partial a_9}\Pi = 0$$

Evaluating the partial differential equations for the energy optimization produces a system of linear equations. Eq. F-24 shows the matrix form of this equation considering a single element. Eq. F-25 shows the equation for all of the elements in a model.

$$U_m \cdot a + U_b = 0 \text{ Linear equation for optimized degrees of freedom for a single element} \qquad \text{Eq. F-24}$$

Where:
$U_m$—Array constants determined with the partial differential equations
$U_b$—Vector constants determined with the partial differential equations $$U_M \cdot a + U_B = 0 \text{ Linear equation for optimized degrees of freedom for all of the elements} \qquad \text{Eq. F-25}$$

or $$a = U_M^{-1} \cdot (-U_B)$$

Where:
$U_M$—Array constants summed for all of the elements in the model
$U_B$—Vector constants summed for all of the elements in the model This energy optimization follows the same strategy as that described in Section A. The degrees of freedom in this Section are complementary to those in Section A. Combining the two sets of degrees of freedom produces a 31 degree of freedom element that addresses displacements in all three directions.

Discussion

As noted in the Outline, this Section provides a relatively simple theoretical description of a plane stress analysis with the new method. Though this example has a different governing equation, different displacement equations, a different strain energy equation, and external work equations, the overall approach follows the same (new method) strategy as that described in Section A. The degrees of freedom in this Section are complementary to those in Section A. Consequently, combining the two sets of degrees of freedom produces a 31 degree of freedom element that addresses displacements in all three directions.

Section G

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects.

The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium include nonvolatile memory circuits (such as a flash memory circuit or a mask read-only memory circuit), volatile memory circuits (such as a static random access memory circuit and a dynamic random access memory circuit), and secondary storage, such as magnetic storage (such as magnetic tape or hard disk drive) and optical storage.

The apparatuses and methods described in this application may be partially or fully implemented by a special purpose computer created by configuring a general purpose computer to execute one or more particular solutions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

None of the elements recited in the claims is intended to be a means-plus-function element within the meaning of 35 U.S.C. § 112(f) unless an element is expressly recited using the phrase "means for", or in the case of a method claim using the phrases "operation for" or "step for".

What is claimed is:

1. A method of designing a physical structure, the method comprising:
   storing a structural model of the physical structure;
   defining a mesh for the structural model, wherein the mesh includes a plurality of finite elements, and wherein each element of the finite elements is defined by a plurality of edges of the element;
   identifying a governing differential equation for each of the plurality of finite elements;
   for each element of the plurality of finite elements:
      identifying a plurality of complementary functions that exactly satisfy the corresponding governing differential equation,
      wherein each of the plurality of complementary functions for the finite element is associated with a respective scalar multiplier, and
      wherein a count of the respective scalar multipliers for the element establishes a number of degrees of freedom of the element;
   determining an applied stimulus for the physical structure, wherein the applied stimulus includes at least one of an applied mechanical force, an applied mechanical stress, an applied mechanical strain, an applied mechanical torque, an applied mechanical moment, an applied translational displacement, and an applied rotational displacement;
   generating an energy optimization model that minimizes a difference between internal energy of the plurality of finite elements and external energy of the plurality of finite elements,
      wherein an internal energy of each finite element of the plurality of finite elements is based on strain energy in a volume of the finite element (i) defined by the edges of the finite element and (ii) resulting from deformations of the finite element by the corresponding plurality of complementary functions,
      wherein an external energy of each finite element of the plurality of finite elements is based on external work done by external stimulus acting on the finite element as deformed by the corresponding plurality of complementary functions,
      wherein the external stimulus is based on the applied stimulus,
      wherein generating the energy optimization model includes, for each element of the plurality of finite elements:
         determining a difference expression between the internal energy of the element and the external energy of the element, and
         for each degree of freedom of the element, generating a set of equation parameters by calculating a partial differential of the difference expression with respect to the respective scalar multiplier, and
      wherein generating the energy optimization model includes transforming the sets of equation parameters for each of the degrees of freedom of the plurality of finite elements into a first matrix;
   solving the energy optimization model for the respective scalar multipliers, wherein solving the energy optimization model includes transforming the first matrix using an inversion operation;
   calculating a physical parameter of interest of the physical structure in response to the applied stimulus, wherein the physical parameter of interest includes at least one of a mechanical strain on the physical structure, a mechanical stress on the physical structure, a mechanical force on the physical structure, a mechanical moment of the physical structure, a mechanical torque of the physical structure, a translational displacement of the physical structure, and a rotational displacement of the physical structure, and wherein the physical parameter of interest is calculated based on the solved scalar multipliers;

determining whether the physical parameter of interest satisfies a design parameter of the physical structure; and in response to the physical parameter of interest not satisfying the design parameter, updating the structural model of the physical structure.

2. The method of claim 1 wherein: the external stimulus includes at least one applied boundary condition, the at least one applied boundary condition includes at least one of a force, and a displacement, and the at least one applied boundary condition is applied to selected ones of the edges of the plurality of finite elements.

3. The method of claim 1 wherein the physical parameter of interest is calculated from the complementary functions as scaled by the solved scalar multipliers.

4. The method of claim 1 further comprising:
in response to the physical parameter of interest not meeting the design parameter, repeating the defining, the solving, the calculating, and the updating the structural model of the physical structure until a final design of the physical structure is reached.

5. The method of claim 4 further comprising:
manufacturing the physical structure based on the final design.

6. The method of claim 1 wherein, for each of the finite elements in a first class of finite element, the corresponding governing differential equation is a first predefined governing differential equation.

7. The method of claim 6 wherein the first class is one of (i) plate elements, (ii) shell elements, (iii) beam elements, and (iv) brick elements.

8. The method of claim 1 wherein:
the method further comprises identifying, for each differential equation of the governing differential equations, a particular solution to the differential equation; and
the energy optimization model is further based on the particular solutions to the governing differential equations.

9. The method of claim 1 wherein:
each of the plurality of finite elements is characterized by an element shape from a set of element shapes; and
for each element shape of the set of element shapes, an area mapping array defines volumes for the element shape for determination of the internal energy.

10. The method of claim 9 wherein, for each element shape of the plurality of finite elements, the area mapping array selectively defines voids in the element shape.

11. The method of claim 1 wherein the external energy of each finite element of the plurality of finite elements is based on (i) external work done on the finite element by the external stimulus acting on (ii) edges of the finite element as deformed by the corresponding plurality of complementary functions.

12. The method of claim 11 wherein:
each of the plurality of finite elements is characterized by an element shape from a set of element shapes; and
for each element shape of the plurality of finite elements, an edge mapping array defines edges for determination of the external energy.

13. The method of claim 1 wherein the mesh is generated by overlaying a grid on the structural model, wherein the grid is one of (i) a radial grid and (ii) a rectangular grid.

14. The method of claim 1 wherein the external energy of at least one of the plurality of finite elements is based on established boundary conditions.

15. The method of claim 14 wherein each of the edges of each of the plurality of finite elements is adapted to allow for a corresponding one of the boundary conditions to be established.

16. The method of claim 14 wherein each of the edges of each of the plurality of finite elements is adapted to allow for a load to be applied.

17. The method of claim 14 wherein the solving permits the established boundary conditions to be violated.

18. The method of claim 1 wherein the solved scalar multipliers represent an exact solution to the governing differential equations.

19. A non-transitory computer-readable medium storing instructions executable on a processor, wherein the instructions include:
storing a structural model of a physical structure;
defining a mesh for the structural model, wherein the mesh includes a plurality of finite elements, and wherein each element of the finite elements is defined by a plurality of edges of the element;
identifying a governing differential equation for each of the plurality of finite elements;
for each element of the plurality of finite elements:
identifying a plurality of complementary functions that exactly satisfy the corresponding governing differential equation,
wherein each of the plurality of complementary functions for the finite element is associated with a respective scalar multiplier, and
wherein a count of the respective scalar multipliers for the element establishes a number of degrees of freedom of the element;
determining an applied stimulus for the physical structure, wherein the applied stimulus includes at least one of an applied mechanical force, an applied mechanical stress, an applied mechanical strain, an applied mechanical torque, an applied mechanical moment, an applied translational displacement, and an applied rotational displacement;
generating an energy optimization model that minimizes a difference between internal energy of the plurality of finite elements and external energy of the plurality of finite elements,
wherein an internal energy of each finite element of the plurality of finite elements is based on strain energy in a volume of the finite element (i) defined by the edges of the finite element and (ii) resulting from deformations of the finite element by the corresponding plurality of complementary functions,
wherein an external energy of each finite element of the plurality of finite elements is based on external work done by external stimulus acting on the finite element as deformed by the corresponding plurality of complementary functions,
wherein the external stimulus is based on the applied stimulus,
wherein generating the energy optimization model includes, for each element of the plurality of finite elements:
determining a difference expression between the internal energy of the element and the external energy of the element, and
for each degree of freedom of the element, generating a set of equation parameters by calculating a partial differential of the difference expression with respect to the respective scalar multiplier, and wherein generating the energy optimization model includes transforming the sets of equation parameters for each of the degrees of freedom of the plurality of finite elements into a first matrix;

solving the energy optimization model for the respective scalar multipliers, wherein solving the energy optimization model includes transforming the first matrix using an inversion operation;

calculating a physical parameter of interest of the physical structure in response to the applied stimulus, wherein the physical parameter of interest includes at least one of a mechanical strain on the physical structure, a mechanical stress on the physical structure, a mechanical force on the physical structure, a mechanical moment of the physical structure, a mechanical torque of the physical structure, a translational displacement of the physical structure, and a rotational displacement of the physical structure, and wherein the physical parameter of interest is calculated based on the solved scalar multipliers;

determining whether the physical parameter of interest satisfies a design parameter of the physical structure; and in response to the physical parameter of interest not satisfying the design parameter, updating the structural model of the physical structure.

20. An apparatus comprising a processor configured to execute instructions from a computer-readable storage medium, the instructions including:

storing a structural model of a physical structure;

defining a mesh for the structural model, wherein the mesh includes a plurality of finite elements, and wherein each element of the finite elements is defined by a plurality of edges of the element;

identifying a governing differential equation for each of the plurality of finite elements;

for each element of the plurality of finite elements:
  identifying a plurality of complementary functions that exactly satisfy the corresponding governing differential equation,
  wherein each of the plurality of complementary functions for the finite element is associated with a respective scalar multiplier, and
  wherein a count of the respective scalar multipliers for the element establishes a number of degrees of freedom of the element;

determining an applied stimulus for the physical structure, wherein the applied stimulus includes at least one of an applied mechanical force, an applied mechanical stress, an applied mechanical strain, an applied mechanical torque, an applied mechanical moment, an applied translational displacement, and an applied rotational displacement;

generating an energy optimization model that minimizes a difference between internal energy of the plurality of finite elements and external energy of the plurality of finite elements,
  wherein an internal energy of each finite element of the plurality of finite elements is based on strain energy in a volume of the finite element (i) defined by the edges of the finite element and (ii) resulting from deformations of the finite element by the corresponding plurality of complementary functions,
  wherein an external energy of each finite element of the plurality of finite elements is based on external work done by external stimulus acting on the finite element as deformed by the corresponding plurality of complementary functions,
  wherein the external stimulus is based on the applied stimulus,
  wherein generating the energy optimization model includes, for each element of the plurality of finite elements:
    determining a difference expression between the internal energy of the element and the external energy of the element, and
    for each degree of freedom of the element, generating a set of equation parameters by calculating a partial differential of the difference expression with respect to the respective scalar multiplier, and
  wherein generating the energy optimization model includes transforming the sets of equation parameters for each of the degrees of freedom of the plurality of finite elements into a first matrix;

solving the energy optimization model for the respective scalar multipliers, wherein solving the energy optimization model includes transforming the first matrix using an inversion operation;

calculating a physical parameter of interest of the physical structure in response to the applied stimulus, wherein the physical parameter of interest includes at least one of a mechanical strain on the physical structure, a mechanical stress on the physical structure, a mechanical force on the physical structure, a mechanical moment of the physical structure, a mechanical torque of the physical structure, a translational displacement of the physical structure, and a rotational displacement of the physical structure, and wherein the physical parameter of interest is calculated based on the solved scalar multipliers;

determining whether the physical parameter of interest satisfies a design parameter of the physical structure; and in response to the physical parameter of interest not satisfying the design parameter, updating the structural model of the physical structure.

* * * * *